United States Patent
Huh et al.

(10) Patent No.: US 11,059,908 B2
(45) Date of Patent: Jul. 13, 2021

(54) LOW-VISCOSITY ANTIGEN BINDING PROTEINS AND METHODS OF MAKING THEM

(71) Applicant: AMGEN INC., Thousand Oaks, CA (US)

(72) Inventors: Joon Hoi Huh, Culver City, CA (US); Riki Stevenson, Ventura, CA (US); Pavel Bondarenko, Thousand Oaks, CA (US); Andrew Nichols, Calabasas, CA (US); Da Ren, Thousand Oaks, CA (US); Neeraj Jagdish Agrawal, Natick, MA (US)

(73) Assignee: AMGEN INC., Thousand Oaks, CA (US)

( * ) Notice: Subject to any disclaimer, the term of this patent is extended or adjusted under 35 U.S.C. 154(b) by 117 days.

(21) Appl. No.: 16/338,292

(22) PCT Filed: Sep. 28, 2017

(86) PCT No.: PCT/US2017/053967
§ 371 (c)(1),
(2) Date: Mar. 29, 2019

(87) PCT Pub. No.: WO2018/064307
PCT Pub. Date: Apr. 5, 2018

(65) Prior Publication Data
US 2019/0233543 A1      Aug. 1, 2019

Related U.S. Application Data

(60) Provisional application No. 62/546,469, filed on Aug. 16, 2017, provisional application No. 62/430,773, filed on Dec. 6, 2016, provisional application No. 62/401,770, filed on Sep. 29, 2016.

(51) Int. Cl.
*C07K 16/40* (2006.01)
*C07K 16/28* (2006.01)
*G01N 11/14* (2006.01)

(52) U.S. Cl.
CPC .......... *C07K 16/40* (2013.01); *C07K 16/2869* (2013.01); *C07K 2317/21* (2013.01); *C07K 2317/24* (2013.01); *C07K 2317/52* (2013.01); *C07K 2317/55* (2013.01); *C07K 2317/90* (2013.01); *C07K 2317/92* (2013.01); *C07K 2317/94* (2013.01); *G01N 11/14* (2013.01)

(58) Field of Classification Search
CPC .......... C07K 16/40; C07K 16/2869; C07K 2317/94; C07K 2317/52; C07K 2317/90; C07K 2317/21; C07K 2317/24; C07K 2317/55; C07K 2317/92
See application file for complete search history.

(56) References Cited

U.S. PATENT DOCUMENTS

| 4,816,397 A | 3/1989 | Boss et al. |
| 4,816,567 A | 3/1989 | Cabilly et al. |
| 5,939,598 A | 8/1999 | Kucherlapati et al. |
| 8,545,849 B2 | 10/2013 | Borras et al. |
| 10,294,303 B2 | 5/2019 | Yie et al. |
| 2017/0275370 A1* | 9/2017 | Yie ................. A61K 39/3955 |
| 2019/0276546 A1 | 9/2019 | Yie et al. |

FOREIGN PATENT DOCUMENTS

| EP | 0 173 494 A2 | 3/1986 |
| EP | 0 171 496 B1 | 5/1993 |
| GB | 2 177 096 B | 5/1989 |

OTHER PUBLICATIONS

U.S. Appl. No. 62/387,486, Yie, J. et al., Amgen SEQ ID No. 74 of the cited application and SEQ ID No. 71 of the cited application.(p. 45 of Spec).
Carraway, K. L. and Koshland, Jr., D. E., "Carbodiimide modification of proteins," Methods Enzymol., 25:616-623 (1972).
Chaudhri, A. et al., "The role of amino acid sequence in the self-association of therapeutic monoclonal antibodies: insights from coarse-grained modeling," The Journal of Physical Chemistry B, 117(5):1269-1279 (2013).
Cheng, W. et al., "Linking the solution viscosity of an IgG2 monoclonal antibody to its structure as a function of pH and temperature," J. Pharm Sci., 102(12):4291-4304 (2013).
Chothia, C. et al., "Structural repertoire of the human $V_H$ segments," J. Mol. Biol., 227(3):799-817 (1992).
Chothia, C. et al., "Canonical structures for the hypervariable regions of immunoglobulins," J. Mol. Biol., 196:901-917 (1987).
Connolly, B. D. et al., "Weak interactions govern the viscosity of concentrated antibody solutions: high-throughput analysis using the diffusion interaction parameter," Biophys. J., 103(1):69-78 (2012).
Diebolder, C. A. et al., "Complement is Activated by IgG Hexamers Assembled at the Cell Surface," Science, 343(6176):1260-1263 (2014).
Edelman, G. M. et al., "The covalent structure of an entire gamma immunoglobulin molecule," Proc. Natl. Acad. Sci. U.S.A., 63(1):78-85 (1969).
Ewert, S. et al., "Stability improvement of antibodies for extracellular and intracellular applications: CDR grafting to stable frameworks and structure-based framework engineering," Methods, 34(2):184-199 (2004).

(Continued)

*Primary Examiner* — Sharon X Wen
(74) *Attorney, Agent, or Firm* — Timothy J. Gaul

(57) ABSTRACT

The present invention concerns a method for preparing antigen binding proteins with reduced viscosity. The method proceeds by replacing residues in high viscosity variable domain subfamilies with residues in correlating low viscosity subfamilies. The method further comprises substituting residues in the Fc domain with residues associated with low viscosity and adding charged residues to the C-terminus of the Fc domain. The present invention further concerns antigen binding proteins produced by this method.

9 Claims, 28 Drawing Sheets
Specification includes a Sequence Listing.

(56) References Cited

OTHER PUBLICATIONS

Ewert, S. et al., "Structure-based improvement of the biophysical properties of immunoglobulin $V_H$ domains with a generalizable approach," Biochemistry, 42:1517-1528 (2003).

Ewert, S. et al., "Biophysical properties of human antibody variable domains," J. Mol. Biol., 325:531-553 (2003).

Ford, C. F. et al., "Fusion tails for the recovery and purification of recombinant proteins," Protein Expression and Purification, 2(2-3):95-107 (1991).

Grussenmeyer, T. et al., "Complexes of polyoma virus medium T antigen and cellular proteins," Proc. Natl. Acad. Sci. USA, 82:7952 (1985).

Guo, Z. et al., "Structure-activity relationship for hydrophobic salts as viscosity-lowering excipients for concentrated solutions of monoclonal antibodies," Pharm Res., 29:3102-3109 (2012).

Honegger, A. et al., "Yet another numbering scheme for immunoglobulin variable domains: an automatic modeling and analysis tool," J. Mol. Biol., 309:657-670 (2001).

Hopp, T. P. et al., A Short Polypeptide Marker Sequence Useful for Recombinant Protein Identification and Purification, Nature Biotechnology, 6:1204-1210 (1988).

Horton, J. D., Cohen, J. C. & Hobbs, H. H., "Molecular Biology of $PCSK_9$: Its Role in LDL Metabolism," Trends Biochem. Sci., 32(2):71-77. doi:10.1016/j.tibs.2006.12.008, Seidah & Prat (2007).

Jackson, S. et al., "The Crystal Structure of PCSK9: a Regulator of Plasma LDL-Cholesterol," Structure, 15:545-552 (2007).

Jefferis, R. and Lefranc, M-P., Human immunoglobulin allotypes: possible implications for immunogenicity, mAbs, 1:332-338 (2009).

Kabat, E. A. et al., Sequences of Proteins of Immunological Interest, Fifth Edition, Public Health Service, National Institutes of Health, Bethesda, MD, Publication No. 91-3242 (1991) Table of Contents Only).

Kanai, S. et al., "Reversible self-association of a concentrated monoclonal antibody solution mediated by Fab-Fab interaction that impacts solution viscosity," Journal of Pharmaceutical Sciences, 97(10):4219-4227 (2008).

Ketchem, R. R. et al., "Mitigation of monoclonal antibody viscosity by modification of protein surface charge," Abstracts of Papers; ACS National Meeting & Exposition, American Chemical Society, US, $243^{rd}$, p. 1, (2012) URL:http://abstracts.acs.org/chem/243nm/program/view.php?obj_id=122153&terms=abstract.

Lemaigre, F. P. et al., "Transcriptional control of genes that regulate glycolysis and gluconeogenesis in adult liver," Biochem. J., 303:1-14 (1994).

Li, L. et al., "Concentration dependent viscosity of monoclonal antibody solutions: explaining experimental behavior in terms of molecular properties," Pharm. Res., 31:3161-3178 (2014).

Loeken, M. R., "Effects of mutation of the CREB binding site of the somatostatin promoter on cyclic AMP responsiveness in CV-1 cells," Gene Expr., 3(3):253-264(12) (1993).

McGehee, R. E. et al., "Differentiation-specific element: a cis-acting developmental switch required for the sustained transcriptional expression of the angiotensinogen gene during hormonal-induced differentiation of 3T3-L1 fibroblasts to adipocytes," Mol. Endocrinol., 7(4):551-560 (1993).

Morrison, S. L. et al., "Chimeric human antibody molecules: mouse antigen-binding domains with human constant region domains," Proc. Natl. Acad. Sci. U.S.A., 81(21):6851-6855 (1984).

Neergaard, M. S. et al., "Viscosity of high concentration protein formulations of monoclonal antibodies of IgG1 and IgG4 subclass—prediction of viscosity through protein—protein interaction measurements," Eur J. Pharm. Sci., 49:400-410 (2013).

Nilsson, B. et al., "Expression and purification of recombinant insulin-like growth factors from Escherichia coli," Methods Enzymol., 198:3-16 (1991).

Nilsson, B. et al., "Immobilization and purification of enzymes with staphylococcal protein A gene fusion vectors," EMBO J., 4(4):1075-1080 (1985).

O'Reilly, M. A. et al., "Identification of an activating transcription factor (ATF) binding site in the human transforming growth factor-β2 promoter," J. Biol. Chem., 267(28):19938-19943 (1992).

Paul, W., ed., Fundamental Immunology, Chapter 7, $2^{nd}$ Edition, Raven Press, NY (1989).

Ropartz, C., Schanfield, M. S., Steinberg, A. G., "Review of the notation for the allotypic and related markers of human immunoglobulins," WHO meeting on human immunoglobulin allotypic markers, Held Jul. 16-19, 1974, Rouen, France, Report Amended Jun. 1976, J. Immunogenet, 3:357-362 (1976).

Rothlisberger, D. et al., "Domain interactions in the Fab fragment: a comparative evaluation of the single-chain Fv and Fab format engineered with variable domains of different stability," J. Mol. Biol., 347:773-789 (2005).

Seidah, N. G. & Prat, A., "The proprotein convertases are potential targets in the treatment of dyslipidemia," J. Mol. Med. (Berl), 85(7):685-696 (2007).

Shukla, A. A. et al., "Downstream processing of monoclonal antibodie—Application of platform approaches," J. Chrom. B, 848:28-39 (2007).

Singh, S. N. et al., "Dipole-Dipole Interaction in Antibody Solutions: Correlation with Viscosity Behavior at High Concentrations," Pharm. Res., 31(9):2549-2558 (2014).

Smith, D. B. et al., "Single-step purification of polypeptides expressed in Escherichia coli as fusions with glutathione S-transferase," Gene, 67(1):31-40 (1988).

Takeda, S. et al., "Construction of chimaeric processed immunoglobulin genes containing mouse variable and human constant region sequences," Nature, 314:452-454 (1985).

Tomlinson, I. M. et al., "The structural repertoire of the human V kappa domain," EMBO J., 14:4628-4638 (1995).

Treisman, R. "The SRE: a growth factor response transcriptional regulator, Seminars in Cancer Biol.," 1(1):47-58 (1990).

Tseng, C. C. et al., "Postprandial stimulation of insulin release by glucose-dependent insulinotropic polypeptide (GIP). Effect of a specific glucose-dependent insulinotropic polypeptide receptor antagonist in the rat," J. Clin. Invest., 98(11):2440-2445 (1996).

Van Den Bremer, E. T. J. et al., "Human IgG is produced in a pro-form that requires clipping of C-terminal lysines for maximal complement activation," mAbs, 7(4):672-680 (2015).

Vidarsson, G. et al., "IgG subclasses and allotypes: from structure to effector functions," Front. Immunol., 5:1-17 (2014).

Yadav, S. et al., "The influence of charge distribution on self-association and viscosity behavior of monoclonal antibody solutions," Mol. Pharm., 9(4):791-802 (2012).

Yadav, S. et al., "Viscosity behavior of high-concentration monoclonal antibody solutions: correlation with interaction parameter and electroviscous effects," J. Pharm. Sci., 101(3):998-1011 (2012).

Yadav, S. et al., "Establishing a Link Between Amino Acid Sequences and Self-Associating Viscoelastic Behavior of Two Closely Related Monoclonal Antibodies," Pharm. Res., 28(7):1750-1764 (2011).

Ye, J. et al., "Characterization of a Silencer Regulatory Element in the Human Interferon-γ Promoter,", J Biol Chem., 269(41):25728-25734 (1994).

\* cited by examiner

| Target (informal name) | mAb | Conc. mg/ml | Visc. cP | HC Type (including allotypes) | LC Type | VL Germline | VH Germline | pI | HC SEQ ID NO | LC SEQ ID NO |
|---|---|---|---|---|---|---|---|---|---|---|
| anti-amyloid | A | 142.2 | 5.0 | IgG1 (f) (R;EM) | Kappa | VK2\|A23 | VH2\|2-26 | 9.0 | 168 | 166 |
| GMCSF (247) | B | 139.7 | 5.6 | IgG2 | Kappa | VK3\|A27 | VH1\|1-02 | 8.7 | 4 | 2 |
| CGRPR | C | 136.6 | 6.3 | IgG2 | Lambda | VL1\|1g | VH3\|3-15 | 8.6 | 180 | 178 |
| RANKL | D | 152.7 | 6.6 | IgG2 | Kappa | VK3\|A27 | VH3\|3-23 | 8.6 | 172 | 170 |
| Sclerostin (27H6) | E | 145.0 | 6.7 | IgG2 | Kappa | VK2\|O1 | VH3\|3-48 | 6.6 | 8 | 6 |
| IL-1R1 | F | 153.9 | 6.7 | IgG2 | Kappa | VK6\|A10 | VH5\|5-51 | 7.4 | 12 | 10 |
| Myostatin | G | 141.0 | 6.8 | IgG1 (z) (K;EM) | Kappa | VK1\|O18 | VH3\|3-07 | 8.7 | 16 | 14 |
| B7RP1 | H | 137.5 | 7.7 | IgG2 | Kappa | VK1\|L15 | VH3\|3-07 | 7.7 | 20 | 18 |
| Amyloid | I | 140.6 | 8.2 | IgG1 (za) (K;DL) | Kappa | VK2\|A17 | VH2\|2-70 | 8.7 | 24 | 22 |
| GMCSF (3.112) | J | 156.0 | 8.2 | IgG2 | Kappa | VK3\|A27 | VH1\|1-02 | 8.8 | 28 | 26 |
| CGRP (32H7) | K | 159.5 | 8.3 | IgG2 | Kappa | VK3\|A27 | VH3\|3-33 | 8.7 | 32 | 30 |
| CGRP (3B6.2) | L | 161.1 | 8.4 | IgG2 | Lambda | VL3\|3l | VH1\|1-02 | 8.6 | 36 | 34 |
| PCSK9 (8A3.1) | M | 150.0 | 9.1 | IgG2 | Kappa | VK2\|A19 | VH3\|3-07 | 6.7 | 40 | 38 |
| PCSK9 (492) | N | 150.0 | 9.2 | IgG2 | Kappa | VK2\|A19 | VH3\|3-07 | 6.9 | 44 | 42 |
| CGRP | O | 155.2 | 9.6 | IgG2 | Lambda | VL1\|1b | VH3\|3-33 | 8.8 | 48 | 46 |
| Hepcidin | P | 147.1 | 9.9 | IgG2 | Lambda | VL3\|3r | VH3\|3-33 | 7.3 | 52 | 50 |
| TNFR p55 | Q | 157.0 | 10.0 | IgG2 | Kappa | VK3\|A27 | VH3\|3-23 | 8.2 | 56 | 54 |
| OX40L | R | 144.5 | 10.0 | IgG2 | Kappa | VK2\|A23 | VH3\|3-33 | 8.7 | 60 | 58 |
| HGF | S | 155.8 | 10.6 | IgG2 | Kappa | VK3\|L16 | VH4\|4-59 | 8.1 | 64 | 62 |
| GMCSF | T | 162.5 | 11.0 | IgG2 | Kappa | VK4\|B3 | VH1\|1-02 | 8.1 | 68 | 66 |
| Glucagon R | V | 146.0 | 12.1 | IgG2 | Kappa | VK1\|A30 | VH3\|3-33 | 8.4 | 72 | 70 |
| GMCSF (4.381) | U | 144.5 | 12.1 | IgG2 | Kappa | VK3\|A27 | VH1\|1-02 | 8.4 | 76 | 74 |

FIGURE 1A

| Target (Informal name) | mAb | Conc. mg/ml | Visc. cP | HC Type (including allotypes) | LC Type | VL Germline | VH Germline | pI | HC SEQ ID NO | LC SEQ ID NO |
|---|---|---|---|---|---|---|---|---|---|---|
| Sclerostin (13F3) | W | 155.0 | 12.1 | IgG2 | Kappa | VK1\|L19 | VH1\|1-46 | 7.8 | 80 | 78 |
| CD-22 | X | 143.7 | 12.2 | IgG1 (f) (R;EM) | Kappa | VK1\|O18 | VH1\|1-69 | 8.8 | 84 | 82 |
| INFgR | Y | 154.2 | 12.2 | IgG1 (za) (K;DL) | Kappa | VK3\|A27 | VH5\|5-51 | 8.8 | 88 | 86 |
| Ang2 | Z | 151.5 | 12.4 | IgG2 | Kappa | VK2\|A19 | VH3\|3-48 | 7.4 | 92 | 90 |
| TRAILR2 | AA | 158.3 | 12.5 | IgG1 (f) (R;EM) | Kappa | VK3\|A27 | VH4\|4-30 | 8.7 | 96 | 94 |
| EGFR | AB | 141.7 | 14.0 | IgG2 | Kappa | VK1\|O18 | VH4\|4-61 | 6.8 | 100 | 98 |
| IL-4R | AC | 145.8 | 15.2 | IgG2 | Kappa | VK3\|A27 | VH3\|3-48 | 8.6 | 104 | 102 |
| IL-15 | AD | 149.0 | 16.3 | IgG1 (f) (R;EM) | Kappa | VK3\|A27 | VH5\|5-51 | 8.8 | 108 | 106 |
| IGF1R | AE | 159.2 | 17.3 | IgG1 (za) (K;DL) | Kappa | VK2\|A19 | VH4\|4-04 | 8.6 | 112 | 110 |
| IL-17R | AF | 150.9 | 19.1 | IgG2 | Kappa | VK3\|L16 | VH1\|1-18 | 8.6 | 116 | 114 |
| Dkk1 (6.37.5) | AG | 159.4 | 19.6 | IgG2 | Kappa | VK2\|A2 | VH3\|3-33 | 8.2 | 120 | 118 |
| Sclerostin | AH | 134.8 | 20.9 | IgG2 | Kappa | VK1\|O2 | VH1\|1-e | 7.4 | 124 | 122 |
| TSLP | AI | 134.2 | 21.4 | IgG2 | Lambda | VL3\|3h | VH3\|3-33 | 7.2 | 128 | 126 |
| Dkk1 (11H10) | AJ | 145.3 | 22.5 | IgG2 | Kappa | VK3\|L6 | VH3\|3-48 | 8.2 | 132 | 130 |
| PCSK9 | AK | 145.2 | 22.8 | IgG2 | Lambda | VL2\|2a2 | VH1\|1-18 | 8.1 | 136 | 134 |
| GIPR (2G10.006) | AQ | 150.0 | 19.1 | IgG1 (z) (K;EM) | Kappa | VK3\|L16 | VH3\|3-33 | 8.1 | 160 | 158 |
| Activin | AL | 133.9 | 29.4 | IgG2 | Lambda | VL3\|3r | VH1\|1-18 | 7.0 | 140 | 138 |
| Sclerostin (2B8) | AM | 150.0 | 30.0 | IgG2 | Lambda | VL6\|6a | VH3\|3-33 | 6.7 | 144 | 142 |
| Sclerostin | AN | 141.4 | 30.4 | IgG2 | Kappa | VK1\|O2 | VH1\|1-18 | 6.8 | 148 | 146 |
| c-fms | AO | 146.9 | 32.1 | IgG2 | Kappa | VK4\|B3 | VH1\|1-18 | 6.6 | 152 | 150 |
| α4β7 | AP | 154.9 | 32.7 | IgG2 | Kappa | VK1\|L19 | VH1\|1-24 | 6.5 | 156 | 154 |

FIGURE 1B

| Target (informal name) | mAb | SEQ ID NOS | | | | | | | |
|---|---|---|---|---|---|---|---|---|---|
| | | HC FR1 | HC FR2 | HC FR3 | HC FR4 | LC FR1 | LC FR2 | LC FR3 | LC FR4 |
| anti-amyloid | A | 280 | 281 | 282 | 283 | 189 | 190 | 191 | 192 |
| GMCSF (247) | B | 300 | 285 | 301 | 276 | 197 | 194 | 198 | 196 |
| CGRPR | C | 316 | 317 | 318 | 287 | 257 | 258 | 259 | 250 |
| RANKL | D | 291 | 292 | 293 | 276 | 193 | 194 | 195 | 196 |
| Sclerostin (27H6) | E | 304 | 292 | 349 | 276 | 246 | 225 | 226 | 188 |
| IL-1R1 | F | 277 | 278 | 279 | 276 | 185 | 186 | 187 | 188 |
| Myostatin | G | 304 | 289 | 346 | 287 | 205 | 206 | 219 | 231 |
| B7RP1 | H | 304 | 289 | 305 | 276 | 205 | 229 | 207 | 196 |
| Amyloid | I | 333 | 281 | 334 | 276 | 235 | 236 | 226 | 237 |
| GMCSF (3.112) | J | 344 | 285 | 345 | 283 | 193 | 194 | 201 | 196 |
| CGRP (32H7) | K | 302 | 289 | 338 | 287 | 193 | 194 | 198 | 231 |
| CGRP (3B6.2) | L | 299 | 285 | 339 | 287 | 266 | 267 | 268 | 269 |
| PCSK9 (8A3.1) | M | 304 | 289 | 315 | 287 | 227 | 225 | 226 | 188 |
| PCSK9 (492) | N | 304 | 289 | 314 | 287 | 227 | 225 | 228 | 188 |
| CGRP | O | 302 | 289 | 306 | 287 | 254 | 255 | 256 | 250 |
| Hepcidin | P | 302 | 289 | 303 | 283 | 263 | 264 | 265 | 250 |
| TNFR p55 ) | Q | 291 | 292 | 293 | 276 | 193 | 199 | 198 | 196 |
| OX40L | R | 302 | 289 | 303 | 276 | 189 | 190 | 213 | 214 |
| HGF | S | 273 | 274 | 275 | 276 | 181 | 182 | 183 | 184 |
| GMCSF | T | 299 | 285 | 301 | 276 | 215 | 211 | 216 | 217 |
| Glucagon R | V | 302 | 289 | 310 | 287 | 205 | 222 | 223 | 188 |
| GMCSF (4.381) | U | 299 | 285 | 301 | 276 | 193 | 202 | 203 | 204 |

FIGURE 1C

| Target (Informal name) | mAb | SEQ ID NOS | | | | | | | |
|---|---|---|---|---|---|---|---|---|---|
| | | HC FR1 | HC FR2 | HC FR3 | HC FR4 | LC FR1 | LC FR2 | LC FR3 | LC FR4 |
| Sclerostin (13F3) | W | 347 | 285 | 348 | 276 | 208 | 245 | 207 | 214 |
| CD-22 | X | 307 | 308 | 309 | 287 | 218 | 206 | 219 | 220 |
| INFγR | Y | 329 | 330 | 331 | 332 | 193 | 194 | 198 | 214 |
| Ang2 | Z | 326 | 292 | 305 | 276 | 227 | 225 | 226 | 231 |
| TRAILR2 | AA | 319 | 320 | 321 | 287 | 193 | 200 | 198 | 196 |
| EGFR | AB | 335 | 336 | 337 | 283 | 205 | 206 | 221 | 188 |
| IL-4R | AC | 304 | 292 | 305 | 276 | 193 | 194 | 198 | 196 |
| IL-15 | AD | 322 | 323 | 324 | 276 | 193 | 194 | 198 | 230 |
| IGF1R | AE | 311 | 312 | 313 | 283 | 224 | 225 | 226 | 196 |
| IL-17R | AF | 299 | 285 | 328 | 276 | 181 | 232 | 233 | 188 |
| Dkk1 (6.37.5) | AG | 302 | 289 | 341 | 276 | 240 | 241 | 242 | 243 |
| Sclerostin | AH | 294 | 285 | 295 | 276 | 205 | 206 | 207 | 196 |
| TSLP | AI | 288 | 289 | 290 | 283 | 251 | 252 | 253 | 250 |
| Dkk1 (11H10) | AJ | 340 | 292 | 305 | 287 | 238 | 194 | 239 | 231 |
| PCSK9 | AK | 284 | 285 | 286 | 287 | 247 | 248 | 249 | 250 |
| GIPR (2G10.006) | AQ | 302 | 342 | 303 | 276 | 181 | 194 | 234 | 188 |
| Activin | AL | 299 | 285 | 325 | 283 | 260 | 261 | 262 | 250 |
| Sclerostin (2B8) | AM | 302 | 289 | 303 | 287 | 270 | 271 | 272 | 250 |
| Sclerostin | AN | 327 | 285 | 328 | 287 | 205 | 206 | 207 | 188 |
| c-fms | AO | 299 | 285 | 328 | 276 | 210 | 211 | 212 | 214 |
| α4β7 | AP | 296 | 297 | 298 | 276 | 208 | 206 | 209 | 196 |
| c-kit | BA | 299 | 285 | 295 | 276 | 210 | 211 | 212 | 188 |

FIGURE 1D

| Chain | High viscosity subfamily | Low viscosity subfamily | p-value | Residues in high viscosity subfamily, positions in Aho numbering, residues in low viscosity subfamily | | | | |
|---|---|---|---|---|---|---|---|---|
| | | | | FR1 | CDR1 | FR2 | CDR2 | FR3 |
| Heavy | VH1\|1-18 | VH1\|1-02 | 0.0002 | | S33G, G40Y, S42H | | S59N, Y61N, N65S, N67G, | T82R, T86I, R94S, S95R |
| Heavy | VH3\|3-33 | VH3\|3-07 | 0.076 | Q1E, R17G | G40W, M41_, H42S | | V57S/Q, W/S59K/R, Y60Q, N67E | S85A |
| Light | VK3\|L16 | VK3\|A27 | 0.031 | M4L, V13L | _33S | | D58G | A76D, S95R, Q97E, S98P |

FIGURE 2

| VH1\|1-18 and VH1\|1-02 Global sequence parameters | | | | | CDR1 | | | CDR2 | | | | | FR3 | | | | | | | | | |
|---|---|---|---|---|---|---|---|---|---|---|---|---|---|---|---|---|---|---|---|---|---|---|
| | | | | | 32 | 33 | 35 | 52 | 53 | 54 | 55 | 57 | 67 | 68 | 69 | 70 | 71 | 72 | 73 | 74 | 75 | |
| | | | | | 31 | 33 | 35 | 52 | a | 53 | 54 | 56 | 66 | 67 | 68 | 69 | 70 | 71 | 72 | 73 | 74 | |
| | | | | | 31 | 33 | 35 | 52 | a | 53 | 54 | 56 | 66 | 67 | 68 | 69 | 70 | 71 | 72 | 73 | 74 | |
| mAbs | Visc, cP | pI | VL | VH1 | 33 | 40 | 42 | 59 | 60 | 61 | 65 | 67 | 77 | 78 | 79 | 80 | 81 | 82 | 83 | 84 | 85 |
| VBase | | | | VH1\|1-02 | G | Y | H | N | P | N | S | G | R | V | T | M | T | R | D | T | S |
| B | 5.8 | 8.7 | VK3\|A27 | VH1\|1-02 | G | Y | H | N | P | N | S | G | R | V | T | M | T | R | D | T | S |
| J | 8.2 | 8.8 | VK3\|A27 | VH1\|1-02 | G | Y | H | N | P | N | S | G | R | V | T | M | T | R | D | T | S |
| L | 8.4 | 8.6 | VL3\|3l | VH1\|1-02 | G | Y | H | N | P | N | S | G | R | V | T | M | T | R | D | T | S |
| T | 11.0 | 8.1 | VK4\|B3 | VH1\|1-02 | G | Y | H | N | P | N | S | G | R | V | T | M | T | R | D | T | S |
| U | 12.1 | 8.4 | VK3\|A27 | VH1\|1-02 | G | Y | H | N | P | N | S | G | R | V | T | M | T | R | D | T | S |
| AF | 19.1 | 8.6 | VK3\|L16 | VH1\|1-18 | R | G | S | S | T | Y | S | N | R | V | T | M | T | I | D | T | S |
| AK | 22.8 | 8.1 | VL2\|2a2 | VH1\|1-18 | S | G | S | S | F | Y | N | N | R | G | T | M | T | I | D | P | S |
| AL | 28.4 | 7.0 | VL3\|3r | VH1\|1-18 | S | G | S | I | P | Y | N | N | R | V | T | M | T | I | D | T | S |
| AN | 30.4 | 6.6 | VK1\|O2 | VH1\|1-18 | D | N | H | N | P | N | S | G | R | V | T | M | T | I | D | T | S |
| AO | 32.1 | 6.6 | VK4\|B3 | VH1\|1-18 | S | G | S | S | A | Y | N | N | R | V | T | M | T | I | D | T | S |
| Vbase | | | | VH1\|1-18 | S | G | S | S | A | Y | N | N | R | V | T | M | T | I | D | T | S |
| p-value | 0.0002 | 0.03 | | | | | | | | | | | | | | | | | | | |

| FR3 | | | | | | | | | | | | | | | | | | | | | | | | VH | VL | Schem |
|---|---|---|---|---|---|---|---|---|---|---|---|---|---|---|---|---|---|---|---|---|---|---|---|---|---|---|
| 76 | 77 | 78 | 79 | 80 | 81 | 82 | 83 | 84 | 85 | 86 | 87 | 88 | 89 | 90 | 91 | 92 | 93 | 94 | 95 | 96 | 97 | 98 | | 52 | 12 | EU |
| 75 | 76 | 77 | 78 | 79 | 80 | 81 | 82 | a | b | c | 83 | 84 | 85 | 86 | 87 | 88 | 89 | 90 | 91 | 92 | 93 | 94 | | 50 | 13 | Kabat |
| 75 | 76 | 77 | 78 | 79 | 80 | 81 | 82 | a | b | c | 83 | 84 | 85 | 86 | 87 | 88 | 89 | 90 | 91 | 92 | 93 | 94 | | 52 | 13 | Chothia |
| 86 | 87 | 88 | 89 | 90 | 91 | 92 | 93 | 94 | 95 | 96 | 97 | 98 | 99 | 100 | 101 | 102 | 103 | 104 | 105 | 106 | 107 | 108 | | 59 | 13 | Aho |
| I | S | T | A | Y | M | E | L | S | R | L | R | S | D | D | T | A | V | Y | Y | C | A | R | | | | |
| I | S | T | A | Y | M | E | L | S | R | L | R | S | D | D | T | A | V | Y | Y | C | A | R | | N | L | |
| I | S | T | A | S | M | E | L | S | R | L | R | S | D | D | T | A | V | Y | F | C | A | R | | N | L | |
| I | S | T | A | Y | M | E | L | S | R | L | R | S | D | D | T | A | V | Y | F | C | A | R | | N | V | |
| I | S | T | A | Y | M | E | L | S | R | L | R | S | D | D | T | A | V | Y | Y | C | A | R | | N | L | |
| I | S | T | A | Y | M | E | L | R | S | L | R | S | D | D | T | A | V | Y | Y | C | A | R | | S | V | |
| I | S | T | A | Y | M | E | L | R | S | L | R | S | D | D | T | A | V | Y | Y | C | A | R | | S | G | |
| I | S | T | A | Y | M | E | L | R | S | L | R | S | D | D | T | A | V | Y | F | C | A | R | | I | V | |
| I | S | T | A | Y | M | E | L | R | S | L | R | S | D | D | T | A | V | Y | Y | C | A | R | | N | A | |
| I | S | T | A | Y | M | E | L | R | S | L | R | S | D | D | T | A | V | Y | Y | C | A | R | | S | V | |
| I | S | T | A | Y | M | E | L | R | S | L | R | S | D | D | T | A | V | Y | Y | C | A | R | | | | |

FIGURE 9

| mAb mutant symbols | Heavy chain mutations | Light chain mutations |
|---|---|---|
| AK | AK_HC | AK_LC |
| AK (82 94 95) | AK_HC: [T82R, R94S, S95R] | AK_LC |
| AK (59 82 94 95) | AK_HC: [S59K, T82R, R94S, S95R] | AK_LC |
| AK (82 94 95 13) | AK_HC: [T82R, R94S, S95R] | AK_LC: [G13L] |
| AK (59 82 94 95 13) | AK_HC: [S59K, T82R, R94S, S95R] | AK_LC: [G13L] |
| AO | AO_HC | AO_LC |
| AO (82 94 95) | AO_HC: [T82R, R94S, S95R] | AO_LC |
| AO (59 82 94 95) | AO_HC: [S59K, T82R, R94S, S95R] | AO_LC |
| AO (82 94 95 13) | AO_HC: [T82R, R94S, S95R] | AO_LC: [V13L] |
| AO (59 82 94 95 13) | AO_HC: [S59K, T82R, R94S, S95R] | AO_LC: [V13L] |

FIGURE 10

| VH3\|3-07 and VH3\|3-33 Global Sequence Parameters | | | | | FR1 | | CDR1 | | | CDR2 | | | | FR3 | Scheme |
|---|---|---|---|---|---|---|---|---|---|---|---|---|---|---|---|
| | | | | | 1 | 16 | 33 | 34 | 35 | 50 | 52 | 53 | 57 | 75 | EU |
| | | | | | 1 | 16 | 33 | 34 | 35 | 50 | 52 | 52a | 56 | 74 | Kabat |
| | | | | | 1 | 16 | 33 | 34 | 35 | 50 | 52 | 52a | 56 | 74 | Chothia |
| mAb | Visc, cP | pI | VL | VH3 | 1 | 17 | 40 | 41 | 42 | 57 | 59 | 60 | 67 | 85 | Aho |
| VBase | | | | VH3\|3-07 | E | G | W | M | S | N | K | Q | E | A | |
| G | 6.8 | 8.7 | VK1\|O18 | VH3\|3-07 | E | G | W | | N | Q | R | L | A | A | |
| H | 7.7 | 7.7 | VK1\|L15 | VH3\|3-07 | E | G | W | | S | Y | K | Q | E | A | |
| K | 8.3 | 8.7 | VK3\|A27 | VH3\|3-33 | Q | R | G | M | H | V | W | Y | N | S | |
| M | 9.1 | 6.7 | VK2\|A19 | VH3\|3-07 | E | G | W | | S | S | K | Q | E | A | |
| N | 9.2 | 6.9 | VK2\|A19 | VH3\|3-07 | E | G | W | | S | S | K | Q | E | A | |
| O | 9.6 | 8.8 | VL1\|1b | VH3\|3-33 | Q | R | G | M | H | V | S | F | I | S | |
| P | 9.9 | 7.3 | VL3\|3r | VH3\|3-33 | Q | R | G | M | H | V | W | Y | N | S | |
| R | 10.0 | 8.7 | VK2\|A23 | VH3\|3-33 | Q | R | G | M | H | V | W | Y | N | S | |
| V | 12.1 | 8.4 | VK1\|A30 | VH3\|3-33 | Q | R | G | M | H | V | W | Y | N | S | |
| AG | 19.6 | 8.2 | VK2\|A2 | VH3\|3-33 | Q | R | G | M | H | V | S | Y | D | A | |
| AI | 21.4 | 7.2 | VL3\|3h | VH3\|3-33 | Q | R | G | M | H | V | W | Y | N | S | |
| AQ | 19.1 | 8.1 | VK3\|L16 | VH3\|3-33 | Q | R | G | M | H | A | W | F | D | S | |
| AM | 30.0 | 6.7 | VL6\|6a | VH3\|3-33 | Q | R | A | M | H | V | W | Y | N | S | |
| VBase | | | | VH3\|3-33 | Q | R | G | M | H | V | W | Y | N | S | |
| p-value | 0.076 | 0.300 | | | | | | | | | | | | | |

FIGURE 11

| VK3|A27 and VK3|L Global Sequence Parameters | | | | | FR1 | | CDR1 | | CDR2 | FR3 | | | | Scheme |
|---|---|---|---|---|---|---|---|---|---|---|---|---|---|---|
| | | | | | 4 | 12 | 31 | 33 | 51 | 66 | 85 | 87 | 88 | EU |
| | | | | | 4 | 12 | 31 | 33 | 51 | 65 | 82b | 83 | 84 | Kabat |
| | | | | | 4 | 12 | 31 | 33 | 51 | 65 | 82b | 83 | 84 | Chothia |
| mAb | Visc, cP | pI | VH | VK3 | 4 | 13 | 33 | 40 | 58 | 76 | 95 | 97 | 98 | Aho |
| VBase | | | | VK3|A27 | L | L | S | Y | G | D | R | E | P | |
| B | 5.6 | 8.7 | VH1|1-02 | VK3|A27 | L | L | S | Y | G | D | R | E | P | |
| D | 6.6 | 8.6 | VH3|3-23 | VK3|A27 | L | L | G | Y | G | D | R | E | P | |
| J | 8.2 | 8.8 | VH1|1-02 | VK3|A27 | L | L | S | Y | G | D | R | E | P | |
| K | 8.3 | 8.7 | VH3|3-33 | VK3|A27 | L | L | S | Y | G | D | R | E | P | |
| Q | 10.0 | 8.2 | VH3|3-23 | VK3|A27 | L | L | S | Y | G | D | R | E | P | |
| S | 10.6 | 8.1 | VH4|4-59 | VK3|L16 | M | V | - | N | G | A | S | Q | S | |
| U | 12.1 | 8.4 | VH1|1-02 | VK3|A27 | L | L | N | Y | G | D | R | E | P | |
| Y | 12.2 | 8.8 | VH5|5-51 | VK3|A27 | L | L | S | Y | G | D | R | E | P | |
| AA | 12.5 | 8.7 | VH4|4-30 | VK3|A27 | L | L | R | Y | G | D | R | E | P | |
| AC | 15.2 | 8.6 | VH3|3-48 | VK3|A27 | L | L | N | Y | G | D | R | E | P | |
| AD | 16.3 | 8.8 | VH5|5-51 | VK3|A27 | L | L | S | Y | G | D | R | E | P | |
| AF | 19.1 | 8.6 | VH1|1-18 | VK3|L16 | M | V | - | N | D | A | S | Q | S | |
| AJ | 22.5 | 8.2 | VH3|3-48 | VK3|L6 | L | L | - | Y | D | A | S | E | P | |
| AQ | 19.1 | 8.1 | VH3|3-33 | VK3|L16 | M | V | - | N | G | A | S | Q | S | |
| Vbase | | | | VK3|L16 | M | V | - | N | G | A | S | Q | S | |
| p-value | 0.007 | 0.011 | | | | | | | | | | | | |

FIGURE 12

| Sample | Viscosity (cP) @ 1000s-1 @ 25C | Relative viscosity |
|---|---|---|
| Antibody AK | 43.7 | 100% |
| Fab Mutant | 25.6 | 59% |
| Fc Mutant | 34.8 | 80% |
| Double Mutant | 22.6 | 52% |

FIGURE 15

| Protein | Target | Monomer | Dimer | Other | Viscosity at 150 mg/mL at 25°C |
|---------|--------|---------|-------|-------|-------------------------------|
| ASA1 |  | Yes | Yes | No | ~ 2-4 cP in A5 |
| ASA2 |  | Yes | Yes | No | ~ 2-4 cP in A5 |
| Ab BA | C-kit | Yes | Yes | Yes | ~50 cP in A52Su |
| Ab AH | sclerostin | Yes | Yes | Yes | ~22 cP in A52Su |
| Ab AN | sclerostin | Yes | Yes | Yes | ~30 cP in A52Su |

FIGURE 17

| AQ mutant symbols | AQ HC mutations in Aho (Linear) numbering | AQ LC mutations in Aho (Linear) numbering | Conc, mg/mL | Visc, cP | STDEV, cP | Visc Rel to AQ |
|---|---|---|---|---|---|---|
| AQ | AQ_HC | AQ_LC | 151.1 | 19.1 | 0.6 | 1 |
| AQ (HC 1, 17, 85) | AQ_HC: Q1(1)E, R17(16)G, S85(75)A | AQ_LC | 151.7 | 15.8 | 0.8 | 0.87 |
| AQ (LC 4 13 76 95 97 98) | AQ_HC: | AQ_LC: M4(4)L, V13(13)L, A76(60)D, S95(77)R, Q97(79)E, S98(80)P | 149.1 | 12.7 | 0.4 | 0.67 |
| AQ (HC 1, 17, 85) (LC 4 13 76 95 97 98) | AQ_HC: Q1(1)E, R17(16)G, S85(75)A | AQ_LC: M4(4)L, V13(13)L, A76(60)D, S95(77)R, Q97(79)E, S98(80)P | 152.6 | 24.2 | 1 | 1.26 |

| Group # | Test Material | Dose Level (mg/kg) | Dose Volume (mL/kg) | Dose Concentration (mg/mL) | # Animals |
|---|---|---|---|---|---|
| 1 | Antibody AK (control) | 10 | 0.071 | 140 | 4 |
| | Diluent (procedural control) | 0 | 0.071 | 0 | |
| 2 | Antibody AK (Fab mutation) | 10 | 0.048 | 210 | 4 |
| | Diluent (procedural control) | 0 | 0.048 | 0 | |
| 3 | Antibody AK (Fc mutation) | 10 | 0.048 | 210 | 4 |
| 4 | Antibody AK (Fab and Fc double mutation) | 10 | 0.048 | 210 | 4 |

FIGURE 21

| Dose Group and Level | $T_{max}$ (Day) | $C_{max}$ (µg/mL) | $AUC_{last}$ (day*µg/mL) | $AUC_{last/D}$ (day*kg*µg/mL*mg) |
|---|---|---|---|---|
| Antibody AK 10 mg/kg | 2.5 | 87.8 | 923 | 92.3 |
| Antibody AK (Fab mutation) 10 mg/kg | 2.5 | 91.1 | 807 | 80.7 |
| Antibody AK (Fc mutation) 10 mg/kg | 0.81 | 125 | 1020 | 102 |
| Antibody AK (Fab + Fc mutation) 10 mg/kg | 1 | 112 | 740 | 74.0 |

FIGURE 22

| Animal # | pretest (Day 1 CLAB) | 1.02 | 2 | 3 | 4 | 6 | 8 | 11 | 15 | 18 | 22 | 25 | 29 | 36 | 43 |
|---|---|---|---|---|---|---|---|---|---|---|---|---|---|---|---|
| 1001 | 100.00% | 101.75% | 66.67% | 40.35% | 36.84% | 29.82% | 33.33% | 29.82% | 15.79% | 24.56% | 21.05% | 22.81% | 31.58% | 57.89% | 59.65% |
| 1002 | 100.00% | 95.00% | 52.50% | 45.00% | 37.50% | 37.50% | 47.50% | 20.00% | 7.50% | 50.00% | 32.50% | 30.00% | 42.50% | 60.00% | 70.00% |
| 1003 | 100.00% | 111.11% | 58.33% | 27.78% | 27.78% | 22.22% | 22.22% | 36.11% | 8.33% | 25.00% | 22.22% | 19.44% | 61.11% | 97.22% | 97.22% |
| 1004 | 100.00% | 105.97% | 52.24% | 35.82% | 32.84% | 29.85% | 19.40% | 14.93% | 4.48% | 4.48% | 19.40% | 19.40% | 83.58% | 98.51% | 100.00% |
| mean | 100.00% | 103.50% | 57.50% | 37.50% | 34.00% | 30.00% | 29.50% | 24.00% | 9.00% | 23.00% | 23.00% | 22.50% | 56.50% | 79.00% | 82.00% |
| 2001 | 100.00% | 106.52% | 58.70% | 34.78% | 26.09% | 28.26% | 30.43% | 28.26% | 21.74% | 52.17% | 32.61% | 39.13% | 39.13% | 54.35% | 69.57% |
| 2002 | 100.00% | 100.00% | 48.57% | 34.29% | 31.43% | 28.57% | 25.71% | 8.57% | 8.57% | 25.71% | 28.57% | 42.86% | 65.71% | 120.00% | 102.86% |
| 2003 | 100.00% | 110.34% | 63.79% | 32.76% | 32.76% | 24.14% | 13.79% | 18.97% | 5.17% | 15.52% | 18.97% | 24.14% | 41.38% | 60.34% | 67.24% |
| 2004 | 100.00% | 114.29% | 62.86% | 37.14% | 31.43% | 25.71% | 22.86% | 28.57% | 20.00% | 22.86% | 31.43% | 31.43% | 48.57% | 65.71% | 77.14% |
| mean | 100.00% | 108.05% | 59.20% | 34.48% | 30.46% | 26.44% | 22.41% | 21.26% | 13.22% | 28.74% | 27.01% | 33.33% | 47.13% | 71.84% | 77.01% |
| 3001 | 102.63% | 63.16% | 42.11% | 31.58% | 28.95% | 23.68% | 18.42% | 7.89% | 23.68% | 28.95% | 76.32% | 113.16% | 126.32% | 97.37% | 94.87% |
| 3002 | 104.17% | 50.00% | 29.17% | 27.08% | 29.17% | 18.75% | 14.58% | 6.25% | 16.67% | 25.00% | 52.08% | 81.25% | 89.58% | 79.17% | 76.00% |
| 3003 | 100.00% | 37.21% | 18.60% | 18.60% | 6.98% | 6.98% | 6.98% | 6.98% | 6.98% | 39.53% | 67.44% | 116.28% | 95.35% | 102.33% | 102.33% |
| 3004 | 100.00% | 55.00% | 40.00% | 32.50% | 27.50% | 25.00% | 27.50% | 20.00% | 22.50% | 25.00% | 22.50% | 32.50% | 37.50% | 50.00% | 50.00% |
| mean | 100.00% | 101.78% | 50.89% | 31.95% | 27.22% | 23.08% | 18.34% | 16.57% | 10.06% | 17.16% | 29.59% | 54.44% | 85.80% | 86.98% | 82.25% |
| 4001 | 100.00% | 105.88% | 76.47% | 56.86% | 47.06% | 45.10% | 35.29% | 39.22% | 25.49% | 31.37% | 31.37% | 37.25% | 64.71% | 92.16% | 96.08% |
| 4002 | 100.00% | 102.17% | 54.35% | 39.13% | 32.61% | 30.43% | 21.74% | 28.26% | 15.22% | 28.26% | 28.26% | 34.78% | 34.78% | 67.39% | 82.61% |
| 4003 | 100.00% | 94.92% | 54.24% | 35.59% | 30.51% | 20.34% | 22.03% | 27.12% | 15.25% | 23.73% | 57.63% | 45.76% | 67.80% | 74.58% | 81.36% |
| 4104 | 100.00% | 102.99% | 56.72% | 32.84% | 34.33% | 35.82% | 28.36% | 29.85% | 31.34% | 25.37% | 28.36% | 26.87% | 44.78% | 55.22% | 59.70% |
| mean | 100.00% | 101.35% | 60.09% | 40.36% | 35.87% | 32.74% | 26.91% | 30.94% | 22.42% | 26.91% | 36.77% | 35.87% | 53.36% | 71.30% | 78.48% |

LDL-C % pretest * — Days post dose

FIGURE 23

SEQUENCE LISTING

```
<160> NUMBER OF SEQ ID NOS: 383

<210> SEQ ID NO 1
<211> LENGTH: 705
<212> TYPE: DNA
<213> ORGANISM: Homo sapiens

<400> SEQUENCE: 1
atggaaaccc cggcgcagct gctgtttctg ctgctgctgt ggctgccgga taccaccggc    60
gaaattgtgt tgacgcagtc tccaggcacc ctgtctttgt ctccagggga cagagccacc   120
ctctcctgca gggccagtca gagtgttagt agcagctact ttgcctggta ccagcagaaa   180
cctggccagg ctcccaggct cctcatttat ggtgcatcca gtagggccac tggcatccca   240
gacaggttca gtggcagtgg gtctgggaca gacttcactc tcaccatcag cagactggag   300
cctgaagatt ttgcagtgta ttactgtcag cagtatgata ggtcacctcg acgttcggc    360 caagggacca aggtggaaat caaacgtacg gtggctgcac catctgtctt catcttcccg   420
ccatctgatg agcagttgaa atctggaact gcctctgttg tgtgcctgct gaataacttc   480
tatcccagag aggccaaagt acagtggaag gtggataacg ccctccaatc gggtaactcc   540
caggagagtg tcacagagca ggacagcaag gacagcacct acagcctcag cagcaccctg   600
acgctgagca agcagacta cgagaaacac aaagtctacg cctgcgaagt cacccatcag   660
ggcctgagct cgcccgtcac aaagagcttc aacaggggag agtgt               705

<210> SEQ ID NO 2
<211> LENGTH: 235
<212> TYPE: PRT
<213> ORGANISM: Homo sapiens

<400> SEQUENCE: 2

Met Glu Thr Pro Ala Gln Leu Leu Phe Leu Leu Leu Trp Leu Pro
1               5                  10                  15

Asp Thr Thr Gly Glu Ile Val Leu Thr Gln Ser Pro Gly Thr Leu Ser
            20                  25                  30

Leu Ser Pro Gly Asp Arg Ala Thr Leu Ser Cys Arg Ala Ser Gln Ser
        35                  40                  45

Val Ser Ser Ser Tyr Phe Ala Trp Tyr Gln Gln Lys Pro Gly Gln Ala
    50                  55                  60

Pro Arg Leu Leu Ile Tyr Gly Ala Ser Ser Arg Ala Thr Gly Ile Pro
65                  70                  75                  80
```

Asp Arg Phe Ser Gly Ser Gly Ser Gly Thr Asp Phe Thr Leu Thr Ile
                85                  90                  95

Ser Arg Leu Glu Pro Glu Asp Phe Ala Val Tyr Tyr Cys Gln Gln Tyr
            100                 105                 110

Asp Arg Ser Pro Arg Thr Phe Gly Gln Gly Thr Lys Val Glu Ile Lys
        115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235

<210> SEQ ID NO 3
<211> LENGTH: 1389
<212> TYPE: DNA
<213> ORGANISM: Homo sapiens

<400> SEQUENCE: 3
atggattgga cctggcgtat tctgtttctg gtggcggcgg cgaccggcgc gcatagccag      60
gtgcagctgg tgcagtctgg ggctgaggtg aagaagcctg ggcctcagt gaaggtctcc     120 tgtaagtctt ctggatacac cttcaccggc tactatatgc actgggtgcg acaggcccct    180
ggacaagggc ttgagtggat gggatggatc aaccctaaca gtggtggcac aaactatgca    240
cagaagttta agggcagggt caccatgacc aggacacgt ccatcagcac agcctacatg    300
gagctgagca gctgagatc tgacgacacg gccgtgtatt actgtgcgag agataagtgg    360
ctggacggct ttgactactg gggccaggga accctggtca ccgtctcctc agctagcacc    420
aagggcccat cggtcttccc cctggcgccc tgctccagga gcacctccga gagcacagcg    480
gccctgggct gcctggtcaa ggactacttc cccgaaccgg tgacggtgtc gtggaactca    540
ggcgctctga ccagcggcgt gcacaccttc ccagctgtcc tacagtcctc aggactctac    600
tccctcagca gcgtggtgac cgtgccctcc agcaacttcg gcacccagac ctacacctgc    660
aacgtagatc acaagcccag caacaccaag gtggacaaga cagttgagcg caaatgttgt    720
gtcgagtgcc caccgtgccc agcaccacct gtggcaggac cgtcagtctt cctcttcccc    780
ccaaaaccca aggacaccct catgatctcc cggacccctg aggtcacgtg cgtggtggtg    840
gacgtgagcc acgaagaccc cgaggtccag ttcaactggt acgtggacgg cgtggaggtg    900
cataatgcca agacaaagcc acgggaggag cagttcaaca gcacgttccg tgtggtcagc    960
gtcctcaccg ttgtgcacca ggactggctg aacggcaagg agtacaagtg caaggtctcc   1020
aacaaaggcc tcccagcccc catcgagaaa accatctcca aaccaaagg gcagccccga    1080 gaaccacagg tgtacaccct gcccccatcc cgggaggaga tgaccaagaa ccaggtcagc   1140
ctgacctgcc tggtcaaagg cttctacccc agcgacatcg ccgtggagtg ggagagcaat    1200
gggcagccgg agaacaacta caagaccaca cctcccatgc tggactccga cggctccttc   1260

-continued

```
ttcctctaca gcaagctcac cgtggacaag agcaggtggc agcagggaa cgtcttctca    1320 tgctccgtga tgcatgaggc tctgcacaac cactacacgc agaagagcct ctccctgtct    1380
ccgggtaaa                                                              1389
```

<210> SEQ ID NO 4
<211> LENGTH: 463
<212> TYPE: PRT
<213> ORGANISM: Homo sapiens

<400> SEQUENCE: 4

```
Met Asp Trp Thr Trp Arg Ile Leu Phe Leu Val Ala Ala Ala Thr Gly
1               5                   10                  15

Ala His Ser Gln Val Gln Leu Val Gln Ser Gly Ala Glu Val Lys Lys
                20                  25                  30

Pro Gly Ala Ser Val Lys Val Ser Cys Lys Ser Ser Gly Tyr Thr Phe
            35                  40                  45

Thr Gly Tyr Tyr Met His Trp Val Arg Gln Ala Pro Gly Gln Gly Leu
        50                  55                  60

Glu Trp Met Gly Trp Ile Asn Pro Asn Ser Gly Gly Thr Asn Tyr Ala
65                  70                  75                  80

Gln Lys Phe Lys Gly Arg Val Thr Met Thr Arg Asp Thr Ser Ile Ser
                85                  90                  95

Thr Ala Tyr Met Glu Leu Ser Arg Leu Arg Ser Asp Asp Thr Ala Val
            100                 105                 110

Tyr Tyr Cys Ala Arg Asp Lys Trp Leu Asp Gly Phe Asp Tyr Trp Gly
        115                 120                 125

Gln Gly Thr Leu Val Thr Val Ser Ser Ala Ser Thr Lys Gly Pro Ser
    130                 135                 140

Val Phe Pro Leu Ala Pro Cys Ser Arg Ser Thr Ser Glu Ser Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Asn Phe Gly Thr Gln Thr Tyr Thr Cys Asn Val Asp His
    210                 215                 220

Lys Pro Ser Asn Thr Lys Val Asp Lys Thr Val Glu Arg Lys Cys Cys
225                 230                 235                 240

Val Glu Cys Pro Pro Cys Pro Ala Pro Pro Val Ala Gly Pro Ser Val
                245                 250                 255

Phe Leu Phe Pro Pro Lys Pro Lys Asp Thr Leu Met Ile Ser Arg Thr
            260                 265                 270

Pro Glu Val Thr Cys Val Val Val Asp Val Ser His Glu Asp Pro Glu
        275                 280                 285

Val Gln Phe Asn Trp Tyr Val Asp Gly Val Glu Val His Asn Ala Lys
    290                 295                 300

Thr Lys Pro Arg Glu Glu Gln Phe Asn Ser Thr Phe Arg Val Val Ser
305                 310                 315                 320

Val Leu Thr Val Val His Gln Asp Trp Leu Asn Gly Lys Glu Tyr Lys
                325                 330                 335

Cys Lys Val Ser Asn Lys Gly Leu Pro Ala Pro Ile Glu Lys Thr Ile
```

Ser Lys Thr Lys Gly Gln Pro Arg Glu Pro Gln Val Tyr Thr Leu Pro
                355                 360                 365

Pro Ser Arg Glu Glu Met Thr Lys Asn Gln Val Ser Leu Thr Cys Leu
        370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Met Leu Asp Ser
                405                 410                 415

Asp Gly Ser Phe Phe Leu Tyr Ser Lys Leu Thr Val Asp Lys Ser Arg
            420                 425                 430

Trp Gln Gln Gly Asn Val Phe Ser Cys Ser Val Met His Glu Ala Leu
        435                 440                 445

His Asn His Tyr Thr Gln Lys Ser Leu Ser Leu Ser Pro Gly Lys
    450                 455                 460

<210> SEQ ID NO 5
<211> LENGTH: 726
<212> TYPE: DNA
<213> ORGANISM: Homo sapiens

<400> SEQUENCE: 5

```
atggacatga gggtgcccgc tcagctcctg gggctcctgc tgctgtggct gagaggtgcg      60
cgctgtgata ttgtgatgac ccagactcca ctctccctgc ccgtcacccc tggagagccg     120
gcctccatct cctgcaggtc tagtcagagc ctcttgaata gtgttgatgg aagcaccaat     180
ttggactggt atctgcagaa gccagggcag tctccacagc tcctgatcta tacgctttcc     240
tatcgggcct ctggagtccc agacaggttc agtggcagtg gtcaggcac tgacttcaca     300
ctgaaaatca gcagggtgga ggctgaggat gttggagttt attactgcat gcaacgtata     360
gagtttccgc tcactttcgg cggagggacc aaggtggaga tcaaacgtac ggtggctgca     420
ccatctgtct tcatcttccc gccatctgat gagcagttga aatctggaac tgcctctgtt     480
gtgtgcctgc tgaataactt ctatcccaga gaggccaaag tacagtggaa ggtggataac     540
gccctccaat cgggtaactc ccaggagagt gtcacagagc aggacagcaa ggacagcacc     600
tacagcctca gcagcaccct gacgctgagc aaagcagact acgagaaaca caaagtctac     660
gcctgcgaag tcacccatca gggcctgagc tcgcccgtca caaagagctt caacagggga     720
gagtgt                                                                 726
```

<210> SEQ ID NO 6
<211> LENGTH: 242
<212> TYPE: PRT
<213> ORGANISM: Homo sapiens

<400> SEQUENCE: 6

Met Asp Met Arg Val Pro Ala Gln Leu Leu Gly Leu Leu Leu Leu Trp
1               5                   10                  15

Leu Arg Gly Ala Arg Cys Asp Ile Val Met Thr Gln Thr Pro Leu Ser
            20                  25                  30

Leu Pro Val Thr Pro Gly Glu Pro Ala Ser Ile Ser Cys Arg Ser Ser
        35                  40                  45

Gln Ser Leu Leu Asn Ser Val Asp Gly Ser Thr Asn Leu Asp Trp Tyr
    50                  55                  60

Leu Gln Lys Pro Gly Gln Ser Pro Gln Leu Leu Ile Tyr Thr Leu Ser
65                  70                  75                  80

Tyr Arg Ala Ser Gly Val Pro Asp Arg Phe Ser Gly Ser Gly Ser Gly
            85                  90                  95

Thr Asp Phe Thr Leu Lys Ile Ser Arg Val Glu Ala Glu Asp Val Gly
        100                 105                 110

Val Tyr Tyr Cys Met Gln Arg Ile Glu Phe Pro Leu Thr Phe Gly Gly
    115                 120                 125

Gly Thr Lys Val Glu Ile Lys Arg Thr Val Ala Ala Pro Ser Val Phe
130                 135                 140

Ile Phe Pro Pro Ser Asp Glu Gln Leu Lys Ser Gly Thr Ala Ser Val
145                 150                 155                 160

Val Cys Leu Leu Asn Asn Phe Tyr Pro Arg Glu Ala Lys Val Gln Trp
            165                 170                 175

Lys Val Asp Asn Ala Leu Gln Ser Gly Asn Ser Gln Glu Ser Val Thr
        180                 185                 190

Glu Gln Asp Ser Lys Asp Ser Thr Tyr Ser Leu Ser Ser Thr Leu Thr
    195                 200                 205

Leu Ser Lys Ala Asp Tyr Glu Lys His Lys Val Tyr Ala Cys Glu Val
210                 215                 220

Thr His Gln Gly Leu Ser Ser Pro Val Thr Lys Ser Phe Asn Arg Gly
225                 230                 235                 240

Glu Cys

<210> SEQ ID NO 7
<211> LENGTH: 1395
<212> TYPE: DNA
<213> ORGANISM: Homo sapiens

<400> SEQUENCE: 7

```
atggagttgg ggctgtgctg ggttttcctt gttgctattt tagaaggtgt ccagtgtgag     60
gtgcagctgg tggagtctgg gggaggcttg gtacagcctg ggggtccct gagactctcc    120
tgtgcagcct ctggattcac cttcagtagc tatagcatga actgggtccg ccaggctcca    180
gggaaggggc tggagtgggt ttcatacatt agtagtagtg gtagttccat atactacgca    240
gactctgtga agggccgatt caccatctcc agagacaatg ccaagaactc actgtatctg    300
caaatgaaca gcctgagaga cgaggacacg gctgtgtatt actgtgcgag agagaggtac    360
tacggtgaca cgccctttga ctactggggc cagggaaccc tggtcaccgt ctctagtgcc    420
tccaccaagg gcccatcggt cttccccctg gcgccctgct ccaggagcac ctccgagagc    480
acagcggccc tgggctgcct ggtcaaggac tacttccccg aaccggtgac ggtgtcgtgg    540
aactcaggcg ctctgaccag cggcgtgcac accttcccag ctgtcctaca gtcctcagga    600
ctctactccc tcagcagcgt ggtgaccgtg ccctccagca acttcggcac ccagacctac    660
acctgcaacg tagatcacaa gcccagcaac accaaggtgg acaagacagt tgagcgcaaa    720
tgttgtgtcg agtgcccacc gtgcccagca ccacctgtgg caggaccgtc agtcttcctc    780
ttccccccaa aacccaagga caccctcatg atctcccgga cccctgaggt cacgtgcgtg    840
gtggtggacg tgagccacga agaccccgag gtccagttca actggtacgt ggacggcgtg    900
gaggtgcata atgccaagac aaagccacgg gaggagcagt tcaacagcac gttccgtgtg    960
gtcagcgtcc tcaccgttgt gcaccaggac tggctgaacg gcaaggagta caagtgcaag   1020
gtctccaaca aaggcctccc agcccccatc gagaaaacca tctccaaaac caagggcag   1080
ccccgagaac cacaggtgta caccctgccc ccatcccggg aggagatgac caagaaccag   1140
```

```
gtcagcctga cctgcctggt caaaggcttc taccccagcg acatcgccgt ggagtgggag    1200
agcaatgggc agccggagaa caactacaag accacacctc ccatgctgga ctccgacggc    1260
tccttcttcc tctacagcaa gctcaccgtg gacaagagca ggtggcagca ggggaacgtc    1320
ttctcatgct ccgtgatgca tgaggctctg cacaaccact acacgcagaa gagcctctcc    1380
ctgtctccgg gtaaa                                                     1395
```

<210> SEQ ID NO 8
<211> LENGTH: 465
<212> TYPE: PRT
<213> ORGANISM: Homo sapiens

<400> SEQUENCE: 8

```
Met Glu Leu Gly Leu Cys Trp Val Phe Leu Val Ala Ile Leu Glu Gly
1               5                   10                  15

Val Gln Cys Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Ser Tyr Ser Met Asn Trp Val Arg Gln Ala Pro Gly Lys Gly Leu
    50                  55                  60

Glu Trp Val Ser Tyr Ile Ser Ser Ser Gly Ser Ser Ile Tyr Tyr Ala
65                  70                  75                  80

Asp Ser Val Lys Gly Arg Phe Thr Ile Ser Arg Asp Asn Ala Lys Asn
                85                  90                  95

Ser Leu Tyr Leu Gln Met Asn Ser Leu Arg Asp Glu Asp Thr Ala Val
            100                 105                 110

Tyr Tyr Cys Ala Arg Glu Arg Tyr Gly Asp Thr Pro Phe Asp Tyr
        115                 120                 125

Trp Gly Gln Gly Thr Leu Val Thr Val Ser Ser Ala Ser Thr Lys Gly
130                 135                 140

Pro Ser Val Phe Pro Leu Ala Pro Cys Ser Arg Ser Thr Ser Glu Ser
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Asn Phe Gly Thr Gln Thr Tyr Thr Cys Asn Val
    210                 215                 220

Asp His Lys Pro Ser Asn Thr Lys Val Asp Lys Thr Val Glu Arg Lys
225                 230                 235                 240

Cys Cys Val Glu Cys Pro Pro Cys Pro Ala Pro Pro Val Ala Gly Pro
                245                 250                 255

Ser Val Phe Leu Phe Pro Pro Lys Pro Lys Asp Thr Leu Met Ile Ser
            260                 265                 270

Arg Thr Pro Glu Val Thr Cys Val Val Val Asp Val Ser His Glu Asp
        275                 280                 285

Pro Glu Val Gln Phe Asn Trp Tyr Val Asp Gly Val Glu Val His Asn
    290                 295                 300

Ala Lys Thr Lys Pro Arg Glu Glu Gln Phe Asn Ser Thr Phe Arg Val
305                 310                 315                 320

Val Ser Val Leu Thr Val Val His Gln Asp Trp Leu Asn Gly Lys Glu
```

```
                325                 330                 335
Tyr Lys Cys Lys Val Ser Asn Lys Gly Leu Pro Ala Pro Ile Glu Lys
            340                 345                 350

Thr Ile Ser Lys Thr Lys Gly Gln Pro Arg Glu Pro Gln Val Tyr Thr
        355                 360                 365

Leu Pro Pro Ser Arg Glu Glu Met Thr Lys Asn Gln Val Ser Leu Thr
    370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Met Leu
                405                 410                 415

Asp Ser Asp Gly Ser Phe Phe Leu Tyr Ser Lys Leu Thr Val Asp Lys
            420                 425                 430

Ser Arg Trp Gln Gln Gly Asn Val Phe Ser Cys Ser Val Met His Glu
        435                 440                 445

Ala Leu His Asn His Tyr Thr Gln Lys Ser Leu Ser Leu Ser Pro Gly
    450                 455                 460

Lys
465

<210> SEQ ID NO 9
<211> LENGTH: 699
<212> TYPE: DNA
<213> ORGANISM: Homo sapiens

<400> SEQUENCE: 9
atgtcgccat cacaactcat tgggtttctg ctgctctggg ttccagcctc caggggtgaa      60
attgtgctga ctcagtctcc agactttcag tctgtgactc caaaggagaa agtcaccatc     120
acctgccggg ccagtcagag cattggtagt agcttacact ggtaccagca gaaaccagat     180
cagtctccaa agctcctcat caagtatgct cccagtcct tctcagggt cccctcgagg       240 ttcagtggca gtggatctgg gacagatttc accctcacca tcaatagcct ggaagctgaa     300
gatgctgcag tgtattactg tcatcagagt agtagtttac ctctcacttt cggcggaggg     360
accaaggtgg agatcaaacg aactgtggct gcaccatctg tcttcatctt cccgccatct     420
gatgagcagt tgaaatctgg aactgcctct gttgtgtgcc tgctgaataa cttctatccc     480
agagaggcca aagtacagtg gaaggtggat aacgccctcc aatcgggtaa ctcccaggag     540
agtgtcacag agcaggacag caaggacagc acctacagcc tcagcagcac cctgacgctg     600
agcaaagcag actacgagaa acacaaagtc tacgcctgcg aagtcaccca tcagggcctg     660
agctcgcccg tcacaaagag cttcaacagg ggagagtgt                            699

<210> SEQ ID NO 10
<211> LENGTH: 233
<212> TYPE: PRT
<213> ORGANISM: Homo sapiens

<400> SEQUENCE: 10

Met Ser Pro Ser Gln Leu Ile Gly Phe Leu Leu Leu Trp Val Pro Ala
1               5                   10                  15

Ser Arg Gly Glu Ile Val Leu Thr Gln Ser Pro Asp Phe Gln Ser Val
            20                  25                  30

Thr Pro Lys Glu Lys Val Thr Ile Thr Cys Arg Ala Ser Gln Ser Ile
        35                  40                  45

Gly Ser Ser Leu His Trp Tyr Gln Gln Lys Pro Asp Gln Ser Pro Lys
```

```
                    50                  55                  60
Leu Leu Ile Lys Tyr Ala Ser Gln Ser Phe Ser Gly Val Pro Ser Arg
 65                  70                  75                  80

Phe Ser Gly Ser Gly Ser Gly Thr Asp Phe Thr Leu Thr Ile Asn Ser
                 85                  90                  95

Leu Glu Ala Glu Asp Ala Ala Ala Tyr Tyr Cys His Gln Ser Ser Ser
            100                 105                 110

Leu Pro Leu Thr Phe Gly Gly Gly Thr Lys Val Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230
```

<210> SEQ ID NO 11
<211> LENGTH: 1389
<212> TYPE: DNA
<213> ORGANISM: Homo sapiens

<400> SEQUENCE: 11

```
atgggtcaa ccgccatcct cgccctcctc ctggctgttc tccaaggagt ctgtgccgag    60
gtgcagctga tgcagtctgg agcagaggtg aaaaagcccg ggagtctct gaagatctcc   120
tgtaagggtt ctggatacag cttttccttc actggatcg cctgggtgcg ccagatgccc   180
gggaaaggcc tggagtggat ggggatcatc atcctggtg cctctgatac agatacagc   240
ccgtccttcc aaggccaggt caccatctca gccgacaact ccaacagcgc cacctacctg   300
cagtggagca gcctgaaggc ctcggacacc gccatgtatt tctgtgcgag acaaagggaa   360
ctcgactact tgactactg gggccaggga accctggtca ccgtctctag tgcctccacc   420
aagggcccat cggtcttccc cctggcgccc tgctccagga gcacctccga gagcacagcg   480
gccctgggct gcctggtcaa ggactacttc cccgaaccgg tgacggtgtc gtggaactca   540
ggcgctctga ccagcggcgt gcacaccttc ccagctgtcc tacagtcctc aggactctac   600
tccctcagca gcgtggtgac cgtgccctcc agcaacttcg cacccagac ctacacctgc   660
aacgtagatc acaagcccag caacaccaag gtggacaaga cagttgagcg caaatgttgt   720
gtcgagtgcc caccgtgccc agcaccacct gtggcaggac cgtcagtctt cctcttcccc   780
ccaaaaccca aggacaccct catgatctcc cggacccctg aggtcacgtg cgtggtggtg   840
gacgtgagcc acgaagaccc cgaggtccag ttcaactggt acgtggacgg cgtggaggtg   900
cataatgcca agacaaagcc acgggaggag cagttcaaca gcacgttccg tgtggtcagc   960
gtcctcaccg ttgtgcacca ggactggctg aacggcaagg agtacaagtg caaggtctcc  1020
aacaaaggcc tcccagcccc catcgagaaa accatctcca aaaccaaagg gcagccccga  1080
```

```
gaaccacagg tgtacaccct gcccccatcc cgggaggaga tgaccaagaa ccaggtcagc    1140
ctgacctgcc tggtcaaagg cttctacccc agcgacatcg ccgtggagtg ggagagcaat    1200
gggcagccgg agaacaacta caagaccaca cctcccatgc tggactccga cggctccttc    1260
ttcctctaca gcaagctcac cgtggacaag agcaggtggc agcaggggaa cgtcttctca    1320
tgctccgtga tgcatgaggc tctgcacaac cactacacgc agaagagcct ctccctgtct    1380
ccgggtaaa                                                              1389
```

<210> SEQ ID NO 12
<211> LENGTH: 463
<212> TYPE: PRT
<213> ORGANISM: Homo sapiens

<400> SEQUENCE: 12

```
Met Gly Ser Thr Ala Ile Leu Ala Leu Leu Ala Val Leu Gln Gly
1               5                   10                  15

Val Cys Ala Glu Val Gln Leu Met Gln Ser Gly Ala Glu Val Lys Lys
            20                  25                  30

Pro Gly Glu Ser Leu Lys Ile Ser Cys Lys Gly Ser Gly Tyr Ser Phe
        35                  40                  45

Ser Phe His Trp Ile Ala Trp Val Arg Gln Met Pro Gly Lys Gly Leu
    50                  55                  60

Glu Trp Met Gly Ile Ile His Pro Gly Ala Ser Asp Thr Arg Tyr Ser
65                  70                  75                  80

Pro Ser Phe Gln Gly Gln Val Thr Ile Ser Ala Asp Asn Ser Asn Ser
                85                  90                  95

Ala Thr Tyr Leu Gln Trp Ser Ser Leu Lys Ala Ser Asp Thr Ala Met
            100                 105                 110

Tyr Phe Cys Ala Arg Gln Arg Glu Leu Asp Tyr Phe Asp Tyr Trp Gly
        115                 120                 125

Gln Gly Thr Leu Val Thr Val Ser Ser Ala Ser Thr Lys Gly Pro Ser
    130                 135                 140

Val Phe Pro Leu Ala Pro Cys Ser Arg Ser Thr Ser Glu Ser Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Asn Phe Gly Thr Gln Thr Tyr Thr Cys Asn Val Asp His
    210                 215                 220

Lys Pro Ser Asn Thr Lys Val Asp Lys Thr Val Glu Arg Lys Cys Cys
225                 230                 235                 240

Val Glu Cys Pro Pro Cys Pro Ala Pro Pro Val Ala Gly Pro Ser Val
                245                 250                 255

Phe Leu Phe Pro Pro Lys Pro Lys Asp Thr Leu Met Ile Ser Arg Thr
            260                 265                 270

Pro Glu Val Thr Cys Val Val Asp Val Ser His Glu Asp Pro Glu
        275                 280                 285

Val Gln Phe Asn Trp Tyr Val Asp Gly Val Glu Val His Asn Ala Lys
    290                 295                 300

Thr Lys Pro Arg Glu Glu Gln Phe Asn Ser Thr Phe Arg Val Val Ser
305                 310                 315                 320
```

Val Leu Thr Val Val His Gln Asp Trp Leu Asn Gly Lys Glu Tyr Lys
            325                 330                 335

Cys Lys Val Ser Asn Lys Gly Leu Pro Ala Pro Ile Glu Lys Thr Ile
        340                 345                 350

Ser Lys Thr Lys Gly Gln Pro Arg Glu Pro Gln Val Tyr Thr Leu Pro
        355                 360                 365

Pro Ser Arg Glu Glu Met Thr Lys Asn Gln Val Ser Leu Thr Cys Leu
    370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Met Leu Asp Ser
            405                 410                 415

Asp Gly Ser Phe Phe Leu Tyr Ser Lys Leu Thr Val Asp Lys Ser Arg
        420                 425                 430

Trp Gln Gln Gly Asn Val Phe Ser Cys Ser Val Met His Glu Ala Leu
    435                 440                 445

His Asn His Tyr Thr Gln Lys Ser Leu Ser Leu Ser Pro Gly Lys
        450                 455                 460

<210> SEQ ID NO 13
<211> LENGTH: 708
<212> TYPE: DNA
<213> ORGANISM: Homo sapiens

<400> SEQUENCE: 13
atggacatga gggtccccgc tcagctcctg gggctcctgc tgctgtggct gagaggtgcg      60
cgctgtgata tccagatgac ccaatcccct tctagtctgt ccgcttctgt gggcgacagg     120
gttacaataa cttgcaaagc gagccaggac atcaacaaat atgtggcttg gtatcagcaa     180
aaacccggca aggcaccaaa attgctcatt tattacacgt catggctcca gcctggtgta     240
cctagcaggt tttccggctc cggctcaggt accgacttta cttcactat ctcctcactg      300 cagccggagg acattgccac atactactgt ctccaatatg ataacttgtt gtatactttt     360
gggcaaggaa ctaagctcga gatcaaacgt acggtggctg caccatctgt cttcatcttc     420
ccgccatctg atgagcagtt gaaatctgga actgcctctg ttgtgtgcct gctgaataac     480
ttctatccca gagaggccaa agtacagtgg aaggtggata acgccctcca atcgggtaac     540
tcccaggaga gtgtcacaga gcaggacagc aaggacagca cctacagcct cagcagcacc     600
ctgacgctga gcaaagcaga ctacgagaaa cacaaagtct acgcctgcga agtcacccat     660
cagggcctga gctcgcccgt cacaaagagc ttcaacaggg gagagtgt                   708

<210> SEQ ID NO 14
<211> LENGTH: 236
<212> TYPE: PRT
<213> ORGANISM: Homo sapiens

<400> SEQUENCE: 14

Met Asp Met Arg Val Pro Ala Gln Leu Leu Gly Leu Leu Leu Leu Trp
1               5                   10                  15

Leu Arg Gly Ala Arg Cys Asp Ile Gln Met Thr Gln Ser Pro Ser Ser
            20                  25                  30

Leu Ser Ala Ser Val Gly Asp Arg Val Thr Ile Thr Cys Lys Ala Ser
        35                  40                  45

Gln Asp Ile Asn Lys Tyr Val Ala Trp Tyr Gln Gln Lys Pro Gly Lys
    50                  55                  60

```
Ala Pro Lys Leu Leu Ile Tyr Tyr Thr Ser Trp Leu Gln Pro Gly Val
 65                  70                  75                  80

Pro Ser Arg Phe Ser Gly Ser Gly Ser Gly Thr Asp Phe Thr Phe Thr
             85                  90                  95

Ile Ser Ser Leu Gln Pro Glu Asp Ile Ala Thr Tyr Tyr Cys Leu Gln
            100                 105                 110

Tyr Asp Asn Leu Leu Tyr Thr Phe Gly Gln Gly Thr Lys Leu Glu Ile
            115                 120                 125

Lys Arg Thr Val Ala Ala Pro Ser Val Phe Ile Phe Pro Pro Ser Asp
130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
            195                 200                 205

Glu Lys His Lys Val Tyr Ala Cys Glu Val Thr His Gln Gly Leu Ser
210                 215                 220

Ser Pro Val Thr Lys Ser Phe Asn Arg Gly Glu Cys
225                 230                 235

<210> SEQ ID NO 15
<211> LENGTH: 1401
<212> TYPE: DNA
<213> ORGANISM: Homo sapiens

<400> SEQUENCE: 15
atggacatga gggtgcccgc tcagctcctg gggctcctgc tgctgtggct gagaggtgcg      60
cgctgtgagg ttcagcttgt ggagtctggc ggcggcctgg tgcagccagg cggttcactc     120
aggctgagct gtgctgcatc agggttcacc ttcagccgtt actggatgaa ctgggtgcgg     180
caagcacccg ggaaaggcct ggagtgggtg gctcagattc gcttgaaaag tgacaattat     240
gccactcact atgcagaaag cgtgaagggg cgctttacaa tttctagaga caacgccaaa     300
aactcactgt acctgcagat gaacagcctc agagctgagg atacagctgt gtattattgt     360
actgaggggc tcgactattg gggacagggc acgacagtga ccgtctctag tgcctccacc     420
aagggcccat cggtcttccc cctggcaccc tcctccaaga gcacctctgg gggcacagcg     480
gccctgggct gcctggtcaa ggactacttc cccgaaccgg tgacggtgtc gtggaactca     540
ggcgccctga ccagcggcgt gcacaccttc cggctgtcc tacagtcctc aggactctac     600
tccctcagca gcgtggtgac cgtgccctcc agcagcttgg gcacccagac ctacatctgc     660
aacgtgaatc acaagcccag caacaccaag gtggacaaga agttgagcc caaatcttgt     720 gacaaaactc acacatgccc accgtgccca gcacctgaac tcctggggg accgtcagtc     780 ttcctcttcc cccaaaaacc caaggacacc ctcatgatct cccggacccc tgaggtcaca     840
tgcgtggtgg tggacgtgag ccacgaagac cctgaggtca agttcaactg gtacgtggac     900
ggcgtggagg tgcataatgc caagacaaag ccgcgggagg agcagtacaa cagcacgtac     960
cgtgtggtca gcgtcctcac cgtcctgcac caggactggc tgaatggcaa ggagtacaag    1020
tgcaaggtct ccaacaaagc cctcccagcc ccatcgaga aaaccatctc caaagccaaa    1080
gggcagcccc gagaaccaca ggtgtacacc ctgcccccat cccgggagga gatgaccaag    1140
```

```
aaccaggtca gcctgacctg cctggtcaaa ggcttctatc ccagcgacat cgccgtggag    1200
tgggagagca atgggcagcc ggagaacaac tacaagacca cgcctcccgt gctggactcc    1260
gacggctcct tcttcctcta tagcaagctc accgtggaca agagcaggtg gcagcagggg    1320
aacgtcttct catgctccgt gatgcatgag gctctgcaca accactacac gcagaagagc    1380
ctctccctgt ctccgggtaa a                                              1401
```

<210> SEQ ID NO 16
<211> LENGTH: 467
<212> TYPE: PRT
<213> ORGANISM: Homo sapiens

<400> SEQUENCE: 16

```
Met Asp Met Arg Val Pro Ala Gln Leu Leu Gly Leu Leu Leu Leu Trp
1               5                   10                  15

Leu Arg Gly Ala Arg Cys Glu Val Gln Leu Val Glu Ser Gly Gly Gly
            20                  25                  30

Leu Val Gln Pro Gly Gly Ser Leu Arg Leu Ser Cys Ala Ala Ser Gly
        35                  40                  45

Phe Thr Phe Ser Arg Tyr Trp Met Asn Trp Val Arg Gln Ala Pro Gly
    50                  55                  60

Lys Gly Leu Glu Trp Val Ala Gln Ile Arg Leu Lys Ser Asp Asn Tyr
65                  70                  75                  80

Ala Thr His Tyr Ala Glu Ser Val Lys Gly Arg Phe Thr Ile Ser Arg
                85                  90                  95

Asp Asn Ala Lys Asn Ser Leu Tyr Leu Gln Met Asn Ser Leu Arg Ala
            100                 105                 110

Glu Asp Thr Ala Val Tyr Tyr Cys Thr Glu Gly Leu Asp Tyr Trp Gly
        115                 120                 125

Gln Gly Thr Thr Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Leu Gly Thr Gln Thr Tyr Ile Cys Asn Val Asn His
    210                 215                 220

Lys Pro Ser Asn Thr Lys Val Asp Lys Lys Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320
```

```
Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Glu Glu Met Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
    450                 455                 460

Pro Gly Lys
465

<210> SEQ ID NO 17
<211> LENGTH: 708
<212> TYPE: DNA
<213> ORGANISM: Homo sapiens

<400> SEQUENCE: 17
atggacatga gggtcctcgc tcagctcctg gggctcctgc tgctctgttt cccaggtgcc      60
agatgtgaca tccagatgac ccagtctcca tcctcactgt ctgcatctgt aggagacaga     120
gtcaccatca cttgtcgggc gagtcagggt attagcaact ggttagcctg gtatcagcag     180
aaaccagaga aagcccctaa gtccctgatc tatgctgcat ccagtttgca aagtggggtc     240
ccatcaaggt tcagcggcag tggatctggg acagatttca ctctcaccat cagcagcctg     300
cagcctgaag attttgcaac ttattactgc aacagtatg atagttaccc tcggacgttc      360
ggccaaggga ccaaggtgga aatcaaacga actgtggctg caccatctgt cttcatcttc     420
ccgccatctg atgagcagtt gaaatctgga actgcctctg ttgtgtgcct gctgaataac     480
ttctatccca gagaggccaa agtacagtgg aaggtggata acgccctcca atcgggtaac     540
tcccaggaga gtgtcacaga gcaggacagc aaggacagca cctacagcct cagcagcacc     600
ctgacgctga gcaaagcaga ctacgagaaa cacaaagtct acgcctgcga agtcacccat     660
cagggcctga gctcgcccgt cacaaagagc ttcaacaggg gagagtgt                  708

<210> SEQ ID NO 18
<211> LENGTH: 236
<212> TYPE: PRT
<213> ORGANISM: Homo sapiens

<400> SEQUENCE: 18

Met Asp Met Arg Val Leu Ala Gln Leu Leu Gly Leu Leu Leu Leu Cys
1               5                   10                  15

Phe Pro Gly Ala Arg Cys Asp Ile Gln Met Thr Gln Ser Pro Ser Ser
            20                  25                  30

Leu Ser Ala Ser Val Gly Asp Arg Val Thr Ile Thr Cys Arg Ala Ser
        35                  40                  45
```

Gln Gly Ile Ser Asn Trp Leu Ala Trp Tyr Gln Gln Lys Pro Glu Lys
            50                  55                  60

Ala Pro Lys Ser Leu Ile Tyr Ala Ala Ser Ser Leu Gln Ser Gly Val
 65                  70                  75                  80

Pro Ser Arg Phe Ser Gly Ser Gly Ser Gly Thr Asp Phe Thr Leu Thr
                 85                  90                  95

Ile Ser Ser Leu Gln Pro Glu Asp Phe Ala Thr Tyr Tyr Cys Gln Gln
            100                 105                 110

Tyr Asp Ser Tyr Pro Arg Thr Phe Gly Gln Gly Thr Lys Val Glu Ile
            115                 120                 125

Lys Arg Thr Val Ala Ala Pro Ser Val Phe Ile Phe Pro Pro Ser Asp
130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
            195                 200                 205

Glu Lys His Lys Val Tyr Ala Cys Glu Val Thr His Gln Gly Leu Ser
210                 215                 220

Ser Pro Val Thr Lys Ser Phe Asn Arg Gly Glu Cys
225                 230                 235

<210> SEQ ID NO 19
<211> LENGTH: 1398
<212> TYPE: DNA
<213> ORGANISM: Homo sapiens

<400> SEQUENCE: 19
atggagttgg ggctgaactg ggttttcctt gttgctattt tagaaggtgt ccactgtgag      60
gtgcagctgg tggagtctgg gggaggcttg gtccagcctg gggggtccct gagactctcc     120
tgtgcagctt ctggatttac ctttagtagt tattggatga gttgggtccg ccaggctcca     180
gggaaagggc tggagtgggt ggcctacata aagcaagatg aaatgagaa atactatgtg      240 gactctgtga agggccgatt caccatctcc agagacaacg ccaagaactc attgtatctg     300
caaatgaaca gcctgagagc cgaggacacg gctgtgtatt actgtgcgag ggaagggata     360
ctttggttcg gggacttacc gacgttctgg ggccagggaa ccctggtcac cgtctctagt     420
gcctccacca agggcccatc ggtcttcccc ctggcgccct gctccaggag cacctccgag     480
agcacagcgg ccctgggctg cctggtcaag gactacttcc ccgaaccggt gacggtgtcg     540
tggaactcag gcgctctgac cagcggcgtg cacaccttcc cagctgtcct acagtcctca     600
ggactctact ccctcagcag cgtggtgacc gtgccctcca gcaacttcgg cacccagacc     660
tacacctgca acgtagatca caagcccagc aacaccaagg tggacaagac agttgagcgc     720
aaatgttgtg tcgagtgccc accgtgccca gcaccacctg tggcaggacc gtcagtcttc     780
ctcttccccc caaaacccaa ggacaccctc atgatctccc ggacccctga ggtcacgtgc     840
gtggtggtgg acgtgagcca cgaagacccc gaggtccagt tcaactggta cgtggacggc     900
gtggaggtgc ataatgccaa gacaaagcca cgggaggagc agttcaacag cacgttccgt     960
gtggtcagcg tcctcaccgt tgtgcaccag gactggctga acggcaagga gtacaagtgc    1020
aaggtctcca acaaaggcct cccagccccc atcgagaaaa ccatctccaa aaccaagggg    1080

```
cagccccgag aaccacaggt gtacaccctg cccccatccc gggaggagat gaccaagaac    1140
caggtcagcc tgacctgcct ggtcaaaggc ttctacccca gcgacatcgc cgtggagtgg    1200
gagagcaatg ggcagccgga gaacaactac aagaccacac ctcccatgct ggactccgac    1260
ggctccttct tcctctacag caagctcacc gtggacaaga gcaggtggca gcagggaac     1320 gtcttctcat gctccgtgat gcatgaggct ctgcacaacc actacacgca gaagagcctc    1380
tccctgtctc cgggtaaa                                                  1398
```

<210> SEQ ID NO 20
<211> LENGTH: 466
<212> TYPE: PRT
<213> ORGANISM: Homo sapiens

<400> SEQUENCE: 20

```
Met Glu Leu Gly Leu Asn Trp Val Phe Leu Val Ala Ile Leu Glu Gly
1               5                   10                  15

Val His Cys Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Ser Tyr Trp Met Ser Trp Val Arg Gln Ala Pro Gly Lys Gly Leu
    50                  55                  60

Glu Trp Val Ala Tyr Ile Lys Gln Asp Gly Asn Glu Lys Tyr Tyr Val
65                  70                  75                  80

Asp Ser Val Lys Gly Arg Phe Thr Ile Ser Arg Asp Asn Ala Lys Asn
                85                  90                  95

Ser Leu Tyr Leu Gln Met Asn Ser Leu Arg Ala Glu Asp Thr Ala Val
            100                 105                 110

Tyr Tyr Cys Ala Arg Glu Gly Ile Leu Trp Phe Gly Asp Leu Pro Thr
        115                 120                 125

Phe Trp Gly Gln Gly Thr Leu Val Thr Val Ser Ala Ser Thr Lys
    130                 135                 140

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Asn Phe Gly Thr Gln Thr Tyr Thr Cys Asn
    210                 215                 220

Val Asp His Lys Pro Ser Asn Thr Lys Val Asp Lys Thr Val Glu Arg
225                 230                 235                 240

Lys Cys Cys Val Glu Cys Pro Pro Cys Pro Ala Pro Pro Val Ala Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
        275                 280                 285

Asp Pro Glu Val Gln Phe Asn Trp Tyr Val Asp Gly Val Glu Val His
    290                 295                 300

Asn Ala Lys Thr Lys Pro Arg Glu Glu Gln Phe Asn Ser Thr Phe Arg
```

Val Val Ser Val Leu Thr Val Val His Gln Asp Trp Leu Asn Gly Lys
                325                 330                 335

Glu Tyr Lys Cys Lys Val Ser Asn Lys Gly Leu Pro Ala Pro Ile Glu
            340                 345                 350

Lys Thr Ile Ser Lys Thr Lys Gly Gln Pro Arg Glu Pro Gln Val Tyr
        355                 360                 365

Thr Leu Pro Pro Ser Arg Glu Glu Met Thr Lys Asn Gln Val Ser Leu
    370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Met
                405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
        435                 440                 445

Glu Ala Leu His Asn His Tyr Thr Gln Lys Ser Leu Ser Leu Ser Pro
    450                 455                 460

Gly Lys
465

<210> SEQ ID NO 21
<211> LENGTH: 723
<212> TYPE: DNA
<213> ORGANISM: Homo sapiens

<400> SEQUENCE: 21

```
atggacatga ggctccctgc tcagctcctg gggctgctaa tgctctgggt cccaggatcc    60
agtggggatg ttctgatgac tcagtctcca ctctccctgc ccgtcaccct tggacagccg   120
gcctccatct cctgcaggtc tagtcaaagc atcgtacaca gtaacggaaa cacctacttg   180
gagtggtatc tgcagaggcc aggccaatct ccaaagctcc taatttataa ggtttctaac   240
cggttctctg ggtcccccaga cagattcagc ggcagtgggt caggcactga tttcacactg   300
aaaatcagca gggtggaggc tgaggatgtt ggggtttatt actgcttcca aggtagccac   360
gttcctctga cgttcggcgc agggaccaag ctggaaatca aacggactgt ggctgcacca   420
tctgtcttca tcttcccgcc atctgatgag cagttgaaat ctggaactgc ctctgttgtg   480
tgcctgctga taacttcta tcccagagag gccaaagtac agtggaaggt ggataacgcc   540
ctccaatcgg gtaactccca ggagagtgtc acagagcagg acagcaagga cagcacctac   600
agcctcagca gcaccctgac gctgagcaaa gcagactacg agaaacacaa agtctacgcc   660
tgcgaagtca cccatcaggg cctgagctcg cccgtcacaa agagcttcaa caggggagag   720
tgt                                                                 723
```

<210> SEQ ID NO 22
<211> LENGTH: 241
<212> TYPE: PRT
<213> ORGANISM: Homo sapiens

<400> SEQUENCE: 22

Met Asp Met Arg Leu Pro Ala Gln Leu Leu Gly Leu Leu Met Leu Trp
1               5                   10                  15

Val Pro Gly Ser Ser Gly Asp Val Leu Met Thr Gln Ser Pro Leu Ser
            20                  25                  30

Leu Pro Val Thr Leu Gly Gln Pro Ala Ser Ile Ser Cys Arg Ser Ser
                35                  40                  45

Gln Ser Ile Val His Ser Asn Gly Asn Thr Tyr Leu Glu Trp Tyr Leu
 50                  55                  60

Gln Arg Pro Gly Gln Ser Pro Lys Leu Leu Ile Tyr Lys Val Ser Asn
65                  70                  75                  80

Arg Phe Ser Gly Val Pro Asp Arg Phe Ser Gly Ser Gly Ser Gly Thr
                85                  90                  95

Asp Phe Thr Leu Lys Ile Ser Arg Val Glu Ala Glu Asp Val Gly Val
                100                 105                 110

Tyr Tyr Cys Phe Gln Gly Ser His Val Pro Leu Thr Phe Gly Ala Gly
                115                 120                 125

Thr Lys Leu Glu Ile Lys Arg Thr Val Ala Ala Pro Ser Val Phe Ile
130                 135                 140

Phe Pro Pro Ser Asp Glu Gln Leu Lys Ser Gly Thr Ala Ser Val Val
145                 150                 155                 160

Cys Leu Leu Asn Asn Phe Tyr Pro Arg Glu Ala Lys Val Gln Trp Lys
                165                 170                 175

Val Asp Asn Ala Leu Gln Ser Gly Asn Ser Gln Glu Ser Val Thr Glu
                180                 185                 190

Gln Asp Ser Lys Asp Ser Thr Tyr Ser Leu Ser Ser Thr Leu Thr Leu
                195                 200                 205

Ser Lys Ala Asp Tyr Glu Lys His Lys Val Tyr Ala Cys Glu Val Thr
210                 215                 220

His Gln Gly Leu Ser Ser Pro Val Thr Lys Ser Phe Asn Arg Gly Glu
225                 230                 235                 240

Cys

<210> SEQ ID NO 23
<211> LENGTH: 1410
<212> TYPE: DNA
<213> ORGANISM: Homo sapiens

<400> SEQUENCE: 23

```
atggacacac tttgctccac gctcctgctg ctgaccatcc cttcatgggt cttgtcccag      60
gtcaccttga aggagtctgg tcctgcgctg gtgaaaccca cacagaccct cacgctgacc     120
tgcaccttct ctgggttctc actccgcact agtggaatgg gcgtgggctg atccgtcag     180
cccccaggaa aggccctgga gtggcttgcc cacatttggt gggatgatga taagagctac     240
aacccatctc tgaagagcca gctcaccatc tctaaggaca cctccaaaaa ccaggtggtc     300
cttacaatga ccaacatgga ccctgtggac acagccacat attactgtgc acgcagaaac     360
tattactacg acgactactt cgcctactgg ggccagggca ccctggtcac cgtctctagt     420
gcctccacca agggcccatc ggtcttcccc ctggcaccct cctccaagag cacctctggg     480
ggcacagcgg ccctgggctg cctggtcaag gactacttcc ccgaaccggt gacggtgtcg     540
tggaactcag gcgccctgac cagcggcgtg cacaccttcc cggctgtcct acagtcctca     600
ggactctact ccctcagcag cgtggtgacc gtgccctcca gcagcttggg cacccagacc     660
tacatctgca acgtgaatca caagcccagc aacaccaagg tggacaagaa agttgagccc     720
aaatcttgtg acaaaactca cacatgccca ccgtgcccag cacctgaact cctgggggga     780
ccgtcagtct tcctcttccc cccaaaaccc aaggacaccc tcatgatctc ccggacccct     840
gaggtcacat gcgtggtggt ggacgtgagc cacgaagacc ctgaggtcaa gttcaactgg     900
```

-continued

```
tacgtggacg gcgtggaggt gcataatgcc aagacaaagc cgcgggagga gcagtacaac    960
agcacgtacc gtgtggtcag cgtcctcacc gtcctgcacc aggactggct gaatggcaag   1020
gagtacaagt gcaaggtctc caacaaagcc ctcccagccc ccatcgagaa aaccatctcc   1080
aaagccaaag ggcagccccg agaaccacag gtgtacaccc tgcccccatc ccgggatgag   1140
ctgaccaaga accaggtcag cctgacctgc ctggtcaaag gcttctatcc cagcgacatc   1200
gccgtggagt gggagagcaa tgggcagccg gagaacaact acaagaccac gcctcccgtg   1260
ctggactccg acggctcctt cttcctctat agcaagctca ccgtggacaa gagcaggtgg   1320
cagcagggga acgtcttctc atgctccgtg atgcatgagg ctctgcacaa ccactacacg   1380
cagaagagcc tctccctgtc tccgggtaaa                                    1410
```

<210> SEQ ID NO 24
<211> LENGTH: 470
<212> TYPE: PRT
<213> ORGANISM: Homo sapiens

<400> SEQUENCE: 24

```
Met Asp Thr Leu Cys Ser Thr Leu Leu Leu Thr Ile Pro Ser Trp
1               5                   10                  15

Val Leu Ser Gln Val Thr Leu Lys Glu Ser Gly Pro Ala Leu Val Lys
            20                  25                  30

Pro Thr Gln Thr Leu Thr Leu Thr Cys Thr Phe Ser Gly Phe Ser Leu
        35                  40                  45

Arg Thr Ser Gly Met Gly Val Gly Trp Ile Arg Gln Pro Pro Gly Lys
    50                  55                  60

Ala Leu Glu Trp Leu Ala His Ile Trp Trp Asp Asp Lys Ser Tyr
65                  70                  75                  80

Asn Pro Ser Leu Lys Ser Gln Leu Thr Ile Ser Lys Asp Thr Ser Lys
                85                  90                  95

Asn Gln Val Val Leu Thr Met Thr Asn Met Asp Pro Val Asp Thr Ala
            100                 105                 110

Thr Tyr Tyr Cys Ala Arg Arg Asn Tyr Tyr Asp Asp Tyr Phe Ala
        115                 120                 125

Tyr Trp Gly Gln Gly Thr Leu Val Thr Val Ser Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Leu Gly Thr Gln Thr Tyr Ile Cys Asn
    210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
```

```
                275                 280                 285
Val Ser His Glu Asp Pro Glu Val Lys Phe Asn Trp Tyr Val Asp Gly
        290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
        340                 345                 350

Ala Pro Ile Glu Lys Thr Ile Ser Lys Ala Lys Gly Gln Pro Arg Glu
                355                 360                 365

Pro Gln Val Tyr Thr Leu Pro Pro Ser Arg Asp Glu Leu Thr Lys Asn
        370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
        420                 425                 430

Leu Thr Val Asp Lys Ser Arg Trp Gln Gln Gly Asn Val Phe Ser Cys
                435                 440                 445

Ser Val Met His Glu Ala Leu His Asn His Tyr Thr Gln Lys Ser Leu
        450                 455                 460

Ser Leu Ser Pro Gly Lys
465                 470

<210> SEQ ID NO 25
<211> LENGTH: 705
<212> TYPE: DNA
<213> ORGANISM: Homo sapiens

<400> SEQUENCE: 25
atggaaaccc cggcgcagct gctgtttctg ctgctgctgt ggctgccgga taccaccggc      60
gaaattgtgt tgacgcagtc tccaggcacc ctgtctttgt ctccagggga agagccacc     120 ctctcctgca gggccagtca gagtgttagc agcagctact cgcctggta ccaacagaaa     180 cctggccagg ctcccaggct cctcatctat ggtacatcca gcagggccac tggcatccca   240
gacaggttca gtggcagtgg gtctgggaca gacttcactc tcaccgtcag cagactggag   300
cctgaggatt ttgcagtgta ttactgtcag cagtatgata ggtcacctcg gacgttcggc   360
caagggacca aggtggaaat caaacgtacg gtggctgcac catctgtctt catcttcccg   420
ccatctgatg agcagttgaa atctggaact gcctctgttg tgtgcctgct gaataacttc   480
tatcccagag aggccaaagt acagtggaag gtggataacg ccctccaatc gggtaactcc   540
caggagagtg tcacagagca ggacagcaag gacagcacct acagcctcag cagcaccctg   600
acgctgagca aagcagacta cgagaaacac aaagtctacg cctgcgaagt cacccatcag   660
ggcctgagct cgcccgtcac aaagagcttc aacaggggag agtgt                   705

<210> SEQ ID NO 26
<211> LENGTH: 235
<212> TYPE: PRT
<213> ORGANISM: Homo sapiens

<400> SEQUENCE: 26

Met Glu Thr Pro Ala Gln Leu Leu Phe Leu Leu Leu Leu Trp Leu Pro
```

```
1               5                   10                  15
Asp Thr Thr Gly Glu Ile Val Leu Thr Gln Ser Pro Gly Thr Leu Ser
                20                  25                  30
Leu Ser Pro Gly Glu Arg Ala Thr Leu Ser Cys Arg Ala Ser Gln Ser
            35                  40                  45
Val Ser Ser Ser Tyr Phe Ala Trp Tyr Gln Gln Lys Pro Gly Gln Ala
        50                  55                  60
Pro Arg Leu Leu Ile Tyr Gly Thr Ser Arg Ala Thr Gly Ile Pro
65                  70                  75                  80
Asp Arg Phe Ser Gly Ser Gly Ser Gly Thr Asp Phe Thr Leu Thr Val
                85                  90                  95
Ser Arg Leu Glu Pro Glu Asp Phe Ala Val Tyr Tyr Cys Gln Gln Tyr
            100                 105                 110
Asp Arg Ser Pro Arg Thr Phe Gly Gln Gly Thr Lys Val Glu Ile Lys
            115                 120                 125
Arg Thr Val Ala Ala Pro Ser Val Phe Ile Phe Pro Pro Ser Asp Glu
130                 135                 140
Gln Leu Lys Ser Gly Thr Ala Ser Val Val Cys Leu Leu Asn Asn Phe
145                 150                 155                 160
Tyr Pro Arg Glu Ala Lys Val Gln Trp Lys Val Asp Asn Ala Leu Gln
                165                 170                 175
Ser Gly Asn Ser Gln Glu Ser Val Thr Glu Gln Asp Ser Lys Asp Ser
            180                 185                 190
Thr Tyr Ser Leu Ser Ser Thr Leu Thr Leu Ser Lys Ala Asp Tyr Glu
        195                 200                 205
Lys His Lys Val Tyr Ala Cys Glu Val Thr His Gln Gly Leu Ser Ser
    210                 215                 220
Pro Val Thr Lys Ser Phe Asn Arg Gly Glu Cys
225                 230                 235
```

<210> SEQ ID NO 27
<211> LENGTH: 1389
<212> TYPE: DNA
<213> ORGANISM: Homo sapiens

<400> SEQUENCE: 27

```
atggattgga cctggcgtat tctgtttctg gtggcggcgg cgaccggcgc gcatagccag     60
gtgcagttgg tgcagtctgg ggctgcggtg aagaagcctg ggcctcagt gaaggtctcc    120
tgcaaggctt ctggatacac cttcaccggc tactatatac actgggtgcg acaggcccct    180
ggacaagggc ttgagtggat gggatggatc aaccctaaca gtggtggcac aaactatgca    240
caaaagtttc agggcagggt caccatgacc agggacacgt ccatcagcac agcctccatg    300
gaactgagca ggctgagatc tgacgacacg gccgtttatt tctgtgcgag agatcggtgg    360
ctggatgctt ttgatatctg gggccaaggg acaatggtca ccgtctcttc tgctagcacc    420
aagggcccat cggtcttccc cctggcgccc tgctccagga gcacctccga gagcacagcg    480
gccctgggct gcctggtcaa ggactacttc cccgaaccgg tgacggtgtc gtggaactca    540
ggcgctctga ccagcggcgt gcacaccttc ccagctgtcc tacagtcctc aggactctac    600
tccctcagca gcgtggtgac cgtgccctcc agcaacttcg gcacccagac ctacacctgc    660
aacgtagatc acaagcccag caacaccaag gtggacaaga cagttgagcg caaatgttgt    720
gtcgagtgcc caccgtgccc agcaccacct gtggcaggac cgtcagtctt cctcttcccc    780
ccaaaaccca aggacaccct catgatctcc cggacccctg aggtcacgtg cgtggtggtg    840
```

-continued

```
gacgtgagcc acgaagaccc cgaggtccag ttcaactggt acgtggacgg cgtggaggtg    900
cataatgcca agacaaagcc acgggaggag cagttcaaca gcacgttccg tgtggtcagc    960
gtcctcaccg ttgtgcacca ggactggctg aacggcaagg agtacaagtg caaggtctcc   1020
aacaaaggcc tcccagcccc catcgagaaa accatctcca aaaccaaagg cagccccga    1080
gaaccacagg tgtacaccct gcccccatcc cgggaggaga tgaccaagaa ccaggtcagc   1140
ctgacctgcc tggtcaaagg cttctacccc agcgacatcg ccgtggagtg ggagagcaat   1200
gggcagccgg agaacaacta caagaccaca cctcccatgc tggactccga cggctccttc   1260
ttcctctaca gcaagctcac cgtggacaag agcaggtggc agcaggggaa cgtcttctca   1320
tgctccgtga tgcatgaggc tctgcacaac cactacacgc agaagagcct ctccctgtct   1380
ccgggtaaa                                                           1389
```

<210> SEQ ID NO 28
<211> LENGTH: 463
<212> TYPE: PRT
<213> ORGANISM: Homo sapiens

<400> SEQUENCE: 28

```
Met Asp Trp Thr Trp Arg Ile Leu Phe Leu Val Ala Ala Thr Gly
1               5                   10                  15

Ala His Ser Gln Val Gln Leu Val Gln Ser Gly Ala Ala Val Lys Lys
            20                  25                  30

Pro Gly Ala Ser Val Lys Val Ser Cys Lys Ala Ser Gly Tyr Thr Phe
        35                  40                  45

Thr Gly Tyr Tyr Ile His Trp Val Arg Gln Ala Pro Gly Gln Gly Leu
    50                  55                  60

Glu Trp Met Gly Trp Ile Asn Pro Asn Ser Gly Gly Thr Asn Tyr Ala
65                  70                  75                  80

Gln Lys Phe Gln Gly Arg Val Thr Met Thr Arg Asp Thr Ser Ile Ser
                85                  90                  95

Thr Ala Ser Met Glu Leu Ser Arg Leu Arg Ser Asp Asp Thr Ala Val
            100                 105                 110

Tyr Phe Cys Ala Arg Asp Arg Trp Leu Asp Ala Phe Asp Ile Trp Gly
        115                 120                 125

Gln Gly Thr Met Val Thr Val Ser Ser Ala Ser Thr Lys Gly Pro Ser
    130                 135                 140

Val Phe Pro Leu Ala Pro Cys Ser Arg Ser Thr Ser Glu Ser Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Asn Phe Gly Thr Gln Thr Tyr Thr Cys Asn Val Asp His
    210                 215                 220

Lys Pro Ser Asn Thr Lys Val Asp Lys Thr Val Glu Arg Lys Cys Cys
225                 230                 235                 240

Val Glu Cys Pro Pro Cys Pro Ala Pro Pro Val Ala Gly Pro Ser Val
                245                 250                 255

Phe Leu Phe Pro Pro Lys Pro Lys Asp Thr Leu Met Ile Ser Arg Thr
            260                 265                 270
```

```
Pro Glu Val Thr Cys Val Val Asp Val Ser His Glu Asp Pro Glu
            275                 280                 285

Val Gln Phe Asn Trp Tyr Val Asp Gly Val Glu Val His Asn Ala Lys
    290                 295                 300

Thr Lys Pro Arg Glu Glu Gln Phe Asn Ser Thr Phe Arg Val Val Ser
305                 310                 315                 320

Val Leu Thr Val Val His Gln Asp Trp Leu Asn Gly Lys Glu Tyr Lys
                325                 330                 335

Cys Lys Val Ser Asn Lys Gly Leu Pro Ala Pro Ile Glu Lys Thr Ile
            340                 345                 350

Ser Lys Thr Lys Gly Gln Pro Arg Glu Pro Gln Val Tyr Thr Leu Pro
        355                 360                 365

Pro Ser Arg Glu Glu Met Thr Lys Asn Gln Val Ser Leu Thr Cys Leu
370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Met Leu Asp Ser
                405                 410                 415

Asp Gly Ser Phe Phe Leu Tyr Ser Lys Leu Thr Val Asp Lys Ser Arg
            420                 425                 430

Trp Gln Gln Gly Asn Val Phe Ser Cys Ser Val Met His Glu Ala Leu
        435                 440                 445

His Asn His Tyr Thr Gln Lys Ser Leu Ser Leu Ser Pro Gly Lys
    450                 455                 460

<210> SEQ ID NO 29
<211> LENGTH: 705
<212> TYPE: DNA
<213> ORGANISM: Homo sapiens

<400> SEQUENCE: 29
atggaaaccc cagctcagct tctcttcctc ctgctactct ggctcccaga taccaccgga     60
gaaattgtgt tgacgcagtc tccaggcacc ctgtctttgt ctccagggga aagagccacc    120
ctctcctgca gggccagtca gagtgttagc agcggctact taacctggta ccagcagaaa    180
cctggccagg ctcccagact cctcatctat ggtgcatcca gcagggccac tggcatccca    240
gacaggttca gtggcagtgg gtctgggacg gacttcactc tcaccatcag cagactggag    300
cctgaagatt ttgcagtgta ttactgtcag cagtatggta actcactgag caggtttggc    360
caggggacca agctggagat caaacgtacg gtggctgcac catctgtctt catcttcccg    420
ccatctgatg agcagttgaa atctggaact gcctctgttg tgtgcctgct gaataacttc    480
tatcccagag aggccaaagt acagtggaag gtggataacg ccctccaatc gggtaactcc    540
caggagagtg tcacagagca ggacagcaag gacagcacct acagcctcag cagcaccctg    600
acgctgagca agcagactac gagaaacac aaagtctacg cctgcgaagt cacccatcag    660
ggcctgagct cgcccgtcac aaagagcttc aacaggggag agtgt              705

<210> SEQ ID NO 30
<211> LENGTH: 235
<212> TYPE: PRT
<213> ORGANISM: Homo sapiens

<400> SEQUENCE: 30

Met Glu Thr Pro Ala Gln Leu Leu Phe Leu Leu Leu Leu Trp Leu Pro
1               5                   10                  15
```

Asp Thr Thr Gly Glu Ile Val Leu Thr Gln Ser Pro Gly Thr Leu Ser
         20                  25                  30

Leu Ser Pro Gly Glu Arg Ala Thr Leu Ser Cys Arg Ala Ser Gln Ser
     35                  40                  45

Val Ser Ser Gly Tyr Leu Thr Trp Tyr Gln Gln Lys Pro Gly Gln Ala
 50                  55                  60

Pro Arg Leu Leu Ile Tyr Gly Ala Ser Ser Arg Ala Thr Gly Ile Pro
 65                  70                  75                  80

Asp Arg Phe Ser Gly Ser Gly Ser Gly Thr Asp Phe Thr Leu Thr Ile
                 85                  90                  95

Ser Arg Leu Glu Pro Glu Asp Phe Ala Val Tyr Tyr Cys Gln Gln Tyr
             100                 105                 110

Gly Asn Ser Leu Ser Arg Phe Gly Gln Gly Thr Lys Leu Glu Ile Lys
             115                 120                 125

Arg Thr Val Ala Ala Pro Ser Val Phe Ile Phe Pro Pro Ser Asp Glu
130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
             165                 170                 175

Ser Gly Asn Ser Gln Glu Ser Val Thr Glu Gln Asp Ser Lys Asp Ser
             180                 185                 190

Thr Tyr Ser Leu Ser Ser Thr Leu Thr Leu Ser Lys Ala Asp Tyr Glu
         195                 200                 205

Lys His Lys Val Tyr Ala Cys Glu Val Thr His Gln Gly Leu Ser Ser
     210                 215                 220

Pro Val Thr Lys Ser Phe Asn Arg Gly Glu Cys
225                 230                 235

<210> SEQ ID NO 31
<211> LENGTH: 1422
<212> TYPE: DNA
<213> ORGANISM: Homo sapiens

<400> SEQUENCE: 31

```
atggacatga gggtgcccgc tcagctcctg gggctcctgc tgctgtggct gagaggtgcg    60
cgctgtcagg tgcagctggt ggagtctggg ggaggcgtgg tccagcctgg aggtccctg   120
agactctcct gtgcagcgtc tggattcacc ttcagtagct atggcatgca ctgggtccgc   180
caggctccag gcaaggggct ggagtgggtg gcagttatat ggtatgatgg aagtaataaa   240
tactatgcag actccgtgaa gggccgattc atcatctcca gagataaatc caagaacacg   300
ctgtatctgc aaatgaacag cctgagagcc gaggacacgg ctgtgtatta ctgtgcgaga   360
gcggggggta tagcagcagc tggcctctac tactactacg gtatggacgt ctggggccaa   420
gggaccacgg tcaccgtctc tagtgcctcc accaagggcc catcggtctt ccccctggcg   480
ccctgctcca ggagcacctc cgagagcaca gcggccctgg gctgcctggt caaggactac   540
ttccccgaac cggtgacggt gtcgtggaac tcaggcgctc tgaccagcgg cgtgcacacc   600
ttcccagctg tcctacagtc ctcaggactc tactccctca gcagcgtggt gaccgtgccc   660
tccagcaact tcggcaccca gacctacacc tgcaacgtag atcacaagcc cagcaacacc   720
aaggtggaca gacagttgag cgcaaatgtt gtgtcgagt gcccaccgtg cccagcacca   780
cctgtggcag gaccgtcagt cttcctcttc cccccaaaac ccaaggacac cctcatgatc   840
```

```
tcccggaccc ctgaggtcac gtgcgtggtg gtggacgtga gccacgaaga ccccgaggtc      900
cagttcaact ggtacgtgga cggcgtggag gtgcataatg ccaagacaaa gccacgggag      960
gagcagttca acagcacgtt ccgtgtggtc agcgtcctca ccgttgtgca ccaggactgg     1020
ctgaacggca aggagtacaa gtgcaaggtc tccaacaaag cctcccagc ccccatcgag      1080 aaaaccatct ccaaaaccaa agggcagccc cgagaaccac aggtgtacac cctgccccca     1140
tcccgggagg agatgaccaa gaaccaggtc agcctgacct gcctggtcaa aggcttctac     1200
cccagcgaca tcgccgtgga gtgggagagc aatgggcagc cggagaacaa ctacaagacc     1260
acacctccca tgctggactc cgacggctcc ttcttcctct acagcaagct caccgtggac     1320
aagagcaggt ggcagcaggg gaacgtcttc tcatgctccg tgatgcatga ggctctgcac     1380
aaccactaca cgcagaagag cctctccctg tctccgggta aa                        1422
```

<210> SEQ ID NO 32
<211> LENGTH: 474
<212> TYPE: PRT
<213> ORGANISM: Homo sapiens

<400> SEQUENCE: 32

```
Met Asp Met Arg Val Pro Ala Gln Leu Leu Gly Leu Leu Leu Leu Trp
1               5                   10                  15

Leu Arg Gly Ala Arg Cys Gln Val Gln Leu Val Glu Ser Gly Gly Gly
            20                  25                  30

Val Val Gln Pro Gly Arg Ser Leu Arg Leu Ser Cys Ala Ala Ser Gly
        35                  40                  45

Phe Thr Phe Ser Ser Tyr Gly Met His Trp Val Arg Gln Ala Pro Gly
    50                  55                  60

Lys Gly Leu Glu Trp Val Ala Val Ile Trp Tyr Asp Gly Ser Asn Lys
65                  70                  75                  80

Tyr Tyr Ala Asp Ser Val Lys Gly Arg Phe Ile Ile Ser Arg Asp Lys
                85                  90                  95

Ser Lys Asn Thr Leu Tyr Leu Gln Met Asn Ser Leu Arg Ala Glu Asp
            100                 105                 110

Thr Ala Val Tyr Tyr Cys Ala Arg Ala Gly Gly Ile Ala Ala Ala Gly
        115                 120                 125

Leu Tyr Tyr Tyr Gly Met Asp Val Trp Gly Gln Gly Thr Thr Val
    130                 135                 140

Thr Val Ser Ser Ala Ser Thr Lys Gly Pro Ser Val Phe Pro Leu Ala
145                 150                 155                 160

Pro Cys Ser Arg Ser Thr Ser Glu Ser Thr Ala Ala Leu Gly Cys Leu
                165                 170                 175

Val Lys Asp Tyr Phe Pro Glu Pro Val Thr Val Ser Trp Asn Ser Gly
            180                 185                 190

Ala Leu Thr Ser Gly Val His Thr Phe Pro Ala Val Leu Gln Ser Ser
        195                 200                 205

Gly Leu Tyr Ser Leu Ser Ser Val Val Thr Val Pro Ser Ser Asn Phe
    210                 215                 220

Gly Thr Gln Thr Tyr Thr Cys Asn Val Asp His Lys Pro Ser Asn Thr
225                 230                 235                 240

Lys Val Asp Lys Thr Val Glu Arg Lys Cys Cys Val Glu Cys Pro Pro
                245                 250                 255

Cys Pro Ala Pro Pro Val Ala Gly Pro Ser Val Phe Leu Phe Pro Pro
            260                 265                 270
```

Lys Pro Lys Asp Thr Leu Met Ile Ser Arg Thr Pro Glu Val Thr Cys
            275                 280                 285

Val Val Val Asp Val Ser His Glu Asp Pro Glu Val Gln Phe Asn Trp
        290                 295                 300

Tyr Val Asp Gly Val Glu Val His Asn Ala Lys Thr Lys Pro Arg Glu
305                 310                 315                 320

Glu Gln Phe Asn Ser Thr Phe Arg Val Val Ser Val Leu Thr Val Val
                325                 330                 335

His Gln Asp Trp Leu Asn Gly Lys Glu Tyr Lys Cys Lys Val Ser Asn
            340                 345                 350

Lys Gly Leu Pro Ala Pro Ile Glu Lys Thr Ile Ser Lys Thr Lys Gly
        355                 360                 365

Gln Pro Arg Glu Pro Gln Val Tyr Thr Leu Pro Pro Ser Arg Glu Glu
    370                 375                 380

Met Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
                405                 410                 415

Asn Tyr Lys Thr Thr Pro Pro Met Leu Asp Ser Asp Gly Ser Phe Phe
            420                 425                 430

Leu Tyr Ser Lys Leu Thr Val Asp Lys Ser Arg Trp Gln Gln Gly Asn
        435                 440                 445

Val Phe Ser Cys Ser Val Met His Glu Ala Leu His Asn His Tyr Thr
    450                 455                 460

Gln Lys Ser Leu Ser Leu Ser Pro Gly Lys
465                 470

<210> SEQ ID NO 33
<211> LENGTH: 806
<212> TYPE: DNA
<213> ORGANISM: Homo sapiens

<400> SEQUENCE: 33
atgacatcca ctttgccttt ctctccacag gtgtccactc ccaggtccaa gtttaaacgg    60
atctctagcg aattccctct agagtcgact agaccaccat ggacatgagg gtgcccgctc   120
agctcctggg gctcctgctg ctgtggctga aggtgcgcg ctgttcttct gagctgactc    180
aggaccctac tgtgtctgtg gccttgggac agacagtcaa atcacatgc caaggagaca    240 gcctcagaag ttttttatgca agctggtacc agcagaagcc aggacaggcc cctgtacttg   300
tcttctatgg taaaaacaac cggccctcag ggatcccaga ccgattctct ggctccagct   360
caggaaacac agcttccttg accatcactg gggctcaggc ggaagatgag gctgactatt   420
attgtaattc ccgggacagc agtgtttacc atctggtact cggcggaggg accaagctga   480
ccgtcctagg tcagcccaag gccaaccca ctgtcactct gttcccgccc tcctctgagg   540
agctccaagc caacaaggcc acactagtgt gtctgatcag tgacttctac cgggagctg    600 tgacagtggc ctggaaggca gatggcagcc ccgtcaaggc gggagtggag accaccaaac   660
cctccaaaca gagcaacaac aagtacgcgg ccagcagcta cctgagcctg acgcccgagc   720
agtggaagtc ccacagaagc tacagctgcc aggtcacgca tgaagggagc accgtggaga   780
agacagtggc ccctacagaa tgttca                                         806

<210> SEQ ID NO 34
<211> LENGTH: 236
<212> TYPE: PRT

<213> ORGANISM: Homo sapiens

<400> SEQUENCE: 34

Met Asp Met Arg Val Pro Ala Gln Leu Leu Gly Leu Leu Leu Leu Trp
1               5                   10                  15

Leu Arg Gly Ala Arg Cys Ser Ser Glu Leu Thr Gln Asp Pro Thr Val
            20                  25                  30

Ser Val Ala Leu Gly Gln Thr Val Lys Ile Thr Cys Gln Gly Asp Ser
        35                  40                  45

Leu Arg Ser Phe Tyr Ala Ser Trp Tyr Gln Gln Lys Pro Gly Gln Ala
    50                  55                  60

Pro Val Leu Val Phe Tyr Gly Lys Asn Asn Arg Pro Ser Gly Ile Pro
65                  70                  75                  80

Asp Arg Phe Ser Gly Ser Ser Ser Gly Asn Thr Ala Ser Leu Thr Ile
                85                  90                  95

Thr Gly Ala Gln Ala Glu Asp Glu Ala Asp Tyr Tyr Cys Asn Ser Arg
            100                 105                 110

Asp Ser Ser Val Tyr His Leu Val Leu Gly Gly Gly Thr Lys Leu Thr
        115                 120                 125

Val Leu Gly Gln Pro Lys Ala Asn Pro Thr Val Thr Leu Phe Pro Pro
    130                 135                 140

Ser Ser Glu Glu Leu Gln Ala Asn Lys Ala Thr Leu Val Cys Leu Ile
145                 150                 155                 160

Ser Asp Phe Tyr Pro Gly Ala Val Thr Val Ala Trp Lys Ala Asp Gly
                165                 170                 175

Ser Pro Val Lys Ala Gly Val Glu Thr Thr Lys Pro Ser Lys Gln Ser
            180                 185                 190

Asn Asn Lys Tyr Ala Ala Ser Ser Tyr Leu Ser Leu Thr Pro Glu Gln
        195                 200                 205

Trp Lys Ser His Arg Ser Tyr Ser Cys Gln Val Thr His Glu Gly Ser
    210                 215                 220

Thr Val Glu Lys Thr Val Ala Pro Thr Glu Cys Ser
225                 230                 235

<210> SEQ ID NO 35
<211> LENGTH: 1434
<212> TYPE: DNA
<213> ORGANISM: Homo sapiens

<400> SEQUENCE: 35
atggacatga gggtgcccgc tcagctcctg gggctcctgc tgctgtggct gagaggtgcg     60
cgctgtcagg tgcagttggt gcagtctggg gctgaggtga agaagcctgg ggcctcagtg    120
aaggtctcct gcaaggcttc tggatacacc ttcaccggct actatatgca ctgggtgcga    180
caggcccctg gacaagggct tgagtggatg ggatggatca accctaacag tggtggcaca    240
aactatgcac agaagtttca ggcagggtc accatgacca gggacacgtc catcagcaca    300
gcctacatgg agctgagcag gctgagatct gacgacacgg ccgtgtattt ctgtgcgaga    360
gatcaaatga gtattattat gcttcgggga gttttttccc cttactatta cggtatggac    420
gtctggggcc aagggaccac ggtcaccgtc tctagtgcct ccaccaaggg cccatcggtc    480
ttccccctgg cgccctgctc caggagcacc tccgagagca cagcggccct gggctgcctg    540
gtcaaggact acttccccga accggtgacg gtgtcgtgga actcaggcgc tctgaccagc    600
ggcgtgcaca ccttcccagc tgtcctacag tcctcaggac tctactccct cagcagcgtg    660

```
gtgaccgtgc cctccagcaa cttcggcacc cagacctaca cctgcaacgt agatcacaag    720
cccagcaaca ccaaggtgga caagacagtt gagcgcaaat gttgtgtcga gtgcccaccg    780
tgcccagcac cacctgtggc aggaccgtca gtcttcctct ccccccaaa acccaaggac     840 accctcatga tctcccggac ccctgaggtc acgtgcgtgg tggtggacgt gagccacgaa    900
gaccccgagg tccagttcaa ctggtacgtg gacggcgtgg aggtgcataa tgccaagaca    960
aagccacggg aggagcagtt caacagcacg ttccgtgtgg tcagcgtcct caccgttgtg   1020
caccaggact ggctgaacgg caaggagtac aagtgcaagg tctccaacaa aggcctccca   1080
gcccccatcg agaaaaccat ctccaaaacc aaagggcagc cccgagaacc acaggtgtac   1140
accctgcccc catcccggga ggagatgacc aagaaccagg tcagcctgac ctgcctggtc   1200
aaaggcttct accccagcga catcgccgtg gagtgggaga gcaatgggca gccggagaac   1260
aactacaaga ccacacctcc catgctggac tccgacggct ccttcttcct ctacagcaag   1320
ctcaccgtgg acaagagcag gtggcagcag gggaacgtct tctcatgctc cgtgatgcat   1380
gaggctctgc acaaccacta cacgcagaag agcctctccc tgtctccggg taaa         1434
```

<210> SEQ ID NO 36
<211> LENGTH: 478
<212> TYPE: PRT
<213> ORGANISM: Homo sapiens

<400> SEQUENCE: 36

```
Met Asp Met Arg Val Pro Ala Gln Leu Leu Gly Leu Leu Leu Leu Trp
1               5                   10                  15

Leu Arg Gly Ala Arg Cys Gln Val Gln Leu Val Gln Ser Gly Ala Glu
            20                  25                  30

Val Lys Lys Pro Gly Ala Ser Val Lys Val Ser Cys Lys Ala Ser Gly
        35                  40                  45

Tyr Thr Phe Thr Gly Tyr Tyr Met His Trp Val Arg Gln Ala Pro Gly
    50                  55                  60

Gln Gly Leu Glu Trp Met Gly Trp Ile Asn Pro Asn Ser Gly Gly Thr
65                  70                  75                  80

Asn Tyr Ala Gln Lys Phe Gln Gly Arg Val Thr Met Thr Arg Asp Thr
                85                  90                  95

Ser Ile Ser Thr Ala Tyr Met Glu Leu Ser Arg Leu Arg Ser Asp Asp
            100                 105                 110

Thr Ala Val Tyr Phe Cys Ala Arg Asp Gln Met Ser Ile Ile Met Leu
        115                 120                 125

Arg Gly Val Phe Pro Pro Tyr Tyr Gly Met Asp Val Trp Gly Gln
    130                 135                 140

Gly Thr Thr Val Thr Val Ser Ser Ala Ser Thr Lys Gly Pro Ser Val
145                 150                 155                 160

Phe Pro Leu Ala Pro Cys Ser Arg Ser Thr Ser Glu Ser Thr Ala Ala
                165                 170                 175

Leu Gly Cys Leu Val Lys Asp Tyr Phe Pro Glu Pro Val Thr Val Ser
            180                 185                 190

Trp Asn Ser Gly Ala Leu Thr Ser Gly Val His Thr Phe Pro Ala Val
        195                 200                 205

Leu Gln Ser Ser Gly Leu Tyr Ser Leu Ser Ser Val Val Thr Val Pro
    210                 215                 220

Ser Ser Asn Phe Gly Thr Gln Thr Tyr Thr Cys Asn Val Asp His Lys
225                 230                 235                 240
```

```
Pro Ser Asn Thr Lys Val Asp Lys Thr Val Glu Arg Lys Cys Cys Val
            245                 250                 255

Glu Cys Pro Pro Cys Pro Ala Pro Pro Val Ala Gly Pro Ser Val Phe
        260                 265                 270

Leu Phe Pro Pro Lys Pro Lys Asp Thr Leu Met Ile Ser Arg Thr Pro
        275                 280                 285

Glu Val Thr Cys Val Val Val Asp Val Ser His Glu Asp Pro Glu Val
        290                 295                 300

Gln Phe Asn Trp Tyr Val Asp Gly Val Glu Val His Asn Ala Lys Thr
305                 310                 315                 320

Lys Pro Arg Glu Glu Gln Phe Asn Ser Thr Phe Arg Val Val Ser Val
                325                 330                 335

Leu Thr Val Val His Gln Asp Trp Leu Asn Gly Lys Glu Tyr Lys Cys
            340                 345                 350

Lys Val Ser Asn Lys Gly Leu Pro Ala Pro Ile Glu Lys Thr Ile Ser
            355                 360                 365

Lys Thr Lys Gly Gln Pro Arg Glu Pro Gln Val Tyr Thr Leu Pro Pro
        370                 375                 380

Ser Arg Glu Glu Met Thr Lys Asn Gln Val Ser Leu Thr Cys Leu Val
385                 390                 395                 400

Lys Gly Phe Tyr Pro Ser Asp Ile Ala Val Glu Trp Glu Ser Asn Gly
                405                 410                 415

Gln Pro Glu Asn Asn Tyr Lys Thr Thr Pro Pro Met Leu Asp Ser Asp
            420                 425                 430

Gly Ser Phe Phe Leu Tyr Ser Lys Leu Thr Val Asp Lys Ser Arg Trp
        435                 440                 445

Gln Gln Gly Asn Val Phe Ser Cys Ser Val Met His Glu Ala Leu His
450                 455                 460

Asn His Tyr Thr Gln Lys Ser Leu Ser Leu Ser Pro Gly Lys
            465                 470                 475

<210> SEQ ID NO 37
<211> LENGTH: 723
<212> TYPE: DNA
<213> ORGANISM: Homo sapiens

<400> SEQUENCE: 37
atggacatga gggtgcccgc tcagctcctg gggctcctgc tgctgtggct gagaggtgcc      60
agatgtgata ttgtgatgac tcagtctcca ctctccctgc ccgtcacccc tggagagccg     120
gcctccatct cctgcaggtc tagtcagagc ctcctgcata gtaatggata caactatttg     180
gattggtacc tgcagaagcc agggcagtct ccacagctcc tgatctattt gggttctaat     240
cgggcctccg ggtccctga caggttcagt ggcagtggat caggcacaga ttttacactg     300
aaaatcagca gagtggaggc tgaggatgtt ggggtttatt actgcatgca agctctacaa     360
actccgctca ctttcggcgg agggaccaag gtagagatca aacggactgt ggctgcacca     420
tctgtcttca tcttcccgcc atctgatgag cagttgaaat ctggaactgc ctctgttgtg     480
tgcctgctga ataacttcta tcccagagag gccaaagtac agtggaaggt ggataacgcc     540
ctccaatcgg gtaactccca ggagagtgtc acagagcagg acagcaagga cagcacctac     600
agcctcagca gcaccctgac gctgagcaaa gcagactacg agaaacacaa agtctacgcc     660
tgcgaagtca cccatcaggg cctgagctcg cccgtcacaa agagcttcaa caggggagag     720
tgt                                                                  723
```

<210> SEQ ID NO 38
<211> LENGTH: 241
<212> TYPE: PRT
<213> ORGANISM: Homo sapiens

<400> SEQUENCE: 38

Met Asp Met Arg Val Pro Ala Gln Leu Leu Gly Leu Leu Leu Leu Trp
1               5                   10                  15

Leu Arg Gly Ala Arg Cys Asp Ile Val Met Thr Gln Ser Pro Leu Ser
            20                  25                  30

Leu Pro Val Thr Pro Gly Glu Pro Ala Ser Ile Ser Cys Arg Ser Ser
        35                  40                  45

Gln Ser Leu Leu His Ser Asn Gly Tyr Asn Tyr Leu Asp Trp Tyr Leu
    50                  55                  60

Gln Lys Pro Gly Gln Ser Pro Gln Leu Leu Ile Tyr Leu Gly Ser Asn
65                  70                  75                  80

Arg Ala Ser Gly Val Pro Asp Arg Phe Ser Gly Ser Gly Ser Gly Thr
                85                  90                  95

Asp Phe Thr Leu Lys Ile Ser Arg Val Glu Ala Glu Asp Val Gly Val
            100                 105                 110

Tyr Tyr Cys Met Gln Ala Leu Gln Thr Pro Leu Thr Phe Gly Gly Gly
        115                 120                 125

Thr Lys Val Glu Ile Lys Arg Thr Val Ala Ala Pro Ser Val Phe Ile
    130                 135                 140

Phe Pro Pro Ser Asp Glu Gln Leu Lys Ser Gly Thr Ala Ser Val Val
145                 150                 155                 160

Cys Leu Leu Asn Asn Phe Tyr Pro Arg Glu Ala Lys Val Gln Trp Lys
                165                 170                 175

Val Asp Asn Ala Leu Gln Ser Gly Asn Ser Gln Glu Ser Val Thr Glu
            180                 185                 190

Gln Asp Ser Lys Asp Ser Thr Tyr Ser Leu Ser Ser Thr Leu Thr Leu
        195                 200                 205

Ser Lys Ala Asp Tyr Glu Lys His Lys Val Tyr Ala Cys Glu Val Thr
    210                 215                 220

His Gln Gly Leu Ser Ser Pro Val Thr Lys Ser Phe Asn Arg Gly Glu
225                 230                 235                 240

Cys

<210> SEQ ID NO 39
<211> LENGTH: 1425
<212> TYPE: DNA
<213> ORGANISM: Homo sapiens

<400> SEQUENCE: 39
atggacatga gggtgcccgc tcagctcctg gggctcctgc tgctgtggct gagaggtgcc      60
agatgtgagg tgcagctggt ggagtctggg ggaggcttgg tccagcctgg ggggtccctg     120
agactctcct gtgcagcctc cggattcacc tttagtagct attggatgag ctgggtccgc     180
caggctccag ggaaggggct ggagtgggtg gccagcataa acaagatgg aagtgagaaa     240 tactatgtgg actctgtgaa gggccgattc accatctcca gagacaacgc caggaactca     300
ctgtatctgc aaatgaacag cctgagagcc gaggacacgg ctgtgtatta ctgtgcgaga     360
gatcttgtat aatggtgta tgatatagac tactactact acggtatgga cgtctggggc     420
caagggacca cggtcaccgt ctcctcagcc tccaccaagg gcccatcggt cttccccctg     480

```
gcgccctgct ccaggagcac ctccgagagc acagcggccc tgggctgcct ggtcaaggac    540
tacttccccg aaccggtgac ggtgtcgtgg aactcaggcg ctctgaccag cggcgtgcac    600
accttcccag ctgtcctaca gtcctcagga ctctactccc tcagcagcgt ggtgaccgtg    660
ccctccagca acttcggcac ccagacctac acctgcaacg tagatcacaa gcccagcaac    720
accaaggtgg acaagacagt tgagcgcaaa tgttgtgtcg agtgcccacc gtgcccagca    780
ccacctgtgg caggaccgtc agtcttcctc ttccccccaa aacccaagga caccctcatg    840
atctcccgga cccctgaggt cacgtgcgtg gtggtggacg tgagccacga agaccccgag    900
gtccagttca actggtacgt ggacggcgtg gaggtgcata atgccaagac aaagccacgg    960
gaggagcagt tcaacagcac gttccgtgtg gtcagcgtcc tcaccgttgt gcaccaggac   1020
tggctgaacg gcaaggagta caagtgcaag gtctccaaca aaggcctccc agcccccatc   1080
gagaaaacca tctccaaaac caaagggcag ccccgagaac acaggtgta caccctgccc   1140 ccatcccggg aggagatgac caagaaccag gtcagcctga cctgcctggt caaaggcttc   1200
taccccagcg acatcgccgt ggagtgggag agcaatgggc agccggagaa caactacaag   1260
accacacctc ccatgctgga ctccgacggc tccttcttcc tctacagcaa gctcaccgtg   1320
gacaagagca ggtggcagca ggggaacgtc ttctcatgct ccgtgatgca tgaggctctg   1380
cacaaccact acacgcagaa gagcctctcc ctgtctccgg gtaaa             1425
```

<210> SEQ ID NO 40  
<211> LENGTH: 475  
<212> TYPE: PRT  
<213> ORGANISM: Homo sapiens

<400> SEQUENCE: 40

```
Met Asp Met Arg Val Pro Ala Gln Leu Leu Gly Leu Leu Leu Leu Trp
1               5                   10                  15

Leu Arg Gly Ala Arg Cys Glu Val Gln Leu Val Glu Ser Gly Gly Gly
            20                  25                  30

Leu Val Gln Pro Gly Gly Ser Leu Arg Leu Ser Cys Ala Ala Ser Gly
        35                  40                  45

Phe Thr Phe Ser Ser Tyr Trp Met Ser Trp Val Arg Gln Ala Pro Gly
    50                  55                  60

Lys Gly Leu Glu Trp Val Ala Ser Ile Lys Gln Asp Gly Ser Glu Lys
65                  70                  75                  80

Tyr Tyr Val Asp Ser Val Lys Gly Arg Phe Thr Ile Ser Arg Asp Asn
                85                  90                  95

Ala Arg Asn Ser Leu Tyr Leu Gln Met Asn Ser Leu Arg Ala Glu Asp
            100                 105                 110

Thr Ala Val Tyr Tyr Cys Ala Arg Asp Leu Val Leu Met Val Tyr Asp
        115                 120                 125

Ile Asp Tyr Tyr Tyr Gly Met Asp Val Trp Gly Gln Gly Thr Thr
    130                 135                 140

Val Thr Val Ser Ser Ala Ser Thr Lys Gly Pro Ser Val Phe Pro Leu
145                 150                 155                 160

Ala Pro Cys Ser Arg Ser Thr Ser Glu Ser Thr Ala Ala Leu Gly Cys
                165                 170                 175

Leu Val Lys Asp Tyr Phe Pro Glu Pro Val Thr Val Ser Trp Asn Ser
            180                 185                 190

Gly Ala Leu Thr Ser Gly Val His Thr Phe Pro Ala Val Leu Gln Ser
        195                 200                 205
```

Ser Gly Leu Tyr Ser Leu Ser Ser Val Val Thr Val Pro Ser Ser Asn
    210                 215                 220

Phe Gly Thr Gln Thr Tyr Thr Cys Asn Val Asp His Lys Pro Ser Asn
225                 230                 235                 240

Thr Lys Val Asp Lys Thr Val Glu Arg Lys Cys Cys Val Glu Cys Pro
                245                 250                 255

Pro Cys Pro Ala Pro Pro Val Ala Gly Pro Ser Val Phe Leu Phe Pro
            260                 265                 270

Pro Lys Pro Lys Asp Thr Leu Met Ile Ser Arg Thr Pro Glu Val Thr
        275                 280                 285

Cys Val Val Val Asp Val Ser His Glu Asp Pro Glu Val Gln Phe Asn
290                 295                 300

Trp Tyr Val Asp Gly Val Glu Val His Asn Ala Lys Thr Lys Pro Arg
305                 310                 315                 320

Glu Glu Gln Phe Asn Ser Thr Phe Arg Val Val Ser Val Leu Thr Val
                325                 330                 335

Val His Gln Asp Trp Leu Asn Gly Lys Glu Tyr Lys Cys Lys Val Ser
            340                 345                 350

Asn Lys Gly Leu Pro Ala Pro Ile Glu Lys Thr Ile Ser Lys Thr Lys
        355                 360                 365

Gly Gln Pro Arg Glu Pro Gln Val Tyr Thr Leu Pro Pro Ser Arg Glu
370                 375                 380

Glu Met Thr Lys Asn Gln Val Ser Leu Thr Cys Leu Val Lys Gly Phe
385                 390                 395                 400

Tyr Pro Ser Asp Ile Ala Val Glu Trp Glu Ser Asn Gly Gln Pro Glu
                405                 410                 415

Asn Asn Tyr Lys Thr Thr Pro Pro Met Leu Asp Ser Asp Gly Ser Phe
            420                 425                 430

Phe Leu Tyr Ser Lys Leu Thr Val Asp Lys Ser Arg Trp Gln Gln Gly
        435                 440                 445

Asn Val Phe Ser Cys Ser Val Met His Glu Ala Leu His Asn His Tyr
450                 455                 460

Thr Gln Lys Ser Leu Ser Leu Ser Pro Gly Lys
465                 470                 475

<210> SEQ ID NO 41
<211> LENGTH: 723
<212> TYPE: DNA
<213> ORGANISM: Homo sapiens

<400> SEQUENCE: 41
atggacatga gggtgcccgc tcagctcctg gggctcctgc tgctgtggct gagaggtgcc      60
agatgtgata ttgtgatgac tcagtctcca ctctccctgc ccgtcacccc tggagagccg     120
gcctccatct cctgcaggtc tagtcagagc ctcctgcata gtaatgggta caactatttg     180
gattggtacc tgcagaagcc agggcagtct ccacagctcc tgatctattt gggttctaat     240
cgggcctccg ggtccctga caggttcagt ggcagtggat caggcacaga tcttacactg     300
aaaatcagca gagtggaggc tgaggatgtt ggagtttatt actgcatgca aactctacaa     360
actccgctca ctttcggcgg agggaccaag gtagagatca aacggactgt ggctgcacca     420
tctgtcttca tcttcccgcc atctgatgag cagttgaaat ctggaactgc ctctgttgtg     480
tgcctgctga ataacttcta tcccagagag gccaaagtac agtggaaggt ggataacgcc     540
ctccaatcgg gtaactccca ggagagtgtc acagagcagg acagcaagga cagcacctac     600

```
agcctcagca gcaccctgac gctgagcaaa gcagactacg agaaacacaa agtctacgcc      660
tgcgaagtca cccatcaggg cctgagctcg cccgtcacaa agagcttcaa caggggagag      720
tgt                                                                    723
```

<210> SEQ ID NO 42
<211> LENGTH: 241
<212> TYPE: PRT
<213> ORGANISM: Homo sapiens

<400> SEQUENCE: 42

```
Met Asp Met Arg Val Pro Ala Gln Leu Leu Gly Leu Leu Leu Leu Trp
1               5                   10                  15

Leu Arg Gly Ala Arg Cys Asp Ile Val Met Thr Gln Ser Pro Leu Ser
            20                  25                  30

Leu Pro Val Thr Pro Gly Glu Pro Ala Ser Ile Ser Cys Arg Ser Ser
        35                  40                  45

Gln Ser Leu Leu His Ser Asn Gly Tyr Asn Tyr Leu Asp Trp Tyr Leu
    50                  55                  60

Gln Lys Pro Gly Gln Ser Pro Gln Leu Leu Ile Tyr Leu Gly Ser Asn
65                  70                  75                  80

Arg Ala Ser Gly Val Pro Asp Arg Phe Ser Gly Ser Gly Ser Gly Thr
                85                  90                  95

His Leu Thr Leu Lys Ile Ser Arg Val Glu Ala Glu Asp Val Gly Val
            100                 105                 110

Tyr Tyr Cys Met Gln Thr Leu Gln Thr Pro Leu Thr Phe Gly Gly Gly
        115                 120                 125

Thr Lys Val Glu Ile Lys Arg Thr Val Ala Ala Pro Ser Val Phe Ile
130                 135                 140

Phe Pro Pro Ser Asp Glu Gln Leu Lys Ser Gly Thr Ala Ser Val Val
145                 150                 155                 160

Cys Leu Leu Asn Asn Phe Tyr Pro Arg Glu Ala Lys Val Gln Trp Lys
                165                 170                 175

Val Asp Asn Ala Leu Gln Ser Gly Asn Ser Gln Glu Ser Val Thr Glu
            180                 185                 190

Gln Asp Ser Lys Asp Ser Thr Tyr Ser Leu Ser Ser Thr Leu Thr Leu
        195                 200                 205

Ser Lys Ala Asp Tyr Glu Lys His Lys Val Tyr Ala Cys Glu Val Thr
    210                 215                 220

His Gln Gly Leu Ser Ser Pro Val Thr Lys Ser Phe Asn Arg Gly Glu
225                 230                 235                 240

Cys
```

<210> SEQ ID NO 43
<211> LENGTH: 1425
<212> TYPE: DNA
<213> ORGANISM: Homo sapiens

<400> SEQUENCE: 43

```
atggacatga gggtgcccgc tcagctcctg gggctcctgc tgctgtggct gagaggtgcc       60
agatgtgagg tgcagctggt ggagtctggg ggaggcttgg tccagcctgg ggggtccctg      120
agactctcct gtgcagcctc cggattcacc tttagtaact attggatgag ctgggtccgc      180
caggctccag ggaaggggct ggagtgggtg gccagcataa acaagatgg aagtgagaaa       240 tactatgtgg actctgtgaa ggccgattc gccatctcca gagacaacgc caagaactca      300
```

| | |
|---|---|
| ctgtttctgc aaatgaacag cctgagagcc gaggacacgg ctgtgtatta ctgtgcgaga | 360 |
| gatcttgtac taatggtgta tgatatagac tactactact acggtatgga cgtctggggc | 420 |
| caagggacca cggtcaccgt ctcctcagcc tccaccaagg gcccatcggt cttccccctg | 480 |
| gcgccctgct ccaggagcac ctccgagagc acagcggccc tgggctgcct ggtcaaggac | 540 |
| tacttccccg aaccggtgac ggtgtcgtgg aactcaggcg ctctgaccag cggcgtgcac | 600 |
| accttcccag ctgtcctaca gtcctcagga ctctactccc tcagcagcgt ggtgaccgtg | 660 |
| ccctccagca acttcggcac ccagacctac acctgcaacg tagatcacaa gcccagcaac | 720 |
| accaaggtgg acaagacagt tgagcgcaaa tgttgtgtcg agtgcccacc gtgcccagca | 780 |
| ccacctgtgg caggaccgtc agtcttcctc ttccccccaa acccaaggga caccctcatg | 840 |
| atctcccgga cccctgaggt cacgtgcgtg gtggtggacg tgagccacga agaccccgag | 900 |
| gtccagttca actggtacgt ggacggcgtg gaggtgcata atgccaagac aaagccacgg | 960 |
| gaggagcagt tcaacagcac gttccgtgtg gtcagcgtcc tcaccgttgt gcaccaggac | 1020 |
| tggctgaacg gcaaggagta caagtgcaag gtctccaaca aaggcctccc agcccccatc | 1080 |
| gagaaaacca tctccaaaac caaagggcag ccccgagaac acaggtgta cacc ctgccc | 1140 |
| ccatcccggg aggagatgac caagaaccag gtcagcctga cctgcctggt caaaggcttc | 1200 |
| taccccagcg acatcgccgt ggagtgggag agcaatgggc agccggagaa caactacaag | 1260 |
| accacacctc ccatgctgga ctccgacggc tccttcttcc tctacagcaa gctcaccgtg | 1320 |
| gacaagagca ggtggcagca ggggaacgtc ttctcatgct ccgtgatgca tgaggctctg | 1380 |
| cacaaccact acacgcagaa gagcctctcc ctgtctccgg gtaaa | 1425 |

<210> SEQ ID NO 44
<211> LENGTH: 475
<212> TYPE: PRT
<213> ORGANISM: Homo sapiens

<400> SEQUENCE: 44

Met Asp Met Arg Val Pro Ala Gln Leu Leu Gly Leu Leu Leu Leu Trp
1               5                   10                  15

Leu Arg Gly Ala Arg Cys Glu Val Gln Leu Val Glu Ser Gly Gly Gly
            20                  25                  30

Leu Val Gln Pro Gly Gly Ser Leu Arg Leu Ser Cys Ala Ala Ser Gly
        35                  40                  45

Phe Thr Phe Ser Asn Tyr Trp Met Ser Trp Val Arg Gln Ala Pro Gly
    50                  55                  60

Lys Gly Leu Glu Trp Val Ala Ser Ile Lys Gln Asp Gly Ser Glu Lys
65                  70                  75                  80

Tyr Tyr Val Asp Ser Val Lys Gly Arg Phe Ala Ile Ser Arg Asp Asn
                85                  90                  95

Ala Lys Asn Ser Leu Phe Leu Gln Met Asn Ser Leu Arg Ala Glu Asp
            100                 105                 110

Thr Ala Val Tyr Tyr Cys Ala Arg Asp Leu Val Leu Met Val Tyr Asp
        115                 120                 125

Ile Asp Tyr Tyr Tyr Gly Met Asp Val Trp Gly Gln Gly Thr Thr
    130                 135                 140

Val Thr Val Ser Ser Ala Ser Thr Lys Gly Pro Ser Val Phe Pro Leu
145                 150                 155                 160

Ala Pro Cys Ser Arg Ser Thr Ser Glu Ser Thr Ala Ala Leu Gly Cys
                165                 170                 175

Leu Val Lys Asp Tyr Phe Pro Glu Pro Val Thr Val Ser Trp Asn Ser
            180                 185                 190

Gly Ala Leu Thr Ser Gly Val His Thr Phe Pro Ala Val Leu Gln Ser
        195                 200                 205

Ser Gly Leu Tyr Ser Leu Ser Ser Val Val Thr Val Pro Ser Ser Asn
    210                 215                 220

Phe Gly Thr Gln Thr Tyr Thr Cys Asn Val Asp His Lys Pro Ser Asn
225                 230                 235                 240

Thr Lys Val Asp Lys Thr Val Glu Arg Lys Cys Cys Val Glu Cys Pro
                245                 250                 255

Pro Cys Pro Ala Pro Pro Val Ala Gly Pro Ser Val Phe Leu Phe Pro
            260                 265                 270

Pro Lys Pro Lys Asp Thr Leu Met Ile Ser Arg Thr Pro Glu Val Thr
        275                 280                 285

Cys Val Val Val Asp Val Ser His Glu Asp Pro Glu Val Gln Phe Asn
    290                 295                 300

Trp Tyr Val Asp Gly Val Glu Val His Asn Ala Lys Thr Lys Pro Arg
305                 310                 315                 320

Glu Glu Gln Phe Asn Ser Thr Phe Arg Val Val Ser Val Leu Thr Val
                325                 330                 335

Val His Gln Asp Trp Leu Asn Gly Lys Glu Tyr Lys Cys Lys Val Ser
            340                 345                 350

Asn Lys Gly Leu Pro Ala Pro Ile Glu Lys Thr Ile Ser Lys Thr Lys
        355                 360                 365

Gly Gln Pro Arg Glu Pro Gln Val Tyr Thr Leu Pro Pro Ser Arg Glu
    370                 375                 380

Glu Met Thr Lys Asn Gln Val Ser Leu Thr Cys Leu Val Lys Gly Phe
385                 390                 395                 400

Tyr Pro Ser Asp Ile Ala Val Glu Trp Glu Ser Asn Gly Gln Pro Glu
                405                 410                 415

Asn Asn Tyr Lys Thr Thr Pro Pro Met Leu Asp Ser Asp Gly Ser Phe
            420                 425                 430

Phe Leu Tyr Ser Lys Leu Thr Val Asp Lys Ser Arg Trp Gln Gln Gly
        435                 440                 445

Asn Val Phe Ser Cys Ser Val Met His Glu Ala Leu His Asn His Tyr
    450                 455                 460

Thr Gln Lys Ser Leu Ser Leu Ser Pro Gly Lys
465                 470                 475

<210> SEQ ID NO 45
<211> LENGTH: 705
<212> TYPE: DNA
<213> ORGANISM: Homo sapiens

<400> SEQUENCE: 45

```
atgacttgtt ctccactgct gctgactctg ctgattcatt gtactggttc ttgggcgcag      60
tctgtgttga cgcagccgcc ctcagtgtct gcggccccag gacagaaggt caccatctcc     120
tgctctggaa gcagctccaa cattgggaat aattatgtat cctggtacca gcagctccca     180
ggaacagccc ccaaactcct catttatgac aataataagc gaccctcagg gattcctgac     240
cgattctctg gctccaagtc tggcacgtca accaccctgg gcatcaccgg actccagact     300
ggggacgagg ccgattatta ctgcggaaca tgggatagcc gcctgagtgc tgtggttttc     360
ggcggaggga ccaagctgac cgtcctaggt cagcccaagg ccaaccccac tgtcactctg     420
```

```
ttcccgccct cctctgagga gctccaagcc aacaaggcca cactagtgtg tctgatcagt    480
gacttctacc cgggagctgt gacagtggcc tggaaggcag atggcagccc cgtcaaggcg    540
ggagtggaga ccaccaaacc ctccaaacag agcaacaaca agtacgcggc cagcagctac    600
ctgagcctga cgcccgagca gtggaagtcc cacagaagct acagctgcca ggtcacgcat    660
gaagggagca ccgtggagaa gacagtggcc cctacagaat gttca                   705
```

<210> SEQ ID NO 46
<211> LENGTH: 235
<212> TYPE: PRT
<213> ORGANISM: Homo sapiens

<400> SEQUENCE: 46

```
Met Thr Cys Ser Pro Leu Leu Thr Leu Leu Ile His Cys Thr Gly
1               5                   10                  15

Ser Trp Ala Gln Ser Val Leu Thr Gln Pro Pro Ser Val Ser Ala Ala
            20                  25                  30

Pro Gly Gln Lys Val Thr Ile Ser Cys Ser Gly Ser Ser Ser Asn Ile
            35                  40                  45

Gly Asn Asn Tyr Val Ser Trp Tyr Gln Gln Leu Pro Gly Thr Ala Pro
    50                  55                  60

Lys Leu Leu Ile Tyr Asp Asn Asn Lys Arg Pro Ser Gly Ile Pro Asp
65                  70                  75                  80

Arg Phe Ser Gly Ser Lys Ser Gly Thr Ser Thr Thr Leu Gly Ile Thr
                85                  90                  95

Gly Leu Gln Thr Gly Asp Glu Ala Asp Tyr Tyr Cys Gly Thr Trp Asp
            100                 105                 110

Ser Arg Leu Ser Ala Val Val Phe Gly Gly Gly Thr Lys Leu Thr Val
        115                 120                 125

Leu Gly Gln Pro Lys Ala Asn Pro Thr Val Thr Leu Phe Pro Pro Ser
130                 135                 140

Ser Glu Glu Leu Gln Ala Asn Lys Ala Thr Leu Val Cys Leu Ile Ser
145                 150                 155                 160

Asp Phe Tyr Pro Gly Ala Val Thr Val Ala Trp Lys Ala Asp Gly Ser
                165                 170                 175

Pro Val Lys Ala Gly Val Glu Thr Thr Lys Pro Ser Lys Gln Ser Asn
            180                 185                 190

Asn Lys Tyr Ala Ala Ser Ser Tyr Leu Ser Leu Thr Pro Glu Gln Trp
        195                 200                 205

Lys Ser His Arg Ser Tyr Ser Cys Gln Val Thr His Glu Gly Ser Thr
    210                 215                 220

Val Glu Lys Thr Val Ala Pro Thr Glu Cys Ser
225                 230                 235
```

<210> SEQ ID NO 47
<211> LENGTH: 1425
<212> TYPE: DNA
<213> ORGANISM: Homo sapiens

<400> SEQUENCE: 47

```
atggaatttg gtctgtcttg gtatttctg gttgctctgc tgcgtggcgt gcagtgccag    60
gtgcagctgg tggaatctgg gggaggcgtg gtccagcctg ggaggtccct gagactctcc   120
tgtgcagcct ctggattcac cttcagtagc tttggcatgc actgggtccg ccaggctcca   180 ggcaagggc tggagtgggt ggcagttata tcatttgatg aagtattaa gtattctgta    240
```

```
gactccgtga agggccgatt caccatctcc agagacaatt caaagaacac gctgtttctg    300
caaatgaaca gcctgcgagc cgaggacacg gctgtgtatt actgtgcgag agatcggctc    360
aattactatg atagtagtgg ttattatcac tacaaatact acggtatggc cgtctggggc    420
caagggacca cggtcaccgt ctctagtgcc tccaccaagg gcccatcggt cttccccctg    480
gcgccctgct ccaggagcac ctccgagagc acagcggccc tgggctgcct ggtcaaggac    540
tacttccccg aaccggtgac ggtgtcgtgg aactcaggcg ctctgaccag cggcgtgcac    600
accttcccag ctgtcctaca gtcctcagga ctctactccc tcagcagcgt ggtgaccgtg    660
ccctccagca cttcggcac ccagacctac acctgcaacg tagatcacaa gcccagcaac    720
accaaggtgg acaagacagt tgagcgcaaa tgttgtgtcg agtgcccacc gtgcccagca    780
ccacctgtgg caggaccgtc agtcttcctc ttccccccaa acccaaggga cacccctcatg    840 atctcccgga cccctgaggt cacgtgcgtg gtggtggacg tgagccacga agaccccgag    900
gtccagttca actggtacgt ggacggcgtg gaggtgcata atgccaagac aaagccacgg    960
gaggagcagt tcaacagcac gttccgtgtg gtcagcgtcc tcaccgttgt gcaccaggac   1020
tggctgaacg gcaaggagta caagtgcaag gtctccaaca aaggcctccc agccccatc    1080 gagaaaacca tctccaaaac caaagggcag ccccgagaac acaggtgta caccctgccc   1140 ccatcccggg aggagatgac caagaaccag gtcagcctga cctgcctggt caaaggcttc   1200
taccccagcg acatcgccgt ggagtgggag agcaatgggc agccggagaa caactacaag   1260
accacacctc ccatgctgga ctccgacggc tccttcttcc tctacagcaa gctcaccgtg   1320
gacaagagca ggtggcagca ggggaacgtc ttctcatgct ccgtgatgca tgaggctctg   1380
cacaaccact acacgcagaa gagcctctcc ctgtctccgg gtaaa               1425
```

<210> SEQ ID NO 48
<211> LENGTH: 475
<212> TYPE: PRT
<213> ORGANISM: Homo sapiens

<400> SEQUENCE: 48

```
Met Glu Phe Gly Leu Ser Trp Val Phe Leu Val Ala Leu Leu Arg Gly
1               5                   10                  15

Val Gln Cys Gln Val Gln Leu Val Glu Ser Gly Gly Gly Val Val Gln
                20                  25                  30

Pro Gly Arg Ser Leu Arg Leu Ser Cys Ala Ala Ser Gly Phe Thr Phe
            35                  40                  45

Ser Ser Phe Gly Met His Trp Val Arg Gln Ala Pro Gly Lys Gly Leu
        50                  55                  60

Glu Trp Val Ala Val Ile Ser Phe Asp Gly Ser Ile Lys Tyr Ser Val
65                  70                  75                  80

Asp Ser Val Lys Gly Arg Phe Thr Ile Ser Arg Asp Asn Ser Lys Asn
                85                  90                  95

Thr Leu Phe Leu Gln Met Asn Ser Leu Arg Ala Glu Asp Thr Ala Val
            100                 105                 110

Tyr Tyr Cys Ala Arg Asp Arg Leu Asn Tyr Tyr Asp Ser Ser Gly Tyr
        115                 120                 125

Tyr His Tyr Lys Tyr Tyr Gly Met Ala Val Trp Gly Gln Gly Thr Thr
    130                 135                 140

Val Thr Val Ser Ser Ala Ser Thr Lys Gly Pro Ser Val Phe Pro Leu
145                 150                 155                 160

Ala Pro Cys Ser Arg Ser Thr Ser Glu Ser Thr Ala Ala Leu Gly Cys
```

```
                    165                 170                 175
Leu Val Lys Asp Tyr Phe Pro Glu Pro Val Thr Val Ser Trp Asn Ser
                180                 185                 190

Gly Ala Leu Thr Ser Gly Val His Thr Phe Pro Ala Val Leu Gln Ser
            195                 200                 205

Ser Gly Leu Tyr Ser Leu Ser Ser Val Val Thr Val Pro Ser Ser Asn
        210                 215                 220

Phe Gly Thr Gln Thr Tyr Thr Cys Asn Val Asp His Lys Pro Ser Asn
225                 230                 235                 240

Thr Lys Val Asp Lys Thr Val Glu Arg Lys Cys Cys Val Glu Cys Pro
                245                 250                 255

Pro Cys Pro Ala Pro Pro Val Ala Gly Pro Ser Val Phe Leu Phe Pro
                260                 265                 270

Pro Lys Pro Lys Asp Thr Leu Met Ile Ser Arg Thr Pro Glu Val Thr
                275                 280                 285

Cys Val Val Val Asp Val Ser His Glu Asp Pro Glu Val Gln Phe Asn
            290                 295                 300

Trp Tyr Val Asp Gly Val Glu Val His Asn Ala Lys Thr Lys Pro Arg
305                 310                 315                 320

Glu Glu Gln Phe Asn Ser Thr Phe Arg Val Val Ser Val Leu Thr Val
                325                 330                 335

Val His Gln Asp Trp Leu Asn Gly Lys Glu Tyr Lys Cys Lys Val Ser
            340                 345                 350

Asn Lys Gly Leu Pro Ala Pro Ile Glu Lys Thr Ile Ser Lys Thr Lys
                355                 360                 365

Gly Gln Pro Arg Glu Pro Gln Val Tyr Thr Leu Pro Pro Ser Arg Glu
            370                 375                 380

Glu Met Thr Lys Asn Gln Val Ser Leu Thr Cys Leu Val Lys Gly Phe
385                 390                 395                 400

Tyr Pro Ser Asp Ile Ala Val Glu Trp Glu Ser Asn Gly Gln Pro Glu
                405                 410                 415

Asn Asn Tyr Lys Thr Thr Pro Pro Met Leu Asp Ser Asp Gly Ser Phe
                420                 425                 430

Phe Leu Tyr Ser Lys Leu Thr Val Asp Lys Ser Arg Trp Gln Gln Gly
            435                 440                 445

Asn Val Phe Ser Cys Ser Val Met His Glu Ala Leu His Asn His Tyr
        450                 455                 460

Thr Gln Lys Ser Leu Ser Leu Ser Pro Gly Lys
465                 470                 475

<210> SEQ ID NO 49
<211> LENGTH: 702
<212> TYPE: DNA
<213> ORGANISM: Homo sapiens

<400> SEQUENCE: 49
atggacatga gggtgcccgc tcagctcctg ggctcctgc tgctgtggct gagaggtgcc      60
agatgttatg agctgactca gccaccctca gtgtccgtgt ccccaggaca gacagccacc     120
atcacctgct ctggagataa attgggggaa agatatgcgc ttggtatca gcagaggcca     180 ggccagtccc ctgtactggt catctatcaa gatatcaagc ggccctcagg gatccctgag     240
cgattctctg gctccaactc tgggaacaca gccactctga ccatcagcgg gacccaggct     300
atggatgagg ctgactattt ctgtcaggcg tggtacagca gcaccaatgt gcttttcggc     360
```

```
ggagggacca agctgaccgt cctaggtcag cccaaggctg ccccctcggt cactctgttc    420
ccgccctcct ctgaggagct tcaagccaac aaggccacac tggtgtgtct cataagtgac    480
ttctacccgg gagccgtgac agtggcctgg aaggcagata gcagcccgt caaggcggga     540 gtggagacca ccacaccctc caaacaaagc aacaacaagt acgcggccag cagctatctg    600
agcctgacgc ctgagcagtg gaagtcccac agaagctaca gctgccaggt cacgcatgaa    660
gggagcaccg tggagaagac agtggcccct acagaatgtt ca                      702
```

```
<210> SEQ ID NO 50
<211> LENGTH: 234
<212> TYPE: PRT
<213> ORGANISM: Homo sapiens

<400> SEQUENCE: 50

Met Asp Met Arg Val Pro Ala Gln Leu Leu Gly Leu Leu Leu Leu Trp
1               5                   10                  15

Leu Arg Gly Ala Arg Cys Tyr Glu Leu Thr Gln Pro Pro Ser Val Ser
            20                  25                  30

Val Ser Pro Gly Gln Thr Ala Thr Ile Thr Cys Ser Gly Asp Lys Leu
        35                  40                  45

Gly Glu Arg Tyr Ala Ser Trp Tyr Gln Gln Arg Pro Gly Gln Ser Pro
    50                  55                  60

Val Leu Val Ile Tyr Gln Asp Ile Lys Arg Pro Ser Gly Ile Pro Glu
65                  70                  75                  80

Arg Phe Ser Gly Ser Asn Ser Gly Asn Thr Ala Thr Leu Thr Ile Ser
                85                  90                  95

Gly Thr Gln Ala Met Asp Glu Ala Asp Tyr Phe Cys Gln Ala Trp Tyr
            100                 105                 110

Ser Ser Thr Asn Val Leu Phe Gly Gly Gly Thr Lys Leu Thr Val Leu
        115                 120                 125

Gly Gln Pro Lys Ala Ala Pro Ser Val Thr Leu Phe Pro Pro Ser Ser
    130                 135                 140

Glu Glu Leu Gln Ala Asn Lys Ala Thr Leu Val Cys Leu Ile Ser Asp
145                 150                 155                 160

Phe Tyr Pro Gly Ala Val Thr Val Ala Trp Lys Ala Asp Ser Ser Pro
                165                 170                 175

Val Lys Ala Gly Val Glu Thr Thr Thr Pro Ser Lys Gln Ser Asn Asn
            180                 185                 190

Lys Tyr Ala Ala Ser Ser Tyr Leu Ser Leu Thr Pro Glu Gln Trp Lys
        195                 200                 205

Ser His Arg Ser Tyr Ser Cys Gln Val Thr His Glu Gly Ser Thr Val
    210                 215                 220

Glu Lys Thr Val Ala Pro Thr Glu Cys Ser
225                 230
```

```
<210> SEQ ID NO 51
<211> LENGTH: 1398
<212> TYPE: DNA
<213> ORGANISM: Homo sapiens

<400> SEQUENCE: 51
atggagtttg ggctgagctg gtttttcctc gttgctcttt taagaggtgt ccagtgtcag    60
gtgcagctgg tggagtctgg gggaggcgtg gtccagcctg gaggtccct gagactctcc    120 tgtgcagcgt ctggattcac cttcagtagc tatggcatgc actgggtccg ccaggctcca    180
```

-continued

| | |
|---|---|
| ggcaaggggc tggagtgggt ggcagttata tggtatgctg aaagtaataa atactacgca | 240 |
| gactccgtga agggccgatt caccatctcc agagacaatt ccaagaacac gctgtatctg | 300 |
| caaatgaaca gcctgagagc cgaggacacg gctgtgtatt actgtgcgag agcccaggag | 360 |
| ggtatagccc ctgacgcttt tgatatctgg ggccaaggaa caatggtcac cgtctcttca | 420 |
| gcctccacca agggcccatc ggtcttcccc ctggcgccct gctccaggag cacctccgag | 480 |
| agcacagcgg ccctgggctg cctggtcaag gactacttcc ccgaaccggt gacggtgtcg | 540 |
| tggaactcag gcgctctgac cagcggcgtg cacaccttcc cagctgtcct acagtcctca | 600 |
| ggactctact ccctcagcag cgtggtgacc gtgccctcca gcaacttcgg cacccagacc | 660 |
| tacacctgca acgtagatca caagcccagc aacaccaagg tggacaagac agttgagcgc | 720 |
| aaatgttgtg tcgagtgccc accgtgccca gcaccacctg tggcaggacc gtcagtcttc | 780 |
| ctcttccccc caaaacccaa ggacaccctc atgatctccc ggacccctga ggtcacgtgc | 840 |
| gtggtggtgg acgtgagcca cgaagacccc gaggtccagt tcaactggta cgtggacggc | 900 |
| gtggaggtgc ataatgccaa gacaaagcca cgggaggagc agttcaacag cacgttccgt | 960 |
| gtggtcagcg tcctcaccgt tgtgcaccag gactggctga acggcaagga gtacaagtgc | 1020 |
| aaggtctcca acaaaggcct cccagccccc atcgagaaaa ccatctccaa aaccaaaggg | 1080 |
| cagccccgag aaccacaggt gtacaccctg cccccatccc gggaggagat gaccaagaac | 1140 |
| caggtcagcc tgacctgcct ggtcaaaggc ttctacccca gcgacatcgc cgtggagtgg | 1200 |
| gagagcaatg ggcagccgga gaacaactac aagaccacac ctcccatgct ggactccgac | 1260 |
| ggctccttct tcctctacag caagctcacc gtggacaaga gcaggtggca gcaggggaac | 1320 |
| gtcttctcat gctccgtgat gcatgaggct ctgcacaacc actacacgca gaagagcctc | 1380 |
| tccctgtctc cgggtaaa | 1398 |

<210> SEQ ID NO 52
<211> LENGTH: 466
<212> TYPE: PRT
<213> ORGANISM: Homo sapiens

<400> SEQUENCE: 52

Met Glu Phe Gly Leu Ser Trp Val Phe Leu Val Ala Leu Leu Arg Gly
1               5                   10                  15

Val Gln Cys Gln Val Gln Leu Val Glu Ser Gly Gly Gly Val Val Gln
            20                  25                  30

Pro Gly Arg Ser Leu Arg Leu Ser Cys Ala Ala Ser Gly Phe Thr Phe
        35                  40                  45

Ser Ser Tyr Gly Met His Trp Val Arg Gln Ala Pro Gly Lys Gly Leu
    50                  55                  60

Glu Trp Val Ala Val Ile Trp Tyr Ala Glu Ser Asn Lys Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Ala Gln Glu Gly Ile Ala Pro Asp Ala Phe Asp
        115                 120                 125

Ile Trp Gly Gln Gly Thr Met Val Thr Val Ser Ser Ala Ser Thr Lys
    130                 135                 140

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Asn Phe Gly Thr Gln Thr Tyr Thr Cys Asn
    210                 215                 220

Val Asp His Lys Pro Ser Asn Thr Lys Val Asp Lys Thr Val Glu Arg
225                 230                 235                 240

Lys Cys Cys Val Glu Cys Pro Pro Cys Pro Ala Pro Pro Val Ala Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
        275                 280                 285

Asp Pro Glu Val Gln Phe Asn Trp Tyr Val Asp Gly Val Glu Val His
    290                 295                 300

Asn Ala Lys Thr Lys Pro Arg Glu Glu Gln Phe Asn Ser Thr Phe Arg
305                 310                 315                 320

Val Val Ser Val Leu Thr Val Val His Gln Asp Trp Leu Asn Gly Lys
                325                 330                 335

Glu Tyr Lys Cys Lys Val Ser Asn Lys Gly Leu Pro Ala Pro Ile Glu
            340                 345                 350

Lys Thr Ile Ser Lys Thr Lys Gly Gln Pro Arg Glu Pro Gln Val Tyr
        355                 360                 365

Thr Leu Pro Pro Ser Arg Glu Glu Met Thr Lys Asn Gln Val Ser Leu
    370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Met
                405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
        435                 440                 445

Glu Ala Leu His Asn His Tyr Thr Gln Lys Ser Leu Ser Leu Ser Pro
    450                 455                 460

Gly Lys
465

<210> SEQ ID NO 53
<211> LENGTH: 702
<212> TYPE: DNA
<213> ORGANISM: Homo sapiens

<400> SEQUENCE: 53
atggggtcaa ccgccatcct tggcctcctc ctggctgtcc tgcagggagg gcgcgccgaa      60
attgtgttga cgcagtctcc aggcaccctg tctttgtctc caggggaaag agccaccctc     120
tcctgcaggg ccagtcagag tgttagcagc agctacttag cctggcacca gcagaaacct     180
ggccaggctc ccaggctcct catctatggt gcatccagca gggccactgg catcccagac     240
aggttcagtg gcagtgggtc tgggacagac ttcactctca ccatcagcag actggagcct     300

```
gaagattttg cagtgtatta ctgtcagcag tatggtagct caccgtggac gttcggccaa    360
gggaccaagg tggaaatcaa acgtacggtg gctgcaccat ctgtcttcat cttcccgcca    420
tctgatgagc agttgaaatc tggaactgcc tctgttgtgt gcctgctgaa taacttctat    480
cccagagagg ccaaagtaca gtggaaggtg gataacgccc tccaatcggg taactcccag    540
gagagtgtca cagagcagga cagcaaggac agcacctaca gcctcagcag caccctgacg    600
ctgagcaaag cagactacga aaacacaaa gtctacgcct gcgaagtcac ccatcagggc    660
ctgagctcgc ccgtcacaaa gagcttcaac aggggagagt gt                     702
```

```
<210> SEQ ID NO 54
<211> LENGTH: 234
<212> TYPE: PRT
<213> ORGANISM: Homo sapiens

<400> SEQUENCE: 54

Met Gly Ser Thr Ala Ile Leu Gly Leu Leu Leu Ala Val Leu Gln Gly
1               5                   10                  15

Gly Arg Ala Glu Ile Val Leu Thr Gln Ser Pro Gly Thr Leu Ser Leu
            20                  25                  30

Ser Pro Gly Glu Arg Ala Thr Leu Ser Cys Arg Ala Ser Gln Ser Val
        35                  40                  45

Ser Ser Ser Tyr Leu Ala Trp His Gln Gln Lys Pro Gly Gln Ala Pro
    50                  55                  60

Arg Leu Leu Ile Tyr Gly Ala Ser Ser Arg Ala Thr Gly Ile Pro Asp
65                  70                  75                  80

Arg Phe Ser Gly Ser Gly Ser Gly Thr Asp Phe Thr Leu Thr Ile Ser
                85                  90                  95

Arg Leu Glu Pro Glu Asp Phe Ala Val Tyr Tyr Cys Gln Gln Tyr Gly
            100                 105                 110

Ser Ser Pro Trp Thr Phe Gly Gln Gly Thr Lys Val Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230
```

```
<210> SEQ ID NO 55
<211> LENGTH: 1389
<212> TYPE: DNA
<213> ORGANISM: Homo sapiens

<400> SEQUENCE: 55
atggggtcaa ccgccatcct tggcctcctc ctggctgtcc tgcagggagg gcgcgccgag     60
gtgcagctat tggagtctgg gggaggcttg gtacagcctg gggggtccct gagactctcc    120
```

```
tgtgcagcct ctggattcac ctttagcacc tatgtcatga gctgggtccg ccaggctcca    180
gggaagggc tggagtgggt ctcaagtatt agtggtagtg gtcttggctc atactacgca     240
gactccgtga agggccggtt caccatctcc agagacaatt ccaagaacac gctgtatctg    300
caaatgaaca gcctgagagc cgaggacacg gccgtatatt actgtgcgaa agaggcccat    360
cggggccct ttgactactg gggccaggga accctggtca ccgtctcctc agctagcacc     420
aagggcccat cggtcttccc cctggcgccc tgctccagga gcacctccga gagcacagcg    480
gccctgggct gcctggtcaa ggactacttc cccgaaccgg tgacggtgtc gtggaactca    540
ggcgctctga ccagcggcgt gcacaccttc ccagctgtcc tacagtcctc aggactctac    600
tccctcagca gcgtggtgac cgtgccctcc agcaacttcg gcacccagac ctacacctgc    660
aacgtagatc acaagcccag caacaccaag gtggacaaga cagttgagcg caaatgttgt    720
gtcgagtgcc caccgtgccc agcaccacct gtggcaggac cgtcagtctt cctcttcccc    780
ccaaaaccca aggacaccct catgatctcc cggacccctg aggtcacgtg cgtggtggtg    840
gacgtgagcc acgaagaccc cgaggtccag ttcaactggt acgtggacgg cgtggaggtg    900
cataatgcca agacaaagcc acgggaggag cagttcaaca gcacgttccg tgtggtcagc    960
gtcctcaccg ttgtgcacca ggactggctg aacggcaagg agtacaagtg caaggtctcc   1020
aacaaaggcc tcccagcccc catcgagaaa accatctcca aaaccaaagg cagcccga    1080
gaaccacagg tgtacaccct gcccccatcc cgggaggaga tgaccaagaa ccaggtcagc   1140
ctgacctgcc tggtcaaagg cttctacccc agcgacatcg ccgtggagtg ggagagcaat   1200
gggcagccgg agaacaacta caagaccaca cctcccatgc tggactccga cggctccttc   1260
ttcctctaca gcaagctcac cgtggacaag agcaggtggc agcaggggaa cgtcttctca   1320
tgctccgtga tgcatgaggc tctgcacaac cactacacgc agaagagcct ctccctgtct   1380
ccgggtaaa                                                            1389
```

<210> SEQ ID NO 56
<211> LENGTH: 463
<212> TYPE: PRT
<213> ORGANISM: Homo sapiens

<400> SEQUENCE: 56

```
Met Gly Ser Thr Ala Ile Leu Gly Leu Leu Ala Val Leu Gln Gly
1               5                   10                  15

Gly Arg Ala Glu Val Gln Leu Leu Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Thr Tyr Val Met Ser Trp Val Arg Gln Ala Pro Gly Lys Gly Leu
    50                  55                  60

Glu Trp Val Ser Ser Ile Ser Gly Ser Gly Leu Gly Ser Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Lys Glu Ala His Arg Gly Pro Phe Asp Tyr Trp Gly
        115                 120                 125

Gln Gly Thr Leu Val Thr Val Ser Ser Ala Ser Thr Lys Gly Pro Ser
    130                 135                 140
```

Val Phe Pro Leu Ala Pro Cys Ser Arg Ser Thr Ser Glu Ser Thr Ala
145                 150                 155                 160

Ala Leu Gly Cys Leu Val Lys Asp Tyr Phe Pro Glu Pro Val Thr Val
            165                 170                 175

Ser Trp Asn Ser Gly Ala Leu Thr Ser Gly Val His Thr Phe Pro Ala
        180                 185                 190

Val Leu Gln Ser Ser Gly Leu Tyr Ser Leu Ser Ser Val Val Thr Val
    195                 200                 205

Pro Ser Ser Asn Phe Gly Thr Gln Thr Tyr Thr Cys Asn Val Asp His
210                 215                 220

Lys Pro Ser Asn Thr Lys Val Asp Lys Thr Val Glu Arg Lys Cys Cys
225                 230                 235                 240

Val Glu Cys Pro Pro Cys Pro Ala Pro Pro Val Ala Gly Pro Ser Val
                245                 250                 255

Phe Leu Phe Pro Pro Lys Pro Lys Asp Thr Leu Met Ile Ser Arg Thr
            260                 265                 270

Pro Glu Val Thr Cys Val Val Val Asp Val Ser His Glu Asp Pro Glu
        275                 280                 285

Val Gln Phe Asn Trp Tyr Val Asp Gly Val Glu Val His Asn Ala Lys
    290                 295                 300

Thr Lys Pro Arg Glu Glu Gln Phe Asn Ser Thr Phe Arg Val Val Ser
305                 310                 315                 320

Val Leu Thr Val Val His Gln Asp Trp Leu Asn Gly Lys Glu Tyr Lys
                325                 330                 335

Cys Lys Val Ser Asn Lys Gly Leu Pro Ala Pro Ile Glu Lys Thr Ile
            340                 345                 350

Ser Lys Thr Lys Gly Gln Pro Arg Glu Pro Gln Val Tyr Thr Leu Pro
        355                 360                 365

Pro Ser Arg Glu Glu Met Thr Lys Asn Gln Val Ser Leu Thr Cys Leu
370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Met Leu Asp Ser
                405                 410                 415

Asp Gly Ser Phe Phe Leu Tyr Ser Lys Leu Thr Val Asp Lys Ser Arg
            420                 425                 430

Trp Gln Gln Gly Asn Val Phe Ser Cys Ser Val Met His Glu Ala Leu
        435                 440                 445

His Asn His Tyr Thr Gln Lys Ser Leu Ser Leu Ser Pro Gly Lys
450                 455                 460

<210> SEQ ID NO 57
<211> LENGTH: 721
<212> TYPE: DNA
<213> ORGANISM: Homo sapiens

<400> SEQUENCE: 57
atgaggctcc ttgctcagct tctggggctg ctaatgctct gggtccctgg atccagtggg      60
gatattgtga tgacccagac tccactctcc tcacctgtca cccttggaca gccggcctcc     120
atctcctgca ggtctagtca agcctcgta cacagtgatg aaacaccta cttgagttgg       180 cttcagcaga ggccaggcca gcctccaaga ctcctaattt ataagaaatt taaccggttc     240
tctggggtcc cagacagatt cagtggcagt ggggcaggga cagatttcac actgaaaatc     300
agcagggtgg aagctgagga tgtcggggtt tattactgca tgcaagctac acaaattcct     360

```
ctcactttcg ccctgggac caaagtggat atcaaacgaa ctgtggctgc accatctgtc      420
ttcatcttcc cgccatctga tgagcagttg aaatctggaa ctgcctctgt tgtgtgcctg      480
ctgaataact tctatcccag agaggccaaa gtacagtgga aggtggataa cgccctccaa      540
tcgggtaact cccaggagag tgtcacagag caggacagca aggacagcac ctacagcctc      600
agcagcaccc tgacgctgag caaagcagac tacgagaaac acaaagtcta cgcctgcgaa      660
gtcacccatc agggcctgag ctcgcccgtc acaaagagct tcaacagggg agagtgttga      720
g                                                                      721
```

```
<210> SEQ ID NO 58
<211> LENGTH: 239
<212> TYPE: PRT
<213> ORGANISM: Homo sapiens

<400> SEQUENCE: 58

Met Arg Leu Leu Ala Gln Leu Leu Gly Leu Leu Met Leu Trp Val Pro
1               5                   10                  15

Gly Ser Ser Gly Asp Ile Val Met Thr Gln Thr Pro Leu Ser Ser Pro
            20                  25                  30

Val Thr Leu Gly Gln Pro Ala Ser Ile Ser Cys Arg Ser Ser Gln Ser
        35                  40                  45

Leu Val His Ser Asp Gly Asn Thr Tyr Leu Ser Trp Leu Gln Gln Arg
    50                  55                  60

Pro Gly Gln Pro Pro Arg Leu Leu Ile Tyr Lys Lys Phe Asn Arg Phe
65                  70                  75                  80

Ser Gly Val Pro Asp Arg Phe Ser Gly Ser Gly Ala Gly Thr Asp Phe
                85                  90                  95

Thr Leu Lys Ile Ser Arg Val Glu Ala Glu Asp Val Gly Val Tyr Tyr
            100                 105                 110

Cys Met Gln Ala Thr Gln Ile Pro Leu Thr Phe Gly Pro Gly Thr Lys
        115                 120                 125

Val Asp Ile Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235
```

```
<210> SEQ ID NO 59
<211> LENGTH: 1416
<212> TYPE: DNA
<213> ORGANISM: Homo sapiens

<400> SEQUENCE: 59
atggagtttg ggctgagctg ggttttcctc gttgctcttt taagaggtgt ccagtgtcag      60
gtgcagctgg tggagtctgg gggaggcgtg gtccagcctg gaggtccct gagactctcc     120
```

```
tgtgcagcgt ctggattcac cttcagtttc tatggcatgc actgggtccg ccaggctcca    180
ggcaaggggc tggagtgggt ggcagttata tggtatgatg gaagtaataa atactatgca    240
gactccgtga agggccgatt caccatctcc agagacaatt ccaagaacac gctgtatctg    300
caaatgaaca gcctgagagc cgaggacacg gctgtgtatt actgtgcgag gggggttat    360
gattacgttt gggggagtta tcgccgtaac tccgactttg actactgggg ccagggaacc    420
ctggtcaccg tctctagtgc ctccaccaag ggcccatcgg tcttcccct ggcgccctgc    480
tccaggagca cctccgagag cacagcggcc ctgggctgcc tggtcaagga ctacttcccc    540
gaaccggtga cggtgtcgtg gaactcaggc gctctgacca gcggcgtgca caccttccca    600
gctgtcctac agtcctcagg actctactcc ctcagcagcg tggtgaccgt gcctccagc    660
aacttcggca cccagaccta cacctgcaac gtagatcaca agcccagcaa caccaaggtg    720
gacaagacag ttgagcgcaa atgttgtgtc gagtgcccac cgtgcccagc accacctgtg    780
gcaggaccgt cagtcttcct cttcccccca aaacccaagg acaccctcat gatctcccgg    840
acccctgagg tcacgtgcgt ggtggtggac gtgagccacg aagaccccga ggtccagttc    900
aactggtacg tggacggcgt ggaggtgcat aatgccaaga caaagccacg ggaggagcag    960
ttcaacagca cgttccgtgt ggtcagcgtc ctcaccgttg tgcaccagga ctggctgaac   1020
ggcaaggagt acaagtgcaa ggtctccaac aaaggcctcc cagcccccat cgagaaaacc   1080
atctccaaaa ccaaagggca gccccgagaa ccacaggtgt acaccctgcc cccatcccgg   1140
gaggagatga ccaagaacca ggtcagcctg acctgcctgg tcaaaggctt ctaccccagc   1200
gacatcgccg tggagtggga gagcaatggg cagccggaga caactacaa gaccacacct   1260
cccatgctgg actccgacgg ctccttcttc ctctacagca agctcaccgt ggacaagagc   1320
aggtggcagc aggggaacgt cttctcatgc tccgtgatgc atgaggctct gcacaaccac   1380
tacacgcaga agagcctctc cctgtctccg ggtaaa                              1416
```

<210> SEQ ID NO 60
<211> LENGTH: 472
<212> TYPE: PRT
<213> ORGANISM: Homo sapiens

<400> SEQUENCE: 60

Met Glu Phe Gly Leu Ser Trp Val Phe Leu Val Ala Leu Leu Arg Gly
1               5                   10                  15

Val Gln Cys Gln Val Gln Leu Val Glu Ser Gly Gly Gly Val Val Gln
                20                  25                  30

Pro Gly Arg Ser Leu Arg Leu Ser Cys Ala Ala Ser Gly Phe Thr Phe
            35                  40                  45

Ser Phe Tyr Gly Met His Trp Val Arg Gln Ala Pro Gly Lys Gly Leu
        50                  55                  60

Glu Trp Val Ala Val Ile Trp Tyr Asp Gly Ser Asn Lys Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Thr Ala Val
                100                 105                 110

Tyr Tyr Cys Ala Arg Gly Gly Tyr Asp Tyr Val Trp Gly Ser Tyr Arg
            115                 120                 125

Arg Asn Ser Asp Phe Asp Tyr Trp Gly Gln Gly Thr Leu Val Thr Val
        130                 135                 140

Ser Ser Ala Ser Thr Lys Gly Pro Ser Val Phe Pro Leu Ala Pro Cys
145                 150                 155                 160

Ser Arg Ser Thr Ser Glu Ser Thr Ala Ala Leu Gly Cys Leu Val Lys
            165                 170                 175

Asp Tyr Phe Pro Glu Pro Val Thr Val Ser Trp Asn Ser Gly Ala Leu
        180                 185                 190

Thr Ser Gly Val His Thr Phe Pro Ala Val Leu Gln Ser Ser Gly Leu
    195                 200                 205

Tyr Ser Leu Ser Ser Val Val Thr Val Pro Ser Ser Asn Phe Gly Thr
210                 215                 220

Gln Thr Tyr Thr Cys Asn Val Asp His Lys Pro Ser Asn Thr Lys Val
225                 230                 235                 240

Asp Lys Thr Val Glu Arg Lys Cys Cys Val Glu Cys Pro Pro Cys Pro
            245                 250                 255

Ala Pro Pro Val Ala Gly Pro Ser Val Phe Leu Phe Pro Pro Lys Pro
        260                 265                 270

Lys Asp Thr Leu Met Ile Ser Arg Thr Pro Glu Val Thr Cys Val Val
    275                 280                 285

Val Asp Val Ser His Glu Asp Pro Glu Val Gln Phe Asn Trp Tyr Val
290                 295                 300

Asp Gly Val Glu Val His Asn Ala Lys Thr Lys Pro Arg Glu Glu Gln
305                 310                 315                 320

Phe Asn Ser Thr Phe Arg Val Val Ser Val Leu Thr Val Val His Gln
            325                 330                 335

Asp Trp Leu Asn Gly Lys Glu Tyr Lys Cys Lys Val Ser Asn Lys Gly
        340                 345                 350

Leu Pro Ala Pro Ile Glu Lys Thr Ile Ser Lys Thr Lys Gly Gln Pro
    355                 360                 365

Arg Glu Pro Gln Val Tyr Thr Leu Pro Pro Ser Arg Glu Glu Met Thr
370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
            405                 410                 415

Lys Thr Thr Pro Pro Met Leu Asp Ser Asp Gly Ser Phe Phe Leu Tyr
        420                 425                 430

Ser Lys Leu Thr Val Asp Lys Ser Arg Trp Gln Gln Gly Asn Val Phe
    435                 440                 445

Ser Cys Ser Val Met His Glu Ala Leu His Asn His Tyr Thr Gln Lys
450                 455                 460

Ser Leu Ser Leu Ser Pro Gly Lys
465                 470

<210> SEQ ID NO 61
<211> LENGTH: 705
<212> TYPE: DNA
<213> ORGANISM: Homo sapiens

<400> SEQUENCE: 61

```
atggaagccc cagctcagct tctcttcctc ctgctactct ggctcccaga taccactgga      60
gaaatagtga tgacgcagtc tccagccacc ctgtctgtgt ctccagggga aagagccacc     120
ctctcctgca gggccagtca gagtgttgac agcaacttag cctggtaccg gcagaaacct     180
ggccaggctc ccaggctcct catctatggt gcatccacca gggccactgg tatcccagcc     240
```

```
aggttcagtg gcagtgggtc tgggactgag ttcactctca ccatcagcag cctgcagtct      300
gaagattttg cagtttatta ctgtcagcag tatattaact ggcctccgat caccttcggc      360
caagggacac gactggagat taaacgaact gtggctgcac catctgtctt catcttcccg      420
ccatctgatg agcagttgaa atctggaact gcctctgttg tgtgcctgct gaataacttc      480
tatcccagag aggccaaagt acagtggaag gtggataacg ccctccaatc gggtaactcc      540
caggagagtg tcacagagca ggacagcaag gacagcacct acagcctcag cagcaccctg      600
acgctgagca aagcagacta cgagaaacac aaagtctacg cctgcgaagt cacccatcag      660
ggcctgagct cgcccgtcac aaagagcttc aacaggggag agtgt                     705
```

<210> SEQ ID NO 62
<211> LENGTH: 235
<212> TYPE: PRT
<213> ORGANISM: Homo sapiens

<400> SEQUENCE: 62

```
Met Glu Ala Pro Ala Gln Leu Leu Phe Leu Leu Leu Leu Trp Leu Pro
1               5                   10                  15

Asp Thr Thr Gly Glu Ile Val Met Thr Gln Ser Pro Ala Thr Leu Ser
            20                  25                  30

Val Ser Pro Gly Glu Arg Ala Thr Leu Ser Cys Arg Ala Ser Gln Ser
        35                  40                  45

Val Asp Ser Asn Leu Ala Trp Tyr Arg Gln Lys Pro Gly Gln Ala Pro
    50                  55                  60

Arg Leu Leu Ile Tyr Gly Ala Ser Thr Arg Ala Thr Gly Ile Pro Ala
65                  70                  75                  80

Arg Phe Ser Gly Ser Gly Ser Gly Thr Glu Phe Thr Leu Thr Ile Ser
                85                  90                  95

Ser Leu Gln Ser Glu Asp Phe Ala Val Tyr Tyr Cys Gln Gln Tyr Ile
            100                 105                 110

Asn Trp Pro Pro Ile Thr Phe Gly Gln Gly Thr Arg Leu Glu Ile Lys
        115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235
```

<210> SEQ ID NO 63
<211> LENGTH: 1395
<212> TYPE: DNA
<213> ORGANISM: Homo sapiens

<400> SEQUENCE: 63

```
atgaaacacc tgtggttctt ccttctcctg gtggcagctc ccagatgggt cctgtcccag       60
```

```
gtgcagctgc aggagtcggg cccaggactg gtgaagcctt cggagaccct gtccctcacc    120
tgcactgtct ctggtggctc catcagtatt tactactgga gctggatccg gcagccccca    180
gggaagggac tggagtggat tgggtatgtc tattacagtg ggagcaccaa ttacaacccc    240
tccctcaaga gtcgagtcac catatcagta gacacgtcca agaaccagtt ctccctgaag    300
ctgaactctg tgaccgctgc ggacacggcc gtgtattact gtgcgagagg gggatacgat    360
ttttggagtg gttattttga ctactggggc cagggaaccc tggtcaccgt ctctagtgcc    420
tccaccaagg gcccatcggt cttccccctg gcgccctgct ccaggagcac ctccgagagc    480
acagcggccc tgggctgcct ggtcaaggac tacttccccg aaccggtgac ggtgtcgtgg    540
aactcaggcg ctctgaccag cggcgtgcac accttcccag ctgtcctaca gtcctcagga    600
ctctactccc tcagcagcgt ggtgaccgtg ccctccagca acttcggcac ccagacctac    660
acctgcaacg tagatcacaa gcccagcaac accaaggtgg acaagacagt tgagcgcaaa    720
tgttgtgtcg agtgcccacc gtgcccagca ccacctgtgg caggaccgtc agtcttcctc    780
ttccccccaa aacccaagga caccctcatg atctcccgga cccctgaggt cacgtgcgtg    840
gtggtggacg tgagccacga agaccccgag gtccagttca actggtacgt ggacggcgtg    900
gaggtgcata atgccaagac aaagccacgg gaggagcagt tcaacagcac gttccgtgtg    960
gtcagcgtcc tcaccgttgt gcaccaggac tggctgaacg gcaaggagta caagtgcaag   1020
gtctccaaca aaggcctccc agcccccatc gagaaaacca tctccaaaac caaagggcag   1080
ccccgagaac acaggtgta caccctgccc ccatcccggg aggagatgac caagaaccag   1140
gtcagcctga cctgcctggt caaaggcttc taccccagcg acatcgccgt ggagtgggag   1200
agcaatgggc agccggagaa caactacaag accacacctc ccatgctgga ctccgacggc   1260
tccttcttcc tctacagcaa gctcaccgtg gacaagagca ggtggcagca ggggaacgtc   1320
ttctcatgct ccgtgatgca tgaggctctg cacaaccact acacgcagaa gagcctctcc   1380
ctgtctccgg gtaaa                                                    1395
```

<210> SEQ ID NO 64
<211> LENGTH: 465
<212> TYPE: PRT
<213> ORGANISM: Homo sapiens

<400> SEQUENCE: 64

```
Met Lys His Leu Trp Phe Phe Leu Leu Leu Val Ala Ala Pro Arg Trp
1               5                   10                  15

Val Leu Ser Gln Val Gln Leu Gln Glu Ser Gly Pro Gly Leu Val Lys
            20                  25                  30

Pro Ser Glu Thr Leu Ser Leu Thr Cys Thr Val Ser Gly Gly Ser Ile
        35                  40                  45

Ser Ile Tyr Tyr Trp Ser Trp Ile Arg Gln Pro Pro Gly Lys Gly Leu
    50                  55                  60

Glu Trp Ile Gly Tyr Val Tyr Tyr Ser Gly Ser Thr Asn Tyr Asn Pro
65                  70                  75                  80

Ser Leu Lys Ser Arg Val Thr Ile Ser Val Asp Thr Ser Lys Asn Gln
                85                  90                  95

Phe Ser Leu Lys Leu Asn Ser Val Thr Ala Ala Asp Thr Ala Val Tyr
            100                 105                 110

Tyr Cys Ala Arg Gly Gly Tyr Asp Phe Trp Ser Gly Tyr Phe Asp Tyr
        115                 120                 125
```

```
Trp Gly Gln Gly Thr Leu Val Thr Val Ser Ser Ala Ser Thr Lys Gly
            130                 135                 140
Pro Ser Val Phe Pro Leu Ala Pro Cys Ser Arg Ser Thr Ser Glu Ser
145                 150                 155                 160
Thr Ala Ala Leu Gly Cys Leu Val Lys Asp Tyr Phe Pro Glu Pro Val
                165                 170                 175
Thr Val Ser Trp Asn Ser Gly Ala Leu Thr Ser Gly Val His Thr Phe
            180                 185                 190
Pro Ala Val Leu Gln Ser Ser Gly Leu Tyr Ser Leu Ser Ser Val Val
                195                 200                 205
Thr Val Pro Ser Ser Asn Phe Gly Thr Gln Thr Tyr Thr Cys Asn Val
210                 215                 220
Asp His Lys Pro Ser Asn Thr Lys Val Asp Lys Thr Val Glu Arg Lys
225                 230                 235                 240
Cys Cys Val Glu Cys Pro Pro Cys Pro Ala Pro Pro Val Ala Gly Pro
                245                 250                 255
Ser Val Phe Leu Phe Pro Pro Lys Pro Lys Asp Thr Leu Met Ile Ser
                260                 265                 270
Arg Thr Pro Glu Val Thr Cys Val Val Val Asp Val Ser His Glu Asp
                275                 280                 285
Pro Glu Val Gln Phe Asn Trp Tyr Val Asp Gly Val Glu Val His Asn
            290                 295                 300
Ala Lys Thr Lys Pro Arg Glu Glu Gln Phe Asn Ser Thr Phe Arg Val
305                 310                 315                 320
Val Ser Val Leu Thr Val Val His Gln Asp Trp Leu Asn Gly Lys Glu
                325                 330                 335
Tyr Lys Cys Lys Val Ser Asn Lys Gly Leu Pro Ala Pro Ile Glu Lys
                340                 345                 350
Thr Ile Ser Lys Thr Lys Gly Gln Pro Arg Glu Pro Gln Val Tyr Thr
            355                 360                 365
Leu Pro Pro Ser Arg Glu Glu Met Thr Lys Asn Gln Val Ser Leu Thr
370                 375                 380
Cys Leu Val Lys Gly Phe Tyr Pro Ser Asp Ile Ala Val Glu Trp Glu
385                 390                 395                 400
Ser Asn Gly Gln Pro Glu Asn Asn Tyr Lys Thr Thr Pro Pro Met Leu
                405                 410                 415
Asp Ser Asp Gly Ser Phe Phe Leu Tyr Ser Lys Leu Thr Val Asp Lys
                420                 425                 430
Ser Arg Trp Gln Gln Gly Asn Val Phe Ser Cys Ser Val Met His Glu
            435                 440                 445
Ala Leu His Asn His Tyr Thr Gln Lys Ser Leu Ser Leu Ser Pro Gly
450                 455                 460
Lys
465

<210> SEQ ID NO 65
<211> LENGTH: 723
<212> TYPE: DNA
<213> ORGANISM: Homo sapiens

<400> SEQUENCE: 65
atggtgctgc agacccaggt gtttattagc ctgctgctgt ggattagcgg cgcgtatggc      60
gacatcgtgc tgacccagtc tccagactcc ctggctgtgt ctctgggcga gagggccacc     120
atcaactgca gtccagccca gagtatttta tacagctcca gcaatgagaa cttcttaact     180
```

```
tggtaccagc agaaaccagg acagcctcct aagctgctca tttactgggc atctacccgg    240
gaatccgggg tccctgaccg attcagtggc agcgggtctg ggacagattt cactctcacc    300
atcagcagcc tgcagcctga agatgtggca gtttattact gtcagcaata ttttagtgtt    360
tttcggacgt tcggccaagg gaccagggtg gaaatcaaac gtacggtggc tgcaccatct    420
gtcttcatct tcccgccatc tgatgagcag ttgaaatctg gaactgcctc tgttgtgtgc    480
ctgctgaata acttctatcc cagagaggcc aaagtacagt ggaaggtgga taacgccctc    540
caatcgggta actcccagga gagtgtcaca gagcaggaca gcaaggacag cacctacagc    600
ctcagcagca ccctgacgct gagcaaagca gactacgaga acacaaagt ctacgcctgc     660 gaagtcaccc atcagggcct gagctcgccc gtcacaaaga gcttcaacag gggagagtgt    720
tag                                                                  723
```

```
<210> SEQ ID NO 66
<211> LENGTH: 240
<212> TYPE: PRT
<213> ORGANISM: Homo sapiens

<400> SEQUENCE: 66
```

```
Met Val Leu Gln Thr Gln Val Phe Ile Ser Leu Leu Leu Trp Ile Ser
1               5                   10                  15

Gly Ala Tyr Gly Asp Ile Val Leu Thr Gln Ser Pro Asp Ser Leu Ala
            20                  25                  30

Val Ser Leu Gly Glu Arg Ala Thr Ile Asn Cys Lys Ser Ser Gln Ser
        35                  40                  45

Ile Leu Tyr Ser Ser Ser Asn Glu Asn Phe Leu Thr Trp Tyr Gln Gln
    50                  55                  60

Lys Pro Gly Gln Pro Pro Lys Leu Leu Ile Tyr Trp Ala Ser Thr Arg
65                  70                  75                  80

Glu Ser Gly Val Pro Asp Arg Phe Ser Gly Ser Gly Ser Gly Thr Asp
                85                  90                  95

Phe Thr Leu Thr Ile Ser Ser Leu Gln Pro Glu Asp Val Ala Val Tyr
            100                 105                 110

Tyr Cys Gln Gln Tyr Phe Ser Val Phe Arg Thr Phe Gly Gln Gly Thr
        115                 120                 125

Arg Val Glu Ile Lys Arg Thr Val Ala Ala Pro Ser Val Phe Ile Phe
    130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
    210                 215                 220

Gln Gly Leu Ser Ser Pro Val Thr Lys Ser Phe Asn Arg Gly Glu Cys
225                 230                 235                 240
```

```
<210> SEQ ID NO 67
<211> LENGTH: 1395
<212> TYPE: DNA
<213> ORGANISM: Homo sapiens
```

<400> SEQUENCE: 67

```
atggattgga cctggcgtat tctgtttctg gtggcggcgg cgaccggcgc gcatagccag      60
gtgcagctgg tgcagtctgg ggctgaggtg aagaagcctg ggcctcagt gaaggtctcc     120
tgcaaggctt ctggatacac cttcaccggc tactatatac actgggtgcg acaggcccct    180
ggacaagggc ttgagtggat gggatggatc aaccctaaca gtggtggcac aaactctgca    240
cagaagtttc ggggcagggt caccatgacc agggacacgt ccatcagcac agcctacatg    300
gagctgagca ggctgagatc tgacgacacg gccgtgtatt actgtgcgcg agagggtgga    360
tacagctatg gttactttga ctactgggc agggaaccc tggtcaccgt ctcctcagct      420
agcaccaagg gcccatcggt cttccccctg gcgccctgct ccaggagcac ctccgagagc    480
acagcggccc tgggctgcct ggtcaaggac tacttcccg aaccggtgac ggtgtcgtgg     540
aactcaggcg ctctgaccag cggcgtgcac accttccag ctgtcctaca gtcctcagga    600
ctctactccc tcagcagcgt ggtgaccgtg ccctccagca acttcggcac ccagacctac    660
acctgcaacg tagatcacaa gcccagcaac accaaggtgg acaagacagt tgagcgcaaa    720
tgttgtgtcg agtgcccacc gtgcccagca ccacctgtgg caggaccgtc agtcttcctc    780
ttccccccaa aacccaagga caccctcatg atctcccgga cccctgaggt cacgtgcgtg    840
gtggtggacg tgagccacga agaccccgag gtccagttca actggtacgt ggacggcgtg    900
gaggtgcata atgccaagac aaagccacgg gaggagcagt tcaacagcac gttccgtgtg    960
gtcagcgtcc tcaccgttgt gcaccaggac tggctgaacg gcaaggagta caagtgcaag   1020
gtctccaaca aaggcctccc agcccccatc gagaaaacca tctccaaaac caaagggcag   1080
ccccgagaac cacaggtgta caccctgccc ccatcccggg aggagatgac caagaaccag   1140
gtcagcctga cctgcctggt caaaggcttc taccccagcg acatcgccgt ggagtgggag   1200
agcaatgggc agccggagaa caactacaag accacacctc ccatgctgga ctccgacggc   1260
tccttcttcc tctacagcaa gctcaccgtg gacaagagca ggtggcagca ggggaacgtc   1320
ttctcatgct ccgtgatgca tgaggctctg cacaaccact acacgcagaa gagcctctcc   1380
ctgtctccgg gtaaa                                                    1395
```

<210> SEQ ID NO 68
<211> LENGTH: 465
<212> TYPE: PRT
<213> ORGANISM: Homo sapiens

<400> SEQUENCE: 68

```
Met Asp Trp Thr Trp Arg Ile Leu Phe Leu Val Ala Ala Thr Gly
1               5                   10                  15

Ala His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Gly Tyr Tyr Ile His Trp Val Arg Gln Ala Pro Gly Gln Gly Leu
    50                  55                  60

Glu Trp Met Gly Trp Ile Asn Pro Asn Ser Gly Gly Thr Asn Ser Ala
65                  70                  75                  80

Gln Lys Phe Arg Gly Arg Val Thr Met Thr Arg Asp Thr Ser Ile Ser
                85                  90                  95

Thr Ala Tyr Met Glu Leu Ser Arg Leu Arg Ser Asp Asp Thr Ala Val
            100                 105                 110
```

Tyr Tyr Cys Ala Arg Glu Gly Gly Tyr Ser Tyr Gly Tyr Phe Asp Tyr
            115                 120                 125

Trp Gly Gln Gly Thr Leu Val Thr Val Ser Ser Ala Ser Thr Lys Gly
        130                 135                 140

Pro Ser Val Phe Pro Leu Ala Pro Cys Ser Arg Ser Thr Ser Glu Ser
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Asn Phe Gly Thr Gln Thr Tyr Thr Cys Asn Val
210                 215                 220

Asp His Lys Pro Ser Asn Thr Lys Val Asp Lys Thr Val Glu Arg Lys
225                 230                 235                 240

Cys Cys Val Glu Cys Pro Pro Cys Pro Ala Pro Pro Val Ala Gly Pro
                245                 250                 255

Ser Val Phe Leu Phe Pro Pro Lys Pro Lys Asp Thr Leu Met Ile Ser
            260                 265                 270

Arg Thr Pro Glu Val Thr Cys Val Val Asp Val Ser His Glu Asp
        275                 280                 285

Pro Glu Val Gln Phe Asn Trp Tyr Val Asp Gly Val Glu Val His Asn
290                 295                 300

Ala Lys Thr Lys Pro Arg Glu Glu Gln Phe Asn Ser Thr Phe Arg Val
305                 310                 315                 320

Val Ser Val Leu Thr Val Val His Gln Asp Trp Leu Asn Gly Lys Glu
                325                 330                 335

Tyr Lys Cys Lys Val Ser Asn Lys Gly Leu Pro Ala Pro Ile Glu Lys
            340                 345                 350

Thr Ile Ser Lys Thr Lys Gly Gln Pro Arg Glu Pro Gln Val Tyr Thr
        355                 360                 365

Leu Pro Pro Ser Arg Glu Glu Met Thr Lys Asn Gln Val Ser Leu Thr
370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Met Leu
                405                 410                 415

Asp Ser Asp Gly Ser Phe Phe Leu Tyr Ser Lys Leu Thr Val Asp Lys
            420                 425                 430

Ser Arg Trp Gln Gln Gly Asn Val Phe Ser Cys Ser Val Met His Glu
        435                 440                 445

Ala Leu His Asn His Tyr Thr Gln Lys Ser Leu Ser Leu Ser Pro Gly
450                 455                 460

Lys
465

<210> SEQ ID NO 69
<211> LENGTH: 708
<212> TYPE: DNA
<213> ORGANISM: Homo sapiens

<400> SEQUENCE: 69
atggacatga gggtccccgc tcagctcctg gggctcctgc tgctctggtt cccaggtgcc      60

```
aggtgtgaca tccagatgac ccagtctcca tcctccctgt ctgcatctgt aggagacaga      120
gtcaccatca cttgccgggc aagtcagggc attagaaatg atttaggctg gtatcagcag      180
aaaccaggga agcccctaa gcgcctgatc tatgctgcat ccagtttgca aagtggggtc       240
ccatcaaggt tcagcggcag tggatctggg acagaattca ctctcacaat cagcagtgtg      300
cagcctgaag attttgtaac ttattactgt ctacagcata atagtaaccc tctcactttc      360
ggcggaggga ccaaggtgga gatcaaacga actgtggctg caccatctgt cttcatcttc      420
ccgccatctg atgagcagtt gaaatctgga actgcctctg ttgtgtgcct gctgaataac      480
ttctatccca gagaggccaa agtacagtgg aaggtggata acgccctcca atcgggtaac      540
tcccaggaga gtgtcacaga gcaggacagc aaggacagca cctacagcct cagcagcacc      600
ctgacgctga gcaaagcaga ctacgagaaa cacaaagtct acgcctgcga agtcacccat      660
cagggcctga gctcgcccgt cacaaagagc ttcaacaggg gagagtgt                    708
```

<210> SEQ ID NO 70
<211> LENGTH: 236
<212> TYPE: PRT
<213> ORGANISM: Homo sapiens

<400> SEQUENCE: 70

```
Met Asp Met Arg Val Pro Ala Gln Leu Leu Gly Leu Leu Leu Leu Trp
1               5                   10                  15

Phe Pro Gly Ala Arg Cys Asp Ile Gln Met Thr Gln Ser Pro Ser Ser
            20                  25                  30

Leu Ser Ala Ser Val Gly Asp Arg Val Thr Ile Thr Cys Arg Ala Ser
        35                  40                  45

Gln Gly Ile Arg Asn Asp Leu Gly Trp Tyr Gln Gln Lys Pro Gly Lys
    50                  55                  60

Ala Pro Lys Arg Leu Ile Tyr Ala Ala Ser Ser Leu Gln Ser Gly Val
65                  70                  75                  80

Pro Ser Arg Phe Ser Gly Ser Gly Ser Gly Thr Glu Phe Thr Leu Thr
                85                  90                  95

Ile Ser Ser Val Gln Pro Glu Asp Phe Val Thr Tyr Tyr Cys Leu Gln
            100                 105                 110

His Asn Ser Asn Pro Leu Thr Phe Gly Gly Gly Thr Lys Val Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235
```

<210> SEQ ID NO 71
<211> LENGTH: 1419

```
<212> TYPE: DNA
<213> ORGANISM: Homo sapiens

<400> SEQUENCE: 71
atggagtttg ggctgagctg ggttttcctc gttgctcttt taagaggtgt ccagtgtcag    60
gtgcagctgg tggagtctgg gggaggcgtg gtccagcctg gaggtccct gagactctcc    120
tgtgcagcgt ctggattcac cttcagtagc tatggcatgc actgggtccg ccaggctcca    180
ggcaaggggc tggagtgggt ggcagttatg tggtatgatg aagtaataa agactatgta    240
gactccgtga agggccgatt caccatctcc agagacaatt ccaagaacac gctgtatctg    300
caaatgaacc gcctgagagc cgaggacacg gctgtgtatt actgtgcgag agaaaaagat    360
cattacgaca ttttgactgg ttataactac tactacggtc tggacgtctg gggccaaggg    420
accacggtca ccgtctcctc agcctccacc aagggcccat cggtcttccc cctggcgccc    480
tgctccagga gcacctccga gagcacagcg gccctgggct gcctggtcaa ggactacttc    540
cccgaaccgg tgacggtgtc gtggaactca ggcgctctga ccagcggcgt gcacaccttc    600
ccagctgtcc tacagtcctc aggactctac tccctcagca gcgtggtgac cgtgccctcc    660
agcaacttcg gcacccagac ctacacctgc aacgtagatc acaagcccag caacaccaag    720
gtggacaaga cagttgagcg caaatgttgt gtcgagtgcc caccgtgccc agcaccacct    780
gtggcaggac cgtcagtctt cctcttcccc ccaaaaccca aggacaccct catgatctcc    840
cggacccctg aggtcacgtg cgtggtggtg gacgtgagcc acgaagaccc cgaggtccag    900
ttcaactggt acgtggacgg cgtggaggtg cataatgcca agacaaagcc acgggaggag    960
cagttcaaca gcacgttccg tgtggtcagc gtcctcaccg ttgtgcacca ggactggctg   1020
aacggcaagg agtacaagtg caaggtctcc aacaaaggcc tcccagcccc catcgagaaa   1080
accatctcca aaaccaaagg gcagcccga gaaccacagg tgtacaccct gcccccatcc   1140
cgggaggaga tgaccaagaa ccaggtcagc ctgacctgcc tggtcaaagg cttctacccc   1200
agcgacatcg ccgtggagtg ggagagcaat gggcagccgg agaacaacta caagaccaca   1260
cctcccatgc tggactccga cggctccttc ttcctctaca gcaagctcac cgtggacaag   1320
agcaggtgga gcaggggaa cgtcttctca tgctccgtga tgcatgaggc tctgcacaac   1380
cactacacgc agaagagcct ctccctgtct ccgggtaaa                          1419

<210> SEQ ID NO 72
<211> LENGTH: 473
<212> TYPE: PRT
<213> ORGANISM: Homo sapiens

<400> SEQUENCE: 72

Met Glu Phe Gly Leu Ser Trp Val Phe Leu Val Ala Leu Leu Arg Gly
1               5                   10                  15

Val Gln Cys Gln Val Gln Leu Val Glu Ser Gly Gly Gly Val Val Gln
                20                  25                  30

Pro Gly Arg Ser Leu Arg Leu Ser Cys Ala Ala Ser Gly Phe Thr Phe
            35                  40                  45

Ser Ser Tyr Gly Met His Trp Val Arg Gln Ala Pro Gly Lys Gly Leu
        50                  55                  60

Glu Trp Val Ala Val Met Trp Tyr Asp Gly Ser Asn Lys Asp Tyr Val
65                  70                  75                  80

Asp Ser Val Lys Gly Arg Phe Thr Ile Ser Arg Asp Asn Ser Lys Asn
                85                  90                  95
```

```
Thr Leu Tyr Leu Gln Met Asn Arg Leu Arg Ala Glu Asp Thr Ala Val
            100                 105                 110

Tyr Tyr Cys Ala Arg Glu Lys Asp His Tyr Asp Ile Leu Thr Gly Tyr
        115                 120                 125

Asn Tyr Tyr Gly Leu Asp Val Trp Gly Gln Gly Thr Thr Val Thr
    130                 135                 140

Val Ser Ser Ala Ser Thr Lys Gly Pro Ser Val Phe Pro Leu Ala Pro
145                 150                 155                 160

Cys Ser Arg Ser Thr Ser Glu Ser Thr Ala Ala Leu Gly Cys Leu Val
                165                 170                 175

Lys Asp Tyr Phe Pro Glu Pro Val Thr Val Ser Trp Asn Ser Gly Ala
            180                 185                 190

Leu Thr Ser Gly Val His Thr Phe Pro Ala Val Leu Gln Ser Ser Gly
        195                 200                 205

Leu Tyr Ser Leu Ser Ser Val Val Thr Val Pro Ser Ser Asn Phe Gly
    210                 215                 220

Thr Gln Thr Tyr Thr Cys Asn Val Asp His Lys Pro Ser Asn Thr Lys
225                 230                 235                 240

Val Asp Lys Thr Val Glu Arg Lys Cys Cys Val Glu Cys Pro Pro Cys
                245                 250                 255

Pro Ala Pro Pro Val Ala Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Gln Phe Asn Trp Tyr
    290                 295                 300

Val Asp Gly Val Glu Val His Asn Ala Lys Thr Lys Pro Arg Glu Glu
305                 310                 315                 320

Gln Phe Asn Ser Thr Phe Arg Val Val Ser Val Leu Thr Val Val His
                325                 330                 335

Gln Asp Trp Leu Asn Gly Lys Glu Tyr Lys Cys Lys Val Ser Asn Lys
            340                 345                 350

Gly Leu Pro Ala Pro Ile Glu Lys Thr Ile Ser Lys Thr Lys Gly Gln
        355                 360                 365

Pro Arg Glu Pro Gln Val Tyr Thr Leu Pro Pro Ser Arg Glu Glu Met
    370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Met Leu Asp Ser Asp Gly Ser Phe Phe Leu
            420                 425                 430

Tyr Ser Lys Leu Thr Val Asp Lys Ser Arg Trp Gln Gln Gly Asn Val
        435                 440                 445

Phe Ser Cys Ser Val Met His Glu Ala Leu His Asn His Tyr Thr Gln
    450                 455                 460

Lys Ser Leu Ser Leu Ser Pro Gly Lys
465                 470

<210> SEQ ID NO 73
<211> LENGTH: 705
<212> TYPE: DNA
<213> ORGANISM: Homo sapiens

<400> SEQUENCE: 73
```

```
atggaaaccc cggcgcagct gctgtttctg ctgctgctgt ggctgccgga taccaccggc      60
gaaattgtgt tgacgcagtc tccaggcacc ctgtctttgt ctccagggga aagagccacc     120
ctctcctgca gggccagtca gtatattagc aacacctatt tagcctggtt ccagcagaaa     180
cctggccagg ctcccaggct cctcatctat ggtgcagcca ccagggccac tggcatccca     240
gacaggttca gtggcagtgg gtctgggaca gacttcactt tcaccatcag cagactggag     300
cctgaagatt ttgcagtgta ttactgtcag cagtatggta gctcaccgtg gacgttcggc     360
caagggacca cggtggaaat caaacgtacg gtggctgcac catctgtctt catcttcccg     420
ccatctgatg agcagttgaa atctggaact gcctctgttg tgtgcctgct gaataacttc     480
tatcccagag aggccaaagt acagtggaag gtggataacg ccctccaatc gggtaactcc     540
caggagagtg tcacagagca ggacagcaag gacagcacct acagcctcag cagcaccctg     600
acgctgagca agcagactac gagaaacac aaagtctacg cctgcgaagt cacccatcag     660
ggcctgagct cgcccgtcac aaagagcttc aacaggggag agtgt                     705
```

<210> SEQ ID NO 74
<211> LENGTH: 235
<212> TYPE: PRT
<213> ORGANISM: Homo sapiens

<400> SEQUENCE: 74

```
Met Glu Thr Pro Ala Gln Leu Leu Phe Leu Leu Leu Trp Leu Pro
1               5                   10                  15

Asp Thr Thr Gly Glu Ile Val Leu Thr Gln Ser Pro Gly Thr Leu Ser
            20                  25                  30

Leu Ser Pro Gly Glu Arg Ala Thr Leu Ser Cys Arg Ala Ser Gln Tyr
            35                  40                  45

Ile Ser Asn Thr Tyr Leu Ala Trp Phe Gln Gln Lys Pro Gly Gln Ala
        50                  55                  60

Pro Arg Leu Leu Ile Tyr Gly Ala Ala Thr Arg Ala Thr Gly Ile Pro
65                  70                  75                  80

Asp Arg Phe Ser Gly Ser Gly Ser Gly Thr Asp Phe Thr Phe Thr Ile
                85                  90                  95

Ser Arg Leu Glu Pro Glu Asp Phe Ala Val Tyr Tyr Cys Gln Gln Tyr
            100                 105                 110

Gly Ser Ser Pro Trp Thr Phe Gly Gln Gly Thr Thr Val Glu Ile Lys
        115                 120                 125

Arg Thr Val Ala Ala Pro Ser Val Phe Ile Phe Pro Pro Ser Asp Glu
130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235
```

<210> SEQ ID NO 75
<211> LENGTH: 1389
<212> TYPE: DNA
<213> ORGANISM: Homo sapiens

<400> SEQUENCE: 75

| | | | | | | |
|---|---|---|---|---|---|---|
| atggattgga | cctggcgtat | tctgtttctg | gtggcggcgg | cgaccggcgc | gcatagccag | 60 |
| gtgcagttgg | tgcagtctgg | ggctgaggtg | aagaagcctg | ggcctcagt | gaaggtctcc | 120 |
| tgcaaggctt | ctggatacac | cttcaccggc | tactatatgc | actgggtgcg | acaggcccct | 180 |
| ggacaagggc | ttgagtggat | gggatggatc | aaccctaaca | gtggtggcac | aaactatgca | 240 |
| cagaggtttc | ggggcagggt | caccatgacc | agggacacgt | ccatcagcac | agcctacatg | 300 |
| gaactgagca | ggctgagatc | tgacgacacg | gccgtgtatt | actgtgcgag | agccccgtat | 360 |
| gactggacct | ttgactactg | gggccaggga | accctggtca | ccgtctcctc | agctagcacc | 420 |
| aagggcccat | cggtcttccc | cctggcgccc | tgctccagga | gcacctccga | gagcacagcg | 480 |
| gccctgggct | gcctggtcaa | ggactacttc | cccgaaccgg | tgacggtgtc | gtggaactca | 540 |
| ggcgctctga | ccagcggcgt | gcacaccttc | ccagctgtcc | tacagtcctc | aggactctac | 600 |
| tccctcagca | gcgtggtgac | cgtgccctcc | agcaacttcg | gcacccagac | ctacacctgc | 660 |
| aacgtagatc | acaagcccag | caacaccaag | gtggacaaga | cagttgagcg | caaatgttgt | 720 |
| gtcgagtgcc | caccgtgccc | agcaccacct | gtggcaggac | cgtcagtctt | cctcttcccc | 780 |
| ccaaaaccca | aggacaccct | catgatctcc | cggacccctg | aggtcacgtg | cgtggtggtg | 840 |
| gacgtgagcc | acgaagaccc | cgaggtccag | ttcaactggt | acgtggacgg | cgtggaggtg | 900 |
| cataatgcca | agacaaagcc | acgggaggag | cagttcaaca | gcacgttccg | tgtggtcagc | 960 |
| gtcctcaccg | ttgtgcacca | ggactggctg | aacggcaagg | agtacaagtg | caaggtctcc | 1020 |
| aacaaaggcc | tcccagcccc | catcgagaaa | accatctcca | aaaccaaagg | gcagccccga | 1080 |
| gaaccacagg | tgtacaccct | gccccatcc | cgggaggaga | tgaccaagaa | ccaggtcagc | 1140 |
| ctgacctgcc | tggtcaaagg | cttctacccc | agcgacatcg | ccgtggagtg | ggagagcaat | 1200 |
| gggcagccgg | agaacaacta | caagaccaca | cctcccatgc | tggactccga | cggctccttc | 1260 |
| ttcctctaca | gcaagctcac | cgtggacaag | agcaggtggc | agcaggggaa | cgtcttctca | 1320 |
| tgctccgtga | tgcatgaggc | tctgcacaac | cactacacgc | agaagagcct | ctccctgtct | 1380 |
| ccgggtaaa | | | | | | 1389 |

<210> SEQ ID NO 76
<211> LENGTH: 463
<212> TYPE: PRT
<213> ORGANISM: Homo sapiens

<400> SEQUENCE: 76

Met Asp Trp Thr Trp Arg Ile Leu Phe Leu Val Ala Ala Thr Gly
1               5                   10                  15

Ala His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Gly Tyr Tyr Met His Trp Val Arg Gln Ala Pro Gly Gln Gly Leu
    50                  55                  60

Glu Trp Met Gly Trp Ile Asn Pro Asn Ser Gly Gly Thr Asn Tyr Ala
65                  70                  75                  80

Gln Arg Phe Arg Gly Arg Val Thr Met Thr Arg Asp Thr Ser Ile Ser

```
            85                  90                  95
Thr Ala Tyr Met Glu Leu Ser Arg Leu Arg Ser Asp Asp Thr Ala Val
            100                 105                 110
Tyr Tyr Cys Ala Arg Ala Pro Tyr Asp Trp Thr Phe Asp Tyr Trp Gly
            115                 120                 125
Gln Gly Thr Leu Val Thr Val Ser Ser Ala Ser Thr Lys Gly Pro Ser
130                 135                 140
Val Phe Pro Leu Ala Pro Cys Ser Arg Ser Thr Ser Glu Ser Thr Ala
145                 150                 155                 160
Ala Leu Gly Cys Leu Val Lys Asp Tyr Phe Pro Glu Pro Val Thr Val
                165                 170                 175
Ser Trp Asn Ser Gly Ala Leu Thr Ser Gly Val His Thr Phe Pro Ala
            180                 185                 190
Val Leu Gln Ser Ser Gly Leu Tyr Ser Leu Ser Ser Val Val Thr Val
            195                 200                 205
Pro Ser Ser Asn Phe Gly Thr Gln Thr Tyr Thr Cys Asn Val Asp His
            210                 215                 220
Lys Pro Ser Asn Thr Lys Val Asp Lys Thr Val Glu Arg Lys Cys Cys
225                 230                 235                 240
Val Glu Cys Pro Pro Cys Pro Ala Pro Pro Val Ala Gly Pro Ser Val
                245                 250                 255
Phe Leu Phe Pro Pro Lys Pro Lys Asp Thr Leu Met Ile Ser Arg Thr
            260                 265                 270
Pro Glu Val Thr Cys Val Val Val Asp Val Ser His Glu Asp Pro Glu
            275                 280                 285
Val Gln Phe Asn Trp Tyr Val Asp Gly Val Glu Val His Asn Ala Lys
            290                 295                 300
Thr Lys Pro Arg Glu Glu Gln Phe Asn Ser Thr Phe Arg Val Val Ser
305                 310                 315                 320
Val Leu Thr Val Val His Gln Asp Trp Leu Asn Gly Lys Glu Tyr Lys
                325                 330                 335
Cys Lys Val Ser Asn Lys Gly Leu Pro Ala Pro Ile Glu Lys Thr Ile
            340                 345                 350
Ser Lys Thr Lys Gly Gln Pro Arg Glu Pro Gln Val Tyr Thr Leu Pro
            355                 360                 365
Pro Ser Arg Glu Glu Met Thr Lys Asn Gln Val Ser Leu Thr Cys Leu
            370                 375                 380
Val Lys Gly Phe Tyr Pro Ser Asp Ile Ala Val Glu Trp Glu Ser Asn
385                 390                 395                 400
Gly Gln Pro Glu Asn Asn Tyr Lys Thr Thr Pro Pro Met Leu Asp Ser
                405                 410                 415
Asp Gly Ser Phe Phe Leu Tyr Ser Lys Leu Thr Val Asp Lys Ser Arg
            420                 425                 430
Trp Gln Gln Gly Asn Val Phe Ser Cys Ser Val Met His Glu Ala Leu
            435                 440                 445
His Asn His Tyr Thr Gln Lys Ser Leu Ser Leu Ser Pro Gly Lys
            450                 455                 460

<210> SEQ ID NO 77
<211> LENGTH: 708
<212> TYPE: DNA
<213> ORGANISM: Homo sapiens

<400> SEQUENCE: 77
```

-continued

```
atggacatga gggtgcccgc tcagctcctg gggctcctgc tgctgtggct gagaggtgcg      60
cgctgtgaca tccagatgac ccagtctcca tcttccgtgt ctgcatctgt aggagacaga     120
gtcaccatca cttgtcgggc gagtcagggt attagcaact ggttagcctg gtatcagcag     180
aaaccaggga cagcccctaa actcctgatc tatgctgcat ccagtttgca aagtggggtc     240
ccatcaaggt tcagcggcag tggatctggg acagatttca ctctcaccat cagcagcctg     300
cagcctgaag attttgcaac ttactattgt caacaggcta acagtttccc attcactttc     360
ggccctggga ccaaagtgga tatcaaacgt acggtggctg caccatctgt cttcatcttc     420
ccgccatctg atgagcagtt gaaatctgga actgcctctg ttgtgtgcct gctgaataac     480
ttctatccca gagaggccaa agtacagtgg aaggtggata acgccctcca atcgggtaac     540
tcccaggaga gtgtcacaga gcaggacagc aaggacagca cctacagcct cagcagcacc     600
ctgacgctga gcaaagcaga ctacgagaaa cacaaagtct acgcctgcga agtcacccat     660
cagggcctga gctcgcccgt cacaaagagc ttcaacaggg gagagtgt                  708
```

<210> SEQ ID NO 78
<211> LENGTH: 236
<212> TYPE: PRT
<213> ORGANISM: Homo sapiens

<400> SEQUENCE: 78

Met Asp Met Arg Val Pro Ala Gln Leu Leu Gly Leu Leu Leu Leu Trp
1               5                   10                  15

Leu Arg Gly Ala Arg Cys Asp Ile Gln Met Thr Gln Ser Pro Ser Ser
            20                  25                  30

Val Ser Ala Ser Val Gly Asp Arg Val Thr Ile Thr Cys Arg Ala Ser
        35                  40                  45

Gln Gly Ile Ser Asn Trp Leu Ala Trp Tyr Gln Gln Lys Pro Gly Thr
    50                  55                  60

Ala Pro Lys Leu Leu Ile Tyr Ala Ala Ser Ser Leu Gln Ser Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Thr Tyr Tyr Cys Gln Gln
            100                 105                 110

Ala Asn Ser Phe Pro Phe Thr Phe Gly Pro Gly Thr Lys Val Asp Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 79

```
<211> LENGTH: 1407
<212> TYPE: DNA
<213> ORGANISM: Homo sapiens

<400> SEQUENCE: 79
atggacatga gggtgcccgc tcagctcctg gggctcctgc tgctgtggct gagaggtgcg      60
cgctgtcagg tgcagttggt gcagtctggg actgaggtga agaagcctgg ggcctcaatg     120
aaggtttcct gcaaggcatc tggatacacc ttcaccagct attatatgca ctgggtgcga     180
caggcccctg gacaagggct tgagtggatg gaataatca accctagtgg tgatagcaca     240
agctacgcac agaagttcca gggcagagtc accatgacca gggacacgtc cacgaacaca     300
gtctacatgg agctgagcag cctgagatct gaggacacgg ccatgtatta ctgtgcgaga     360
gatgtagagg ttcggggaat ttctcacttt gactactggg gccagggaac cctggtcacc     420
gtctctagtg cctccaccaa gggcccatcg gtcttcccc tggcgccctg ctccaggagc     480
acctccgaga gcacagcggc cctgggctgc ctggtcaagg actacttccc cgaaccggtg     540
acggtgtcgt ggaactcagg cgctctgacc agcggcgtgc acaccttccc agctgtccta     600
cagtcctcag gactctactc cctcagcagc gtggtgaccg tgccctccag caacttcggc     660
acccagacct acacctgcaa cgtagatcac aagcccagca caccaaggt ggacaagaca     720 gttgagcgca aatgttgtgt cgagtgccca ccgtgccag caccacctgt ggcaggaccg     780
tcagtcttcc tcttcccccc aaaacccaag gacaccctca tgatctcccg gacccctgag     840
gtcacgtgcg tggtggtgga cgtgagccac gaagacccg aggtccagtt caactggtac     900
gtggacggcg tggaggtgca taatgccaag acaaagccac gggaggagca gttcaacagc     960
acgttccgtg tggtcagcgt cctcaccgtt gtgcaccagg actggctgaa cggcaaggag    1020
tacaagtgca aggtctccaa caaaggcctc ccagccccca tcgagaaaac catctccaaa    1080
accaaagggc agccccgaga accacaggtg tacaccctgc ccccatcccg ggaggagatg    1140
accaagaacc aggtcagcct gacctgcctg gtcaaaggct tctacccag cgacatcgcc    1200 gtggagtggg agagcaatgg gcagccggag aacaactaca agaccacacc tcccatgctg    1260
gactccgacg gctccttctt cctctacagc aagctcaccg tggacaagag caggtggcag    1320
caggggaacg tcttctcatg ctccgtgatg catgaggctc tgcacaacca ctacacgcag    1380
aagagcctct ccctgtctcc gggtaaa                                        1407

<210> SEQ ID NO 80
<211> LENGTH: 469
<212> TYPE: PRT
<213> ORGANISM: Homo sapiens

<400> SEQUENCE: 80

Met Asp Met Arg Val Pro Ala Gln Leu Leu Gly Leu Leu Leu Leu Trp
1               5                   10                  15

Leu Arg Gly Ala Arg Cys Gln Val Gln Leu Val Gln Ser Gly Thr Glu
                20                  25                  30

Val Lys Lys Pro Gly Ala Ser Met Lys Val Ser Cys Lys Ala Ser Gly
            35                  40                  45

Tyr Thr Phe Thr Ser Tyr Tyr Met His Trp Val Arg Gln Ala Pro Gly
        50                  55                  60

Gln Gly Leu Glu Trp Met Gly Ile Ile Asn Pro Ser Gly Asp Ser Thr
65                  70                  75                  80

Ser Tyr Ala Gln Lys Phe Gln Gly Arg Val Thr Met Thr Arg Asp Thr
                85                  90                  95
```

Ser Thr Asn Thr Val Tyr Met Glu Leu Ser Ser Leu Arg Ser Glu Asp
            100                 105                 110

Thr Ala Met Tyr Tyr Cys Ala Arg Asp Val Glu Val Arg Gly Ile Ser
            115                 120                 125

His Phe Asp Tyr Trp Gly Gln Gly Thr Leu Val Thr Val Ser Ser Ala
        130                 135                 140

Ser Thr Lys Gly Pro Ser Val Phe Pro Leu Ala Pro Cys Ser Arg Ser
145                 150                 155                 160

Thr Ser Glu Ser Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205

Ser Ser Val Val Thr Val Pro Ser Ser Asn Phe Gly Thr Gln Thr Tyr
    210                 215                 220

Thr Cys Asn Val Asp His Lys Pro Ser Asn Thr Lys Val Asp Lys Thr
225                 230                 235                 240

Val Glu Arg Lys Cys Cys Val Glu Cys Pro Pro Cys Pro Ala Pro Pro
                245                 250                 255

Val Ala Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Gln Phe Asn Trp Tyr Val Asp Gly Val
    290                 295                 300

Glu Val His Asn Ala Lys Thr Lys Pro Arg Glu Glu Gln Phe Asn Ser
305                 310                 315                 320

Thr Phe Arg Val Val Ser Val Leu Thr Val Val His Gln Asp Trp Leu
                325                 330                 335

Asn Gly Lys Glu Tyr Lys Cys Lys Val Ser Asn Lys Gly Leu Pro Ala
            340                 345                 350

Pro Ile Glu Lys Thr Ile Ser Lys Thr Lys Gly Gln Pro Arg Glu Pro
        355                 360                 365

Gln Val Tyr Thr Leu Pro Pro Ser Arg Glu Glu Met Thr Lys Asn Gln
    370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Met Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
        435                 440                 445

Val Met His Glu Ala Leu His Asn His Tyr Thr Gln Lys Ser Leu Ser
    450                 455                 460

Leu Ser Pro Gly Lys
465

<210> SEQ ID NO 81
<211> LENGTH: 714
<212> TYPE: DNA
<213> ORGANISM: Homo sapiens

<400> SEQUENCE: 81

```
atgggatgga gctgtatcat cctcttcttg gtagcaacag ctacaggtgt ccactccgac      60
atccagctga cccagtctcc atcatctctg agcgcatctg ttggagatag ggtcactatg     120
agctgtaagt ccagtcaaag tgttttatac agtgcaaatc acaagaacta cttggcctgg     180
taccagcaga aaccagggaa agcacctaaa ctgctgatct actgggcatc cactaggaa      240
tctggtgtcc cttcgcgatt ctctggcagc ggatctggga cagattttac tttcaccatc     300
agctctcttc aaccagaaga cattgcaaca tattattgtc accaatacct ctcctcgtgg     360
acgttcggtg agggaccaa ggtgcagatc aaacgaactg tggctgcacc atctgtcttc      420
atcttcccgc catctgatga gcagttgaaa tctggaactg cctctgttgt gtgcctgctg     480
aataacttct atcccagaga ggccaaagta cagtggaagg tggataacgc cctccaatcg     540
ggtaactccc aggagagtgt cacagagcag gacagcaagg acagcaccta cagcctcagc     600
agcaccctga cgctgagcaa agcagactac gagaaacaca agtctacgc ctgcgaagtc      660
acccatcagg gcctgagctc gcccgtcaca aagagcttca caggggagag tgt            714
```

<210> SEQ ID NO 82
<211> LENGTH: 238
<212> TYPE: PRT
<213> ORGANISM: Homo sapiens

<400> SEQUENCE: 82

```
Met Gly Trp Ser Cys Ile Ile Leu Phe Leu Val Ala Thr Ala Thr Gly
  1               5                  10                  15
Val His Ser Asp Ile Gln Leu Thr Gln Ser Pro Ser Ser Leu Ser Ala
             20                  25                  30
Ser Val Gly Asp Arg Val Thr Met Ser Cys Lys Ser Ser Gln Ser Val
         35                  40                  45
Leu Tyr Ser Ala Asn His Lys Asn Tyr Leu Ala Trp Tyr Gln Gln Lys
     50                  55                  60
Pro Gly Lys Ala Pro Lys Leu Leu Ile Tyr Trp Ala Ser Thr Arg Glu
 65                  70                  75                  80
Ser Gly Val Pro Ser Arg Phe Ser Gly Ser Gly Ser Gly Thr Asp Phe
                 85                  90                  95
Thr Phe Thr Ile Ser Ser Leu Gln Pro Glu Asp Ile Ala Thr Tyr Tyr
            100                 105                 110
Cys His Gln Tyr Leu Ser Ser Trp Thr Phe Gly Gly Gly Thr Lys Val
        115                 120                 125
Gln Ile Lys Arg Thr Val Ala Ala Pro Ser Val Phe Ile Phe Pro Pro
    130                 135                 140
Ser Asp Glu Gln Leu Lys Ser Gly Thr Ala Ser Val Val Cys Leu Leu
145                 150                 155                 160
Asn Asn Phe Tyr Pro Arg Glu Ala Lys Val Gln Trp Lys Val Asp Asn
                165                 170                 175
Ala Leu Gln Ser Gly Asn Ser Gln Glu Ser Val Thr Glu Gln Asp Ser
            180                 185                 190
Lys Asp Ser Thr Tyr Ser Leu Ser Ser Thr Leu Thr Leu Ser Lys Ala
        195                 200                 205
Asp Tyr Glu Lys His Lys Val Tyr Ala Cys Glu Val Thr His Gln Gly
    210                 215                 220
Leu Ser Ser Pro Val Thr Lys Ser Phe Asn Arg Gly Glu Cys
225                 230                 235
```

-continued

<210> SEQ ID NO 83
<211> LENGTH: 1395
<212> TYPE: DNA
<213> ORGANISM: Homo sapiens

<400> SEQUENCE: 83

| | | | | | |
|---|---|---|---|---|---|
| atgggatgga | gctgtatcat | cctcttcttg | gtagcaacag | ctacaggtgt | ccactcccag | 60 |
| gtccagctgg | tccaatcagg | ggctgaagtc | aagaaacctg | ggtcatcagt | gaaggtctcc | 120 |
| tgcaaggctt | ctggctacac | ctttactagc | tactggctgc | actgggtcag | gcaggcacct | 180 |
| ggacagggtc | tggaatggat | tggatacatt | aatcctagga | atgattatac | tgagtacaat | 240 |
| cagaacttca | aggacaaggc | cacaataact | gcagacgaat | ccaccaatac | agcctacatg | 300 |
| gagctgagca | gcctgaggtc | tgaggacacg | gcattttatt | tttgtgcaag | aagggatatt | 360 |
| actacgttct | actggggcca | aggcaccacg | gtcaccgtct | cctcagcctc | caccaagggc | 420 |
| ccatcggtct | tccccctggc | accctcctcc | aagagcacct | ctgggggcac | agcggccctg | 480 |
| ggctgcctgg | tcaaggacta | cttccccgaa | ccggtgacgg | tgtcgtggaa | ctcaggcgcc | 540 |
| ctgaccagcg | gcgtgcacac | cttcccggct | gtcctacagt | cctcaggact | ctactccctc | 600 |
| agcagcgtgg | tgaccgtgcc | ctccagcagc | ttgggcaccc | agacctacat | ctgcaacgtg | 660 |
| aatcacaagc | ccagcaacac | caaggtggac | aagagagttg | agcccaaatc | ttgtgacaaa | 720 |
| actcacacat | gcccaccgtg | cccagcacct | gaactcctgg | ggggaccgtc | agtcttcctc | 780 |
| ttccccccaa | aacccaagga | caccctcatg | atctcccgga | cccctgaggt | cacatgcgtg | 840 |
| gtggtggacg | tgagccacga | agaccctgag | gtcaagttca | actggtacgt | ggacggcgtg | 900 |
| gaggtgcata | atgccaagac | aaagccgcgg | gaggagcagt | acaacagcac | gtaccgtgtg | 960 |
| gtcagcgtcc | tcaccgtcct | gcaccaggac | tggctgaatg | gcaaggagta | caagtgcaag | 1020 |
| gtctccaaca | aagccctccc | agcccccatc | gagaaaacca | tctccaaagc | caaagggcag | 1080 |
| ccccgagaac | cacaggtgta | caccctgccc | ccatcccggg | aggagatgac | caagaaccag | 1140 |
| gtcagcctga | cctgcctggt | caaaggcttc | tatcccagcg | acatcgccgt | ggagtgggag | 1200 |
| agcaatgggc | agccggagaa | caactacaag | accacgcctc | ccgtgctgga | ctccgacggc | 1260 |
| tccttcttcc | tctatagcaa | gctcaccgtg | gacaagagca | ggtggcagca | ggggaacgtc | 1320 |
| ttctcatgct | ccgtgatgca | tgaggctctg | cacaaccact | acacgcagaa | gagcctctcc | 1380 |
| ctgtctccgg | gtaaa | | | | | 1395 |

<210> SEQ ID NO 84
<211> LENGTH: 465
<212> TYPE: PRT
<213> ORGANISM: Homo sapiens

<400> SEQUENCE: 84

Met Gly Trp Ser Cys Ile Ile Leu Phe Leu Val Ala Thr Ala Thr Gly
1               5                   10                  15

Val His Ser Gln Val Gln Leu Val Gln Ser Gly Ala Glu Val Lys Lys
            20                  25                  30

Pro Gly Ser Ser Val Lys Val Ser Cys Lys Ala Ser Gly Tyr Thr Phe
        35                  40                  45

Thr Ser Tyr Trp Leu His Trp Val Arg Gln Ala Pro Gly Gln Gly Leu
    50                  55                  60

Glu Trp Ile Gly Tyr Ile Asn Pro Arg Asn Asp Tyr Thr Glu Tyr Asn
65                  70                  75                  80

-continued

```
Gln Asn Phe Lys Asp Lys Ala Thr Ile Thr Ala Asp Glu Ser Thr Asn
                 85                  90                  95

Thr Ala Tyr Met Glu Leu Ser Ser Leu Arg Ser Glu Asp Thr Ala Phe
            100                 105                 110

Tyr Phe Cys Ala Arg Arg Asp Ile Thr Thr Phe Tyr Trp Gly Gln Gly
        115                 120                 125

Thr Thr Val Thr Val Ser Ser Ala Ser Thr Lys Gly Pro Ser Val Phe
    130                 135                 140

Pro Leu Ala Pro Ser Ser Lys Ser Thr Ser Gly Gly Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
        195                 200                 205

Ser Ser Leu Gly Thr Gln Thr Tyr Ile Cys Asn Val Asn His Lys Pro
    210                 215                 220

Ser Asn Thr Lys Val Asp Lys Arg Val Glu Pro Lys Ser Cys Asp Lys
225                 230                 235                 240

Thr His Thr Cys Pro Pro Cys Pro Ala Pro Glu Leu Leu Gly Gly Pro
                245                 250                 255

Ser Val Phe Leu Phe Pro Pro Lys Pro Lys Asp Thr Leu Met Ile Ser
            260                 265                 270

Arg Thr Pro Glu Val Thr Cys Val Val Val Asp Val Ser His Glu Asp
        275                 280                 285

Pro Glu Val Lys Phe Asn Trp Tyr Val Asp Gly Val Glu Val His Asn
    290                 295                 300

Ala Lys Thr Lys Pro Arg Glu Glu Gln Tyr Asn Ser Thr Tyr Arg Val
305                 310                 315                 320

Val Ser Val Leu Thr Val Leu His Gln Asp Trp Leu Asn Gly Lys Glu
                325                 330                 335

Tyr Lys Cys Lys Val Ser Asn Lys Ala Leu Pro Ala Pro Ile Glu Lys
            340                 345                 350

Thr Ile Ser Lys Ala Lys Gly Gln Pro Arg Glu Pro Gln Val Tyr Thr
        355                 360                 365

Leu Pro Pro Ser Arg Glu Glu Met Thr Lys Asn Gln Val Ser Leu Thr
    370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
                405                 410                 415

Asp Ser Asp Gly Ser Phe Phe Leu Tyr Ser Lys Leu Thr Val Asp Lys
            420                 425                 430

Ser Arg Trp Gln Gln Gly Asn Val Phe Ser Cys Ser Val Met His Glu
        435                 440                 445

Ala Leu His Asn His Tyr Thr Gln Lys Ser Leu Ser Leu Ser Pro Gly
    450                 455                 460

Lys
465

<210> SEQ ID NO 85
<211> LENGTH: 705
<212> TYPE: DNA
```

<213> ORGANISM: Homo sapiens

<400> SEQUENCE: 85

```
atggaaaccc cagctcagct tctcttcctc ctgctactct ggctcccaga taccaccgga      60
gaaattgtgt tgacgcagtc tccaggcacc ctgtctttgt ctccagggga aagagccacc     120
ctctcctgca gggccagtca gagtgttagc agcagctact tagcctggta ccagcagaaa     180
cctggccagg ctcccaggct cctcatatat ggtgcatcca gcagggccac tggcatccca     240
gacaggttca gtggcagtgg gtctgggaca gacttcactc tcaccatcag cagactggag     300
cctgaagatt ttgcagtgta ttactgtcag cggtctggtg gctcatcatt cactttcggc     360
cctgggacca agtggatat caaacgaact gtggctgcac catctgtctt catcttcccg     420
ccatctgatg agcagttgaa atctggaact gcctctgttg tgtgcctgct gaataacttc     480
tatcccagag aggccaaagt acagtggaag gtggataacg ccctccaatc gggtaactcc     540
caggagagtg tcacagagca ggacagcaag gacagcacct acagcctcag cagcaccctg     600
acgctgagca aagcagacta cgagaaacac aaagtctacg cctgcgaagt cacccatcag     660
ggcctgagct cgcccgtcac aaagagcttc aacaggggag agtgt                     705
```

<210> SEQ ID NO 86
<211> LENGTH: 235
<212> TYPE: PRT
<213> ORGANISM: Homo sapiens

<400> SEQUENCE: 86

```
Met Glu Thr Pro Ala Gln Leu Leu Phe Leu Leu Leu Trp Leu Pro
1               5                   10                  15

Asp Thr Thr Gly Glu Ile Val Leu Thr Gln Ser Pro Gly Thr Leu Ser
            20                  25                  30

Leu Ser Pro Gly Glu Arg Ala Thr Leu Ser Cys Arg Ala Ser Gln Ser
        35                  40                  45

Val Ser Ser Ser Tyr Leu Ala Trp Tyr Gln Gln Lys Pro Gly Gln Ala
    50                  55                  60

Pro Arg Leu Leu Ile Tyr Gly Ala Ser Ser Arg Ala Thr Gly Ile Pro
65                  70                  75                  80

Asp Arg Phe Ser Gly Ser Gly Ser Gly Thr Asp Phe Thr Leu Thr Ile
                85                  90                  95

Ser Arg Leu Glu Pro Glu Asp Phe Ala Val Tyr Tyr Cys Gln Arg Ser
            100                 105                 110

Gly Gly Ser Ser Phe Thr Phe Gly Pro Gly Thr Lys Val Asp Ile Lys
        115                 120                 125

Arg Thr Val Ala Ala Pro Ser Val Phe Ile Phe Pro Pro Ser Asp Glu
130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
```

<210> SEQ ID NO 87
<211> LENGTH: 1398
<212> TYPE: DNA
<213> ORGANISM: Homo sapiens

<400> SEQUENCE: 87

```
atggggtcaa ccgccatcct cgccctcctc ctggctgttc tccaaggagt ctgtgccgag      60
gtgcagctgg tacagtctgg agcagaggtg aaaaagcccg ggagtctct gaagatctcc     120
tgtaagggtt ctggatacaa ctttaccagc tactggatcg gctgggtgcg ccagatgccc    180
gggaaaggcc tggagttgat ggggatcatc tatcctggtg actctgatac cagatacagc    240
ccgtccttcc aaggccaggt caccatctca gccgacaagt ccatcagcac cgcctacctg    300
cagtggagca gcctgaaggc ctcggacacc gccatgtatt actgtggttc ggggagctac    360
ttttacttcg atctctgggg ccgtggcacc ctggtcaccg tctctagtgc ctccaccaag    420
ggcccatcgg tcttccccct ggcaccctcc tccaagagca cctctggggg cacagcggcc    480
ctgggctgcc tggtcaagga ctacttcccc gaaccggtga cggtgtcgtg gaactcaggc    540
gccctgacca gcggcgtgca caccttcccg gctgtcctac agtcctcagg actctactcc    600
ctcagcagcg tggtgaccgt gccctccagc agcttgggca cccagaccta catctgcaac    660
gtgaatcaca agcccagcaa caccaaggtg gacaagaaag ttgagcccaa atcttgtgac    720
aaaactcaca catgcccacc gtgcccagca cctgaactcc tggggggacc gtcagtcttc    780
ctcttccccc caaaacccaa ggacaccctc atgatctccc ggacccctga ggtcacatgc    840
gtggtggtgg acgtgagcca cgaagaccct gaggtcaagt tcaactggta cgtggacggc    900
gtggaggtgc ataatgccaa gacaaagccg cgggaggagc agtacaacag cacgtaccgt    960
gtggtcagcg tcctcaccgt cctgcaccag gactggctga atggcaagga gtacaagtgc   1020
aaggtctcca acaaagccct cccagccccc atcgagaaaa ccatctccaa agccaaaggg   1080
cagccccgag aaccacaggt gtacaccctg cccccatccc gggatgagct gaccaagaac   1140
caggtcagcc tgacctgcct ggtcaaaggc ttctatccca gcgacatcgc cgtggagtgg   1200
gagagcaatg ggcagccgga gaacaactac aagaccacgc ctcccgtgct ggactccgac   1260
ggctccttct tcctctatag caagctcacc gtggacaaga gcaggtggca gcaggggaac   1320
gtcttctcat gctccgtgat gcatgaggct ctgcacaacc actacacgca gaagagcctc   1380
tccctgtctc cgggtaaa                                                  1398
```

<210> SEQ ID NO 88
<211> LENGTH: 466
<212> TYPE: PRT
<213> ORGANISM: Homo sapiens

<400> SEQUENCE: 88

Met Gly Ser Thr Ala Ile Leu Ala Leu Leu Ala Val Leu Gln Gly
1               5                   10                  15

Val Cys Ala Glu Val Gln Leu Val Gln Ser Gly Ala Glu Val Lys Lys
            20                  25                  30

Pro Gly Glu Ser Leu Lys Ile Ser Cys Lys Gly Ser Gly Tyr Asn Phe
        35                  40                  45

Thr Ser Tyr Trp Ile Gly Trp Val Arg Gln Met Pro Gly Lys Gly Leu
    50                  55                  60

Glu Leu Met Gly Ile Ile Tyr Pro Gly Asp Ser Asp Thr Arg Tyr Ser

Pro Ser Phe Gln Gly Gln Val Thr Ile Ser Ala Asp Lys Ser Ile Ser
　　　　　　　　　　85　　　　　　　　　　　90　　　　　　　　　95

Thr Ala Tyr Leu Gln Trp Ser Ser Leu Lys Ala Ser Asp Thr Ala Met
　　　　　　　　100　　　　　　　　　　105　　　　　　　　　110

Tyr Tyr Cys Gly Ser Gly Ser Phe Tyr Phe Asp Leu Trp Gly Arg
　　　　　　115　　　　　　　　　　120　　　　　　　　　125

Gly Thr Leu Val Thr Val Ser Ser Ala Ser Thr Lys Gly Pro Ser Val
　　　　130　　　　　　　　　　135　　　　　　　　　140

Phe Pro Leu Ala Pro Ser Ser Lys Ser Thr Ser Gly Gly Thr Ala Ala
145　　　　　　　　　　150　　　　　　　　　155　　　　　　　　　160

Leu Gly Cys Leu Val Lys Asp Tyr Phe Pro Glu Pro Val Thr Val Ser
　　　　　　　　165　　　　　　　　　　170　　　　　　　　　175

Trp Asn Ser Gly Ala Leu Thr Ser Gly Val His Thr Phe Pro Ala Val
　　　　　　　　180　　　　　　　　　　185　　　　　　　　　190

Leu Gln Ser Ser Gly Leu Tyr Ser Leu Ser Ser Val Val Thr Val Pro
　　　　　　　　195　　　　　　　　　　200　　　　　　　　　205

Ser Ser Ser Leu Gly Thr Gln Thr Tyr Ile Cys Asn Val Asn His Lys
　　　　210　　　　　　　　　　215　　　　　　　　　220

Pro Ser Asn Thr Lys Val Asp Lys Lys Val Glu Pro Lys Ser Cys Asp
225　　　　　　　　　　230　　　　　　　　　235　　　　　　　　　240

Lys Thr His Thr Cys Pro Pro Cys Pro Ala Pro Glu Leu Leu Gly Gly
　　　　　　　　245　　　　　　　　　　250　　　　　　　　　255

Pro Ser Val Phe Leu Phe Pro Pro Lys Pro Lys Asp Thr Leu Met Ile
　　　　　　　　260　　　　　　　　　　265　　　　　　　　　270

Ser Arg Thr Pro Glu Val Thr Cys Val Val Val Asp Val Ser His Glu
　　　　　　　275　　　　　　　　　　280　　　　　　　　　285

Asp Pro Glu Val Lys Phe Asn Trp Tyr Val Asp Gly Val Glu Val His
　　　　290　　　　　　　　　　295　　　　　　　　　300

Asn Ala Lys Thr Lys Pro Arg Glu Glu Gln Tyr Asn Ser Thr Tyr Arg
305　　　　　　　　　　310　　　　　　　　　315　　　　　　　　　320

Val Val Ser Val Leu Thr Val Leu His Gln Asp Trp Leu Asn Gly Lys
　　　　　　　　325　　　　　　　　　　330　　　　　　　　　335

Glu Tyr Lys Cys Lys Val Ser Asn Lys Ala Leu Pro Ala Pro Ile Glu
　　　　　　　　340　　　　　　　　　　345　　　　　　　　　350

Lys Thr Ile Ser Lys Ala Lys Gly Gln Pro Arg Glu Pro Gln Val Tyr
　　　　　　　　355　　　　　　　　　　360　　　　　　　　　365

Thr Leu Pro Pro Ser Arg Asp Glu Leu Thr Lys Asn Gln Val Ser Leu
　　　　370　　　　　　　　　　375　　　　　　　　　380

Thr Cys Leu Val Lys Gly Phe Tyr Pro Ser Asp Ile Ala Val Glu Trp
385　　　　　　　　　　390　　　　　　　　　395　　　　　　　　　400

Glu Ser Asn Gly Gln Pro Glu Asn Asn Tyr Lys Thr Thr Pro Pro Val
　　　　　　　　405　　　　　　　　　　410　　　　　　　　　415

Leu Asp Ser Asp Gly Ser Phe Phe Leu Tyr Ser Lys Leu Thr Val Asp
　　　　　　　　420　　　　　　　　　　425　　　　　　　　　430

Lys Ser Arg Trp Gln Gln Gly Asn Val Phe Ser Cys Ser Val Met His
　　　　　　　　435　　　　　　　　　　440　　　　　　　　　445

Glu Ala Leu His Asn His Tyr Thr Gln Lys Ser Leu Ser Leu Ser Pro
　　　　450　　　　　　　　　　455　　　　　　　　　460

Gly Lys
465

<210> SEQ ID NO 89

```
<211> LENGTH: 723
<212> TYPE: DNA
<213> ORGANISM: Homo sapiens

<400> SEQUENCE: 89
atggacatga gggtgcccgc tcagctcctg gggctcctgc tgctgtggct gagaggtgcg      60
cgctgtgata ttgtgatgac tcagtctcca ctctccctgc ccgtcacccc tggagagccg     120
gcctccatct cctgcaggtc tagtcagagc ctcctgcata gtcatggata caactatttg     180
gattggtacc tgcagaagcc agggcagtct ccacagctcc tgatctattt gggttctaat     240
cgggcctccg gggtccctga caggttcagt ggcagtggat caggcacaga ttttacactg     300
aaaatcagca gagtggaggc tgaggatgtt ggggtttatt actgcatgca aggtacacac     360
tggcctccga cttttggcca ggggaccaag ctggagatca aacgtacggt ggctgcacca     420
tctgtcttca tcttcccgcc atctgatgag cagttgaaat ctggaactgc ctctgttgtg     480
tgcctgctga ataacttcta tcccagagag gccaaagtac agtggaaggt ggataacgcc     540
ctccaatcgg gtaactccca ggagagtgtc acagagcagg acagcaagga cagcacctac     600
agcctcagca gcaccctgac gctgagcaaa gcagactacg agaaacacaa agtctacgcc     660
tgcgaagtca cccatcaggg cctgagctcg cccgtcacaa agagcttcaa caggggagag     720
tgt                                                                   723

<210> SEQ ID NO 90
<211> LENGTH: 241
<212> TYPE: PRT
<213> ORGANISM: Homo sapiens

<400> SEQUENCE: 90

Met Asp Met Arg Val Pro Ala Gln Leu Leu Gly Leu Leu Leu Leu Trp
1               5                   10                  15

Leu Arg Gly Ala Arg Cys Asp Ile Val Met Thr Gln Ser Pro Leu Ser
            20                  25                  30

Leu Pro Val Thr Pro Gly Glu Pro Ala Ser Ile Ser Cys Arg Ser Ser
        35                  40                  45

Gln Ser Leu Leu His Ser His Gly Tyr Asn Tyr Leu Asp Trp Tyr Leu
    50                  55                  60

Gln Lys Pro Gly Gln Ser Pro Gln Leu Leu Ile Tyr Leu Gly Ser Asn
65                  70                  75                  80

Arg Ala Ser Gly Val Pro Asp Arg Phe Ser Gly Ser Gly Ser Gly Thr
                85                  90                  95

Asp Phe Thr Leu Lys Ile Ser Arg Val Glu Ala Glu Asp Val Gly Val
            100                 105                 110

Tyr Tyr Cys Met Gln Gly Thr His Trp Pro Pro Thr Phe Gly Gln Gly
        115                 120                 125

Thr Lys Leu Glu Ile Lys Arg Thr Val Ala Ala Pro Ser Val Phe Ile
    130                 135                 140

Phe Pro Pro Ser Asp Glu Gln Leu Lys Ser Gly Thr Ala Ser Val Val
145                 150                 155                 160

Cys Leu Leu Asn Asn Phe Tyr Pro Arg Glu Ala Lys Val Gln Trp Lys
                165                 170                 175

Val Asp Asn Ala Leu Gln Ser Gly Asn Ser Gln Glu Ser Val Thr Glu
            180                 185                 190

Gln Asp Ser Lys Asp Ser Thr Tyr Ser Leu Ser Ser Thr Leu Thr Leu
        195                 200                 205
```

```
Ser Lys Ala Asp Tyr Glu Lys His Lys Val Tyr Ala Cys Glu Val Thr
    210                 215                 220

His Gln Gly Leu Ser Ser Pro Val Thr Lys Ser Phe Asn Arg Gly Glu
225                 230                 235                 240

Cys
```

<210> SEQ ID NO 91
<211> LENGTH: 1410
<212> TYPE: DNA
<213> ORGANISM: Homo sapiens

<400> SEQUENCE: 91

```
atggacatga gggtgcccgc tcagctcctg gggctcctgc tgctgtggct gagaggtgcg      60
cgctgtgagg tccagctggt gcagtctggg ggaggcgtgg tccagcctgg gaggtccctg     120
agactctcct gtgcagcgtc tggattcacc ttcagtagct atggcatgca ctgggtccgc     180
caggctccag gcaaggggct ggagtgggtt tcatacatta gtagtagtgg tagtaccata     240
tactacgcag actctgtgaa gggccgattc accatctcca gggacaacgc caagaactca     300
ctatatctgc aaatgaacag cctgagagcc gaggacacgg ccgtgtatta ctgtgcgaga     360
gatctgttag attacgatct gttgactggt tatggctact ggggccaggg aaccctggtc     420
accgtctcta gtgcctccac caagggccca tcggtcttcc cctggcgccc tgctccagg      480
agcacctccg agagcacagc ggccctgggc tgcctggtca aggactactt ccccgaaccg     540
gtgacggtgt cgtggaactc aggcgctctg accagcggcg tgcacacctt cccagctgtc     600
ctacagtcct caggactcta ctccctcagc agcgtggtga ccgtgccctc agcaacttc      660
ggcacccaga cctacacctg caacgtagat cacaagccca gcaacaccaa ggtggacaag     720
acagttgagc gcaaatgttg tgtcgagtgc ccaccgtgcc cagcaccacc tgtggcagga     780
ccgtcagtct tcctcttccc cccaaaaccc aaggacaccc tcatgatctc ccggacccct     840
gaggtcacgt gcgtggtggt ggacgtgagc cacgaagacc ccgaggtcca gttcaactgg     900
tacgtggacg gcgtggaggt gcataatgcc aagacaaagc cacgggagga gcagttcaac     960
agcacgttcc gtgtggtcag cgtcctcacc gttgtgcacc aggactggct gaacggcaag    1020
gagtacaagt gcaaggtctc caacaaaggc ctcccagccc ccatcgagaa aaccatctcc    1080
aaaaccaaag ggcagccccg agaaccacag gtgtacaccc tgcccccatc ccgggaggag    1140
atgaccaaga accaggtcag cctgacctgc ctggtcaaag gcttctaccc cagcgacatc    1200
gccgtggagt gggagagcaa tgggcagccg gagaacaact acaagaccac acctcccatg    1260
ctggactccg acggctcctt cttcctctac agcaagctca ccgtggacaa gagcaggtgg    1320
cagcagggga acgtcttctc atgctccgtg atgcatgagg ctctgcacaa ccactacacg    1380
cagaagagcc tctccctgtc tccgggtaaa                                      1410
```

<210> SEQ ID NO 92
<211> LENGTH: 470
<212> TYPE: PRT
<213> ORGANISM: Homo sapiens

<400> SEQUENCE: 92

```
Met Asp Met Arg Val Pro Ala Gln Leu Leu Gly Leu Leu Leu Leu Trp
1               5                   10                  15

Leu Arg Gly Ala Arg Cys Glu Val Gln Leu Val Gln Ser Gly Gly Gly
            20                  25                  30

Val Val Gln Pro Gly Arg Ser Leu Arg Leu Ser Cys Ala Ala Ser Gly
```

-continued

```
                35                  40                  45
Phe Thr Phe Ser Ser Tyr Gly Met His Trp Val Arg Gln Ala Pro Gly
 50                  55                  60
Lys Gly Leu Glu Trp Val Ser Tyr Ile Ser Ser Ser Gly Ser Thr Ile
 65                  70                  75                  80
Tyr Tyr Ala Asp Ser Val Lys Gly Arg Phe Thr Ile Ser Arg Asp Asn
                 85                  90                  95
Ala Lys Asn Ser Leu Tyr Leu Gln Met Asn Ser Leu Arg Ala Glu Asp
                100                 105                 110
Thr Ala Val Tyr Tyr Cys Ala Arg Asp Leu Leu Asp Tyr Asp Leu Leu
                115                 120                 125
Thr Gly Tyr Gly Tyr Trp Gly Gln Gly Thr Leu Val Thr Val Ser Ser
            130                 135                 140
Ala Ser Thr Lys Gly Pro Ser Val Phe Pro Leu Ala Pro Cys Ser Arg
145                 150                 155                 160
Ser Thr Ser Glu Ser Thr Ala Ala Leu Gly Cys Leu Val Lys Asp Tyr
                165                 170                 175
Phe Pro Glu Pro Val Thr Val Ser Trp Asn Ser Gly Ala Leu Thr Ser
                180                 185                 190
Gly Val His Thr Phe Pro Ala Val Leu Gln Ser Ser Gly Leu Tyr Ser
            195                 200                 205
Leu Ser Ser Val Val Thr Val Pro Ser Ser Asn Phe Gly Thr Gln Thr
210                 215                 220
Tyr Thr Cys Asn Val Asp His Lys Pro Ser Asn Thr Lys Val Asp Lys
225                 230                 235                 240
Thr Val Glu Arg Lys Cys Cys Val Glu Cys Pro Pro Cys Pro Ala Pro
                245                 250                 255
Pro Val Ala Gly Pro Ser Val Phe Leu Phe Pro Pro Lys Pro Lys Asp
            260                 265                 270
Thr Leu Met Ile Ser Arg Thr Pro Glu Val Thr Cys Val Val Val Asp
            275                 280                 285
Val Ser His Glu Asp Pro Glu Val Gln Phe Asn Trp Tyr Val Asp Gly
        290                 295                 300
Val Glu Val His Asn Ala Lys Thr Lys Pro Arg Glu Glu Gln Phe Asn
305                 310                 315                 320
Ser Thr Phe Arg Val Val Ser Val Leu Thr Val Val His Gln Asp Trp
                325                 330                 335
Leu Asn Gly Lys Glu Tyr Lys Cys Lys Val Ser Asn Lys Gly Leu Pro
            340                 345                 350
Ala Pro Ile Glu Lys Thr Ile Ser Lys Thr Lys Gly Gln Pro Arg Glu
        355                 360                 365
Pro Gln Val Tyr Thr Leu Pro Pro Ser Arg Glu Glu Met Thr Lys Asn
    370                 375                 380
Gln Val Ser Leu Thr Cys Leu Val Lys Gly Phe Tyr Pro Ser Asp Ile
385                 390                 395                 400
Ala Val Glu Trp Glu Ser Asn Gly Gln Pro Glu Asn Asn Tyr Lys Thr
                405                 410                 415
Thr Pro Pro Met Leu Asp Ser Asp Gly Ser Phe Phe Leu Tyr Ser Lys
            420                 425                 430
Leu Thr Val Asp Lys Ser Arg Trp Gln Gln Gly Asn Val Phe Ser Cys
        435                 440                 445
Ser Val Met His Glu Ala Leu His Asn His Tyr Thr Gln Lys Ser Leu
    450                 455                 460
```

Ser Leu Ser Pro Gly Lys
465             470

<210> SEQ ID NO 93
<211> LENGTH: 705
<212> TYPE: DNA
<213> ORGANISM: Homo sapiens

<400> SEQUENCE: 93

```
atggaaaccc cagcgcagct tctcttcctc ctgctactct ggctcccaga taccaccgga      60
gaaattgtgt tgacgcagtc tccaggcacc ctgtctttgt ctccagggga aagagccacc    120
ctctcctgca gggccagtca gggtattagt agaagctact tagcctggta ccagcagaaa    180
cctggccagg ctcccagcct cctcatctat ggtgcatcca gcagggccac tggcatccca    240
gacaggttca gtggcagtgg gtctgggaca gacttcactc tcaccatcag cagactggag    300
cctgaagatt ttgcagtgta ttactgtcaa caatttggta gttcaccgtg gacgttcggc    360
caagggacca aggtggaaat caaacgaact gtggctgcac catctgtctt catcttcccg    420
ccatctgatg agcagttgaa atctggaact gctagcgttg tgtgcctgct gaataacttc    480
tatcccagag aggccaaagt acagtggaag gtggataacg ccctccaatc gggtaactcc    540
caggagagtg tcacagagca ggacagcaag gacagcacct acagcctcag cagcaccctg    600
acgctgagca agcagactac gagaaacac aaagtctacg cctgcgaagt cacccatcag    660
ggcctgagct cgcccgtcac aaagagcttc aacaggggag agtgt                    705
```

<210> SEQ ID NO 94
<211> LENGTH: 235
<212> TYPE: PRT
<213> ORGANISM: Homo sapiens

<400> SEQUENCE: 94

Met Glu Thr Pro Ala Gln Leu Leu Phe Leu Leu Leu Leu Trp Leu Pro
1               5                   10                  15

Asp Thr Thr Gly Glu Ile Val Leu Thr Gln Ser Pro Gly Thr Leu Ser
            20                  25                  30

Leu Ser Pro Gly Glu Arg Ala Thr Leu Ser Cys Arg Ala Ser Gln Gly
        35                  40                  45

Ile Ser Arg Ser Tyr Leu Ala Trp Tyr Gln Gln Lys Pro Gly Gln Ala
    50                  55                  60

Pro Ser Leu Leu Ile Tyr Gly Ala Ser Ser Arg Ala Thr Gly Ile Pro
65                  70                  75                  80

Asp Arg Phe Ser Gly Ser Gly Ser Gly Thr Asp Phe Thr Leu Thr Ile
                85                  90                  95

Ser Arg Leu Glu Pro Glu Asp Phe Ala Val Tyr Tyr Cys Gln Gln Phe
            100                 105                 110

Gly Ser Ser Pro Trp Thr Phe Gly Gln Gly Thr Lys Val Glu Ile Lys
        115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235

<210> SEQ ID NO 95
<211> LENGTH: 1413
<212> TYPE: DNA
<213> ORGANISM: Homo sapiens

<400> SEQUENCE: 95

| | | | | | |
|---|---|---|---|---|---|
| atgaagcatc | tgtggttctt | cctcctgctg | gtggcagctc | ccagatgggt | cctgtcccag | 60 |
| gtgcagctgc | aggagtcggg | cccaggactg | gtgaagcctt | cacagaccct | gtccctcacc | 120 |
| tgcactgtct | ctggtggctc | catcagcagt | ggtgattact | tctggagctg | gatccgccag | 180 |
| ctcccaggga | agggcctgga | gtggattggg | cacatccata | cagtgggac | acctactac | 240 |
| aatccgtccc | tcaagagtcg | agttaccata | tcagtagaca | cgtctaagaa | gcagttctcc | 300 |
| ctgaggctga | gttctgtgac | tgccgcggac | acggccgtat | attactgtgc | gagagatcga | 360 |
| gggggtgact | actactatgg | tatggacgtc | tggggccaag | ggaccacggt | caccgtctcc | 420 |
| tcagcctcca | ccaagggccc | atccgtcttc | cccctggcac | cctcctccaa | gagcacctct | 480 |
| gggggcacag | cggccctggg | ctgcctggtc | aaggactact | tccccgaacc | ggtgacggtg | 540 |
| tcgtggaact | caggcgccct | gaccagcggc | gtgcacacct | tcccggctgt | cctacagtcc | 600 |
| tcaggactct | actccctcag | cagcgtggtg | accgtgccct | ccagcagctt | gggcacccag | 660 |
| acctacatct | gcaacgtgaa | tcacaagccc | agcaacacca | aggtggacaa | gagagttgag | 720 |
| cccaaatctt | gtgacaaaac | tcacacatgc | ccaccgtgcc | cagcacctga | actcctgggg | 780 |
| ggaccgtcag | tcttcctctt | ccccccaaaa | cccaaggaca | ccctcatgat | ctcccggacc | 840 |
| cctgaggtca | catgcgtggt | ggtggacgtg | agccacgaag | accctgaggt | caagttcaac | 900 |
| tggtacgtgg | acggcgtgga | ggtgcataat | gccaagacaa | agccgcggga | ggagcagtac | 960 |
| aacagcacgt | accgtgtggt | cagcgtcctc | accgtcctgc | accaggactg | gctgaatggc | 1020 |
| aaggagtaca | agtgcaaggt | ctccaacaaa | gccctcccag | cccccatcga | gaaaaccatc | 1080 |
| tccaaagcca | aagggcagcc | ccgagaacca | caggtgtaca | ccctgccccc | atcccgggag | 1140 |
| gagatgacca | agaaccaggt | cagcctgacc | tgcctggtca | aaggcttcta | tcccagcgac | 1200 |
| atcgccgtgg | agtgggagag | caatgggcag | ccggagaaca | actacaagac | cacgcctccc | 1260 |
| gtgctggact | ccgacggctc | cttcttcctc | tatagcaagc | tcaccgtgga | caagagcagg | 1320 |
| tggcagcagg | ggaacgtctt | ctcatgctcc | gtgatgcatg | aggctctgca | caaccactac | 1380 |
| acgcagaaga | gcctctccct | gtctccgggt | aaa | | | 1413 |

<210> SEQ ID NO 96
<211> LENGTH: 471
<212> TYPE: PRT
<213> ORGANISM: Homo sapiens

<400> SEQUENCE: 96

Met Lys His Leu Trp Phe Phe Leu Leu Leu Val Ala Ala Pro Arg Trp
1               5                   10                  15

Val Leu Ser Gln Val Gln Leu Gln Glu Ser Gly Pro Gly Leu Val Lys
            20                  25                  30

```
Pro Ser Gln Thr Leu Ser Leu Thr Cys Thr Val Ser Gly Gly Ser Ile
        35                  40                  45

Ser Ser Gly Asp Tyr Phe Trp Ser Trp Ile Arg Gln Leu Pro Gly Lys
    50                  55                  60

Gly Leu Glu Trp Ile Gly His Ile His Asn Ser Gly Thr Thr Tyr Tyr
 65                  70                  75                  80

Asn Pro Ser Leu Lys Ser Arg Val Thr Ile Ser Val Asp Thr Ser Lys
                85                  90                  95

Lys Gln Phe Ser Leu Arg Leu Ser Ser Val Thr Ala Ala Asp Thr Ala
                100                 105                 110

Val Tyr Tyr Cys Ala Arg Asp Arg Gly Asp Tyr Tyr Gly Met
                115                 120                 125            Gly Met

Asp Val Trp Gly Gln Gly Thr Thr Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
                180                 185                 190

Thr Phe Pro Ala Val Leu Gln Ser Ser Gly Leu Tyr Ser Leu Ser Ser
                195                 200                 205

Val Val Thr Val Pro Ser Ser Ser Leu Gly Thr Gln Thr Tyr Ile Cys
                210                 215                 220

Asn Val Asn His Lys Pro Ser Asn Thr Lys Val Asp Lys Arg Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
                260                 265                 270

Asp Thr Leu Met Ile Ser Arg Thr Pro Glu Val Thr Cys Val Val Val
                275                 280                 285

Asp Val Ser His Glu Asp Pro Glu Val Lys Phe Asn Trp Tyr Val Asp
                290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
                340                 345                 350

Pro Ala Pro Ile Glu Lys Thr Ile Ser Lys Ala Lys Gly Gln Pro Arg
                355                 360                 365

Glu Pro Gln Val Tyr Thr Leu Pro Pro Ser Arg Glu Glu Met Thr Lys
                370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
                420                 425                 430

Lys Leu Thr Val Asp Lys Ser Arg Trp Gln Gln Gly Asn Val Phe Ser
                435                 440                 445
```

```
Cys Ser Val Met His Glu Ala Leu His Asn His Tyr Thr Gln Lys Ser
    450                 455                 460

Leu Ser Leu Ser Pro Gly Lys
465                 470

<210> SEQ ID NO 97
<211> LENGTH: 708
<212> TYPE: DNA
<213> ORGANISM: Homo sapiens

<400> SEQUENCE: 97
atggacatga gggtccctgc tcagctcctg gggctcctgc tgctctggct ctcaggtgcc     60
agatgtgaca tccagatgac ccagtctcca tcctcccctgt ctgcatctgt aggagacaga    120
gtcaccatca cttgccaggc gagtcaggac atcagcaact atttaaattg gtatcagcag    180
aaaccaggga aagcccctaa actcctgatc tacgatgcat ccaatttgga aacaggggtc    240
ccatcaaggt tcagtggaag tggatctggg acagatttta ctttcaccat cagcagcctg    300
cagcctgaag atattgcaac atatttctgt caacactttg atcatctccc gctcgctttc    360
ggcggaggga ccaaggtgga gatcaaacga actgtggctg caccatctgt cttcatcttc    420
ccgccatctg atgagcagtt gaaatctgga actgcctctg ttgtgtgcct gctgaataac    480
ttctatccca gagaggccaa agtacagtgg aaggtggata acgccctcca atcgggtaac    540
tcccaggaga gtgtcacaga gcaggacagc aaggacagca cctacagcct cagcagcacc    600
ctgacgctga gcaaagcaga ctacgagaaa cacaaagtct acgcctgcga agtcacccat    660
cagggcctga gctcgcccgt cacaaagagc ttcaacaggg gagagtgt             708

<210> SEQ ID NO 98
<211> LENGTH: 236
<212> TYPE: PRT
<213> ORGANISM: Homo sapiens

<400> SEQUENCE: 98

Met Asp Met Arg Val Pro Ala Gln Leu Leu Gly Leu Leu Leu Leu Trp
1               5                   10                  15

Leu Ser Gly Ala Arg Cys Asp Ile Gln Met Thr Gln Ser Pro Ser Ser
            20                  25                  30

Leu Ser Ala Ser Val Gly Asp Arg Val Thr Ile Thr Cys Gln Ala Ser
        35                  40                  45

Gln Asp Ile Ser Asn Tyr Leu Asn Trp Tyr Gln Gln Lys Pro Gly Lys
    50                  55                  60

Ala Pro Lys Leu Leu Ile Tyr Asp Ala Ser Asn Leu Glu Thr Gly Val
65                  70                  75                  80

Pro Ser Arg Phe Ser Gly Ser Gly Ser Gly Thr Asp Phe Thr Phe Thr
                85                  90                  95

Ile Ser Ser Leu Gln Pro Glu Asp Ile Ala Thr Tyr Phe Cys Gln His
            100                 105                 110

Phe Asp His Leu Pro Leu Ala Phe Gly Gly Gly Thr Lys Val Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175
```

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 99
<211> LENGTH: 1392
<212> TYPE: DNA
<213> ORGANISM: Homo sapiens

<400> SEQUENCE: 99

| | |
|---|---|
| atgaaacacc tgtggttctt cctcctcctg gtggcagctc ccagatgggt cctgtcccag | 60 |
| gtacagctgc aggagtcggg cccaggactg gtgaagcctt cggagaccct gtccctcacc | 120 |
| tgcactgtct ctggtggctc cgtcagcagt ggtgattact actggacctg gatccggcag | 180 |
| tccccaggga agggactgga gtggattgga cacatctatt acagtgggaa caccaattat | 240 |
| aacccctccc tcaagagtcg actcaccata tcaattgaca cgtccaagac tcagttctcc | 300 |
| ctgaagctga gttctgtgac cgctgcggac acggccattt attactgtgt gcgagatcga | 360 |
| gtgactggtg cttttgatat ctggggccaa gggacaatgg tcaccgtctc ttcagctagc | 420 |
| accaagggcc catcggtctt ccccctggcg ccctgctcca ggagcacctc cgagagcaca | 480 |
| gcggccctgg gctgcctggt caaggactac ttccccgaac cggtgacggt gtcgtggaac | 540 |
| tcaggcgctc tgaccagcgg cgtgcacacc ttcccagctg tcctacagtc ctcaggactc | 600 |
| tactccctca gcagcgtggt gaccgtgccc tccagcaact tcggcaccca gacctacacc | 660 |
| tgcaacgtag atcacaagcc cagcaacacc aaggtggaca agacagttga gcgcaaatgt | 720 |
| tgtgtcgagt gcccaccgtg cccagcacca cctgtggcag accgtcagt cttcctcttc | 780 |
| cccccaaaac ccaaggacac cctcatgatc tcccggaccc ctgaggtcac gtgcgtggtg | 840 |
| gtggacgtga gccacgaaga ccccgaggtc cagttcaact ggtacgtgga cggcgtggag | 900 |
| gtgcataatg ccaagacaaa gccacgggag gagcagttca acagcacgtt ccgtgtggtc | 960 |
| agcgtcctca ccgttgtgca ccaggactgg ctgaacggca aggagtacaa gtgcaaggtc | 1020 |
| tccaacaaag gcctcccagc ccccatcgag aaaaccatct ccaaaaccaa agggcagccc | 1080 |
| cgagaaccac aggtgtacac cctgccccca tcccgggagg agatgaccaa gaaccaggtc | 1140 |
| agcctgacct gcctggtcaa aggcttctac cccagcgaca tcgccgtgga gtgggagagc | 1200 |
| aatgggcagc cggagaacaa ctacaagacc acacctccca tgctggactc cgacggctcc | 1260 |
| ttcttcctct acagcaagct caccgtggac aagagcaggt ggcagcaggg gaacgtcttc | 1320 |
| tcatgctccg tgatgcatga ggctctgcac aaccactaca cgcagaagag cctctccctg | 1380 |
| tctccgggta aa | 1392 |

<210> SEQ ID NO 100
<211> LENGTH: 464
<212> TYPE: PRT
<213> ORGANISM: Homo sapiens

<400> SEQUENCE: 100

Met Lys His Leu Trp Phe Phe Leu Leu Leu Val Ala Ala Pro Arg Trp
1               5                   10                  15

-continued

Val Leu Ser Gln Val Gln Leu Gln Glu Ser Gly Pro Gly Leu Val Lys
            20                  25                  30

Pro Ser Glu Thr Leu Ser Leu Thr Cys Thr Val Ser Gly Gly Ser Val
        35                  40                  45

Ser Ser Gly Asp Tyr Tyr Trp Thr Trp Ile Arg Gln Ser Pro Gly Lys
    50                  55                  60

Gly Leu Glu Trp Ile Gly His Ile Tyr Tyr Ser Gly Asn Thr Asn Tyr
65                  70                  75                  80

Asn Pro Ser Leu Lys Ser Arg Leu Thr Ile Ser Ile Asp Thr Ser Lys
                85                  90                  95

Thr Gln Phe Ser Leu Lys Leu Ser Ser Val Thr Ala Ala Asp Thr Ala
            100                 105                 110

Ile Tyr Tyr Cys Val Arg Asp Arg Val Thr Gly Ala Phe Asp Ile Trp
        115                 120                 125

Gly Gln Gly Thr Met Val Thr Val Ser Ser Ala Ser Thr Lys Gly Pro
    130                 135                 140

Ser Val Phe Pro Leu Ala Pro Cys Ser Arg Ser Thr Ser Glu Ser Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Asn Phe Gly Thr Gln Thr Tyr Thr Cys Asn Val Asp
    210                 215                 220

His Lys Pro Ser Asn Thr Lys Val Asp Lys Thr Val Glu Arg Lys Cys
225                 230                 235                 240

Cys Val Glu Cys Pro Pro Cys Pro Ala Pro Pro Val Ala Gly Pro Ser
                245                 250                 255

Val Phe Leu Phe Pro Pro Lys Pro Lys Asp Thr Leu Met Ile Ser Arg
            260                 265                 270

Thr Pro Glu Val Thr Cys Val Val Val Asp Val Ser His Glu Asp Pro
        275                 280                 285

Glu Val Gln Phe Asn Trp Tyr Val Asp Gly Val Glu Val His Asn Ala
    290                 295                 300

Lys Thr Lys Pro Arg Glu Glu Gln Phe Asn Ser Thr Phe Arg Val Val
305                 310                 315                 320

Ser Val Leu Thr Val Val His Gln Asp Trp Leu Asn Gly Lys Glu Tyr
                325                 330                 335

Lys Cys Lys Val Ser Asn Lys Gly Leu Pro Ala Pro Ile Glu Lys Thr
            340                 345                 350

Ile Ser Lys Thr Lys Gly Gln Pro Arg Glu Pro Gln Val Tyr Thr Leu
        355                 360                 365

Pro Pro Ser Arg Glu Glu Met Thr Lys Asn Gln Val Ser Leu Thr Cys
    370                 375                 380

Leu Val Lys Gly Phe Tyr Pro Ser Asp Ile Ala Val Glu Trp Glu Ser
385                 390                 395                 400

Asn Gly Gln Pro Glu Asn Asn Tyr Lys Thr Thr Pro Pro Met Leu Asp
                405                 410                 415

Ser Asp Gly Ser Phe Phe Leu Tyr Ser Lys Leu Thr Val Asp Lys Ser
            420                 425                 430

Arg Trp Gln Gln Gly Asn Val Phe Ser Cys Ser Val Met His Glu Ala 435                 440                 445
Leu His Asn His Tyr Thr Gln Lys Ser Leu Ser Leu Ser Pro Gly Lys
    450                 455                 460

<210> SEQ ID NO 101
<211> LENGTH: 708
<212> TYPE: DNA
<213> ORGANISM: Homo sapiens

<400> SEQUENCE: 101
atggaaaccc cagcgcagct tctcttcctc ctgctactct ggctcccaga taccgctagc    60
gaaattgtgt tgacgcagtc tccaggcacc ctgtctttgt ctccagggga aagagccacc   120
ctctcctgca gggccagtca gagtgttagc aacagctact tagcctggta ccagcagaaa   180
cctggccagg ctcccaggct cctcatctat ggtgcatcca gcagggcccc tggcatccca   240
gacaggttca gtggcagtgg gtctgggaca gacttcactc tcaccatcag cagactggag   300
cctgaagatt ttgcagtgta ttactgtcag cagtatgatc actcagcagg gtggacgttc   360
ggccaaggga ccaaggtgga gatcaaacgt acggtggctg caccatctgt cttcatcttc   420
ccgccatctg atgagcagtt gaaatctgga actgcctctg ttgtgtgcct gctgaataac   480
ttctatccca gagaggccaa agtacagtgg aaggtggata acgccctcca atcgggtaac   540
tcccaggaga gtgtcacaga gcaggacagc aaggacagca cctacagcct cagcagcacc   600
ctgacgctga gcaaagcaga ctacgagaaa cacaaagtct acgcctgcga agtcacccat   660
cagggcctga gctcgcccgt cacaaagagc ttcaacaggg gagagtgt              708

<210> SEQ ID NO 102
<211> LENGTH: 236
<212> TYPE: PRT
<213> ORGANISM: Homo sapiens

<400> SEQUENCE: 102

Met Glu Thr Pro Ala Gln Leu Leu Phe Leu Leu Leu Trp Leu Pro
1               5                   10                  15

Asp Thr Ala Ser Glu Ile Val Leu Thr Gln Ser Pro Gly Thr Leu Ser
            20                  25                  30

Leu Ser Pro Gly Glu Arg Ala Thr Leu Ser Cys Arg Ala Ser Gln Ser
        35                  40                  45

Val Ser Asn Ser Tyr Leu Ala Trp Tyr Gln Gln Lys Pro Gly Gln Ala
    50                  55                  60

Pro Arg Leu Leu Ile Tyr Gly Ala Ser Ser Arg Ala Pro Gly Ile Pro
65                  70                  75                  80

Asp Arg Phe Ser Gly Ser Gly Ser Gly Thr Asp Phe Thr Leu Thr Ile
                85                  90                  95

Ser Arg Leu Glu Pro Glu Asp Phe Ala Val Tyr Tyr Cys Gln Gln Tyr
            100                 105                 110

Asp His Ser Ala Gly Trp Thr Phe Gly Gln Gly Thr Lys Val Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp

```
                180                 185                 190
Ser Thr Tyr Ser Leu Ser Ser Thr Leu Thr Leu Ser Lys Ala Asp Tyr
            195                 200                 205

Glu Lys His Lys Val Tyr Ala Cys Glu Val Thr His Gln Gly Leu Ser
            210                 215                 220

Ser Pro Val Thr Lys Ser Phe Asn Arg Gly Glu Cys
225                 230                 235

<210> SEQ ID NO 103
<211> LENGTH: 1680
<212> TYPE: DNA
<213> ORGANISM: Homo sapiens

<400> SEQUENCE: 103
atggggtcaa ccgccatcct tggcctcctc ctggctgttc tccaaggagt cgctagcgag     60
gttcagctgg tggagtctgg gggaggcttg gtacagcctg ggggtccct gagactctcc    120 tgtgcagcct ctggattcac cttcagtaga aatgctatgt ctgggttcg ccaggctcca    180 ggaaaaggtc tggagtgggt atcaggtatt ggtactggtg gtgccacaag ctatgcagac    240
tccgtgaagg gccgattcac catctccaga gacaatgcca agaactcctt gtatcttcaa    300
atgaacagcc tgagagccga ggacacggct gtgtattact gtgcaagagg gaggtactac    360
ttcccgtggt ggggccaggg aaccctggtc accgtctcct cagcctccac caagggccca    420
tcggtcttcc ccctggcgcc ctgctccagg agcacctccg agagcacagc ggccctgggc    480
tgcctggtca aggactactt ccccgaaccg gtgacggtgt cgtggaactc aggcgctctg    540
accagcggcg tgcacacctt cccggctgtc ctacagtcct caggactcta ctccctcagc    600
agcgtggtga ccgtgccctc agcaacttc ggcacccaga cctacacctg caacgtagat    660
cacaagccca gcaacaccaa ggtggacaag acagttggtg agaggccagc tcagggaggg    720
agggtgtctg ctggaagcca ggctcagccc tcctgcctgg acgcaccccg gctgtgcagc    780
cccagcccag ggcagcaagg caggccccat ctgtctcctc accggaggc ctctgcccgc    840 cccactcatg ctcagggaga gggtcttctg cttttttcca ccaggctcca ggcaggcaca    900
ggctgggtgc ccctacccca gcccttcac acacaggggc aggtgcttgg ctcagacctg    960
ccaaaagcca tatccgggag gaccctgccc ctgaccgagc gcaaatgttg tgtcgagtgc   1020
ccaccgtgcc cagcaccacc tgtggcagga ccgtcagtct tcctcttccc cccaaaaccc   1080
aaggacaccc tcatgatctc ccggacccct gaggtcacgt gcgtggtggt ggacgtgagc   1140
cacgaagacc ccgaggtcca gttcaactgg tacgtggacg gcgtggaggt gcataatgcc   1200
aagacaaagc cacgggagga gcagttcaac agcacgttcc gtgtggtcag cgtcctcacc   1260
gtcgtgcacc aggactggct gaacggcaag gagtacaagt gcaaggtctc caacaaaggc   1320
ctcccagccc ccatcgagaa aaccatctcc aaaaccaaag gcagccccg agaaccacag   1380 gtgtacaccc tgcccccatc ccgggaggag atgaccaaga accaggtcag cctgacctgc   1440
ctggtcaaag gcttctaccc cagcgacatc gccgtggagt gggagagcaa tgggcagccg   1500
gagaacaact acaagaccac acctcccatg ctggactccg acggctcctt cttcctctac   1560
agcaagctca ccgtggacaa gagcaggtgg cagcagggga acgtcttctc atgctccgtg   1620
atgcatgagg ctctgcacaa ccactacacg cagaagagcc tctccctgtc tccgggtaaa   1680

<210> SEQ ID NO 104
<211> LENGTH: 460
<212> TYPE: PRT
```

<213> ORGANISM: Homo sapiens

<400> SEQUENCE: 104

Met Gly Ser Thr Ala Ile Leu Gly Leu Leu Ala Val Leu Gln Gly
1               5                   10                  15

Val Ala Ser Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Arg Asn Ala Met Phe Trp Val Arg Gln Ala Pro Gly Lys Gly Leu
    50                  55                  60

Glu Trp Val Ser Gly Ile Gly Thr Gly Gly Ala Thr Ser Tyr Ala Asp
65                  70                  75                  80

Ser Val Lys Gly Arg Phe Thr Ile Ser Arg Asp Asn Ala Lys Asn Ser
                85                  90                  95

Leu Tyr Leu Gln Met Asn Ser Leu Arg Ala Glu Asp Thr Ala Val Tyr
            100                 105                 110

Tyr Cys Ala Arg Gly Arg Tyr Tyr Phe Pro Trp Trp Gly Gln Gly Thr
        115                 120                 125

Leu Val Thr Val Ser Ser Ala Ser Thr Lys Gly Pro Ser Val Phe Pro
130                 135                 140

Leu Ala Pro Cys Ser Arg Ser Thr Ser Glu Ser Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205

Asn Phe Gly Thr Gln Thr Tyr Thr Cys Asn Val Asp His Lys Pro Ser
    210                 215                 220

Asn Thr Lys Val Asp Lys Thr Val Glu Arg Lys Cys Cys Val Glu Cys
225                 230                 235                 240

Pro Pro Cys Pro Ala Pro Pro Val Ala Gly Pro Ser Val Phe Leu Phe
                245                 250                 255

Pro Pro Lys Pro Lys Asp Thr Leu Met Ile Ser Arg Thr Pro Glu Val
            260                 265                 270

Thr Cys Val Val Val Asp Val Ser His Glu Asp Pro Glu Val Gln Phe
        275                 280                 285

Asn Trp Tyr Val Asp Gly Val Glu Val His Asn Ala Lys Thr Lys Pro
    290                 295                 300

Arg Glu Glu Gln Phe Asn Ser Thr Phe Arg Val Val Ser Val Leu Thr
305                 310                 315                 320

Val Val His Gln Asp Trp Leu Asn Gly Lys Glu Tyr Lys Cys Lys Val
                325                 330                 335

Ser Asn Lys Gly Leu Pro Ala Pro Ile Glu Lys Thr Ile Ser Lys Thr
            340                 345                 350

Lys Gly Gln Pro Arg Glu Pro Gln Val Tyr Thr Leu Pro Pro Ser Arg
        355                 360                 365

Glu Glu Met Thr Lys Asn Gln Val Ser Leu Thr Cys Leu Val Lys Gly
    370                 375                 380

Phe Tyr Pro Ser Asp Ile Ala Val Glu Trp Glu Ser Asn Gly Gln Pro
385                 390                 395                 400

```
Glu Asn Asn Tyr Lys Thr Thr Pro Pro Met Leu Asp Ser Asp Gly Ser
            405                 410                 415

Phe Phe Leu Tyr Ser Lys Leu Thr Val Asp Lys Ser Arg Trp Gln Gln
        420                 425                 430

Gly Asn Val Phe Ser Cys Ser Val Met His Glu Ala Leu His Asn His
        435                 440                 445

Tyr Thr Gln Lys Ser Leu Ser Leu Ser Pro Gly Lys
    450                 455                 460

<210> SEQ ID NO 105
<211> LENGTH: 702
<212> TYPE: DNA
<213> ORGANISM: Homo sapiens

<400> SEQUENCE: 105
atggaaaccc cagcgcagct tctcttcctc ctgctactct ggctcccaga taccaccgga      60
gaaattgtgt tgacgcagtc tccaggcacc ctgtctttgt ctccagggga aagagccacc     120
ctctcctgca gggccagtca gagtgttagc agcagctact tagcctggta ccagcagaaa     180
cctggccagg ctcccaggct cctcatctat ggtgcatccc gcagggccac tggcatccca     240
gacaggttca gtggcagtgg gtctgggaca gacttcactc tcaccatcag cagactggag     300
cctgaagatt ttgcagtgta ttactgtcag cggtatggta gctcacacac ttttggccag     360
gggaccaagc tggagatcag ccgaactgtg gctgcaccat ctgtcttcat cttcccgcca     420
tctgatgagc agttgaaatc tggaactgcc tctgttgtgt gcctgctgaa taacttctat     480
cccagagagg ccaaagtaca gtggaaggtg gataacgccc tccaatcggg taactcccag     540
gagagtgtca cagagcagga cagcaaggac agcacctaca gcctcagcag caccctgacg     600
ctgagcaaag cagactacga gaaacacaaa gtctacgcct gcgaagtcac ccatcagggc     660
ctgagctcgc ccgtcacaaa gagcttcaac aggggagagt gt                         702

<210> SEQ ID NO 106
<211> LENGTH: 234
<212> TYPE: PRT
<213> ORGANISM: Homo sapiens

<400> SEQUENCE: 106

Met Glu Thr Pro Ala Gln Leu Leu Phe Leu Leu Leu Trp Leu Pro
1               5                   10                  15

Asp Thr Thr Gly Glu Ile Val Leu Thr Gln Ser Pro Gly Thr Leu Ser
            20                  25                  30

Leu Ser Pro Gly Glu Arg Ala Thr Leu Ser Cys Arg Ala Ser Gln Ser
        35                  40                  45

Val Ser Ser Ser Tyr Leu Ala Trp Tyr Gln Gln Lys Pro Gly Gln Ala
    50                  55                  60

Pro Arg Leu Leu Ile Tyr Gly Ala Ser Arg Ala Thr Gly Ile Pro
65                  70                  75                  80

Asp Arg Phe Ser Gly Ser Gly Ser Gly Thr Asp Phe Thr Leu Thr Ile
                85                  90                  95

Ser Arg Leu Glu Pro Glu Asp Phe Ala Val Tyr Tyr Cys Gln Arg Tyr
            100                 105                 110

Gly Ser Ser His Thr Phe Gly Gln Gly Thr Lys Leu Glu Ile Ser Arg
        115                 120                 125

Thr Val Ala Ala Pro Ser Val Phe Ile Phe Pro Pro Ser Asp Glu Gln
    130                 135                 140
```

| Leu | Lys | Ser | Gly | Thr | Ala | Ser | Val | Val | Cys | Leu | Leu | Asn | Asn | Phe | Tyr |
|---|---|---|---|---|---|---|---|---|---|---|---|---|---|---|---|
| 145 | | | | 150 | | | | | 155 | | | | | | 160 |

| Pro | Arg | Glu | Ala | Lys | Val | Gln | Trp | Lys | Val | Asp | Asn | Ala | Leu | Gln | Ser |
|---|---|---|---|---|---|---|---|---|---|---|---|---|---|---|---|
| | | | | 165 | | | | | 170 | | | | | 175 | |

| Gly | Asn | Ser | Gln | Glu | Ser | Val | Thr | Glu | Gln | Asp | Ser | Lys | Asp | Ser | Thr |
|---|---|---|---|---|---|---|---|---|---|---|---|---|---|---|---|
| | | | 180 | | | | | 185 | | | | | 190 | | |

| Tyr | Ser | Leu | Ser | Ser | Thr | Leu | Thr | Leu | Ser | Lys | Ala | Asp | Tyr | Glu | Lys |
|---|---|---|---|---|---|---|---|---|---|---|---|---|---|---|---|
| | | | 195 | | | | | 200 | | | | | 205 | | |

| His | Lys | Val | Tyr | Ala | Cys | Glu | Val | Thr | His | Gln | Gly | Leu | Ser | Ser | Pro |
|---|---|---|---|---|---|---|---|---|---|---|---|---|---|---|---|
| | 210 | | | | | 215 | | | | | 220 | | | | |

| Val | Thr | Lys | Ser | Phe | Asn | Arg | Gly | Glu | Cys |
|---|---|---|---|---|---|---|---|---|---|
| 225 | | | | | 230 | | | | |

<210> SEQ ID NO 107
<211> LENGTH: 1401
<212> TYPE: DNA
<213> ORGANISM: Homo sapiens

<400> SEQUENCE: 107

| | | | | | |
|---|---|---|---|---|---|
| atggggtcaa | ccgccatcct | cgccctcctc | ctggctgttc | tccaaggagt | ctgtgccgag | 60 |
| gtgcagctgg | tgcagtctgg | agcagaggtg | aaaaagcccg | gggagtctct | gaagatctcc | 120 |
| tgtaaggttt | ctggatactt | ctttaccacc | tactggatcg | gctgggtgcg | ccagatgccc | 180 |
| gggaaaggcc | tggagtatat | ggggatcatc | tatcctggtg | actctgatac | cagatacagc | 240 |
| ccgtccttcc | aaggccaggt | caccatctca | gccgacaagt | ccatcagcac | cgcctacctg | 300 |
| cagtggagca | gcctgaaggc | ctcggacacc | gccatgtatt | actgtgcgag | aggggggtaac | 360 |
| tggaactgct | ttgactactg | gggccaggga | accctggtca | ccgtctcctc | agcctccacc | 420 |
| aagggcccat | cggtcttccc | cctggcaccc | tcctccaaga | gcacctctgg | ggcacagcg | 480 |
| gccctgggct | gcctggtcaa | ggactacttc | cccgaaccgg | tgacggtgtc | gtggaactca | 540 |
| ggcgccctga | ccagcggcgt | gcacaccttc | ccggctgtcc | tacagtcctc | aggactctac | 600 |
| tccctcagca | gcgtggtgac | cgtgccctcc | agcagcttgg | gcacccagac | ctacatctgc | 660 |
| aacgtgaatc | acaagcccag | caacaccaag | gtggacaaga | gagttgagcc | caaatcttgt | 720 |
| gacaaaactc | acacatgccc | accgtgccca | gcacctgaac | tcctgggggg | accgtcagtc | 780 |
| ttcctcttcc | ccccaaaacc | caaggacacc | ctcatgatct | cccggacccc | tgaggtcaca | 840 |
| tgcgtggtgg | tggacgtgag | ccacgaagac | cctgaggtca | agttcaactg | gtacgtggac | 900 |
| ggcgtggagg | tgcataatgc | caagacaaag | ccgcgggagg | agcagtacaa | cagcacgtac | 960 |
| cgtgtggtca | gcgtcctcac | cgtcctgcac | caggactggc | tgaatggcaa | ggagtacaag | 1020 |
| tgcaaggtct | ccaacaaagc | cctcccagcc | cccatcgaga | aaaccatctc | caaagccaaa | 1080 |
| gggcagcccc | gagaaccaca | ggtgtacacc | ctgcccccat | cccgggatga | gctgaccaag | 1140 |
| aaccaggtca | gcctgacctg | cctggtcaaa | ggcttctatc | ccagcgacat | cgccgtggag | 1200 |
| tgggagagca | atgggcagcc | ggagaacaac | tacaagacca | cgcctcccgt | gctggactcc | 1260 |
| gacggctcct | tcttcctcta | cagcaagctc | accgtggaca | agagcaggtg | gcagcagggg | 1320 |
| aacgtcttct | catgctccgt | gatgcatgag | gctctgcaca | accactacac | gcagaagagc | 1380 |
| ctctccctgt | ctccgggtaa | a | | | | 1401 |

<210> SEQ ID NO 108
<211> LENGTH: 467
<212> TYPE: PRT
<213> ORGANISM: Homo sapiens

<400> SEQUENCE: 108

Met Gly Ser Thr Ala Ile Leu Ala Leu Leu Ala Val Leu Gln Gly
1               5                   10                  15

Val Cys Ala Glu Val Gln Leu Val Gln Ser Gly Ala Glu Val Lys Lys
            20                  25                  30

Pro Gly Glu Ser Leu Lys Ile Ser Cys Lys Val Ser Gly Tyr Phe Phe
        35                  40                  45

Thr Thr Tyr Trp Ile Gly Trp Val Arg Gln Met Pro Gly Lys Gly Leu
    50                  55                  60

Glu Tyr Met Gly Ile Ile Tyr Pro Gly Asp Ser Asp Thr Arg Tyr Ser
65                  70                  75                  80

Pro Ser Phe Gln Gly Gln Val Thr Ile Ser Ala Asp Lys Ser Ile Ser
                85                  90                  95

Thr Ala Tyr Leu Gln Trp Ser Ser Leu Lys Ala Ser Asp Thr Ala Met
            100                 105                 110

Tyr Tyr Cys Ala Arg Gly Gly Asn Trp Asn Cys Phe Asp Tyr Trp Gly
        115                 120                 125

Gln Gly Thr Leu Val Thr Val Ser Ser Ala Ser Thr Lys Gly Pro Ser
130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Arg Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Asp Glu Leu Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro

```
                        405                 410                 415
Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
            435                 440                 445

His Glu Ala Leu His Asn His Tyr Thr Gln Lys Ser Leu Ser Leu Ser
            450                 455                 460

Pro Gly Lys
465

<210> SEQ ID NO 109
<211> LENGTH: 723
<212> TYPE: DNA
<213> ORGANISM: Homo sapiens

<400> SEQUENCE: 109
atggacatga gggtgcccgc tcagctcctg gggctcctgc tgctgtggct gagaggtgcc      60
agatgtgatg ttgtgatgac tcagtctcca ctctccctgc ccgtcacccc tggagagccg     120
gcctccatct cctgcaggtc tagtcagagc ctcctgcata gtaatggata caactatttg     180
gattggtacc tgcagaagcc agggcagtct ccacagctcc tgatctattt gggttctaat     240
cgggcctccg gggtccctga caggttcagt ggcagtggat caggcacaga ttttacactg     300
aaaatcagca gggtggaggc tgaggatgtt gggctttatt actgcatgca aggtacacac     360
tggcctctga cgttcggcca agggaccaag gtggagatca aacgaactgt ggctgcacca     420
tctgtcttca tcttcccgcc atctgatgag cagttgaaat ctggaactgc ctctgttgtg     480
tgcctgctga ataacttcta tcccagagag gccaaagtac agtggaaggt ggataacgcc     540
ctccaatcgg gtaactccca ggagagtgtc acagagcagg acagcaagga cagcacctac     600
agcctcagca gcaccctgac gctgagcaaa gcagactacg agaaacacaa agtctacgcc     660
tgcgaagtca cccatcaggg cctgagctcg cccgtcacaa agagcttcaa caggggagag     720
tgt                                                                    723

<210> SEQ ID NO 110
<211> LENGTH: 241
<212> TYPE: PRT
<213> ORGANISM: Homo sapiens

<400> SEQUENCE: 110

Met Asp Met Arg Val Pro Ala Gln Leu Leu Gly Leu Leu Leu Leu Trp
1               5                   10                  15

Leu Arg Gly Ala Arg Cys Asp Val Val Met Thr Gln Ser Pro Leu Ser
            20                  25                  30

Leu Pro Val Thr Pro Gly Glu Pro Ala Ser Ile Ser Cys Arg Ser Ser
            35                  40                  45

Gln Ser Leu Leu His Ser Asn Gly Tyr Asn Tyr Leu Asp Trp Tyr Leu
        50                  55                  60

Gln Lys Pro Gly Gln Ser Pro Gln Leu Leu Ile Tyr Leu Gly Ser Asn
65                  70                  75                  80

Arg Ala Ser Gly Val Pro Asp Arg Phe Ser Gly Ser Gly Ser Gly Thr
                85                  90                  95

Asp Phe Thr Leu Lys Ile Ser Arg Val Glu Ala Glu Asp Val Gly Val
            100                 105                 110

Tyr Tyr Cys Met Gln Gly Thr His Trp Pro Leu Thr Phe Gly Gln Gly
            115                 120                 125
```

```
Thr Lys Val Glu Ile Lys Arg Thr Val Ala Ala Pro Ser Val Phe Ile
    130                 135                 140
Phe Pro Pro Ser Asp Glu Gln Leu Lys Ser Gly Thr Ala Ser Val Val
145                 150                 155                 160
Cys Leu Leu Asn Asn Phe Tyr Pro Arg Glu Ala Lys Val Gln Trp Lys
                165                 170                 175
Val Asp Asn Ala Leu Gln Ser Gly Asn Ser Gln Glu Ser Val Thr Glu
            180                 185                 190
Gln Asp Ser Lys Asp Ser Thr Tyr Ser Leu Ser Ser Thr Leu Thr Leu
        195                 200                 205
Ser Lys Ala Asp Tyr Glu Lys His Lys Val Tyr Ala Cys Glu Val Thr
    210                 215                 220
His Gln Gly Leu Ser Ser Pro Val Thr Lys Ser Phe Asn Arg Gly Glu
225                 230                 235                 240
Cys
```

<210> SEQ ID NO 111
<211> LENGTH: 1413
<212> TYPE: DNA
<213> ORGANISM: Homo sapiens

<400> SEQUENCE: 111

```
atggacatga gggtgcccgc tcagctcctg gggctcctgc tgctgtggct gagaggtgcc      60
agatgtcagg tgcagctgca ggagtcgggc ccaggactgg tgaagccttc ggggaccctg     120
tccctcacct gcgctgtctc tggtggctcc atcagcagta gtaactggtg gagttgggtc     180
cgccagcccc cagggaaggg gctggagtgg attggggaaa tctatcatag tgggagcacc     240
aactacaacc cgtccctcaa gagtcgagtc accatatcag tagacaagtc caagaaccag     300
ttctccctga agctgagctc tgtgaccgcc gcggacacgg ccgtgtatta ctgtgcgaga     360
tggaccgggc gtactgatgc ttttgatatc tggggccaag ggacaatggt caccgtctct     420
agtgcctcca ccaagggccc atcggtcttc ccctggcac cctcctccaa gagcacctct     480
gggggcacag cggccctggg ctgcctggtc aaggactact ccccgaacc ggtgacggtg     540
tcgtggaact caggcgccct gaccagcggc gtgcacacct tcccggctgt cctacagtcc     600
tcaggactct actccctcag cagcgtggtg accgtgccct ccagcagctt gggcacccag     660
acctacatct gcaacgtgaa tcacaagccc agcaacacca aggtggacaa gaaagttgag     720
cccaaatctt gtgacaaaac tcacacatgc ccaccgtgcc cagcacctga actcctgggg     780
ggaccgtcag tcttcctctt ccccccaaaa cccaaggaca ccctcatgat ctcccggacc     840
cctgaggtca catgcgtggt ggtggacgtg agccacgaag accctgaggt caagttcaac     900
tggtacgtgg acggcgtgga ggtgcataat gccaagacaa agccgcggga ggagcagtac     960
aacagcacgt accgtgtggt cagcgtcctc accgtcctgc accaggactg gctgaatggc    1020
aaggagtaca agtgcaaggt ctccaacaaa gccctcccag cccccatcga gaaaaccatc    1080
tccaaagcca aagggcagcc ccgagaacca caggtgtaca ccctgccccc atcccgggat    1140
gagctgacca agaaccaggt cagcctgacc tgcctggtca aaggcttcta tcccagcgac    1200
atcgccgtgg agtgggagag caatgggcag ccggagaaca actacaagac cacgcctccc    1260
gtgctggact ccgacggctc cttcttcctc tatagcaagc tcaccgtgga caagagcagg    1320
tggcagcagg ggaacgtctt ctcatgctcc gtgatgcatg aggctctgca caaccactac    1380
acgcagaaga gcctctccct gtctccgggt aaa                                 1413
```

<210> SEQ ID NO 112
<211> LENGTH: 471
<212> TYPE: PRT
<213> ORGANISM: Homo sapiens

<400> SEQUENCE: 112

Met Asp Met Arg Val Pro Ala Gln Leu Leu Gly Leu Leu Leu Leu Trp
1               5                   10                  15

Leu Arg Gly Ala Arg Cys Gln Val Gln Leu Gln Glu Ser Gly Pro Gly
            20                  25                  30

Leu Val Lys Pro Ser Gly Thr Leu Ser Leu Thr Cys Ala Val Ser Gly
        35                  40                  45

Gly Ser Ile Ser Ser Ser Asn Trp Trp Ser Trp Val Arg Gln Pro Pro
    50                  55                  60

Gly Lys Gly Leu Glu Trp Ile Gly Glu Ile Tyr His Ser Gly Ser Thr
65                  70                  75                  80

Asn Tyr Asn Pro Ser Leu Lys Ser Arg Val Thr Ile Ser Val Asp Lys
                85                  90                  95

Ser Lys Asn Gln Phe Ser Leu Lys Leu Ser Ser Val Thr Ala Ala Asp
            100                 105                 110

Thr Ala Val Tyr Tyr Cys Ala Arg Trp Thr Gly Arg Thr Asp Ala Phe
        115                 120                 125

Asp Ile Trp Gly Gln Gly Thr Met Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Lys Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Asp Glu Leu Thr Lys

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
    450                 455                 460

Leu Ser Leu Ser Pro Gly Lys
465             470

<210> SEQ ID NO 113
<211> LENGTH: 702
<212> TYPE: DNA
<213> ORGANISM: Homo sapiens

<400> SEQUENCE: 113
atggaagcgc cggcgcagct tctcttcctc ctgctactct ggctcccaga taccactgga      60
gaaatagtga tgacgcagtc tccagccacc ctgtctgtgt ctcctgggga agagccacc     120 ctctcctgca gggccagtca gagtgttagc agcaacttag cctggttcca gcagaaacct     180
ggccaggctc ccaggcccct catctatgat gcatccacca gggccactgg tgtcccagcc     240
aggttcagtg gcagtgggtc tgggacagac ttcactctca ccatcagcag cctgcagtct     300
gaagattttg cagtttatta ctgtcagcag tatgataact ggccgctcac tttcggcgga     360
gggaccaagg tggagatcaa acgtacggtg gctgcaccat ctgtcttcat cttcccgcca     420
tctgatgagc agttgaaatc tggaactgcc tctgttgtgt gcctgctgaa taacttctat     480
cccagagagg ccaaagtaca gtggaaggtg gataacgccc tccaatcggg taactcccag     540
gagagtgtca cagagcagga cagcaaggac agcacctaca gcctcagcag caccctgacg     600
ctgagcaaag cagactacga aaacacaaa gtctacgcct gcgaagtcac ccatcagggc     660
ctgagctcgc ccgtcacaaa gagcttcaac aggggagagt gt                         702

<210> SEQ ID NO 114
<211> LENGTH: 234
<212> TYPE: PRT
<213> ORGANISM: Homo sapiens

<400> SEQUENCE: 114

Met Glu Ala Pro Ala Gln Leu Leu Phe Leu Leu Leu Leu Trp Leu Pro
1               5                   10                  15

Asp Thr Thr Gly Glu Ile Val Met Thr Gln Ser Pro Ala Thr Leu Ser
            20                  25                  30

Val Ser Pro Gly Glu Arg Ala Thr Leu Ser Cys Arg Ala Ser Gln Ser
        35                  40                  45

Val Ser Ser Asn Leu Ala Trp Phe Gln Gln Lys Pro Gly Gln Ala Pro
    50                  55                  60

Arg Pro Leu Ile Tyr Asp Ala Ser Thr Arg Ala Thr Gly Val Pro Ala
65                  70                  75                  80

Arg Phe Ser Gly Ser Gly Ser Gly Thr Asp Phe Thr Leu Thr Ile Ser
                85                  90                  95

Ser Leu Gln Ser Glu Asp Phe Ala Val Tyr Tyr Cys Gln Gln Tyr Asp

|     | 100 |     |     |     | 105 |     |     |     | 110 |     |     |
| --- | --- | --- | --- | --- | --- | --- | --- | --- | --- | --- | --- |
| Asn | Trp | Pro | Leu | Thr | Phe | Gly | Gly | Thr | Lys | Val | Glu | Ile | Lys | Arg |

Thr Val Ala Ala Pro Ser Val Phe Ile Phe Pro Ser Asp Glu Gln
    130                    135                    140

Leu Lys Ser Gly Thr Ala Ser Val Val Cys Leu Leu Asn Asn Phe Tyr
145                    150                    155                    160

Pro Arg Glu Ala Lys Val Gln Trp Lys Val Asp Asn Ala Leu Gln Ser
                165                    170                    175

Gly Asn Ser Gln Glu Ser Val Thr Glu Gln Asp Ser Lys Asp Ser Thr
                180                    185                    190

Tyr Ser Leu Ser Ser Thr Leu Thr Leu Ser Lys Ala Asp Tyr Glu Lys
    195                  200                    205

His Lys Val Tyr Ala Cys Glu Val Thr His Gln Gly Leu Ser Ser Pro
    210                  215                    220

Val Thr Lys Ser Phe Asn Arg Gly Glu Cys
225                  230

<210> SEQ ID NO 115
<211> LENGTH: 1383
<212> TYPE: DNA
<213> ORGANISM: Homo sapiens

<400> SEQUENCE: 115

```
atggagtgga cctggagggt ccttttcttg gtggcagcag caacaggtgc ccactcccag     60
gttcagctgg tgcagtctgg agctgaggtg aagaagcctg ggcctcagt gaaggtctcc    120
tgcaaggctt ctggttacac ctttaccaga tatggtatca gctgggtgcg acaggcccct    180
ggacaagggc ttgagtggat gggatggatc agcacttaca gtggtaacac aaactatgca    240
cagaagctcc agggcagagt caccatgacc acagacacat ccacgagcac agcctacatg    300
gagctgagga gcctgagatc tgacgacacg gccgtgtatt actgtgcgag acggcagctt    360
tactttgact actggggcca gggaaccctg gtcaccgtct cctcagctag caccaagggc    420
ccatcggtct tccccctggc gccctgctcc aggagcacct ccgagagcac agcggccctg    480
ggctgcctgg tcaaggacta cttccccgaa ccggtgacgg tgtcgtggaa ctcaggcgct    540
ctgaccagcg gcgtgcacac cttcccagct gtcctacagt cctcaggact ctactccctc    600
agcagcgtgg tgaccgtgcc ctccagcaac ttcggcaccc agacctacac ctgcaacgta    660
gatcacaagc ccagcaacac caaggtggac aagacagttg agcgcaaatg ttgtgtcgag    720
tgcccaccgt gcccagcacc acctgtggca ggaccgtcag tcttcctctt ccccccaaaa    780
cccaaggaca ccctcatgat ctcccggacc cctgaggtca cgtgcgtggt ggtggacgtg    840
agccacgaag accccgaggt ccagttcaac tggtacgtgg acggcgtgga ggtgcataat    900
gccaagacaa agccacggga ggagcagttc aacagcacgt tccgtgtggt cagcgtcctc    960
accgttgtgc accaggactg gctgaacggc aaggagtaca agtgcaaggt ctccaacaaa   1020
ggcctcccag cccccatcga gaaaaccatc tccaaaacca agggcagcc cgagaaccca   1080
caggtgtaca ccctgccccc atcccgggag gagatgacca gaaccaggt cagcctgacc   1140
tgcctggtca aaggcttcta ccccagcgac atcgccgtgg agtgggagag caatgggcag   1200
ccggagaaca actacaagac cacacctccc atgctggact ccgacggctc cttcttcctc   1260
tacagcaagc tcaccgtgga caagagcagg tggcagcagg ggaacgtctt ctcatgctcc   1320
gtgatgcatg aggctctgca caaccactac acgcagaaga gcctctccct gtctccgggt   1380
```

<210> SEQ ID NO 116
<211> LENGTH: 461
<212> TYPE: PRT
<213> ORGANISM: Homo sapiens

<400> SEQUENCE: 116

```
Met Glu Trp Thr Trp Arg Val Leu Phe Leu Val Ala Ala Ala Thr Gly
1               5                   10                  15

Ala His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Arg Tyr Gly Ile Ser Trp Val Arg Gln Ala Pro Gly Gln Gly Leu
    50                  55                  60

Glu Trp Met Gly Trp Ile Ser Thr Tyr Ser Gly Asn Thr Asn Tyr Ala
65                  70                  75                  80

Gln Lys Leu Gln Gly Arg Val Thr Met Thr Thr Asp Thr Ser Thr Ser
                85                  90                  95

Thr Ala Tyr Met Glu Leu Arg Ser Leu Arg Ser Asp Asp Thr Ala Val
            100                 105                 110

Tyr Tyr Cys Ala Arg Arg Gln Leu Tyr Phe Asp Tyr Trp Gly Gln Gly
        115                 120                 125

Thr Leu Val Thr Val Ser Ser Ala Ser Thr Lys Gly Pro Ser Val Phe
    130                 135                 140

Pro Leu Ala Pro Cys Ser Arg Ser Thr Ser Glu Ser Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
        195                 200                 205

Ser Asn Phe Gly Thr Gln Thr Tyr Thr Cys Asn Val Asp His Lys Pro
    210                 215                 220

Ser Asn Thr Lys Val Asp Lys Thr Val Glu Arg Lys Cys Cys Val Glu
225                 230                 235                 240

Cys Pro Pro Cys Pro Ala Pro Pro Val Ala Gly Pro Ser Val Phe Leu
                245                 250                 255

Phe Pro Pro Lys Pro Lys Asp Thr Leu Met Ile Ser Arg Thr Pro Glu
            260                 265                 270

Val Thr Cys Val Val Asp Val Ser His Glu Asp Pro Glu Val Gln
        275                 280                 285

Phe Asn Trp Tyr Val Asp Gly Val Glu Val His Asn Ala Lys Thr Lys
    290                 295                 300

Pro Arg Glu Glu Gln Phe Asn Ser Thr Phe Arg Val Val Ser Val Leu
305                 310                 315                 320

Thr Val Val His Gln Asp Trp Leu Asn Gly Lys Glu Tyr Lys Cys Lys
                325                 330                 335

Val Ser Asn Lys Gly Leu Pro Ala Pro Ile Glu Lys Thr Ile Ser Lys
            340                 345                 350

Thr Lys Gly Gln Pro Arg Glu Pro Gln Val Tyr Thr Leu Pro Pro Ser
        355                 360                 365
```

Arg Glu Glu Met Thr Lys Asn Gln Val Ser Leu Thr Cys Leu Val Lys
    370                 375                 380

Gly Phe Tyr Pro Ser Asp Ile Ala Val Glu Trp Glu Ser Asn Gly Gln
385                 390                 395                 400

Pro Glu Asn Asn Tyr Lys Thr Thr Pro Pro Met Leu Asp Ser Asp Gly
                405                 410                 415

Ser Phe Phe Leu Tyr Ser Lys Leu Thr Val Asp Lys Ser Arg Trp Gln
            420                 425                 430

Gln Gly Asn Val Phe Ser Cys Ser Val Met His Glu Ala Leu His Asn
        435                 440                 445

His Tyr Thr Gln Lys Ser Leu Ser Leu Ser Pro Gly Lys
    450                 455                 460

<210> SEQ ID NO 117
<211> LENGTH: 717
<212> TYPE: DNA
<213> ORGANISM: Homo sapiens

<400> SEQUENCE: 117
atgaggctcc ctgctcagct cctggggctg ctaatgctct ggatacctgg atccagtgca     60
gatattgtga tgacccagac tccactctct ctgtccgtca cccctggaca gccggcctcc    120
atctcctgca gtctggtca gagcctcctg catagtgatg gaaagaccta tttgtattgg    180
tacctgcaga agccaggcca gcctccacag ttcctgatct atgaagtttc caaccggttc    240
tctagagtgc cagataggtt cagtggcagc gggtcaggga cagatttcac actgagaatc    300
agccgggtgg aggctgagga tgttggaatt tattactgca tgcaaagtat acagcttccg    360
tggacgttcg gccaagggac ccaggtggaa atcaaacgaa ctgtggctgc accatctgtc    420
ttcatcttcc cgccatctga tgagcagttg aaatctggaa ctgcctctgt tgtgtgcctg    480
ctgaataact tctatcccag agaggccaaa gtacagtgga aggtggataa cgccctccaa    540
tcgggtaact cccaggagag tgtcacagag caggacagca aggacagcac ctacagcctc    600
agcagcaccc tgacgctgag caaagcagac tacgagaaac acaaagtcta cgcctgcgaa    660
gtcacccatc agggcctgag ctcgcccgtc acaaagagct tcaacagggg agagtgt       717

<210> SEQ ID NO 118
<211> LENGTH: 239
<212> TYPE: PRT
<213> ORGANISM: Homo sapiens

<400> SEQUENCE: 118

Met Arg Leu Pro Ala Gln Leu Leu Gly Leu Leu Met Leu Trp Ile Pro
1               5                   10                  15

Gly Ser Ser Ala Asp Ile Val Met Thr Gln Thr Pro Leu Ser Leu Ser
            20                  25                  30

Val Thr Pro Gly Gln Pro Ala Ser Ile Ser Cys Lys Ser Gly Gln Ser
        35                  40                  45

Leu Leu His Ser Asp Gly Lys Thr Tyr Leu Tyr Trp Tyr Leu Gln Lys
    50                  55                  60

Pro Gly Gln Pro Pro Gln Phe Leu Ile Tyr Glu Val Ser Asn Arg Phe
65                  70                  75                  80

Ser Arg Val Pro Asp Arg Phe Ser Gly Ser Gly Ser Gly Thr Asp Phe
                85                  90                  95

Thr Leu Arg Ile Ser Arg Val Glu Ala Glu Asp Val Gly Ile Tyr Tyr
            100                 105                 110

```
Cys Met Gln Ser Ile Gln Leu Pro Trp Thr Phe Gly Gln Gly Thr Gln
            115                 120                 125
Val Glu Ile Lys Arg Thr Val Ala Ala Pro Ser Val Phe Ile Phe Pro
    130                 135                 140
Pro Ser Asp Glu Gln Leu Lys Ser Gly Thr Ala Ser Val Val Cys Leu
145                 150                 155                 160
Leu Asn Asn Phe Tyr Pro Arg Glu Ala Lys Val Gln Trp Lys Val Asp
                165                 170                 175
Asn Ala Leu Gln Ser Gly Asn Ser Gln Glu Ser Val Thr Glu Gln Asp
            180                 185                 190
Ser Lys Asp Ser Thr Tyr Ser Leu Ser Ser Thr Leu Thr Leu Ser Lys
        195                 200                 205
Ala Asp Tyr Glu Lys His Lys Val Tyr Ala Cys Glu Val Thr His Gln
    210                 215                 220
Gly Leu Ser Ser Pro Val Thr Lys Ser Phe Asn Arg Gly Glu Cys
225                 230                 235
```

<210> SEQ ID NO 119
<211> LENGTH: 1377
<212> TYPE: DNA
<213> ORGANISM: Homo sapiens

<400> SEQUENCE: 119

| | | |
|---|---|---|
| atggagtttg ggctgagctg ggttttcctc gttgctcttt taagaggtgt ccagtgtcag | 60 |
| gtgcagctgg tggagtctgg gggaggcgtg gtccagcctg gaggtccct gagactctcc | 120 |
| tgtgcagcct ctggattcac cttcagtggc tatggcatgc actgggtccg ccaggctcca | 180 |
| ggcaaggggc tggagtgggt ggcagttata tcatatgatg gaaatgataa atactatgca | 240 |
| gactccgtga agggccgatt caccatctcc agagacaatg ccaagaacac gctgtatctg | 300 |
| caaatgaaca gcctgagagc tgaggacacg gctgtgtatt actgtgcgag agagctacgg | 360 |
| gtcctctggg gccagggaac cctggtcacc gtctctagtg cctccaccaa gggcccatcg | 420 |
| gtcttccccc tggcgccctg ctccaggagc acctccgaga gcacagcggc cctgggctgc | 480 |
| ctggtcaagg actacttccc cgaaccggtg acggtgtcgt ggaactcagg cgctctgacc | 540 |
| agcggcgtgc acaccttccc agctgtccta cagtcctcag gactctactc cctcagcagc | 600 |
| gtggtgaccg tgccctccag caacttcggc acccagacct acacctgcaa cgtagatcac | 660 |
| aagcccagca acaccaaggt ggacaagaca gttgagcgca aatgttgtgt cgagtgccca | 720 |
| ccgtgcccag caccacctgt ggcaggaccg tcagtcttcc tcttcccccc aaaacccaag | 780 |
| gacacccta tgatctcccg gacccctgag gtcacgtgcg tggtggtgga cgtgagccac | 840 |
| gaagaccccg aggtccagtt caactggtac gtggacggcg tggaggtgca taatgccaag | 900 |
| acaaagccac gggaggagca gttcaacagc acgttccgtg tggtcagcgt cctcaccgtt | 960 |
| gtgcaccagg actggctgaa cggcaaggag tacaagtgca aggtctccaa caaaggcctc | 1020 |
| ccagccccca tcgagaaaac catctccaaa accaaagggc agccccgaga accacaggtg | 1080 |
| tacacccgc cccatcccg ggaggagatg accaagaacc aggtcagcct gacctgcctg | 1140 |
| gtcaaaggct tctaccccag cgacatcgcc gtggagtggg agagcaatgg gcagccggag | 1200 |
| aacaactaca agaccacacc tcccatgctg gactccgacg gctccttctt cctctacagc | 1260 |
| aagctcaccg tggacaagag caggtggcag caggggaacg tcttctcatg ctccgtgatg | 1320 |
| catgaggctc tgcacaacca ctacacgcag aagagcctct ccctgtctcc gggtaaa | 1377 |

```
<210> SEQ ID NO 120
<211> LENGTH: 459
<212> TYPE: PRT
<213> ORGANISM: Homo sapiens

<400> SEQUENCE: 120

Met Glu Phe Gly Leu Ser Trp Val Phe Leu Val Ala Leu Leu Arg Gly
1               5                   10                  15

Val Gln Cys Gln Val Gln Leu Val Glu Ser Gly Gly Gly Val Val Gln
            20                  25                  30

Pro Gly Arg Ser Leu Arg Leu Ser Cys Ala Ala Ser Gly Phe Thr Phe
        35                  40                  45

Ser Gly Tyr Gly Met His Trp Val Arg Gln Ala Pro Gly Lys Gly Leu
    50                  55                  60

Glu Trp Val Ala Val Ile Ser Tyr Asp Gly Asn Asp Lys Tyr Tyr Ala
65                  70                  75                  80

Asp Ser Val Lys Gly Arg Phe Thr Ile Ser Arg Asp Asn Ala Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Glu Leu Arg Val Leu Trp Gly Gln Gly Thr Leu
        115                 120                 125

Val Thr Val Ser Ser Ala Ser Thr Lys Gly Pro Ser Val Phe Pro Leu
    130                 135                 140

Ala Pro Cys Ser Arg Ser Thr Ser Glu Ser Thr Ala Ala Leu Gly Cys
145                 150                 155                 160

Leu Val Lys Asp Tyr Phe Pro Glu Pro Val Thr Val Ser Trp Asn Ser
                165                 170                 175

Gly Ala Leu Thr Ser Gly Val His Thr Phe Pro Ala Val Leu Gln Ser
            180                 185                 190

Ser Gly Leu Tyr Ser Leu Ser Ser Val Val Thr Val Pro Ser Ser Asn
        195                 200                 205

Phe Gly Thr Gln Thr Tyr Thr Cys Asn Val Asp His Lys Pro Ser Asn
    210                 215                 220

Thr Lys Val Asp Lys Thr Val Glu Arg Lys Cys Cys Val Glu Cys Pro
225                 230                 235                 240

Pro Cys Pro Ala Pro Pro Val Ala Gly Pro Ser Val Phe Leu Phe Pro
                245                 250                 255

Pro Lys Pro Lys Asp Thr Leu Met Ile Ser Arg Thr Pro Glu Val Thr
            260                 265                 270

Cys Val Val Val Asp Val Ser His Glu Asp Pro Glu Val Gln Phe Asn
        275                 280                 285

Trp Tyr Val Asp Gly Val Glu Val His Asn Ala Lys Thr Lys Pro Arg
    290                 295                 300

Glu Glu Gln Phe Asn Ser Thr Phe Arg Val Val Ser Val Leu Thr Val
305                 310                 315                 320

Val His Gln Asp Trp Leu Asn Gly Lys Glu Tyr Lys Cys Lys Val Ser
                325                 330                 335

Asn Lys Gly Leu Pro Ala Pro Ile Glu Lys Thr Ile Ser Lys Thr Lys
            340                 345                 350

Gly Gln Pro Arg Glu Pro Gln Val Tyr Thr Leu Pro Pro Ser Arg Glu
        355                 360                 365

Glu Met Thr Lys Asn Gln Val Ser Leu Thr Cys Leu Val Lys Gly Phe
    370                 375                 380
```

```
Tyr Pro Ser Asp Ile Ala Val Glu Trp Glu Ser Asn Gly Gln Pro Glu
385                 390                 395                 400

Asn Asn Tyr Lys Thr Thr Pro Pro Met Leu Asp Ser Asp Gly Ser Phe
            405                 410                 415

Phe Leu Tyr Ser Lys Leu Thr Val Asp Lys Ser Arg Trp Gln Gln Gly
        420                 425                 430

Asn Val Phe Ser Cys Ser Val Met His Glu Ala Leu His Asn His Tyr
            435                 440                 445

Thr Gln Lys Ser Leu Ser Leu Ser Pro Gly Lys
        450                 455

<210> SEQ ID NO 121
<211> LENGTH: 705
<212> TYPE: DNA
<213> ORGANISM: Homo sapiens

<400> SEQUENCE: 121
atggacatga gggtgcccgc tcagctcctg gggctcctgc tgctgtggct gagaggtgcc      60
agatgtgaca tccagatgac ccagtctcca tcctccctgt ctgcatctgt aggtgaccgt     120
gtcaccatca cttgccgcgc aagtcaggat attagcagct atttaaattg gtatcagcag     180
aaaccaggga agcccctaa gctcctgatc tattctactt cccgtttgaa tagtggggtc      240
ccatcacgct tcagtggcag tggctctggg acagatttca ctctcaccat cagcagtctg     300
caacctgaag attttgcaac ttactactgt caacaggata ttaaacaccc tacgttcggt     360
caaggcacca aggtggagat caaacgtacg gtggctgcac catctgtctt catcttcccg     420
ccatctgatg agcagttgaa atctggaact gcctctgttg tgtgcctgct gaataacttc     480
tatcccagag aggccaaagt acagtggaag gtggataacg ccctccaatc gggtaactcc     540
caggagagtg tcacagagca ggacagcaag gacagcacct acagcctcag cagcaccctg     600
acgctgagca agcagactac gagaaacac aaagtctacg cctgcgaagt cacccatcag     660
ggcctgagct cgcccgtcac aaagagcttc aacaggggag agtgt                      705

<210> SEQ ID NO 122
<211> LENGTH: 235
<212> TYPE: PRT
<213> ORGANISM: Homo sapiens

<400> SEQUENCE: 122

Met Asp Met Arg Val Pro Ala Gln Leu Leu Gly Leu Leu Leu Leu Trp
1               5                   10                  15

Leu Arg Gly Ala Arg Cys Asp Ile Gln Met Thr Gln Ser Pro Ser Ser
            20                  25                  30

Leu Ser Ala Ser Val Gly Asp Arg Val Thr Ile Thr Cys Arg Ala Ser
        35                  40                  45

Gln Asp Ile Ser Ser Tyr Leu Asn Trp Tyr Gln Gln Lys Pro Gly Lys
    50                  55                  60

Ala Pro Lys Leu Leu Ile Tyr Ser Thr Ser Arg Leu Asn Ser Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Thr Tyr Tyr Cys Gln Gln
            100                 105                 110

Asp Ile Lys His Pro Thr Phe Gly Gln Gly Thr Lys Val Glu Ile Lys
        115                 120                 125
```

```
Arg Thr Val Ala Ala Pro Ser Val Phe Ile Phe Pro Pro Ser Asp Glu
            130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
            210                 215                 220

Pro Val Thr Lys Ser Phe Asn Arg Gly Glu Cys
225                 230                 235
```

<210> SEQ ID NO 123
<211> LENGTH: 1395
<212> TYPE: DNA
<213> ORGANISM: Homo sapiens

<400> SEQUENCE: 123

```
atggactgga cctggaggat cctcttcttg gtggcagcag ccacaggagc ccactccgag    60
gtgcagctgg tgcagtctgg ggctgaggtg aagaagcctg gtcctcggt gaaggtctcc   120
tgcaaggctt ctggttttac cttcaccgac tatattatgc actgggtgcg tcaggcccct   180
ggtcaagggc ttgagtggat gggctatatc aacccttata atgatgacac cgaatacaac   240
gagaagttca agggccgtgt cacgattacc gcggacaaat ccacgagcac agcctacatg   300
gagctgagca gcctgcgctc tgaggacacg gccgtgtatt actgtgcgcg ttcgatttat   360
tactacgatg cccgtttgc ttactggggc caagggactc tggtcaccgt ctctagtgcc   420
tccaccaagg gcccatcggt cttccccctg gcgccctgct ccaggagcac ctccgagagc   480
acagcggccc tgggctgcct ggtcaaggac tacttcccg aaccggtgac ggtgtcgtgg   540
aactcaggcg ctctgaccag cggcgtgcac accttcccag ctgtcctaca gtcctcagga   600
ctctactccc tcagcagcgt ggtgaccgtg ccctccagca acttcggcac ccagacctac   660
acctgcaacg tagatcacaa gcccagcaac accaaggtgg acaagacagt tgagcgcaaa   720
tgttgtgtcg agtgcccacc gtgcccagca ccacctgtgg caggaccgtc agtcttcctc   780
ttccccccaa aacccaagga caccctcatg atctcccgga cccctgaggt cacgtgcgtg   840
gtggtggacg tgagccacga agaccccgag gtccagttca actggtacgt ggacggcgtg   900
gaggtgcata atgccaagac aaagccacgg gaggagcagt tcaacagcac gttccgtgtg   960
gtcagcgtcc tcaccgttgt gcaccaggac tggctgaacg gcaaggagta caagtgcaag  1020
gtctccaaca aaggcctccc agcccccatc gagaaaacca tctccaaaac caagggcag  1080
ccccgagaac cacaggtgta caccctgccc ccatcccggg aggagatgac caagaaccag  1140
gtcagcctga cctgcctggt caaaggcttc taccccagcg acatcgccgt ggagtgggag  1200
agcaatgggc agccggagaa caactacaag accacacctc ccatgctgga ctccgacggc  1260
tccttcttcc tctacagcaa gctcaccgtg gacaagagca ggtggcagca ggggaacgtc  1320
ttctcatgct ccgtgatgca tgaggctctg cacaaccact acacgcagaa gagcctctcc  1380
ctgtctccgg gtaaa                                                    1395
```

<210> SEQ ID NO 124
<211> LENGTH: 465
<212> TYPE: PRT
<213> ORGANISM: Homo sapiens

<400> SEQUENCE: 124

Met Asp Trp Thr Trp Arg Ile Leu Phe Leu Val Ala Ala Thr Gly
1               5                   10                  15

Ala His Ser Glu Val Gln Leu Val Gln Ser Gly Ala Glu Val Lys Lys
            20                  25                  30

Pro Gly Ser Ser Val Lys Val Ser Cys Lys Ala Ser Gly Phe Thr Phe
        35                  40                  45

Thr Asp Tyr Ile Met His Trp Val Arg Gln Ala Pro Gly Gln Gly Leu
    50                  55                  60

Glu Trp Met Gly Tyr Ile Asn Pro Tyr Asn Asp Asp Thr Glu Tyr Asn
65                  70                  75                  80

Glu Lys Phe Lys Gly Arg Val Thr Ile Thr Ala Asp Lys Ser Thr Ser
                85                  90                  95

Thr Ala Tyr Met Glu Leu Ser Ser Leu Arg Ser Glu Asp Thr Ala Val
            100                 105                 110

Tyr Tyr Cys Ala Arg Ser Ile Tyr Tyr Tyr Asp Ala Pro Phe Ala Tyr
        115                 120                 125

Trp Gly Gln Gly Thr Leu Val Thr Val Ser Ser Ala Ser Thr Lys Gly
    130                 135                 140

Pro Ser Val Phe Pro Leu Ala Pro Cys Ser Arg Ser Thr Ser Glu Ser
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Asn Phe Gly Thr Gln Thr Tyr Thr Cys Asn Val
    210                 215                 220

Asp His Lys Pro Ser Asn Thr Lys Val Asp Lys Thr Val Glu Arg Lys
225                 230                 235                 240

Cys Cys Val Glu Cys Pro Pro Cys Pro Ala Pro Pro Val Ala Gly Pro
                245                 250                 255

Ser Val Phe Leu Phe Pro Pro Lys Pro Lys Asp Thr Leu Met Ile Ser
            260                 265                 270

Arg Thr Pro Glu Val Thr Cys Val Val Val Asp Val Ser His Glu Asp
        275                 280                 285

Pro Glu Val Gln Phe Asn Trp Tyr Val Asp Gly Val Glu Val His Asn
    290                 295                 300

Ala Lys Thr Lys Pro Arg Glu Glu Gln Phe Asn Ser Thr Phe Arg Val
305                 310                 315                 320

Val Ser Val Leu Thr Val Val His Gln Asp Trp Leu Asn Gly Lys Glu
                325                 330                 335

Tyr Lys Cys Lys Val Ser Asn Lys Gly Leu Pro Ala Pro Ile Glu Lys
            340                 345                 350

Thr Ile Ser Lys Thr Lys Gly Gln Pro Arg Glu Pro Gln Val Tyr Thr
        355                 360                 365

Leu Pro Pro Ser Arg Glu Glu Met Thr Lys Asn Gln Val Ser Leu Thr
    370                 375                 380

```
Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Met Leu
        405                 410                 415

Asp Ser Asp Gly Ser Phe Phe Leu Tyr Ser Lys Leu Thr Val Asp Lys
            420                 425                 430

Ser Arg Trp Gln Gln Gly Asn Val Phe Ser Cys Ser Val Met His Glu
        435                 440                 445

Ala Leu His Asn His Tyr Thr Gln Lys Ser Leu Ser Leu Ser Pro Gly
        450                 455                 460

Lys
465

<210> SEQ ID NO 125
<211> LENGTH: 699
<212> TYPE: DNA
<213> ORGANISM: Homo sapiens

<400> SEQUENCE: 125
atggggtcaa ccgccatcct tggcctcctc ctggctgtcc tgcagggagg gcgcgcctcc      60
tatgtgctga ctcagccacc ctcggtgtca gtggccccag acagacggc caggattacc     120 tgtgggggaa acaaccttgg aagtaaaagt gtgcactggt accagcagaa gccaggccag     180
gcccctgtgc tggtcgtcta tgatgatagc accggccct catggatccc tgagcgattc     240
tctggctcca actctgggaa cacggccacc ctgaccatca gcagggcga agccggggat     300 gaggccgact attactgtca ggtgtgggat agtagtagtg atcatgtggt attcggcgga     360
gggaccaagc tgaccgtcct aggccaaccg aaagcggcgc cctcggtcac tctgttcccg     420
ccctcctctg aggagcttca agccaacaag gccacactgg tgtgtctcat aagtgacttc     480
tacccgggag ccgtgacagt ggcctggaag gcagatagca gccccgtcaa ggcgggagtg     540
gagaccacca cacctccaa acaaagcaac aacaagtacg cggccagcag ctatctgagc     600
ctgacgcctg agcagtggaa gtcccacaga agctacagct gccaggtcac gcatgaaggg     660
agcaccgtgg agaagacagt ggcccctaca gaatgttca                            699

<210> SEQ ID NO 126
<211> LENGTH: 233
<212> TYPE: PRT
<213> ORGANISM: Homo sapiens

<400> SEQUENCE: 126

Met Gly Ser Thr Ala Ile Leu Gly Leu Leu Leu Ala Val Leu Gln Gly
1               5                   10                  15

Gly Arg Ala Ser Tyr Val Leu Thr Gln Pro Pro Ser Val Ser Val Ala
            20                  25                  30

Pro Gly Gln Thr Ala Arg Ile Thr Cys Gly Gly Asn Asn Leu Gly Ser
        35                  40                  45

Lys Ser Val His Trp Tyr Gln Gln Lys Pro Gly Gln Ala Pro Val Leu
    50                  55                  60

Val Val Tyr Asp Asp Ser Asp Arg Pro Ser Trp Ile Pro Glu Arg Phe
65                  70                  75                  80

Ser Gly Ser Asn Ser Gly Asn Thr Ala Thr Leu Thr Ile Ser Arg Gly
                85                  90                  95

Glu Ala Gly Asp Glu Ala Asp Tyr Tyr Cys Gln Val Trp Asp Ser Ser
            100                 105                 110
```

```
Ser Asp His Val Val Phe Gly Gly Thr Lys Leu Thr Val Leu Gly
            115                 120                 125

Gln Pro Lys Ala Ala Pro Ser Val Thr Leu Phe Pro Pro Ser Ser Glu
        130                 135                 140

Glu Leu Gln Ala Asn Lys Ala Thr Leu Val Cys Leu Ile Ser Asp Phe
145                 150                 155                 160

Tyr Pro Gly Ala Val Thr Val Ala Trp Lys Ala Asp Ser Ser Pro Val
                165                 170                 175

Lys Ala Gly Val Glu Thr Thr Thr Pro Ser Lys Gln Ser Asn Asn Lys
            180                 185                 190

Tyr Ala Ala Ser Ser Tyr Leu Ser Leu Thr Pro Glu Gln Trp Lys Ser
        195                 200                 205

His Arg Ser Tyr Ser Cys Gln Val Thr His Glu Gly Ser Thr Val Glu
    210                 215                 220

Lys Thr Val Ala Pro Thr Glu Cys Ser
225                 230
```

<210> SEQ ID NO 127
<211> LENGTH: 1401
<212> TYPE: DNA
<213> ORGANISM: Homo sapiens

<400> SEQUENCE: 127

```
atggggtcaa ccgccatcct tggcctcctc ctggctgtcc tgcagggagg gcgcgcccag      60
atgcagctgg tggagtctgg gggaggcgtg gtccagcctg gaggtccct gagactctcc      120
tgtgcagcgt ctggattcac cttcagaacc tatggcatgc actgggtccg ccaggctcca     180
ggcaagggac tggagtgggt ggcagttata tggtatgatg aagtaataa acactatgca     240
gactccgtga agggccgatt caccatcacc agagacaatt ccaagaacac tctgaatctg     300
caaatgaaca gcctgagagc cgaggacacg gctgtgtatt actgtgcgag agccccctcag    360
tgggagctag ttcatgaagc ttttgatatc tggggccaag gacaatggt caccgtctct      420
tcagctagca ccaagggccc atcggtcttc cccctggcgc cctgctccag gagcacctcc     480
gagagcacag cggccctggg ctgcctggtc aaggactact ccccgaacc ggtgacggtg      540
tcgtggaact caggcgctct gaccagcggc gtgcacacct tcccagctgt cctacagtcc    600
tcaggactct actccctcag cagcgtggtg accgtgccct ccagcaactt cggcacccag    660
acctacacct gcaacgtaga tcacaagccc agcaacacca aggtggacaa gacagttgag    720
cgcaaatgtt gtgtcgagtg cccaccgtgc ccagcaccac ctgtggcagg accgtcagtc    780
ttcctcttcc ccccaaaacc caaggacacc ctcatgatct cccggacccc tgaggtcacg    840
tgcgtggtgg tggacgtgag ccacgaagac cccgaggtcc agttcaactg gtacgtggac    900
ggcgtggagg tgcataatgc caagacaaag ccacgggagg agcagttcaa cagcacgttc     960
cgtgtggtca gcgtcctcac cgttgtgcac caggactggc tgaacggcaa ggagtacaag     1020
tgcaaggtct ccaacaaagg cctcccagcc cccatcgaga aaaccatctc caaaaccaaa     1080
gggcagcccc gagaaccaca ggtgtacacc ctgcccccat cccgggagga gatgaccaag     1140
aaccaggtca gcctgacctg cctggtcaaa ggcttctacc ccagcgacat cgccgtggag     1200
tgggagagca atgggcagcc ggagaacaac tacaagacca cacctcccat gctggactcc     1260
gacggctcct tcttcctcta cagcaagctc accgtggaca agagcaggtg gcagcagggg     1320
aacgtcttct catgctccgt gatgcatgag gctctgcaca accactacac gcagaagagc     1380
ctctccctgt ctccgggtaa a                                                1401
```

<210> SEQ ID NO 128
<211> LENGTH: 467
<212> TYPE: PRT
<213> ORGANISM: Homo sapiens

<400> SEQUENCE: 128

Met Gly Ser Thr Ala Ile Leu Gly Leu Leu Ala Val Leu Gln Gly
1               5                   10                  15

Gly Arg Ala Gln Met Gln Leu Val Glu Ser Gly Gly Val Val Gln
                20                  25                  30

Pro Gly Arg Ser Leu Arg Leu Ser Cys Ala Ala Ser Gly Phe Thr Phe
            35                  40                  45

Arg Thr Tyr Gly Met His Trp Val Arg Gln Ala Pro Gly Lys Gly Leu
        50                  55                  60

Glu Trp Val Ala Val Ile Trp Tyr Asp Gly Ser Asn Lys His Tyr Ala
65                  70                  75                  80

Asp Ser Val Lys Gly Arg Phe Thr Ile Thr Arg Asp Asn Ser Lys Asn
                85                  90                  95

Thr Leu Asn Leu Gln Met Asn Ser Leu Arg Ala Glu Asp Thr Ala Val
            100                 105                 110

Tyr Tyr Cys Ala Arg Ala Pro Gln Trp Glu Leu Val His Glu Ala Phe
        115                 120                 125

Asp Ile Trp Gly Gln Gly Thr Met Val Thr Val Ser Ser Ala Ser Thr
130                 135                 140

Lys Gly Pro Ser Val Phe Pro Leu Ala Pro Cys Ser Arg Ser Thr Ser
145                 150                 155                 160

Glu Ser Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Asn Phe Gly Thr Gln Thr Tyr Thr Cys
210                 215                 220

Asn Val Asp His Lys Pro Ser Asn Thr Lys Val Asp Lys Thr Val Glu
225                 230                 235                 240

Arg Lys Cys Cys Val Glu Cys Pro Pro Cys Pro Ala Pro Pro Val Ala
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Gln Phe Asn Trp Tyr Val Asp Gly Val Glu Val
290                 295                 300

His Asn Ala Lys Thr Lys Pro Arg Glu Glu Gln Phe Asn Ser Thr Phe
305                 310                 315                 320

Arg Val Val Ser Val Leu Thr Val Val His Gln Asp Trp Leu Asn Gly
                325                 330                 335

Lys Glu Tyr Lys Cys Lys Val Ser Asn Lys Gly Leu Pro Ala Pro Ile
            340                 345                 350

Glu Lys Thr Ile Ser Lys Thr Lys Gly Gln Pro Arg Glu Pro Gln Val
        355                 360                 365

Tyr Thr Leu Pro Pro Ser Arg Glu Glu Met Thr Lys Asn Gln Val Ser

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
            405                 410                 415

Met Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
            435                 440                 445

His Glu Ala Leu His Asn His Tyr Thr Gln Lys Ser Leu Ser Leu Ser
    450                 455                 460

Pro Gly Lys
465

<210> SEQ ID NO 129
<211> LENGTH: 702
<212> TYPE: DNA
<213> ORGANISM: Homo sapiens

<400> SEQUENCE: 129
atgggtgtgc ctactcatct cctgggtttg ttgctgctct ggattacaca tgccatatgt        60
gatatccgga tgacacagtc tccagcttcc ctgtctgcat ctctgggaga aactgtcaac       120
atcgaatgtc tagcaagtga ggacatttac agtgatttag catggtatca gcagaagcca       180
gggaaatctc ctcagctcct gatctataat gcaaatagct tgcaaaatgg ggtcccttca       240
cggtttagtg gcagtggatc tggcacacag tattctctaa aaataaacag cctgcaatct       300
gaagatgtcg cgacttattt ctgtcaacaa tataacaatt atcctccgac gttcggtgga       360
ggcaccaagc tggaattgaa acgggctgat gctgcaccaa ctgtatctat cttcccacca       420
tccacggaac agttagcaac tggaggtgcc tcagtcgtgt gcctcatgaa caacttctat       480
cccagagaca tcagtgtcaa gtggaagatt gatggcactg aacgacgaga tggtgtcctg       540
gacagtgtta ctgatcagga cagcaaagac agcacgtaca gcatgagcag caccctctcg       600
ttgaccaagg ctgactatga aagtcataac ctctatacct gtgaggttgt tcataagaca       660
tcatcctcac ccgtcgtcaa gagcttcaac aggaatgagt gt                          702

<210> SEQ ID NO 130
<211> LENGTH: 234
<212> TYPE: PRT
<213> ORGANISM: Homo sapiens

<400> SEQUENCE: 130

Met Gly Val Pro Thr His Leu Leu Gly Leu Leu Leu Trp Ile Thr
1               5                   10                  15

His Ala Ile Cys Asp Ile Arg Met Thr Gln Ser Pro Ala Ser Leu Ser
            20                  25                  30

Ala Ser Leu Gly Glu Thr Val Asn Ile Glu Cys Leu Ala Ser Glu Asp
        35                  40                  45

Ile Tyr Ser Asp Leu Ala Trp Tyr Gln Gln Lys Pro Gly Lys Ser Pro
    50                  55                  60

Gln Leu Leu Ile Tyr Asn Ala Asn Ser Leu Gln Asn Gly Val Pro Ser
65                  70                  75                  80

Arg Phe Ser Gly Ser Gly Ser Gly Thr Gln Tyr Ser Leu Lys Ile Asn
                85                  90                  95

Ser Leu Gln Ser Glu Asp Val Ala Thr Tyr Phe Cys Gln Gln Tyr Asn

```
            100                 105                 110
Asn Tyr Pro Pro Thr Phe Gly Gly Thr Lys Leu Glu Leu Lys Arg
        115                 120                 125

Ala Asp Ala Ala Pro Thr Val Ser Ile Phe Pro Ser Thr Glu Gln
130                 135                 140

Leu Ala Thr Gly Gly Ala Ser Val Val Cys Leu Met Asn Asn Phe Tyr
145                 150                 155                 160

Pro Arg Asp Ile Ser Val Lys Trp Lys Ile Asp Gly Thr Glu Arg Arg
                165                 170                 175

Asp Gly Val Leu Asp Ser Val Thr Asp Gln Asp Ser Lys Asp Ser Thr
                180                 185                 190

Tyr Ser Met Ser Ser Thr Leu Ser Leu Thr Lys Ala Asp Tyr Glu Ser
                195                 200                 205

His Asn Leu Tyr Thr Cys Glu Val Val His Lys Thr Ser Ser Ser Pro
        210                 215                 220

Val Val Lys Ser Phe Asn Arg Asn Glu Cys
225                 230

<210> SEQ ID NO 131
<211> LENGTH: 1395
<212> TYPE: DNA
<213> ORGANISM: Homo sapiens

<400> SEQUENCE: 131
atggacatca ggctcagctt ggctttcctt gtccttttca taaaaggtgt ccagtgtgag    60
gtacagctgg tggagtctgg cggaggattg gtacagcctg caaactccct gaaactctcc   120
tgtgcagcct caggattcac tttcagtgac tatgccatgg cctgggtccg ccagtctcca   180
aagaagggtc tggagtgggt cgcaaccatt atttatgatg gtagtagcac ttactatcga   240
gactccgtga agggccgatt cactatctcc agagataatg caaaaagcac cctatacctg   300
caaatggaca gtctgaggtc tgaggacacg gccacttatt actgtgcaac aggtctgggt   360
atagctacgg actactttga ttactggggc caaggagtcc tggtcacagt ctcctcagct   420
gaaacaacag cccccatctgt ctatccactg gctcctggaa ctgctctcaa agtaactcc   480 atggtgaccc tgggatgcct ggtcaagggc tatttccctg agccagtcac cgtgacctgg   540
aactctggag ccctgtccag cggtgtgcac accttcccag ctgtcctgca gtctgggctc   600
tacactctca ccagctcagt gactgtaccc tccagcacct ggcccagcca gaccgtcacc   660
tgcaacgtag cccacccggc cagcagcacc aaggtggaca gaaaattgt gcccagaaac   720 tgtggaggtg attgcaagcc ttgtatatgt acaggctcag aagtatcatc tgtcttcatc   780
ttccccccaa agcccaaaga tgtgctcacc atcactctga ctcctaaggt cacgtgtgtt   840
gtggtagaca ttagccagga cgatcccgag gtccatttca gctggtttgt agatgacgtg   900
gaagtccaca cagctcagac tcgaccacca gaggagcagt tcaacagcac tttccgctca   960
gtcagtgaac tccccatcct gcaccaggac tggctcaatg gcaggacgtt cagatgcaag  1020
gtcaccagtg cagctttccc atcccccatc gagaaaacca tctccaaacc cgaaggcaga  1080
acacaagttc gcatgtata caccatgtca cctaccaagg aagagatgac ccagaatgaa  1140
gtcagtatca cctgcatggt aaaaggcttc tatcccccag acatttatgt ggagtggcag  1200
atgaacgggc agccacagga aaactacaag aacactccac ctacgatgga cacagatggg  1260
agttacttcc tctacagcaa gctcaatgtg aagaaggaaa atggcagca gggaaacacg  1320 ttcacgtgtt ctgtgctgca tgaaggcctg cacaaccacc atactgagaa gagtctctcc  1380
```
cactctccgg gtaaa                                                         1395

<210> SEQ ID NO 132
<211> LENGTH: 465
<212> TYPE: PRT
<213> ORGANISM: Homo sapiens

<400> SEQUENCE: 132

Met Asp Ile Arg Leu Ser Leu Ala Phe Leu Val Leu Phe Ile Lys Gly
1               5                   10                  15

Val Gln Cys Glu Val Gln Leu Val Glu Ser Gly Gly Gly Leu Val Gln
            20                  25                  30

Pro Ala Asn Ser Leu Lys Leu Ser Cys Ala Ala Ser Gly Phe Thr Phe
        35                  40                  45

Ser Asp Tyr Ala Met Ala Trp Val Arg Gln Ser Pro Lys Lys Gly Leu
    50                  55                  60

Glu Trp Val Ala Thr Ile Ile Tyr Asp Gly Ser Ser Thr Tyr Tyr Arg
65                  70                  75                  80

Asp Ser Val Lys Gly Arg Phe Thr Ile Ser Arg Asp Asn Ala Lys Ser
                85                  90                  95

Thr Leu Tyr Leu Gln Met Asp Ser Leu Arg Ser Glu Asp Thr Ala Thr
            100                 105                 110

Tyr Tyr Cys Ala Thr Gly Leu Gly Ile Ala Thr Asp Tyr Phe Asp Tyr
        115                 120                 125

Trp Gly Gln Gly Val Leu Val Thr Val Ser Ser Ala Glu Thr Thr Ala
    130                 135                 140

Pro Ser Val Tyr Pro Leu Ala Pro Gly Thr Ala Leu Lys Ser Asn Ser
145                 150                 155                 160

Met Val Thr Leu Gly Cys Leu Val Lys Gly Tyr Phe Pro Glu Pro Val
                165                 170                 175

Thr Val Thr Trp Asn Ser Gly Ala Leu Ser Ser Gly Val His Thr Phe
            180                 185                 190

Pro Ala Val Leu Gln Ser Gly Leu Tyr Thr Leu Thr Ser Ser Val Thr
        195                 200                 205

Val Pro Ser Ser Thr Trp Pro Ser Gln Thr Val Thr Cys Asn Val Ala
    210                 215                 220

His Pro Ala Ser Ser Thr Lys Val Asp Lys Lys Ile Val Pro Arg Asn
225                 230                 235                 240

Cys Gly Gly Asp Cys Lys Pro Cys Ile Cys Thr Gly Ser Glu Val Ser
                245                 250                 255

Ser Val Phe Ile Phe Pro Pro Lys Pro Lys Asp Val Leu Thr Ile Thr
            260                 265                 270

Leu Thr Pro Lys Val Thr Cys Val Val Asp Ile Ser Gln Asp Asp
        275                 280                 285

Pro Glu Val His Phe Ser Trp Phe Val Asp Val Glu Val His Thr
    290                 295                 300

Ala Gln Thr Arg Pro Pro Glu Glu Gln Phe Asn Ser Thr Phe Arg Ser
305                 310                 315                 320

Val Ser Glu Leu Pro Ile Leu His Gln Asp Trp Leu Asn Gly Arg Thr
                325                 330                 335

Phe Arg Cys Lys Val Thr Ser Ala Ala Phe Pro Ser Pro Ile Glu Lys
            340                 345                 350

Thr Ile Ser Lys Pro Glu Gly Arg Thr Gln Val Pro His Val Tyr Thr
        355                 360                 365

```
Met Ser Pro Thr Lys Glu Glu Met Thr Gln Asn Glu Val Ser Ile Thr
    370                 375                 380
Cys Met Val Lys Gly Phe Tyr Pro Pro Asp Ile Tyr Val Glu Trp Gln
385                 390                 395                 400
Met Asn Gly Gln Pro Gln Glu Asn Tyr Lys Asn Thr Pro Pro Thr Met
                405                 410                 415
Asp Thr Asp Gly Ser Tyr Phe Leu Tyr Ser Lys Leu Asn Val Lys Lys
            420                 425                 430
Glu Lys Trp Gln Gln Gly Asn Thr Phe Thr Cys Ser Val Leu His Glu
        435                 440                 445
Gly Leu His Asn His His Thr Glu Lys Ser Leu Ser His Ser Pro Gly
    450                 455                 460
Lys
465

<210> SEQ ID NO 133
<211> LENGTH: 711
<212> TYPE: DNA
<213> ORGANISM: Homo sapiens

<400> SEQUENCE: 133
atggacatga gggtgcccgc tcagctcctg gggctcctgc tgctgtggct gagaggtgcc      60
agatgtgagt ctgccctgac tcagcctgcc tccgtgtctg ggtctcctgg acagtcgatc     120
accatctcct gcactggaac cagcagtgac gttggtggtt ataactctgt ctcctggtac     180
caacagcacc caggcaaagc ccccaaactc atgatttatg aggtcagtaa tcggccctca     240
ggggtttcta atcgcttctc tggctccaag tctggcaaca cggcctccct gaccatctct     300
gggctccagg ctgaggacga ggctgattat tactgcaatt catatacaag caccagcatg     360
gtattcggcg gagggaccaa gctgaccgtc ctaggtcagc ccaaggctgc ccctcggtc      420 actctgttcc cgccctcctc tgaggagctt caagccaaca ggccacact ggtgtgtctc      480 ataagtgact tctacccggg agccgtgaca gtggcctgga aggcagatag cagccccgtc     540
aaggcgggag tggagaccac cacaccctcc aaacaaagca caacaagta cgcggccagc     600 agctatctga gcctgacgcc tgagcagtgg aagtcccaca gaagctacag ctgccaggtc     660
acgcatgaag ggagcaccgt ggagaagaca gtggccccta cagaatgttc a              711

<210> SEQ ID NO 134
<211> LENGTH: 237
<212> TYPE: PRT
<213> ORGANISM: Homo sapiens

<400> SEQUENCE: 134

Met Asp Met Arg Val Pro Ala Gln Leu Leu Gly Leu Leu Leu Leu Trp
1               5                   10                  15
Leu Arg Gly Ala Arg Cys Glu Ser Ala Leu Thr Gln Pro Ala Ser Val
            20                  25                  30
Ser Gly Ser Pro Gly Gln Ser Ile Thr Ile Ser Cys Thr Gly Thr Ser
        35                  40                  45
Ser Asp Val Gly Gly Tyr Asn Ser Val Ser Trp Tyr Gln Gln His Pro
    50                  55                  60
Gly Lys Ala Pro Lys Leu Met Ile Tyr Glu Val Ser Asn Arg Pro Ser
65                  70                  75                  80
Gly Val Ser Asn Arg Phe Ser Gly Ser Lys Ser Gly Asn Thr Ala Ser
                85                  90                  95
```

Leu Thr Ile Ser Gly Leu Gln Ala Glu Asp Glu Ala Asp Tyr Tyr Cys
            100                 105                 110

Asn Ser Tyr Thr Ser Thr Ser Met Val Phe Gly Gly Gly Thr Lys Leu
            115                 120                 125

Thr Val Leu Gly Gln Pro Lys Ala Ala Pro Ser Val Thr Leu Phe Pro
        130                 135                 140

Pro Ser Ser Glu Glu Leu Gln Ala Asn Lys Ala Thr Leu Val Cys Leu
145                 150                 155                 160

Ile Ser Asp Phe Tyr Pro Gly Ala Val Thr Val Ala Trp Lys Ala Asp
                165                 170                 175

Ser Ser Pro Val Lys Ala Gly Val Glu Thr Thr Thr Pro Ser Lys Gln
            180                 185                 190

Ser Asn Asn Lys Tyr Ala Ala Ser Ser Tyr Leu Ser Leu Thr Pro Glu
        195                 200                 205

Gln Trp Lys Ser His Arg Ser Tyr Ser Cys Gln Val Thr His Glu Gly
210                 215                 220

Ser Thr Val Glu Lys Thr Val Ala Pro Thr Glu Cys Ser
225                 230                 235

<210> SEQ ID NO 135
<211> LENGTH: 1380
<212> TYPE: DNA
<213> ORGANISM: Homo sapiens

<400> SEQUENCE: 135
atggactgga cctggaggat cctttttcttg gtggcagcag ccacaggtgt ccactccgag     60
gttcagctgg tgcagtctgg agctgaggtg aagaagcctg ggcctcagt gaaggtctcc    120 tgcaaggctt ctggttacac cttaaccagc tatggtatca gctgggtgcg acaggcccct    180
ggacaagggc ttgagtggat gggatgggtc agttttttata atggtaacac aaactatgca    240
cagaagctcc agggcagagg caccatgacc acagacccat ccacgagcac agcctacatg    300
gagctgagga gcctgagatc tgacgacacg gccgtgtatt actgtgcgag aggctacggt    360
atggacgtct ggggccaagg gaccacggtc accgtctcct ctgcctccac caagggccca    420
tcggtcttcc ccctggcgcc ctgctccagg agcacctccg agagcacagc ggccctgggc    480
tgcctggtca aggactactt ccccgaaccg gtgacggtgt cgtggaactc aggcgctctg    540
accagcggcg tgcacacctt cccagctgtc ctacagtcct caggactcta ctccctcagc    600
agcgtggtga ccgtgccctc agcaacttc ggcacccaga cctacacctg caacgtagat    660
cacaagccca gcaacaccaa ggtggacaag acagttgagc gcaaatgttg tgtcgagtgc    720
ccaccgtgcc cagcaccacc tgtggcagga ccgtcagtct tcctcttccc cccaaaaccc    780
aaggacaccc tcatgatctc ccggaccct gaggtcacgt gcgtggtggt ggacgtgagc    840
cacgaagacc ccgaggtcca gttcaactgg tacgtggacg gcgtggaggt gcataatgcc    900
aagacaaagc cacgggagga gcagttcaac agcacgttcc gtgtggtcag cgtcctcacc    960
gttgtgcacc aggactggct gaacggcaag gagtacaagt gcaaggtctc caacaaaggc   1020
ctcccagccc ccatcgagaa aaccatctcc aaaaccaaag gcagccccg agaaccacag   1080 gtgtacaccc tgcccccatc ccgggaggag atgaccaaga accaggtcag cctgacctgc   1140
ctggtcaaag gcttctaccc cagcgacatc gccgtggagt gggagagcaa tgggcagccg   1200
gagaacaact acaagaccac acctcccatg ctggactccg acggctcctt cttcctctac   1260
agcaagctca ccgtggacaa gagcaggtgg cagcagggga acgtcttctc atgctccgtg   1320

```
atgcatgagg ctctgcacaa ccactacacg cagaagagcc tctccctgtc tccgggtaaa    1380
```

<210> SEQ ID NO 136
<211> LENGTH: 460
<212> TYPE: PRT
<213> ORGANISM: Homo sapiens

<400> SEQUENCE: 136

```
Met Asp Trp Thr Trp Arg Ile Leu Phe Leu Val Ala Ala Ala Thr Gly
1               5                   10                  15

Val His Ser Glu Val Gln Leu Val Gln Ser Gly Ala Glu Val Lys Lys
            20                  25                  30

Pro Gly Ala Ser Val Lys Val Ser Cys Lys Ala Ser Gly Tyr Thr Leu
        35                  40                  45

Thr Ser Tyr Gly Ile Ser Trp Val Arg Gln Ala Pro Gly Gln Gly Leu
    50                  55                  60

Glu Trp Met Gly Trp Val Ser Phe Tyr Asn Gly Asn Thr Asn Tyr Ala
65                  70                  75                  80

Gln Lys Leu Gln Gly Arg Gly Thr Met Thr Thr Asp Pro Ser Thr Ser
                85                  90                  95

Thr Ala Tyr Met Glu Leu Arg Ser Leu Arg Ser Asp Asp Thr Ala Val
            100                 105                 110

Tyr Tyr Cys Ala Arg Gly Tyr Gly Met Asp Val Trp Gly Gln Gly Thr
        115                 120                 125

Thr Val Thr Val Ser Ser Ala Ser Thr Lys Gly Pro Ser Val Phe Pro
    130                 135                 140

Leu Ala Pro Cys Ser Arg Ser Thr Ser Glu Ser Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205

Asn Phe Gly Thr Gln Thr Tyr Thr Cys Asn Val Asp His Lys Pro Ser
    210                 215                 220

Asn Thr Lys Val Asp Lys Thr Val Glu Arg Lys Cys Cys Val Glu Cys
225                 230                 235                 240

Pro Pro Cys Pro Ala Pro Pro Val Ala Gly Pro Ser Val Phe Leu Phe
                245                 250                 255

Pro Pro Lys Pro Lys Asp Thr Leu Met Ile Ser Arg Thr Pro Glu Val
            260                 265                 270

Thr Cys Val Val Val Asp Val Ser His Glu Asp Pro Glu Val Gln Phe
        275                 280                 285

Asn Trp Tyr Val Asp Gly Val Glu Val His Asn Ala Lys Thr Lys Pro
    290                 295                 300

Arg Glu Glu Gln Phe Asn Ser Thr Phe Arg Val Val Ser Val Leu Thr
305                 310                 315                 320

Val Val His Gln Asp Trp Leu Asn Gly Lys Glu Tyr Lys Cys Lys Val
                325                 330                 335

Ser Asn Lys Gly Leu Pro Ala Pro Ile Glu Lys Thr Ile Ser Lys Thr
            340                 345                 350

Lys Gly Gln Pro Arg Glu Pro Gln Val Tyr Thr Leu Pro Pro Ser Arg
        355                 360                 365
```

```
Glu Glu Met Thr Lys Asn Gln Val Ser Leu Thr Cys Leu Val Lys Gly
    370                 375                 380

Phe Tyr Pro Ser Asp Ile Ala Val Glu Trp Glu Ser Asn Gly Gln Pro
385                 390                 395                 400

Glu Asn Asn Tyr Lys Thr Thr Pro Pro Met Leu Asp Ser Asp Gly Ser
                405                 410                 415

Phe Phe Leu Tyr Ser Lys Leu Thr Val Asp Lys Ser Arg Trp Gln Gln
            420                 425                 430

Gly Asn Val Phe Ser Cys Ser Val Met His Glu Ala Leu His Asn His
            435                 440                 445

Tyr Thr Gln Lys Ser Leu Ser Leu Ser Pro Gly Lys
    450                 455                 460

<210> SEQ ID NO 137
<211> LENGTH: 693
<212> TYPE: DNA
<213> ORGANISM: Homo sapiens

<400> SEQUENCE: 137
atggcatgga tccctctctt cctcggcgtc cttgcttact gcacaggatc cgtggcctcc    60
tatgaggtga ctcaggcacc ctcagtgtcc gtgtcccccag acagacagc cagcatcacc   120 tgctctggag ataaaattgg ggataaatat gcttgttggt atcagcagaa gccaggccag   180
tcccctgtgc tggtcatcta tcaagatagc aagcggccct cagggatccc tgagcgattc   240
tctggctcca actctggaaa cacagccact ctgaccatca gcgggaccca ggctatggat   300
gaggctgact attactgtca ggcgtgggac agcagcactg cggtattcgg cggagggacc   360
aagctgaccg tcctaggtca gcccaaggct gccccctcgg tcactctgtt cccgccctcc   420
tctgaggagc ttcaagccaa caaggccaca ctggtgtgtc tcataagtga cttctacccg   480
ggagccgtga cagtggcctg gaaggcagat agcagccccg tcaaggcggg agtggagacc   540
accacaccct ccaaacaaag caacaacaag tacgcggcca gcagctatct gagcctgacg   600
cctgagcagt ggaagtccca cagaagctac agctgccagg tcacgcatga agggagcacc   660
gtggagaaga cagtggcccc tacagaatgt tca                                693

<210> SEQ ID NO 138
<211> LENGTH: 231
<212> TYPE: PRT
<213> ORGANISM: Homo sapiens

<400> SEQUENCE: 138

Met Ala Trp Ile Pro Leu Phe Leu Gly Val Leu Ala Tyr Cys Thr Gly
1               5                   10                  15

Ser Val Ala Ser Tyr Glu Val Thr Gln Ala Pro Ser Val Ser Val Ser
            20                  25                  30

Pro Gly Gln Thr Ala Ser Ile Thr Cys Ser Gly Asp Lys Leu Gly Asp
        35                  40                  45

Lys Tyr Ala Cys Trp Tyr Gln Gln Lys Pro Gly Gln Ser Pro Val Leu
    50                  55                  60

Val Ile Tyr Gln Asp Ser Lys Arg Pro Ser Gly Ile Pro Glu Arg Phe
65                  70                  75                  80

Ser Gly Ser Asn Ser Gly Asn Thr Ala Thr Leu Thr Ile Ser Gly Thr
                85                  90                  95

Gln Ala Met Asp Glu Ala Asp Tyr Tyr Cys Gln Ala Trp Asp Ser Ser
            100                 105                 110
```

```
Thr Ala Val Phe Gly Gly Thr Lys Leu Thr Val Leu Gly Gln Pro
            115                 120                 125
Lys Ala Ala Pro Ser Val Thr Leu Phe Pro Pro Ser Ser Glu Glu Leu
130                 135                 140
Gln Ala Asn Lys Ala Thr Leu Val Cys Leu Ile Ser Asp Phe Tyr Pro
145                 150                 155                 160
Gly Ala Val Thr Val Ala Trp Lys Ala Asp Ser Ser Pro Val Lys Ala
                165                 170                 175
Gly Val Glu Thr Thr Thr Pro Ser Lys Gln Ser Asn Asn Lys Tyr Ala
            180                 185                 190
Ala Ser Ser Tyr Leu Ser Leu Thr Pro Glu Gln Trp Lys Ser His Arg
        195                 200                 205
Ser Tyr Ser Cys Gln Val Thr His Glu Gly Ser Thr Val Glu Lys Thr
210                 215                 220
Val Ala Pro Thr Glu Cys Ser
225                 230

<210> SEQ ID NO 139
<211> LENGTH: 1401
<212> TYPE: DNA
<213> ORGANISM: Homo sapiens

<400> SEQUENCE: 139
atggactgga cctggagcat cctttctctg gtggcagcag caacaggtgc ccactcccag      60
gttcagctgg tgcagtctgg agctgaggtg aagaagcctg ggcctcagt gaaggtctcc     120
tgcaaggctt ctggttacac ctttaccagt tatggtctca gctgggtgcg acaggcccct     180
ggacaagggc ttgagtggat gggatggatc atcccttaca atggtaacac aaactctgca     240
cagaaactcc agggcagagt caccatgacc acagacacat ccacgagcac agcctacatg     300
gagctgagga gcctgagatc tgacgacacg gccgtgtatt tctgtgcgag agacagggac     360
tacggtgtca attatgatgc ttttgatatc tggggccaag gacaatggt caccgtctct     420
tcagcctcca ccaagggccc atcggtcttc cccctggcgc cctgctccag gagcacctcc     480
gagagcacag cggccctggg ctgcctggtc aaggactact cccccgaacc ggtgacggtg     540
tcgtggaact caggcgctct gaccagcggc gtgcacacct tcccagctgt cctacagtcc     600
tcaggactct actccctcag cagcgtggtg accgtgccct ccagcaactt cggcacccag     660
acctacacct gcaacgtaga tcacaagccc agcaacacca aggtggacaa gacagttgag     720
cgcaaatgtt gtgtcgagtg cccaccgtgc ccagcaccac ctgtggcagg accgtcagtc     780
ttcctcttcc ccccaaaacc caaggacacc ctcatgatct cccggacccc tgaggtcacg     840
tgcgtggtgg tggacgtgag ccacgaagac cccgaggtcc agttcaactg gtacgtggac     900
ggcgtggagg tgcataatgc caagacaaag ccacgggagg agcagttcaa cagcacgttc     960
cgtgtggtca gcgtcctcac cgttgtgcac caggactggc tgaacggcaa ggagtacaag    1020
tgcaaggtct ccaacaaagg cctcccagcc cccatcgaga aaccatctc caaaaccaaa    1080
gggcagcccc gagaaccaca ggtgtacacc ctgcccccat cccgggagga gatgaccaag    1140
aaccaggtca gcctgacctg cctggtcaaa ggcttctacc ccagcgacat cgccgtggag    1200
tgggagagca atgggcagcc ggagaacaac tacaagacca cacctcccat gctggactcc    1260
gacggctcct tcttcctcta cagcaagctc accgtggaca gagcaggtg gcagcagggg    1320
aacgtcttct catgctccgt gatgcatgag gctctgcaca accactacac gcagaagagc    1380
```

-continued

```
ctctccctgt ctccgggtaa a                                              1401
```

<210> SEQ ID NO 140
<211> LENGTH: 467
<212> TYPE: PRT
<213> ORGANISM: Homo sapiens

<400> SEQUENCE: 140

Met Asp Trp Thr Trp Ser Ile Leu Phe Leu Val Ala Ala Thr Gly
1               5                   10                  15

Ala His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Ser Tyr Gly Leu Ser Trp Val Arg Gln Ala Pro Gly Gln Gly Leu
    50                  55                  60

Glu Trp Met Gly Trp Ile Ile Pro Tyr Asn Gly Asn Thr Asn Ser Ala
65                  70                  75                  80

Gln Lys Leu Gln Gly Arg Val Thr Met Thr Thr Asp Thr Ser Thr Ser
                85                  90                  95

Thr Ala Tyr Met Glu Leu Arg Ser Leu Arg Ser Asp Asp Thr Ala Val
            100                 105                 110

Tyr Phe Cys Ala Arg Asp Arg Asp Tyr Gly Val Asn Tyr Asp Ala Phe
        115                 120                 125

Asp Ile Trp Gly Gln Gly Thr Met Val Thr Val Ser Ser Ala Ser Thr
    130                 135                 140

Lys Gly Pro Ser Val Phe Pro Leu Ala Pro Cys Ser Arg Ser Thr Ser
145                 150                 155                 160

Glu Ser Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Asn Phe Gly Thr Gln Thr Tyr Thr Cys
    210                 215                 220

Asn Val Asp His Lys Pro Ser Asn Thr Lys Val Asp Lys Thr Val Glu
225                 230                 235                 240

Arg Lys Cys Cys Val Glu Cys Pro Pro Cys Pro Ala Pro Pro Val Ala
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Asp Val Ser His
        275                 280                 285

Glu Asp Pro Glu Val Gln Phe Asn Trp Tyr Val Asp Gly Val Glu Val
    290                 295                 300

His Asn Ala Lys Thr Lys Pro Arg Glu Glu Gln Phe Asn Ser Thr Phe
305                 310                 315                 320

Arg Val Val Ser Val Leu Thr Val Val His Gln Asp Trp Leu Asn Gly
                325                 330                 335

Lys Glu Tyr Lys Cys Lys Val Ser Asn Lys Gly Leu Pro Ala Pro Ile
            340                 345                 350

Glu Lys Thr Ile Ser Lys Thr Lys Gly Gln Pro Arg Glu Pro Gln Val
        355                 360                 365

| Tyr | Thr | Leu | Pro | Pro | Ser | Arg | Glu | Glu | Met | Thr | Lys | Asn | Gln | Val | Ser |
|---|---|---|---|---|---|---|---|---|---|---|---|---|---|---|---|
| 370 | | | | | 375 | | | | | 380 | | | | | |

| Leu | Thr | Cys | Leu | Val | Lys | Gly | Phe | Tyr | Pro | Ser | Asp | Ile | Ala | Val | Glu |
|---|---|---|---|---|---|---|---|---|---|---|---|---|---|---|---|
| 385 | | | | | 390 | | | | | 395 | | | | | 400 |

| Trp | Glu | Ser | Asn | Gly | Gln | Pro | Glu | Asn | Asn | Tyr | Lys | Thr | Thr | Pro | Pro |
|---|---|---|---|---|---|---|---|---|---|---|---|---|---|---|---|
| | | | | 405 | | | | | 410 | | | | | 415 | |

| Met | Leu | Asp | Ser | Asp | Gly | Ser | Phe | Phe | Leu | Tyr | Ser | Lys | Leu | Thr | Val |
|---|---|---|---|---|---|---|---|---|---|---|---|---|---|---|---|
| | | | 420 | | | | | 425 | | | | | 430 | | |

| Asp | Lys | Ser | Arg | Trp | Gln | Gln | Gly | Asn | Val | Phe | Ser | Cys | Ser | Val | Met |
|---|---|---|---|---|---|---|---|---|---|---|---|---|---|---|---|
| | | 435 | | | | | 440 | | | | | 445 | | | |

| His | Glu | Ala | Leu | His | Asn | His | Tyr | Thr | Gln | Lys | Ser | Leu | Ser | Leu | Ser |
|---|---|---|---|---|---|---|---|---|---|---|---|---|---|---|---|
| | 450 | | | | | 455 | | | | | 460 | | | | |

Pro Gly Lys
465

<210> SEQ ID NO 141
<211> LENGTH: 705
<212> TYPE: DNA
<213> ORGANISM: Homo sapiens

<400> SEQUENCE: 141

```
atggcctggg ctccactact tctcaccctc ctcgctcact gcacaggttc ttgggccaat    60
tttatgctga ctcagcccca ctctgtgtcg gagtctccgg ggaagacggt ggccatctcc   120
tgcacccgca acagtggcag cattgccagc aactctgtgc agtggtacca gcagcgcccg   180
ggcagttccc ccaccactgt gatctttgag gataaccaaa gaccctctgg ggtccctgat   240
cggttctctg gctccatcga cagctcctcc aactctgcct ccctcaccat ctctggtctg   300
aagactgagg acgaggctga ctactactgt cagtcttatg atagcaacaa ttgggtgttc   360
ggcggaggga ccaaactgac cgtcctaggt cagcccaagg ccaaccccac tgtcactctg   420
ttcccgccct cctctgagga gctccaagcc aacaaggcca cactagtgtg tctgatcagt   480
gacttctacc cgggagctgt gacagtggcc tggaaggcag atggcagccc cgtcaaggcg   540
ggagtggaga ccaccaaacc ctccaaacag agcaacaaca gtacgcggc cagcagctac   600
ctgagcctga cgcccgagca gtggaagtcc cacagaagct acagctgcca ggtcacgcat   660
gaagggagca ccgtggagaa gacagtggcc cctacagaat gttca              705
```

<210> SEQ ID NO 142
<211> LENGTH: 235
<212> TYPE: PRT
<213> ORGANISM: Homo sapiens

<400> SEQUENCE: 142

| Met | Ala | Trp | Ala | Pro | Leu | Leu | Leu | Thr | Leu | Leu | Ala | His | Cys | Thr | Gly |
|---|---|---|---|---|---|---|---|---|---|---|---|---|---|---|---|
| 1 | | | | 5 | | | | | 10 | | | | | 15 | |

| Ser | Trp | Ala | Asn | Phe | Met | Leu | Thr | Gln | Pro | His | Ser | Val | Ser | Glu | Ser |
|---|---|---|---|---|---|---|---|---|---|---|---|---|---|---|---|
| | | | 20 | | | | | 25 | | | | | 30 | | |

| Pro | Gly | Lys | Thr | Val | Ala | Ile | Ser | Cys | Thr | Arg | Asn | Ser | Gly | Ser | Ile |
|---|---|---|---|---|---|---|---|---|---|---|---|---|---|---|---|
| | | 35 | | | | | 40 | | | | | 45 | | | |

| Ala | Ser | Asn | Ser | Val | Gln | Trp | Tyr | Gln | Gln | Arg | Pro | Gly | Ser | Ser | Pro |
|---|---|---|---|---|---|---|---|---|---|---|---|---|---|---|---|
| | 50 | | | | | 55 | | | | | 60 | | | | |

| Thr | Thr | Val | Ile | Phe | Glu | Asp | Asn | Gln | Arg | Pro | Ser | Gly | Val | Pro | Asp |
|---|---|---|---|---|---|---|---|---|---|---|---|---|---|---|---|
| 65 | | | | | 70 | | | | | 75 | | | | | 80 |

| Arg | Phe | Ser | Gly | Ser | Ile | Asp | Ser | Ser | Ser | Asn | Ser | Ala | Ser | Leu | Thr |
|---|---|---|---|---|---|---|---|---|---|---|---|---|---|---|---|
| | | | | 85 | | | | | 90 | | | | | 95 | |

```
Ile Ser Gly Leu Lys Thr Glu Asp Glu Ala Asp Tyr Tyr Cys Gln Ser
            100                 105                 110
Tyr Asp Ser Asn Asn Trp Val Phe Gly Gly Gly Thr Lys Leu Thr Val
            115                 120                 125
Leu Gly Gln Pro Lys Ala Asn Pro Thr Val Thr Leu Phe Pro Pro Ser
        130                 135                 140
Ser Glu Glu Leu Gln Ala Asn Lys Ala Thr Leu Val Cys Leu Ile Ser
145                 150                 155                 160
Asp Phe Tyr Pro Gly Ala Val Thr Val Ala Trp Lys Ala Asp Gly Ser
                165                 170                 175
Pro Val Lys Ala Gly Val Glu Thr Thr Lys Pro Ser Lys Gln Ser Asn
            180                 185                 190
Asn Lys Tyr Ala Ala Ser Ser Tyr Leu Ser Leu Thr Pro Glu Gln Trp
        195                 200                 205
Lys Ser His Arg Ser Tyr Ser Cys Gln Val Thr His Glu Gly Ser Thr
210                 215                 220
Val Glu Lys Thr Val Ala Pro Thr Glu Cys Ser
225                 230                 235

<210> SEQ ID NO 143
<211> LENGTH: 1410
<212> TYPE: DNA
<213> ORGANISM: Homo sapiens

<400> SEQUENCE: 143
atggagtttg ggctgagctg ggttttcctc gttgctcttt taagaggtgt ccagtgtcag        60
gtgcagctgg tggagtctgg gggaggcgtg gtccagcctg ggaggtccct gagactctcc       120
tgtgcagcgt ctggattcac cttcagtagc tatgtcatgc actgggtccg ccaggctcca       180
ggcaaggggc tggagtgggt ggctgttata tggtatgatg aagtaataaa atactatgca       240
gactccgtga agggccgatt caccatctcc agagacaatt ccaagaacac gctgtatctg       300
caaatgaaca gcctgagagc cgaggacacg gctgtgtatt actgtgcgag agggggtat        360 gactacggtg aagactacta ctactacggt atggacgtct ggggccaagg gaccacggtc       420
accgtctcta gtgcctccac caagggccca tcggtcttcc cctggcgcc ctgctccagg        480 agcacctccg agagcacagc ggccctgggc tgcctggtca aggactactt ccccgaaccg       540
gtgacggtgt cgtggaactc aggcgctctg accagcggcg tgcacacctt cccagctgtc       600
ctacagtcct caggactcta ctccctcagc agcgtggtga ccgtgccctc agcaacttc        660 ggcacccaga cctacacctg caacgtagat cacaagccca gcaacaccaa ggtggacaag       720
acagttgagc gcaaatgttg tgtcgagtgc ccaccgtgcc cagcaccacc tgtggcagga       780
ccgtcagtct tcctcttccc cccaaaaccc aaggacaccc tcatgatctc ccggacccct       840
gaggtcacgt gcgtggtggt ggacgtgagc cacgaagacc ccgaggtcca gttcaactgg       900
tacgtggacg gcgtggaggt gcataatgcc aagacaaagc cacgggagga gcagttcaac       960
agcacgttcc gtgtggtcag cgtcctcacc gttgtgcacc aggactggct gaacggcaag      1020
gagtacaagt gcaaggtctc caacaaaggc ctcccagccc ccatcgagaa aaccatctcc      1080
aaaaccaaag ggcagccccg agaaccacag gtgtacaccc tgcccccatc ccgggaggag      1140
atgaccaaga accaggtcag cctgacctgc ctggtcaaag gcttctaccc cagcgacatc      1200
gccgtggagt gggagagcaa tgggcagccg gagaacaact acaagaccac acctcccatg      1260
ctggactccg acggctcctt cttcctctac agcaagctca ccgtggacaa gagcaggtgg      1320
```

```
cagcagggga acgtcttctc atgctccgtg atgcatgagg ctctgcacaa ccactacacg    1380
cagaagagcc tctccctgtc tccgggtaaa                                     1410
```

<210> SEQ ID NO 144
<211> LENGTH: 470
<212> TYPE: PRT
<213> ORGANISM: Homo sapiens

<400> SEQUENCE: 144

| Met | Glu | Phe | Gly | Leu | Ser | Trp | Val | Phe | Leu | Val | Ala | Leu | Leu | Arg | Gly |
|---|---|---|---|---|---|---|---|---|---|---|---|---|---|---|---|
| 1 | | | | 5 | | | | | 10 | | | | | 15 | |

Val Gln Cys Gln Val Gln Leu Val Glu Ser Gly Gly Gly Val Val Gln
            20                  25                  30

Pro Gly Arg Ser Leu Arg Leu Ser Cys Ala Ala Ser Gly Phe Thr Phe
        35                  40                  45

Ser Ser Tyr Val Met His Trp Val Arg Gln Ala Pro Gly Lys Gly Leu
    50                  55                  60

Glu Trp Val Ala Val Ile Trp Tyr Asp Gly Ser Asn Lys Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Glu Gly Tyr Asp Tyr Gly Asp Tyr Tyr Tyr
        115                 120                 125

Tyr Gly Met Asp Val Trp Gly Gln Gly Thr Thr Val Thr Val Ser Ser
    130                 135                 140

Ala Ser Thr Lys Gly Pro Ser Val Phe Pro Leu Ala Pro Cys Ser Arg
145                 150                 155                 160

Ser Thr Ser Glu Ser Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
        195                 200                 205

Leu Ser Ser Val Val Thr Val Pro Ser Ser Asn Phe Gly Thr Gln Thr
    210                 215                 220

Tyr Thr Cys Asn Val Asp His Lys Pro Ser Asn Thr Lys Val Asp Lys
225                 230                 235                 240

Thr Val Glu Arg Lys Cys Cys Val Glu Cys Pro Pro Cys Pro Ala Pro
                245                 250                 255

Pro Val Ala Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Gln Phe Asn Trp Tyr Val Asp Gly
    290                 295                 300

Val Glu Val His Asn Ala Lys Thr Lys Pro Arg Glu Glu Gln Phe Asn
305                 310                 315                 320

Ser Thr Phe Arg Val Val Ser Val Leu Thr Val His Gln Asp Trp
                325                 330                 335

Leu Asn Gly Lys Glu Tyr Lys Cys Lys Val Ser Asn Lys Gly Leu Pro
            340                 345                 350

Ala Pro Ile Glu Lys Thr Ile Ser Lys Thr Lys Gly Gln Pro Arg Glu

```
            355                 360                 365
Pro Gln Val Tyr Thr Leu Pro Pro Ser Arg Glu Glu Met Thr Lys Asn
370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                    405                 410                 415

Thr Pro Pro Met Leu Asp Ser Asp Gly Ser Phe Phe Leu Tyr Ser Lys
                420                 425                 430

Leu Thr Val Asp Lys Ser Arg Trp Gln Gln Gly Asn Val Phe Ser Cys
            435                 440                 445

Ser Val Met His Glu Ala Leu His Asn His Tyr Thr Gln Lys Ser Leu
450                 455                 460

Ser Leu Ser Pro Gly Lys
465                 470

<210> SEQ ID NO 145
<211> LENGTH: 708
<212> TYPE: DNA
<213> ORGANISM: Homo sapiens

<400> SEQUENCE: 145
atggacatga gggtccccgc tcagctcctg gggctcctgc tactctggct ccgaggtgcc      60
agatgtgaca tccagatgac ccagtctcca tcctccctct ccgcatccgt aggcgaccgc     120
gtaaccataa catgtagagc atctcaagat atttccaact atttgaattg gtaccaacaa     180
aaacccggca agcacctaa actcctcatt tactatacat caagactcct ctccggcgtt     240
ccatcacgat tctcaggctc cggctccggc acagatttca cactcactat ttcctccctc     300
caaccagaag attttgcaac ctattactgt caacaaggcg atacactccc atacacattc     360
ggcggcggca caaagttga attaaaacgt acggtggctg caccatctgt cttcatcttc     420
ccgccatctg atgagcagtt gaaatctgga actgcctctg ttgtgtgcct gctgaataac     480
ttctatccca gagaggccaa agtacagtgg aaggtggata cgccctcca atcgggtaac     540 tcccaggaga gtgtcacaga gcaggacagc aaggacagca cctacagcct cagcagcacc     600
ctgacgctga gcaaagcaga ctacgagaaa cacaaagtct acgcctgcga agtcacccat     660
cagggcctga gctcgcccgt cacaaagagc ttcaacaggg gagagtgt                  708

<210> SEQ ID NO 146
<211> LENGTH: 236
<212> TYPE: PRT
<213> ORGANISM: Homo sapiens

<400> SEQUENCE: 146

Met Asp Met Arg Val Pro Ala Gln Leu Leu Gly Leu Leu Leu Leu Trp
1               5                   10                  15

Leu Arg Gly Ala Arg Cys Asp Ile Gln Met Thr Gln Ser Pro Ser Ser
                20                  25                  30

Leu Ser Ala Ser Val Gly Asp Arg Val Thr Ile Thr Cys Arg Ala Ser
            35                  40                  45

Gln Asp Ile Ser Asn Tyr Leu Asn Trp Tyr Gln Gln Lys Pro Gly Lys
        50                  55                  60

Ala Pro Lys Leu Leu Ile Tyr Tyr Thr Ser Arg Leu Leu Ser Gly Val
65                  70                  75                  80

Pro Ser Arg Phe Ser Gly Ser Gly Ser Gly Thr Asp Phe Thr Leu Thr
```

|   |   |   | 85 |   |   |   | 90 |   |   |   | 95 |   |   |
|---|---|---|---|---|---|---|---|---|---|---|---|---|---|

Ile Ser Ser Leu Gln Pro Glu Asp Phe Ala Thr Tyr Tyr Cys Gln Gln
                100                 105                 110

Gly Asp Thr Leu Pro Tyr Thr Phe Gly Gly Gly Thr Lys Val Glu Ile
            115                 120                 125

Lys Arg Thr Val Ala Ala Pro Ser Val Phe Ile Phe Pro Pro Ser Asp
130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
            195                 200                 205

Glu Lys His Lys Val Tyr Ala Cys Glu Val Thr His Gln Gly Leu Ser
        210                 215                 220

Ser Pro Val Thr Lys Ser Phe Asn Arg Gly Glu Cys
225                 230                 235

<210> SEQ ID NO 147
<211> LENGTH: 1404
<212> TYPE: DNA
<213> ORGANISM: Homo sapiens

<400> SEQUENCE: 147

```
atggactgga cctggaggat cctcttcttg gtggcagcag ccacaggagc ccactccgag      60
gtgcagctgg tgcagagcgg cgccgaggta aaaaaaccag gagcaagcgt taaagtttct     120
tgtaaagcaa gcggatatac atttacagat tacaacatgc attgggtaag acaagcgcca     180
ggacaaggat tggaatggat gggcgaaatt aaccctaata gtggaggagc aggctacaat     240
caaaaattca agggagagt tacaatgaca acagacacaa gcacttcaac agcatatatg     300
gaactgcgat cacttagaag cgacgataca gctgtatact attgcgcacg acttgggtat     360
gatgatatat atgatgactg gtatttcgat gtttggggcc aggaacaac agttaccgtc     420
tctagtgcct ccaccaaggg cccatcggtc ttccccctgg cgccctgctc caggagcacc     480
tccgagagca cagcggccct gggctgcctg gtcaaggact acttccccga accggtgacg     540
gtgtcgtgga actcaggcgc tctgaccagc ggcgtgcaca ccttcccagc tgtcctacag     600
tcctcaggac tctactccct cagcagcgtg gtgaccgtgc cctccagcaa cttcggcacc     660
cagacctaca cctgcaacgt agatcacaag cccagcaaca ccaaggtgga caagacagtt     720
gagcgcaaat gttgtgtcga gtgcccaccg tgcccagcac cacctgtggc aggaccgtca     780
gtcttcctct tccccccaaa acccaaggac accctcatga tctcccggac ccctgaggtc     840
acgtgcgtgg tggtggacgt gagccacgaa gaccccgagg tccagttcaa ctggtacgtg     900
gacggcgtgg aggtgcataa tgccaagaca aagccacggg aggagcagtt caacagcacg     960
ttccgtgtgg tcagcgtcct caccgttgtg caccaggact ggctgaacgg caaggagtac    1020
aagtgcaagg tctccaacaa aggcctccca gcccccatcg agaaaccat ctccaaaacc    1080
aaagggcagc cccgagaacc acaggtgtac accctgcccc catcccggga ggagatgacc    1140
aagaaccagg tcagcctgac ctgcctggtc aaaggcttct accccagcga catcgccgtg    1200
gagtgggaga gcaatgggca gccggagaac aactacaaga ccacacctcc catgctggac    1260
```

```
tccgacggct ccttcttcct ctacagcaag ctcaccgtgg acaagagcag gtggcagcag    1320
gggaacgtct tctcatgctc cgtgatgcat gaggctctgc acaaccacta cacgcagaag    1380
agcctctccc tgtctccggg taaa                                           1404
```

<210> SEQ ID NO 148
<211> LENGTH: 468
<212> TYPE: PRT
<213> ORGANISM: Homo sapiens

<400> SEQUENCE: 148

```
Met Asp Trp Thr Trp Arg Ile Leu Phe Leu Val Ala Ala Thr Gly
1               5                   10                  15

Ala His Ser Glu Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Asp Tyr Asn Met His Trp Val Arg Gln Ala Pro Gly Gln Gly Leu
    50                  55                  60

Glu Trp Met Gly Glu Ile Asn Pro Asn Ser Gly Gly Ala Gly Tyr Asn
65                  70                  75                  80

Gln Lys Phe Lys Gly Arg Val Thr Met Thr Thr Asp Thr Ser Thr Ser
                85                  90                  95

Thr Ala Tyr Met Glu Leu Arg Ser Leu Arg Ser Asp Asp Thr Ala Val
            100                 105                 110

Tyr Tyr Cys Ala Arg Leu Gly Tyr Asp Asp Ile Tyr Asp Asp Trp Tyr
        115                 120                 125

Phe Asp Val Trp Gly Gln Gly Thr Thr Val Thr Val Ser Ser Ala Ser
    130                 135                 140

Thr Lys Gly Pro Ser Val Phe Pro Leu Ala Pro Cys Ser Arg Ser Thr
145                 150                 155                 160

Ser Glu Ser Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205

Ser Val Val Thr Val Pro Ser Ser Asn Phe Gly Thr Gln Thr Tyr Thr
    210                 215                 220

Cys Asn Val Asp His Lys Pro Ser Asn Thr Lys Val Asp Lys Thr Val
225                 230                 235                 240

Glu Arg Lys Cys Cys Val Glu Cys Pro Pro Cys Pro Ala Pro Pro Val
                245                 250                 255

Ala Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Gln Phe Asn Trp Tyr Val Asp Gly Val Glu
    290                 295                 300

Val His Asn Ala Lys Thr Lys Pro Arg Glu Glu Gln Phe Asn Ser Thr
305                 310                 315                 320

Phe Arg Val Val Ser Val Leu Thr Val Val His Gln Asp Trp Leu Asn
                325                 330                 335

Gly Lys Glu Tyr Lys Cys Lys Val Ser Asn Lys Gly Leu Pro Ala Pro
            340                 345                 350
```

```
Ile Glu Lys Thr Ile Ser Lys Thr Lys Gly Gln Pro Arg Glu Pro Gln
        355                 360                 365

Val Tyr Thr Leu Pro Pro Ser Arg Glu Glu Met Thr Lys Asn Gln Val
    370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Met Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
        435                 440                 445

Met His Glu Ala Leu His Asn His Tyr Thr Gln Lys Ser Leu Ser Leu
    450                 455                 460

Ser Pro Gly Lys
465

<210> SEQ ID NO 149
<211> LENGTH: 720
<212> TYPE: DNA
<213> ORGANISM: Homo sapiens

<400> SEQUENCE: 149
atggtgttgc agacccaggt cttcatttct ctgttgctct ggatctctgg tgcctacggg      60
gacatcgtga tgacccagtc tccagactcc ctggctgtgt ctctgggcga gagggccacc     120
atcaactgca agtccagcca gagtgtttta gacagctccg acaataagaa ctacttagct     180
tggtaccagc agaaaccagg acagcctcct aagctgctca tttactgggc atctaaccgg     240
gaatccgggg tccctgaccg attcagtggc agcgggtctg ggacagattt cactctcacc     300
atcagcagcc tgcaggctga agatgtggca gtttattact gtcagcaata ttatagtgat     360
ccattcactt tcggccctgg gaccaaagtg gatatcaaac gtacggtggc tgcaccatct     420
gtcttcatct tcccgccatc tgatgagcag ttgaaatctg gaactgcctc tgttgtgtgc     480
ctgctgaata acttctatcc cagagaggcc aaagtacagt ggaaggtgga taacgccctc     540
caatcgggta actcccagga gagtgtcaca gagcaggaca gcaaggacag cacctacagc     600
ctcagcagca ccctgacgct gagcaaagca gactacgaga aacacaaagt ctacgcctgc     660
gaagtcaccc atcagggcct gagctcgccc gtcacaaaga gcttcaacag gggagagtgt     720

<210> SEQ ID NO 150
<211> LENGTH: 240
<212> TYPE: PRT
<213> ORGANISM: Homo sapiens

<400> SEQUENCE: 150

Met Val Leu Gln Thr Gln Val Phe Ile Ser Leu Leu Trp Ile Ser
1               5                   10                  15

Gly Ala Tyr Gly Asp Ile Val Met Thr Gln Ser Pro Asp Ser Leu Ala
            20                  25                  30

Val Ser Leu Gly Glu Arg Ala Thr Ile Asn Cys Lys Ser Ser Gln Ser
        35                  40                  45

Val Leu Asp Ser Ser Asp Asn Lys Asn Tyr Leu Ala Trp Tyr Gln Gln
    50                  55                  60

Lys Pro Gly Gln Pro Pro Lys Leu Leu Ile Tyr Trp Ala Ser Asn Arg
65                  70                  75                  80
```

```
Glu Ser Gly Val Pro Asp Arg Phe Ser Gly Ser Gly Thr Asp
                85                  90                  95

Phe Thr Leu Thr Ile Ser Ser Leu Gln Ala Glu Asp Val Ala Val Tyr
            100                 105                 110

Tyr Cys Gln Gln Tyr Tyr Ser Asp Pro Phe Thr Phe Gly Pro Gly Thr
        115                 120                 125

Lys Val Asp Ile Lys Arg Thr Val Ala Ala Pro Ser Val Phe Ile Phe
    130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
    210                 215                 220

Gln Gly Leu Ser Ser Pro Val Thr Lys Ser Phe Asn Arg Gly Glu Cys
225                 230                 235                 240

<210> SEQ ID NO 151
<211> LENGTH: 1395
<212> TYPE: DNA
<213> ORGANISM: Homo sapiens

<400> SEQUENCE: 151
atggactgga cctggagcat ccttttcttg gtggcagcac caacaggtgc ccactcccag      60
gttcagctgg tgcagtctgg agctgaggtg aagaagcctg gggcctcagt gaaggtctcc    120
tgcaaggctt ctggttacac ctttaccagc tatggtatca gctgggtgcg acaggcccct    180
ggacaagggc ttgagtggat gggatggatc agcgcttaca atggtaacac aaactatgca    240
cagaagctcc agggcagagt caccatgacc acagacacat ccacgagcac agcctacatg    300
gagctgagga gcctgagatc tgacgacacg gccgtgtatt actgtgcgag agagtcgtgg    360
ttcggggagg tattctttga ctactggggc cagggaaccc tggtcaccgt ctcctcagct    420
agcaccaagg gcccatcggt cttccccctg gcgccctgct ccaggagcac ctccgagagc    480
acagcggccc tgggctgcct ggtcaaggac tacttccccg aaccggtgac ggtgtcgtgg    540
aactcaggcg ctctgaccag cggcgtgcac accttcccag ctgtcctaca gtcctcagga    600
ctctactccc tcagcagcgt ggtgaccgtg ccctccagca acttcggcac ccagacctac    660
acctgcaacg tagatcacaa gcccagcaac accaaggtgg acaagacagt tgagcgcaaa    720
tgttgtgtcg agtgcccacc gtgcccagca ccacctgtgg caggaccgtc agtcttcctc    780
ttccccccaa acccaaggac acccctcatg atctcccgga cccctgaggt cacgtgcgtg    840
gtggtggacg tgagccacga agaccccgag gtccagttca actggtacgt ggacggcgtg    900
gaggtgcata atgccaagac aaagccacgg gaggagcagt tcaacagcac gttccgtgtg    960
gtcagcgtcc tcaccgttgt gcaccaggac tggctgaacg gcaaggagta caagtgcaag   1020
gtctccaaca aaggcctccc agcccccatc gagaaaacca tctccaaaac caaagggcag   1080
ccccgagaac cacaggtgta caccctgccc ccatcccggg aggagatgac caagaaccag   1140
gtcagcctga cctgcctggt caaaggcttc taccccagcg acatcgccgt ggagtgggag   1200
```

-continued

```
agcaatgggc agccggagaa caactacaag accacacctc ccatgctgga ctccgacggc    1260
tccttcttcc tctacagcaa gctcaccgtg gacaagagca ggtggcagca ggggaacgtc    1320
ttctcatgct ccgtgatgca tgaggctctg cacaaccact acacgcagaa gagcctctcc    1380
ctgtctccgg gtaaa                                                    1395
```

<210> SEQ ID NO 152
<211> LENGTH: 465
<212> TYPE: PRT
<213> ORGANISM: Homo sapiens

<400> SEQUENCE: 152

```
Met Asp Trp Thr Trp Ser Ile Leu Phe Leu Val Ala Ala Pro Thr Gly
1               5                   10                  15

Ala His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Ser Tyr Gly Ile Ser Trp Val Arg Gln Ala Pro Gly Gln Gly Leu
    50                  55                  60

Glu Trp Met Gly Trp Ile Ser Ala Tyr Asn Gly Asn Thr Asn Tyr Ala
65                  70                  75                  80

Gln Lys Leu Gln Gly Arg Val Thr Met Thr Thr Asp Thr Ser Thr Ser
                85                  90                  95

Thr Ala Tyr Met Glu Leu Arg Ser Leu Arg Ser Asp Asp Thr Ala Val
            100                 105                 110

Tyr Tyr Cys Ala Arg Glu Ser Trp Phe Gly Val Phe Phe Asp Tyr
        115                 120                 125

Trp Gly Gln Gly Thr Leu Val Thr Val Ser Ser Ala Ser Thr Lys Gly
    130                 135                 140

Pro Ser Val Phe Pro Leu Ala Pro Cys Ser Arg Ser Thr Ser Glu Ser
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Asn Phe Gly Thr Gln Thr Tyr Thr Cys Asn Val
    210                 215                 220

Asp His Lys Pro Ser Asn Thr Lys Val Asp Lys Thr Val Glu Arg Lys
225                 230                 235                 240

Cys Cys Val Glu Cys Pro Pro Cys Pro Ala Pro Pro Val Ala Gly Pro
                245                 250                 255

Ser Val Phe Leu Phe Pro Pro Lys Pro Lys Asp Thr Leu Met Ile Ser
            260                 265                 270

Arg Thr Pro Glu Val Thr Cys Val Val Val Asp Val Ser His Glu Asp
        275                 280                 285

Pro Glu Val Gln Phe Asn Trp Tyr Val Asp Gly Val Glu Val His Asn
    290                 295                 300

Ala Lys Thr Lys Pro Arg Glu Glu Gln Phe Asn Ser Thr Phe Arg Val
305                 310                 315                 320

Val Ser Val Leu Thr Val Val His Gln Asp Trp Leu Asn Gly Lys Glu
                325                 330                 335
```

```
Tyr Lys Cys Lys Val Ser Asn Lys Gly Leu Pro Ala Pro Ile Glu Lys
            340                 345                 350

Thr Ile Ser Lys Thr Lys Gly Gln Pro Arg Glu Pro Gln Val Tyr Thr
        355                 360                 365

Leu Pro Pro Ser Arg Glu Glu Met Thr Lys Asn Gln Val Ser Leu Thr
    370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Met Leu
                405                 410                 415

Asp Ser Asp Gly Ser Phe Phe Leu Tyr Ser Lys Leu Thr Val Asp Lys
            420                 425                 430

Ser Arg Trp Gln Gln Gly Asn Val Phe Ser Cys Ser Val Met His Glu
        435                 440                 445

Ala Leu His Asn His Tyr Thr Gln Lys Ser Leu Ser Leu Ser Pro Gly
    450                 455                 460

Lys
465

<210> SEQ ID NO 153
<211> LENGTH: 708
<212> TYPE: DNA
<213> ORGANISM: Homo sapiens

<400> SEQUENCE: 153
atggacatga gggtgcccgc tcagctcctg gggctcctgc tgctgtggct gagaggtgcg    60
cgctgtgaca tccagatgac ccagtctcca tcttccgtgt ctgcatctgt aggagacaga   120
gtcaccatca cttgtcgggc gagtcagggt attagcagct ggttagcctg gtatcaacag   180
aaaccaggga aagcccctaa gctcctgatc tatggtgcat ccaatttgga aagtggggtc   240
ccatcaaggt tcagcggcag tggatctggg acagatttca ctctcaccat cagcagcctg   300
cagcctgaag attttgcaaa ttactattgt caacaggcta cagtttccc gtggacgttc    360 ggccaaggga ccaaggtgga aatcaaacgt acggtggctg caccatctgt cttcatcttc   420
ccgccatctg atgagcagtt gaaatctgga actgcctctg ttgtgtgcct gctgaataac   480
ttctatccca gagaggccaa agtacagtgg aaggtggata acgccctcca atcgggtaac   540
tcccaggaga gtgtcacaga gcaggacagc aaggacagca cctacagcct cagcagcacc   600
ctgacgctga gcaaagcaga ctacgagaaa cacaaagtct acgcctgcga agtcacccat   660
cagggcctga gctcgcccgt cacaaagagc ttcaacaggg gagagtgt               708

<210> SEQ ID NO 154
<211> LENGTH: 236
<212> TYPE: PRT
<213> ORGANISM: Homo sapiens

<400> SEQUENCE: 154

Met Asp Met Arg Val Pro Ala Gln Leu Leu Gly Leu Leu Leu Leu Trp
1               5                   10                  15

Leu Arg Gly Ala Arg Cys Asp Ile Gln Met Thr Gln Ser Pro Ser Ser
            20                  25                  30

Val Ser Ala Ser Val Gly Asp Arg Val Thr Ile Thr Cys Arg Ala Ser
        35                  40                  45

Gln Gly Ile Ser Ser Trp Leu Ala Trp Tyr Gln Gln Lys Pro Gly Lys
    50                  55                  60
```

Ala Pro Lys Leu Leu Ile Tyr Gly Ala Ser Asn Leu Glu Ser Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Asn Tyr Tyr Cys Gln Gln
            100                 105                 110

Ala Asn Ser Phe Pro Trp Thr Phe Gly Gln Gly Thr Lys Val Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 155
<211> LENGTH: 1398
<212> TYPE: DNA
<213> ORGANISM: Homo sapiens

<400> SEQUENCE: 155
atggacatga gggtgcccgc tcagctcctg gggctcctgc tgctgtggct gagaggtgcg      60
cgctgtcagg tccagctggt acagtctggg gctgaggtga agaagcctgg ggcctcagtg     120
aaggtctcct gcaaggtttc cggatacacc ctcagtgatt atccatcca ctgggtgcga     180 caggctcctg gaaagggct tgagtggatg ggaggttttg atcctcaaga tggtgaaaca     240
atctacgcac agaagttcca gggcagagtc accatgaccg aggacacatc tacagacaca     300
gcctacatgg agctgagcag cctgaaatct gaggacacgg ccgtgtatta ctgcgcaacg     360
gggagcagct cgtcctggtt cgaccctgg gccagggaa ccctggtcac cgtctctagt      420
gcctccacca agggcccatc ggtcttcccc ctggcgccct gctccaggag cacctccgag     480
agcacagcgg ccctgggctg cctggtcaag gactacttcc ccgaaccggt gacggtgtcg     540
tggaactcag gcgctctgac cagcggcgtg cacaccttcc cagctgtcct acagtcctca     600
ggactctact ccctcagcag cgtggtgacc gtgccctcca gcaacttcgg cacccagacc     660
tacacctgca acgtagatca caagcccagc aacaccaagg tggacaagac agttgagcgc     720
aaatgttgtg tcgagtgccc accgtgccca gcaccacctg tgcaggacc gtcagtcttc     780 ctcttcccc caaaacccaa ggacaccctc atgatctccc ggacccctga ggtcacgtgc     840
gtggtggtgg acgtgagcca cgaagacccc gaggtccagt tcaactggta cgtggacggc     900
gtggaggtgc ataatgccaa gacaaagcca cgggaggagc agttcaacag cacgttccgt     960
gtggtcagcg tcctcaccgt tgtgcaccag gactggctga acggcaagga gtacaagtgc    1020
aaggtctcca acaaaggcct cccagcccc atcgagaaaa ccatctccaa aaccaaaggg    1080
cagccccgag aaccacaggt gtacaccctg cccccatccc gggaggagat gaccaagaac    1140

```
caggtcagcc tgacctgcct ggtcaaaggc ttctacccca gcgacatcgc cgtggagtgg    1200
gagagcaatg ggcagccgga gaacaactac aagaccacac ctcccatgct ggactccgac    1260
ggctccttct tcctctacag caagctcacc gtggacaaga gcaggtggca gcaggggaac    1320
gtcttctcat gctccgtgat gcatgaggct ctgcacaacc actacacgca gaagagcctc    1380
tccctgtctc cgggtaaa                                                  1398
```

<210> SEQ ID NO 156
<211> LENGTH: 466
<212> TYPE: PRT
<213> ORGANISM: Homo sapiens

<400> SEQUENCE: 156

```
Met Asp Met Arg Val Pro Ala Gln Leu Leu Gly Leu Leu Leu Leu Trp
1               5                   10                  15

Leu Arg Gly Ala Arg Cys Gln Val Gln Leu Val Gln Ser Gly Ala Glu
            20                  25                  30

Val Lys Lys Pro Gly Ala Ser Val Lys Val Ser Cys Lys Val Ser Gly
        35                  40                  45

Tyr Thr Leu Ser Asp Leu Ser Ile His Trp Val Arg Gln Ala Pro Gly
    50                  55                  60

Lys Gly Leu Glu Trp Met Gly Gly Phe Asp Pro Gln Asp Gly Glu Thr
65                  70                  75                  80

Ile Tyr Ala Gln Lys Phe Gln Gly Arg Val Thr Met Thr Glu Asp Thr
                85                  90                  95

Ser Thr Asp Thr Ala Tyr Met Glu Leu Ser Ser Leu Lys Ser Glu Asp
            100                 105                 110

Thr Ala Val Tyr Tyr Cys Ala Thr Gly Ser Ser Ser Ser Trp Phe Asp
        115                 120                 125

Pro Trp Gly Gln Gly Thr Leu Val Thr Val Ser Ser Ala Ser Thr Lys
    130                 135                 140

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Asn Phe Gly Thr Gln Thr Tyr Thr Cys Asn
    210                 215                 220

Val Asp His Lys Pro Ser Asn Thr Lys Val Asp Lys Thr Val Glu Arg
225                 230                 235                 240

Lys Cys Cys Val Glu Cys Pro Pro Cys Pro Ala Pro Pro Val Ala Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
        275                 280                 285

Asp Pro Glu Val Gln Phe Asn Trp Tyr Val Asp Gly Val Glu Val His
    290                 295                 300

Asn Ala Lys Thr Lys Pro Arg Glu Glu Gln Phe Asn Ser Thr Phe Arg
305                 310                 315                 320

Val Val Ser Val Leu Thr Val Val His Gln Asp Trp Leu Asn Gly Lys
```

```
                    325                 330                 335
Glu Tyr Lys Cys Lys Val Ser Asn Lys Gly Leu Pro Ala Pro Ile Glu
                340                 345                 350

Lys Thr Ile Ser Lys Thr Lys Gly Gln Pro Arg Glu Pro Gln Val Tyr
            355                 360                 365

Thr Leu Pro Pro Ser Arg Glu Glu Met Thr Lys Asn Gln Val Ser Leu
        370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Met
                405                 410                 415

Leu Asp Ser Asp Gly Ser Phe Phe Leu Tyr Ser Lys Leu Thr Val Asp
                420                 425                 430

Lys Ser Arg Trp Gln Gln Gly Asn Val Phe Ser Cys Ser Val Met His
            435                 440                 445

Glu Ala Leu His Asn His Tyr Thr Gln Lys Ser Leu Ser Leu Ser Pro
        450                 455                 460

Gly Lys
465

<210> SEQ ID NO 157
<211> LENGTH: 702
<212> TYPE: DNA
<213> ORGANISM: Homo sapiens

<400> SEQUENCE: 157
atggagaccc ctgcccagct gctgttcctg ctgctgctgt ggctgcccga cacaaccggc      60
gaaatcgtca tgacacagag ccctgccaca ctgtccgtga gccctggaga gagggctacc     120
ctgagctgca gggcttccca gagcgtgagc agcaacctgg cctggtacca acagaagcct     180
ggccaggccc ctaggctgct gatctacggg gctgctacca gggccaccgg tattcctgcc     240
agggtgtccg gctccggatc cggcaccgag tttaccctga ccatcagcag cctgcagagc     300
gaggacttcg ccgtgtacta ctgtcagcaa tacaacaact ggcccctgac ctttggcggc     360
ggcaccaagg tggagatcaa aggacagtg gccgccccca gcgtgttcat cttccctccc     420
agcgacgagc agctgaagag cggcaccgcc agcgtggtgt gtctgctgaa caacttctac     480
cccagggagg ccaaggtgca gtggaaggtg gacaacgccc tgcagtccgg caactcccag     540
gagtccgtga ccgagcagga ctccaaggac tccacctact ccctgtcctc caccctgacc     600
ctgtccaagg ccgactacga gaagcacaag gtgtacgcct gcgaggtgac ccaccagggc     660
ctgtcctccc ctgtgaccaa gagcttcaac aggggcgagt gc                        702

<210> SEQ ID NO 158
<211> LENGTH: 234
<212> TYPE: PRT
<213> ORGANISM: Homo sapiens

<400> SEQUENCE: 158

Met Glu Thr Pro Ala Gln Leu Leu Phe Leu Leu Leu Leu Trp Leu Pro
1               5                   10                  15

Asp Thr Thr Gly Glu Ile Val Met Thr Gln Ser Pro Ala Thr Leu Ser
            20                  25                  30

Val Ser Pro Gly Glu Arg Ala Thr Leu Ser Cys Arg Ala Ser Gln Ser
        35                  40                  45

Val Ser Ser Asn Leu Ala Trp Tyr Gln Gln Lys Pro Gly Gln Ala Pro
```

```
                 50                  55                  60
Arg Leu Leu Ile Tyr Gly Ala Ala Thr Arg Ala Thr Gly Ile Pro Ala
 65                  70                  75                  80

Arg Val Ser Gly Ser Gly Ser Gly Thr Glu Phe Thr Leu Thr Ile Ser
                 85                  90                  95

Ser Leu Gln Ser Glu Asp Phe Ala Val Tyr Tyr Cys Gln Gln Tyr Asn
            100                 105                 110

Asn Trp Pro Leu Thr Phe Gly Gly Gly Thr Lys Val Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230
```

<210> SEQ ID NO 159
<211> LENGTH: 1416
<212> TYPE: DNA
<213> ORGANISM: Homo sapiens

<400> SEQUENCE: 159

```
atggatatgc gggtccctgc tcagctgctg ggactgctgc tgctgtggct gaggggcgcc    60
aggtgtcagg tgcagctggt cgaaagcgga ggaggagtgg tgcagcccgg aaggtccctg   120
aggctgtcct gcgccgctag cggcttcacc ttttccaact acggcatgca ctgggtgagg   180
caagcccctg gagagggcct ggaatgggtg gctgctatcg gttcgacgc cagcgacaag   240
tactatgccg acgctgtgaa gggccggttc accatcagca ggacaacag caagaacacc   300
ctctacctgc agatgaacag cctccgggcc gaggacaccg ctgtctatta ctgtgccagg   360
gaccaggcca tcttcggagt ggtccccgat tactggggcc agggaaccct ggtgaccgtg   420
tcctccgctt ccacaaaggg acctagcgtg ttccctctgg cccctagcag caagtccaca   480
agcggaggaa cagccgccct gggctgtctc gtgaaggact attttcccga gcccgtgacc   540
gtgtcctgga actccggagc cctgacctcc ggcgtgcata cattcccgc tgtcctgcag   600
tccagcggcc tctactccct gtcctccgtg gtcaccgtgc ctagcagcag cctgggcacc   660
cagacataca tctgcaacgt caaccacaag ccttccaaca ccaaggtgga caagaaggtg   720
gagcccaagt cctgtgacaa gacccacacc tgtcctccct gtcctgctcc tgagctgctg   780
ggaggcccct ccgtcttcct gttccctccc aagcccaagg acaccctgat gatctccagg   840
acccctgaag tgacatgtgt ggtggtggat gtgagccacg aagatcccga ggtgaagttc   900
aactggtacg tggacggcgt ggaggtgcac aacgctaaaa caaagccctg cgaggagcag   960
tacgatccca cctacaggtg cgtgtccgtg tcaccgtgc tccatcagga ctggctgaac  1020
ggaaaagagt acaagtgcaa agtcagcaat aaggccctgc cgcccctat cgagaaaacc  1080
```

```
atcagcaagg ccaaaggcca gcccagggag cctcaggtgt ataccctgcc tccctccagg        1140
gaggagatga ccaagaacca ggtgagcctg acctgcctcg tgaagggctt ttatccctcc        1200
gacatcgctg tggagtggga gagcaatggc cagcctgaaa acaactacaa aaccaccccc        1260
cctgtgctgg atagcgacgg cagcttcttc ctctactcca agctgaccgt cgataagtcc        1320
cggtggcagc agggcaacgt gtttagctgc agcgtgatgc acgaagccct gcataaccac        1380
tacacccaga gagcctgag cctcagcccc ggaaag                                    1416
```

<210> SEQ ID NO 160
<211> LENGTH: 472
<212> TYPE: PRT
<213> ORGANISM: Homo sapiens

<400> SEQUENCE: 160

```
Met Asp Met Arg Val Pro Ala Gln Leu Leu Gly Leu Leu Leu Leu Trp
1               5                   10                  15

Leu Arg Gly Ala Arg Cys Gln Val Gln Leu Val Glu Ser Gly Gly Gly
            20                  25                  30

Val Val Gln Pro Gly Arg Ser Leu Arg Leu Ser Cys Ala Ala Ser Gly
        35                  40                  45

Phe Thr Phe Ser Asn Tyr Gly Met His Trp Val Arg Gln Ala Pro Gly
    50                  55                  60

Glu Gly Leu Glu Trp Val Ala Ala Ile Trp Phe Asp Ala Ser Asp Lys
65                  70                  75                  80

Tyr Tyr Ala Asp Ala Val Lys Gly Arg Phe Thr Ile Ser Arg Asp Asn
                85                  90                  95

Ser Lys Asn Thr Leu Tyr Leu Gln Met Asn Ser Leu Arg Ala Glu Asp
            100                 105                 110

Thr Ala Val Tyr Tyr Cys Ala Arg Asp Gln Ala Ile Phe Gly Val Val
        115                 120                 125

Pro Asp Tyr Trp Gly Gln Gly Thr Leu Val Thr Val Ser Ser Ala Ser
    130                 135                 140

Thr Lys Gly Pro Ser Val Phe Pro Leu Ala Pro Ser Ser Lys Ser Thr
145                 150                 155                 160

Ser Gly Gly Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205

Ser Val Val Thr Val Pro Ser Ser Ser Leu Gly Thr Gln Thr Tyr Ile
    210                 215                 220

Cys Asn Val Asn His Lys Pro Ser Asn Thr Lys Val Asp Lys Lys Val
225                 230                 235                 240

Glu Pro Lys Ser Cys Asp Lys Thr His Thr Cys Pro Pro Cys Pro Ala
                245                 250                 255

Pro Glu Leu Leu Gly Gly Pro Ser Val Phe Leu Phe Pro Pro Lys Pro
            260                 265                 270

Lys Asp Thr Leu Met Ile Ser Arg Thr Pro Glu Val Thr Cys Val Val
        275                 280                 285

Val Asp Val Ser His Glu Asp Pro Glu Val Lys Phe Asn Trp Tyr Val
    290                 295                 300

Asp Gly Val Glu Val His Asn Ala Lys Thr Lys Pro Cys Glu Glu Gln
305                 310                 315                 320
```

```
Tyr Gly Ser Thr Tyr Arg Cys Val Ser Val Leu Thr Val Leu His Gln
                325                 330                 335

Asp Trp Leu Asn Gly Lys Glu Tyr Lys Cys Lys Val Ser Asn Lys Ala
            340                 345                 350

Leu Pro Ala Pro Ile Glu Lys Thr Ile Ser Lys Ala Lys Gly Gln Pro
        355                 360                 365

Arg Glu Pro Gln Val Tyr Thr Leu Pro Pro Ser Arg Glu Glu Met Thr
    370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Pro Pro Val Leu Asp Ser Asp Gly Ser Phe Phe Leu Tyr
            420                 425                 430

Ser Lys Leu Thr Val Asp Lys Ser Arg Trp Gln Gln Gly Asn Val Phe
        435                 440                 445

Ser Cys Ser Val Met His Glu Ala Leu His Asn His Tyr Thr Gln Lys
    450                 455                 460

Ser Leu Ser Leu Ser Pro Gly Lys
465                 470

<210> SEQ ID NO 161
<211> LENGTH: 702
<212> TYPE: DNA
<213> ORGANISM: Homo sapiens

<400> SEQUENCE: 161
atggagaccc ctgcccagct gctgttcctg ctgctgctgt ggctgcccga cacaaccggc    60
gaaatcgtcc tgacacagag ccctgccaca ctgtccctga gccctggaga gagggctacc   120
ctgagctgca gggcttccca gagcgtgagc agcaacctgg cctggtacca acagaagcct   180
ggccaggccc ctaggctgct gatctacggc gctgctacca gggccaccgg tattcctgac   240
agggtgtccg gctccggatc cggcaccgag tttaccctga ccatcagccg cctggagccc   300
gaggacttcg ccgtgtacta ctgtcagcaa tacaacaact ggcccctgac ctttggcggc   360
ggcaccaagg tggagatcaa gaggacagtg gccgccccca gcgtgttcat cttccctccc   420
agcgacgagc agctgaagag cggcaccgcc agcgtggtgt gtctgctgaa caacttctac   480
cccagggagg ccaaggtgca gtggaaggtg gacaacgccc tgcagtccgg caactcccag   540
gagtccgtga ccgagcagga ctccaaggac tccacctact ccctgtcctc caccctgacc   600
ctgtccaagg ccgactacga gaagcacaag gtgtacgcct gcgaggtgac ccaccagggc   660
ctgtcctccc ctgtgaccaa gagcttcaac aggggcgagt gc                      702

<210> SEQ ID NO 162
<211> LENGTH: 234
<212> TYPE: PRT
<213> ORGANISM: Homo sapiens

<400> SEQUENCE: 162

Met Glu Thr Pro Ala Gln Leu Leu Phe Leu Leu Leu Leu Trp Leu Pro
1               5                   10                  15

Asp Thr Thr Gly Glu Ile Val Leu Thr Gln Ser Pro Ala Thr Leu Ser
            20                  25                  30

Leu Ser Pro Gly Glu Arg Ala Thr Leu Ser Cys Arg Ala Ser Gln Ser
        35                  40                  45
```

Val Ser Ser Asn Leu Ala Trp Tyr Gln Gln Lys Pro Gly Gln Ala Pro
 50                  55                  60

Arg Leu Leu Ile Tyr Gly Ala Ala Thr Arg Ala Thr Gly Ile Pro Asp
 65                  70                  75                  80

Arg Val Ser Gly Ser Gly Ser Gly Thr Glu Phe Thr Leu Thr Ile Ser
                 85                  90                  95

Arg Leu Glu Pro Glu Asp Phe Ala Val Tyr Tyr Cys Gln Gln Tyr Asn
                100                 105                 110

Asn Trp Pro Leu Thr Phe Gly Gly Gly Thr Lys Val Glu Ile Lys Arg
            115                 120                 125

Thr Val Ala Ala Pro Ser Val Phe Ile Phe Pro Pro Ser Asp Glu Gln
130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 163
<211> LENGTH: 1416
<212> TYPE: DNA
<213> ORGANISM: Homo sapiens

<400> SEQUENCE: 163

```
atggatatgc gggtccctgc tcagctgctg ggactgctgc tgctgtggct gaggggcgcc      60
aggtgtgagg tgcagctggt cgaaagcgga ggaggagtgg tgcagcccgg agggtccctg     120
aggctgtcct gcgccgctag cggcttcacc ttttccaact acggcatgca ctgggtgagg     180
caagcccctg gagagggcct ggaatgggtg gctgctatct ggttcgacgc cagcgacaag     240
tactatgccg acgctgtgaa gggccggttc accatcagca gggacaacgc caagaacacc     300
ctctacctgc agatgaacag cctccgggcc gaggacaccg ctgtctatta ctgtgccagg     360
gaccaggcca tcttcggagt ggtccccgat tactggggcc agggaaccct ggtgaccgtg     420
tcctccgctt ccacaaaggg acctagcgtg ttccctctgg cccctagcag caagtccaca     480
agcggaggaa cagccgccct gggctgtctc gtgaaggact attttcccga gcccgtgacc     540
gtgtcctgga actccggagc cctgacctcc ggcgtgcata cattccccgc tgtcctgcag     600
tccagcggcc tctactccct gtcctccgtg gtcaccgtgc ctagcagcag cctgggcacc     660
cagacataca tctgcaacgt caaccacaag ccttccaaca ccaaggtgga caagaaggtg     720
gagcccaagt cctgtgacaa gacccacacc tgtcctccct gtcctgctcc tgagctgctg     780
ggaggccccct ccgtcttcct gttccctccc aagcccaagg acaccctgat gatctccagg     840
acccctgaag tgacatgtgt ggtggtggat gtgagccacg aagatcccga ggtgaagttc     900
aactggtacg tggacggcgt ggaggtgcac aacgctaaaa caaagccctg cgaggagcag     960
tacggatcca cctacaggtg cgtgtccgtg ctcaccgtgc tccatcagga ctggctgaac    1020
```

```
ggaaaagagt acaagtgcaa agtcagcaat aaggccctgc ccgcccctat cgagaaaacc    1080
atcagcaagg ccaaaggcca gcccagggag cctcaggtgt ataccctgcc tccctccagg    1140
gaggagatga ccaagaacca ggtgagcctg acctgcctcg tgaagggctt ttatccctcc    1200
gacatcgctg tggagtggga gagcaatggc cagcctgaaa acaactacaa aaccacccc    1260 cctgtgctgg atagcgacgg cagcttcttc ctctactcca agctgaccgt cgataagtcc    1320
cggtggcagc agggcaacgt gtttagctgc agcgtgatgc acgaagccct gcataaccac    1380
tacacccaga agagcctgag cctcagcccc ggaaag                              1416

<210> SEQ ID NO 164
<211> LENGTH: 472
<212> TYPE: PRT
<213> ORGANISM: Homo sapiens

<400> SEQUENCE: 164

Met Asp Met Arg Val Pro Ala Gln Leu Leu Gly Leu Leu Leu Leu Trp
1               5                   10                  15

Leu Arg Gly Ala Arg Cys Glu Val Gln Leu Val Glu Ser Gly Gly Gly
            20                  25                  30

Val Val Gln Pro Gly Gly Ser Leu Arg Leu Ser Cys Ala Ala Ser Gly
        35                  40                  45

Phe Thr Phe Ser Asn Tyr Gly Met His Trp Val Arg Gln Ala Pro Gly
    50                  55                  60

Glu Gly Leu Glu Trp Val Ala Ala Ile Trp Phe Asp Ala Ser Asp Lys
65                  70                  75                  80

Tyr Tyr Ala Asp Ala Val Lys Gly Arg Phe Thr Ile Ser Arg Asp Asn
                85                  90                  95

Ala Lys Asn Thr Leu Tyr Leu Gln Met Asn Ser Leu Arg Ala Glu Asp
            100                 105                 110

Thr Ala Val Tyr Tyr Cys Ala Arg Asp Gln Ala Ile Phe Gly Val Val
        115                 120                 125

Pro Asp Tyr Trp Gly Gln Gly Thr Leu Val Thr Val Ser Ser Ala Ser
    130                 135                 140

Thr Lys Gly Pro Ser Val Phe Pro Leu Ala Pro Ser Ser Lys Ser Thr
145                 150                 155                 160

Ser Gly Gly Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205

Ser Val Val Thr Val Pro Ser Ser Ser Leu Gly Thr Gln Thr Tyr Ile
    210                 215                 220

Cys Asn Val Asn His Lys Pro Ser Asn Thr Lys Val Asp Lys Lys Val
225                 230                 235                 240

Glu Pro Lys Ser Cys Asp Lys Thr His Thr Cys Pro Pro Cys Pro Ala
                245                 250                 255

Pro Glu Leu Leu Gly Gly Pro Ser Val Phe Leu Phe Pro Pro Lys Pro
            260                 265                 270

Lys Asp Thr Leu Met Ile Ser Arg Thr Pro Glu Val Thr Cys Val Val
        275                 280                 285

Val Asp Val Ser His Glu Asp Pro Glu Val Lys Phe Asn Trp Tyr Val
    290                 295                 300
```

Asp Gly Val Glu Val His Asn Ala Lys Thr Lys Pro Cys Glu Glu Gln
305                 310                 315                 320

Tyr Gly Ser Thr Tyr Arg Cys Val Ser Val Leu Thr Val Leu His Gln
            325                 330                 335

Asp Trp Leu Asn Gly Lys Glu Tyr Lys Cys Lys Val Ser Asn Lys Ala
        340                 345                 350

Leu Pro Ala Pro Ile Glu Lys Thr Ile Ser Lys Ala Lys Gly Gln Pro
    355                 360                 365

Arg Glu Pro Gln Val Tyr Thr Leu Pro Pro Ser Arg Glu Glu Met Thr
370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
            405                 410                 415

Lys Thr Thr Pro Pro Val Leu Asp Ser Asp Gly Ser Phe Phe Leu Tyr
        420                 425                 430

Ser Lys Leu Thr Val Asp Lys Ser Arg Trp Gln Gln Gly Asn Val Phe
    435                 440                 445

Ser Cys Ser Val Met His Glu Ala Leu His Asn His Tyr Thr Gln Lys
450                 455                 460

Ser Leu Ser Leu Ser Pro Gly Lys
465                 470

<210> SEQ ID NO 165
<211> LENGTH: 717
<212> TYPE: DNA
<213> ORGANISM: Homo sapiens

<400> SEQUENCE: 165

```
atgaggctcc ctgctcagct cctggggctg ctaatgctct gggtccctgg atccagtggg     60
gatattgtga tgacccagac tccactctcc tcacctgtca cccttggaca gccggcctcc    120
atctcctgca ggtctagtca agcctcgta cacagtgatg gaaacaccta cttgaattgg    180
cttcagcaga ggccaggcca gcctccaaga ctcctaattt ataagatttc taaccggttc    240
tctggggtcc cagacagatt cactggcagt ggggcaggga cagatttcac actgaaaatc    300
agcagggtgg aagctgagga tgtcggggtt tatacctgca tgcaagttac acaatttcct    360
ctcaccttcg gccaagggac acgactggag attaaacgaa ctgtggctgc accatctgtc    420
ttcatcttcc cgccatctga tgagcagttg aaatctggaa ctgcctctgt tgtgtgcctg    480
ctgaataact tctatcccag agaggccaaa gtacagtgga aggtggataa cgccctccaa    540
tcgggtaact cccaggagag tgtcacagag caggacagca aggacagcac ctacagcctc    600
agcagcaccc tgacgctgag caaagcagac tacgagaaac acaaagtcta cgcctgcgaa    660
gtcacccatc agggcctgag ctcgcccgtc acaaagagct tcaacagggg agagtgt      717
```

<210> SEQ ID NO 166
<211> LENGTH: 239
<212> TYPE: PRT
<213> ORGANISM: Homo sapiens

<400> SEQUENCE: 166

Met Arg Leu Pro Ala Gln Leu Leu Gly Leu Leu Met Leu Trp Val Pro
1               5                   10                  15

Gly Ser Ser Gly Asp Ile Val Met Thr Gln Thr Pro Leu Ser Ser Pro
            20                  25                  30

Val Thr Leu Gly Gln Pro Ala Ser Ile Ser Cys Arg Ser Gln Ser
    35                  40                  45

Leu Val His Ser Asp Gly Asn Thr Tyr Leu Asn Trp Leu Gln Gln Arg
50                  55                  60

Pro Gly Gln Pro Pro Arg Leu Leu Ile Tyr Lys Ile Ser Asn Arg Phe
65                  70                  75                  80

Ser Gly Val Pro Asp Arg Phe Thr Gly Ser Gly Ala Gly Thr Asp Phe
                85                  90                  95

Thr Leu Lys Ile Ser Arg Val Glu Ala Glu Asp Val Gly Val Tyr Thr
            100                 105                 110

Cys Met Gln Val Thr Gln Phe Pro Leu Thr Phe Gly Gln Gly Thr Arg
        115                 120                 125

Leu Glu Ile Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235

<210> SEQ ID NO 167
<211> LENGTH: 1410
<212> TYPE: DNA
<213> ORGANISM: Homo sapiens

<400> SEQUENCE: 167
atggacacac tttgctacac actcctgctg ctgaccaccc cttcctgggt cttgtcccag     60
gtcaccttga aggagtctgg tcctgtgctg ctgaaaccca cagagaccct cacgctgacc    120
tgcaccgtct ctgggttctc actcagcaat gctagaatgg gtgtgagctg gatccgtcag    180
ccccagggaa aggccctgga gtggcttgca cacatttttt cgaatgacga aaaatcctac    240
atcacatctc tgaagagcag gctcaccatc tccaaggaca cctccaaaag ccaggtggtc    300
cttaccatga ccaacatgga ccctgtggac acagccacat attactgtgc acggataccc    360
ctacgatccc cgggtgcttt tgatatctgg ggccaaggga caatggtcac cgtctcttca    420
gcctccacca agggcccatc ggtcttcccc ctggcaccct cctccaagag cacctctggg    480
ggcacagcgg ccctgggctg cctggtcaag gactacttcc ccgaaccggt gacggtgtcg    540
tggaactcag gcgccctgac cagcggcgtg cacaccttcc cggctgtcct acagtcctca    600
ggactctact ccctcagcag cgtggtgacc gtgccctcca gcagcttggg cacccagacc    660
tacatctgca acgtgaatca caagcccagc aacaccaagg tggacaagag agttgagccc    720
aaatcttgtg acaaaactca cacatgccca ccgtgcccag cacctgaact cctgggggga    780
ccgtcagtct tcctcttccc cccaaaaccc aaggacaccc tcatgatctc ccggacccct    840
gaggtcacat gcgtggtggt ggacgtgagc cacgaagacc ctgaggtcaa gttcaactgg    900
tacgtggacg gcgtggaggt gcataatgcc aagacaaagc cgcgggagga gcagtacaac    960

```
agcacgtacc gtgtggtcag cgtcctcacc gtcctgcacc aggactggct gaatggcaag    1020
gagtacaagt gcaaggtctc caacaaagcc ctcccagccc ccatcgagaa aaccatctcc    1080
aaagccaaag ggcagccccg agaaccacag gtgtacaccc tgcccccatc ccgggaggag    1140
atgaccaaga accaggtcag cctgacctgc ctggtcaaag gcttctatcc cagcgacatc    1200
gccgtggagt gggagagcaa tgggcagccg gagaacaact acaagaccac gcctcccgtg    1260
ctggactccg acggctcctt cttcctctat agcaagctca ccgtggacaa gagcaggtgg    1320
cagcagggga acgtcttctc atgctccgtg atgcatgagg ctctgcacaa ccactacacg    1380
cagaagagcc tctcactgtc tccgggtaaa                                     1410
```

<210> SEQ ID NO 168
<211> LENGTH: 470
<212> TYPE: PRT
<213> ORGANISM: Homo sapiens

<400> SEQUENCE: 168

```
Met Asp Thr Leu Cys Tyr Thr Leu Leu Leu Thr Thr Pro Ser Trp
1               5                   10                  15

Val Leu Ser Gln Val Thr Leu Lys Glu Ser Gly Pro Val Leu Leu Lys
                20                  25                  30

Pro Thr Glu Thr Leu Thr Leu Thr Cys Thr Val Ser Gly Phe Ser Leu
            35                  40                  45

Ser Asn Ala Arg Met Gly Val Ser Trp Ile Arg Gln Pro Pro Gly Lys
    50                  55                  60

Ala Leu Glu Trp Leu Ala His Ile Phe Ser Asn Asp Glu Lys Ser Tyr
65                  70                  75                  80

Ile Thr Ser Leu Lys Ser Arg Leu Thr Ile Ser Lys Asp Thr Ser Lys
                85                  90                  95

Ser Gln Val Val Leu Thr Met Thr Asn Met Asp Pro Val Asp Thr Ala
            100                 105                 110

Thr Tyr Tyr Cys Ala Arg Ile Pro Leu Arg Ser Pro Gly Ala Phe Asp
        115                 120                 125

Ile Trp Gly Gln Gly Thr Met Val Thr Val Ser Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
    210                 215                 220

Val Asn His Lys Pro Ser Asn Thr Lys Val Asp Lys Arg Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
```

```
    290                 295                 300
Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
            325                 330                 335

Leu Asn Gly Lys Glu Tyr Lys Cys Lys Val Ser Asn Lys Ala Leu Pro
        340                 345                 350

Ala Pro Ile Glu Lys Thr Ile Ser Lys Ala Lys Gly Gln Pro Arg Glu
    355                 360                 365

Pro Gln Val Tyr Thr Leu Pro Pro Ser Arg Glu Glu Met Thr Lys Asn
370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
            405                 410                 415

Thr Pro Pro Val Leu Asp Ser Asp Gly Ser Phe Phe Leu Tyr Ser Lys
        420                 425                 430

Leu Thr Val Asp Lys Ser Arg Trp Gln Gln Gly Asn Val Phe Ser Cys
    435                 440                 445

Ser Val Met His Glu Ala Leu His Asn His Tyr Thr Gln Lys Ser Leu
450                 455                 460

Ser Leu Ser Pro Gly Lys
465                 470

<210> SEQ ID NO 169
<211> LENGTH: 705
<212> TYPE: DNA
<213> ORGANISM: Homo sapiens

<400> SEQUENCE: 169
atggaaaccc cagcgcagct tctcttcctc ctgctactct ggctcccaga taccaccgga      60
gaaattgtgt tgacgcagtc tccaggcacc ctgtctttgt ctccagggga agagccacc     120 ctctcctgta gggccagtca gagtgttcgc ggcaggtact tagcctggta ccagcagaaa     180
cctggccagg ctcccaggct cctcatctat ggtgcatcca gcagggccac tggcatccca     240
gacaggttca gtggcagtgg gtctgggaca gacttcactc tcaccatcag cagactggag     300
cctgaagatt ttgcagtgtt ttactgtcag cagtatggta gttcacctcg acgttcggc     360 caagggacca aggtggaaat caaacgaact gtggctgcac catctgtctt catcttcccg     420
ccatctgatg agcagttgaa atctggaact gcctctgttg tgtgcctgct gaataacttc     480
tatcccagag aggccaaagt acagtggaag gtggataacg ccctccaatc gggtaactcc     540
caggagagtg tcacagagca ggacagcaag gacagcacct acagcctcag cagcaccctg     600
acgctgagca agcagactac gagaaacac aaagtctacg cctgcgaagt cacccatcag     660
ggcctgagct cgcccgtcac aaagagcttc aacaggggag agtgt             705

<210> SEQ ID NO 170
<211> LENGTH: 235
<212> TYPE: PRT
<213> ORGANISM: Homo sapiens

<400> SEQUENCE: 170

Met Glu Thr Pro Ala Gln Leu Leu Phe Leu Leu Leu Leu Trp Leu Pro
1               5                   10                  15

Asp Thr Thr Gly Glu Ile Val Leu Thr Gln Ser Pro Gly Thr Leu Ser
```

```
                20                  25                  30
Leu Ser Pro Gly Glu Arg Ala Thr Leu Ser Cys Arg Ala Ser Gln Ser
                35                  40                  45

Val Arg Gly Arg Tyr Leu Ala Trp Tyr Gln Gln Lys Pro Gly Gln Ala
        50                  55                  60

Pro Arg Leu Leu Ile Tyr Gly Ala Ser Ser Arg Ala Thr Gly Ile Pro
65                  70                  75                  80

Asp Arg Phe Ser Gly Ser Gly Ser Gly Thr Asp Phe Thr Leu Thr Ile
                85                  90                  95

Ser Arg Leu Glu Pro Glu Asp Phe Ala Val Phe Tyr Cys Gln Gln Tyr
                100                 105                 110

Gly Ser Ser Pro Arg Thr Phe Gly Gln Gly Thr Lys Val Glu Ile Lys
            115                 120                 125

Arg Thr Val Ala Ala Pro Ser Val Phe Ile Phe Pro Pro Ser Asp Glu
        130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
                180                 185                 190

Thr Tyr Ser Leu Ser Ser Thr Leu Thr Leu Ser Lys Ala Asp Tyr Glu
            195                 200                 205

Lys His Lys Val Tyr Ala Cys Glu Val Thr His Gln Gly Leu Ser Ser
        210                 215                 220

Pro Val Thr Lys Ser Phe Asn Arg Gly Glu Cys
225                 230                 235

<210> SEQ ID NO 171
<211> LENGTH: 1401
<212> TYPE: DNA
<213> ORGANISM: Homo sapiens

<400> SEQUENCE: 171
atggagtttg ggctgagctg gcttttctt gtggctattt taaaaggtgt ccagtgtgag     60
gtgcagctgt tggagtctgg gggaggcttg gtacagcctg gggggtccct gagactctcc    120
tgtgcagcct ctggattcac ctttagcagc tatgccatga gctgggtccg ccaggctcca    180 gggaagggc tggagtgggt ctcaggtatt actgggagtg gtggtagtac atactacgca    240
gactccgtga agggccggtt caccatctcc agagacaatt ccaagaacac gctgtatctg    300
caaatgaaca gcctgagagc cgaggacacg gccgtatatt actgtgcgaa agatccaggg    360
actacggtga ttatgagttg gttcgacccc tggggccagg gaaccctggt caccgtctcc    420
tcagcctcca ccaagggccc atcggtcttc cccctggcgc cctgctccag agcacctcc    480 gagagcacag cggccctggg ctgcctggtc aaggactact ccccgaacc ggtgacggtg    540 tcgtggaact caggcgctct gaccagcggc gtgcacacct tcccagctgt cctacagtcc    600
tcaggactct actccctcag cagcgtggtg accgtgccct ccagcaactt cggcacccag    660
acctacacct gcaacgtaga tcacaagccc agcaacacca aggtggacaa gacagttgag    720
cgcaaatgtt gtgtcgagtg cccaccgtgc ccagcaccac ctgtggcagg accgtcagtc    780
ttcctcttcc cccaaaaacc caaggacacc ctcatgatct cccggacccc tgaggtcacg    840
tgcgtggtgg tggacgtgag ccacgaagac cccgaggtcc agttcaactg gtacgtggac    900
```

-continued

```
ggcgtggagg tgcataatgc caagacaaag ccacgggagg agcagttcaa cagcacgttc      960
cgtgtggtca gcgtcctcac cgttgtgcac caggactggc tgaacggcaa ggagtacaag     1020
tgcaaggtct ccaacaaagg cctcccagcc cccatcgaga aaaccatctc caaaaccaaa     1080
gggcagcccc gagaaccaca ggtgtacacc ctgcccccat cccgggagga gatgaccaag     1140
aaccaggtca gcctgacctg cctggtcaaa ggcttctacc ccagcgacat cgccgtggag     1200
tgggagagca atgggcagcc ggagaacaac tacaagacca cacctcccat gctggactcc     1260
gacggctcct tcttcctcta cagcaagctc accgtggaca gagcaggtg gcagcagggg     1320 aacgtcttct catgctccgt gatgcatgag gctctgcaca accactacac gcagaagagc     1380
ctctccctgt ctccgggtaa a                                               1401
```

<210> SEQ ID NO 172
<211> LENGTH: 467
<212> TYPE: PRT
<213> ORGANISM: Homo sapiens

<400> SEQUENCE: 172

```
Met Glu Phe Gly Leu Ser Trp Leu Phe Leu Val Ala Ile Leu Lys Gly
1               5                   10                  15

Val Gln Cys Glu Val Gln Leu Leu Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Ser Tyr Ala Met Ser Trp Val Arg Gln Ala Pro Gly Lys Gly Leu
    50                  55                  60

Glu Trp Val Ser Gly Ile Thr Gly Ser Gly Gly Ser Thr Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Lys Asp Pro Gly Thr Thr Val Ile Met Ser Trp Phe
        115                 120                 125

Asp Pro Trp Gly Gln Gly Thr Leu Val Thr Val Ser Ser Ala Ser Thr
    130                 135                 140

Lys Gly Pro Ser Val Phe Pro Leu Ala Pro Cys Ser Arg Ser Thr Ser
145                 150                 155                 160

Glu Ser Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Asn Phe Gly Thr Gln Thr Tyr Thr Cys
    210                 215                 220

Asn Val Asp His Lys Pro Ser Asn Thr Lys Val Asp Lys Thr Val Glu
225                 230                 235                 240

Arg Lys Cys Cys Val Glu Cys Pro Pro Cys Pro Ala Pro Pro Val Ala
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285
```

Glu Asp Pro Glu Val Gln Phe Asn Trp Tyr Val Asp Gly Val Glu Val
            290                 295                 300

His Asn Ala Lys Thr Lys Pro Arg Glu Glu Gln Phe Asn Ser Thr Phe
305                 310                 315                 320

Arg Val Val Ser Val Leu Thr Val Val His Gln Asp Trp Leu Asn Gly
                325                 330                 335

Lys Glu Tyr Lys Cys Lys Val Ser Asn Lys Gly Leu Pro Ala Pro Ile
            340                 345                 350

Glu Lys Thr Ile Ser Lys Thr Lys Gly Gln Pro Arg Glu Pro Gln Val
        355                 360                 365

Tyr Thr Leu Pro Pro Ser Arg Glu Glu Met Thr Lys Asn Gln Val Ser
370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Met Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
450                 455                 460

Pro Gly Lys
465

<210> SEQ ID NO 173
<211> LENGTH: 714
<212> TYPE: DNA
<213> ORGANISM: Homo sapiens

<400> SEQUENCE: 173
atggtgttgc agacccaggt cttcatttct ctgttgctct ggatctctgg tgcctacggg      60
gacatcgtga tgacccagtc tccagactcc ctggctgtgt ctctgggcga gagggccacc     120
atcaactgca gagccagtga aagtgttgat atttatggca atagttttat gcactggtac     180
cagcagaaac caggacagcc tcctaagctg ctcatttacc ttgcatccaa cctagaatct     240
ggggtccctg accgattcag tggcagcggg tctgggacag attcactctc accatcagc     300 agcctgcagg ctgaagatgt ggcagtttat tactgtcagc aaaataatga ggatccgtac     360
acgttcggag gtgggaccaa ggtggaaata aaacgtacgg tggctgcacc atctgtcttc     420
atcttcccgc catctgatga gcagttgaaa tctggaactg cctctgttgt gtgcctgctg     480
aataacttct atcccagaga ggccaaagta cagtggaagg tggataacgc cctccaatcg     540
ggtaactccc aggagagtgt cacagagcag gacagcaagg acagcaccta cagcctcagc     600
agcaccctga cgctgagcaa agcagactac gagaaacaca agtctacgc ctgcgaagtc     660 acccatcagg gcctgagctc gcccgtcaca aagagcttca caggggaga gtgt           714

<210> SEQ ID NO 174
<211> LENGTH: 238
<212> TYPE: PRT
<213> ORGANISM: Homo sapiens

<400> SEQUENCE: 174

Met Val Leu Gln Thr Gln Val Phe Ile Ser Leu Leu Leu Trp Ile Ser
1               5                   10                  15

Gly Ala Tyr Gly Asp Ile Val Met Thr Gln Ser Pro Asp Ser Leu Ala
            20                  25                  30

Val Ser Leu Gly Glu Arg Ala Thr Ile Asn Cys Arg Ala Ser Glu Ser
        35                  40                  45

Val Asp Ile Tyr Gly Asn Ser Phe Met His Trp Tyr Gln Gln Lys Pro
    50                  55                  60

Gly Gln Pro Pro Lys Leu Leu Ile Tyr Leu Ala Ser Asn Leu Glu Ser
65                  70                  75                  80

Gly Val Pro Asp Arg Phe Ser Gly Ser Gly Ser Gly Thr Asp Phe Thr
                85                  90                  95

Leu Thr Ile Ser Ser Leu Gln Ala Glu Asp Val Ala Val Tyr Tyr Cys
            100                 105                 110

Gln Gln Asn Asn Glu Asp Pro Tyr Thr Phe Gly Gly Gly Thr Lys Val
        115                 120                 125

Glu Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235

<210> SEQ ID NO 175
<211> LENGTH: 1398
<212> TYPE: DNA
<213> ORGANISM: Homo sapiens

<400> SEQUENCE: 175

| | | | | | |
|---|---|---|---|---|---|
| atggactgga | cctggagggt | cttctgcttg | ctggcagtgg | ccccaggtgc | ccactcccag | 60 |
| gtgcagctgg | tgcagtctgg | ggctgaggtg | aagaagcctg | ggcctcagt | gaaggtctcc | 120 |
| tgcaaggctt | ctggatacac | cttcaccagt | tacaatatgc | actgggtgcg | ccaggcccct | 180 |
| ggacaagggc | ttgagtggat | gggagttatt | tattcaggaa | atggtgatac | ttcctacaat | 240 |
| cagaagttca | aaggcagggt | caccattacc | gctgacaaat | ccaccagcac | agcctacatg | 300 |
| gagctgagca | gcctgagatc | tgaggacacg | gccgtgtatt | actgtgcgag | agagagggat | 360 |
| actcgttttg | gtaactgggg | ccaagggact | ctggtcaccg | tctctagtgc | ctccaccaag | 420 |
| ggcccatcgg | tcttccccct | ggcaccctcc | tccaagagca | cctctggggg | cacagcggcc | 480 |
| ctgggctgcc | tggtcaagga | ctacttcccc | gaaccggtga | cggtgtcgtg | gaactcaggc | 540 |
| gccctgacca | gcggcgtgca | caccttcccg | gctgtcctac | agtcctcagg | actctactcc | 600 |
| ctcagcagcg | tggtgaccgt | gccctccagc | agcttgggca | cccagaccta | catctgcaac | 660 |
| gtgaatcaca | agcccagcaa | caccaaggtg | gacaagaaag | ttgagcccaa | atcttgtgac | 720 |
| aaaactcaca | catgcccacc | gtgcccagca | cctgaactcc | tggggggacc | gtcagtcttc | 780 |
| ctcttccccc | caaaacccaa | ggacaccctc | atgatctccc | ggacccctga | ggtcacatgc | 840 |

```
gtggtggtgg acgtgagcca cgaagaccct gaggtcaagt tcaactggta cgtggacggc    900
gtggaggtgc ataatgccaa gacaaagccg cgggaggagc agtaccagag cacgtaccgt    960
gtggtcagcg tcctcaccgt cctgcaccag gactggctga atggcaagga gtacaagtgc   1020
aaggtctcca acaaagccct cccagccccc atcgagaaaa ccatctccaa agccaaaggg   1080
cagccccgag aaccacaggt gtacaccctg cccccatccc gggatgagct gaccaagaac   1140
caggtcagcc tgacctgcct ggtcaaaggc ttctatccca gcgacatcgc cgtggagtgg   1200
gagagcaatg ggcagccgga gaacaactac aagaccacgc ctcccgtgct ggactccgac   1260
ggctccttct cctctatag caagctcacc gtggacaaga gcaggtggca gcaggggaac   1320
gtcttctcat gctccgtgat gcatgaggct ctgcacaacc actacacgca gaagagcctc   1380
tccctgtctc cgggtaaa                                                  1398
```

<210> SEQ ID NO 176
<211> LENGTH: 466
<212> TYPE: PRT
<213> ORGANISM: Homo sapiens

<400> SEQUENCE: 176

```
Met Asp Trp Thr Trp Arg Val Phe Cys Leu Leu Ala Val Ala Pro Gly
1               5                   10                  15

Ala His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Ser Tyr Asn Met His Trp Val Arg Gln Ala Pro Gly Gln Gly Leu
    50                  55                  60

Glu Trp Met Gly Val Ile Tyr Ser Gly Asn Gly Asp Thr Ser Tyr Asn
65                  70                  75                  80

Gln Lys Phe Lys Gly Arg Val Thr Ile Thr Ala Asp Lys Ser Thr Ser
                85                  90                  95

Thr Ala Tyr Met Glu Leu Ser Ser Leu Arg Ser Glu Asp Thr Ala Val
            100                 105                 110

Tyr Tyr Cys Ala Arg Glu Arg Asp Thr Arg Phe Gly Asn Trp Gly Gln
        115                 120                 125

Gly Thr Leu Val Thr Val Ser Ser Ala Ser Thr Lys Gly Pro Ser Val
    130                 135                 140

Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205

Ser Ser Ser Leu Gly Thr Gln Thr Tyr Ile Cys Asn Val Asn His Lys
    210                 215                 220

Pro Ser Asn Thr Lys Val Asp Lys Lys Val Glu Pro Lys Ser Cys Asp
225                 230                 235                 240

Lys Thr His Thr Cys Pro Pro Cys Pro Ala Pro Glu Leu Leu Gly Gly
                245                 250                 255

Pro Ser Val Phe Leu Phe Pro Pro Lys Pro Lys Asp Thr Leu Met Ile
            260                 265                 270
```

```
Ser Arg Thr Pro Glu Val Thr Cys Val Val Asp Val Ser His Glu
        275                 280                 285
Asp Pro Glu Val Lys Phe Asn Trp Tyr Val Asp Gly Val Glu Val His
290                 295                 300
Asn Ala Lys Thr Lys Pro Arg Glu Glu Gln Tyr Gln Ser Thr Tyr Arg
305                 310                 315                 320
Val Val Ser Val Leu Thr Val Leu His Gln Asp Trp Leu Asn Gly Lys
                325                 330                 335
Glu Tyr Lys Cys Lys Val Ser Asn Lys Ala Leu Pro Ala Pro Ile Glu
            340                 345                 350
Lys Thr Ile Ser Lys Ala Lys Gly Gln Pro Arg Glu Pro Gln Val Tyr
        355                 360                 365
Thr Leu Pro Pro Ser Arg Asp Glu Leu Thr Lys Asn Gln Val Ser Leu
    370                 375                 380
Thr Cys Leu Val Lys Gly Phe Tyr Pro Ser Asp Ile Ala Val Glu Trp
385                 390                 395                 400
Glu Ser Asn Gly Gln Pro Glu Asn Asn Tyr Lys Thr Thr Pro Pro Val
                405                 410                 415
Leu Asp Ser Asp Gly Ser Phe Phe Leu Tyr Ser Lys Leu Thr Val Asp
            420                 425                 430
Lys Ser Arg Trp Gln Gln Gly Asn Val Phe Ser Cys Ser Val Met His
        435                 440                 445
Glu Ala Leu His Asn His Tyr Thr Gln Lys Ser Leu Ser Leu Ser Pro
    450                 455                 460
Gly Lys
465

<210> SEQ ID NO 177
<211> LENGTH: 705
<212> TYPE: DNA
<213> ORGANISM: Homo sapiens

<400> SEQUENCE: 177
atggcctggg ctctgctgct cctcactctc ctcactcagg acacagggtc ctgggcccag      60
tctgtgctga ctcagtcacc ctcagcgtct gggacccccg ggcagagagt caccatctct     120
tgttctggaa gcagctccaa catcggcagt aattatgtat actggtacca gcagctccca     180
ggagcggccc ccaaactcct catccttagg aataatcagc ggcccctcag ggtccctgac     240
cgattctctg gctccaagtc tggcacctca gcctccctga ccatcagtgg gctccggtcc     300
gaggatgagg ctgactatta ttgtgcagca tgggatgaca gcctgagtgg ttgggtgttc     360
ggcggaggga ccaagctgac cgtcctaggt cagcccaagg ccaacccact gtcactctg      420 ttcccgccct cctctgagga gctccaagcc aacaaggcca cactagtgtg tctgatcagt     480
gacttctacc cgggagctgt gacagtggcc tggaaggcag atggcagccc cgtcaaggcg     540
ggagtggaga ccaccaaacc ctccaaacag agcaacaaca gtacgcggc cagcagctac     600 ctgagcctga cgcccgagca gtggaagtcc cacagaagct acagctgcca ggtcacgcat     660
gaagggagca ccgtggagaa gacagtggcc cctacagaat gttca                     705

<210> SEQ ID NO 178
<211> LENGTH: 235
<212> TYPE: PRT
<213> ORGANISM: Homo sapiens

<400> SEQUENCE: 178
```

```
Met Ala Trp Ala Leu Leu Leu Thr Leu Thr Gln Asp Thr Gly
1               5                   10                  15

Ser Trp Ala Gln Ser Val Leu Thr Gln Ser Pro Ser Ala Ser Gly Thr
            20                  25                  30

Pro Gly Gln Arg Val Thr Ile Ser Cys Ser Gly Ser Ser Ser Asn Ile
            35                  40                  45

Gly Ser Asn Tyr Val Tyr Trp Tyr Gln Gln Leu Pro Gly Ala Ala Pro
    50                  55                  60

Lys Leu Leu Ile Leu Arg Asn Asn Gln Arg Pro Ser Gly Val Pro Asp
65                  70                  75                  80

Arg Phe Ser Gly Ser Lys Ser Gly Thr Ser Ala Ser Leu Thr Ile Ser
                85                  90                  95

Gly Leu Arg Ser Glu Asp Glu Ala Asp Tyr Tyr Cys Ala Ala Trp Asp
            100                 105                 110

Asp Ser Leu Ser Gly Trp Val Phe Gly Gly Gly Thr Lys Leu Thr Val
            115                 120                 125

Leu Gly Gln Pro Lys Ala Asn Pro Thr Val Thr Leu Phe Pro Pro Ser
    130                 135                 140

Ser Glu Glu Leu Gln Ala Asn Lys Ala Thr Leu Val Cys Leu Ile Ser
145                 150                 155                 160

Asp Phe Tyr Pro Gly Ala Val Thr Val Ala Trp Lys Ala Asp Gly Ser
                165                 170                 175

Pro Val Lys Ala Gly Val Glu Thr Thr Lys Pro Ser Lys Gln Ser Asn
            180                 185                 190

Asn Lys Tyr Ala Ala Ser Ser Tyr Leu Ser Leu Thr Pro Glu Gln Trp
    195                 200                 205

Lys Ser His Arg Ser Tyr Ser Cys Gln Val Thr His Glu Gly Ser Thr
210                 215                 220

Val Glu Lys Thr Val Ala Pro Thr Glu Cys Ser
225                 230                 235

<210> SEQ ID NO 179
<211> LENGTH: 1437
<212> TYPE: DNA
<213> ORGANISM: Homo sapiens

<400> SEQUENCE: 179
atggacatga gggtgcccgc tcagctcctg gggctcctgc tgctgtggct gagaggtgcg    60
cgctgtgagg tgcagctggt ggagtctggg ggaggcttgg taaagcctgg ggggtccctt   120
agactctcct gtgcagcctc tggattcact ttcagtaacg cctggatgag ctgggtccgc   180
caggctccag ggaaggggct ggagtgggtt ggccgtatta aaagcaaaac tgatggtggg   240
acaacagact acactgcacc cgtgaaaggc agattcacca tctcaagaga tgattcaaaa   300
aacacgctgt atctgcaaat gaatagcctg aaagccgagg acacagccgt gtattactgt   360
accacagatc ggaccgggta tagcatcagc tggtctagtt actactacta ctacggtatg   420
gacgtctggg gccaagggac cacggtcacc gtctctagtg cctccaccaa gggcccatcg   480
gtcttccccc tggcgccctg ctccaggagc acctccgaga gcacagcggc cctgggctgc   540
ctggtcaagg actacttccc cgaaccggtg acggtgtcgt ggaactcagg cgctctgacc   600
agcggcgtgc acaccttccc agctgtccta cagtcctcag gactctactc cctcagcagc   660
gtggtgaccg tgccctccag caacttcggc acccagacct acacctgcaa cgtagatcac   720
aagcccagca acaccaaggt ggacaagaca gttgagcgca atgttgtgtg cgagtgccca   780
```

-continued

```
ccgtgcccag caccacctgt ggcaggaccg tcagtcttcc tcttcccccc aaaacccaag      840
gacaccctca tgatctcccg gacccctgag gtcacgtgcg tggtggtgga cgtgagccac      900 gaagacccg aggtccagtt caactggtac gtggacggcg tggaggtgca taatgccaag       960
acaaagccac gggaggagca gttcaacagc acgttccgtg tggtcagcgt cctcaccgtt     1020
gtgcaccagg actggctgaa cggcaaggag tacaagtgca aggtctccaa caaaggcctc     1080 ccagcccca tcgagaaaac catctccaaa accaaagggc agccccgaga accacaggtg      1140
tacaccctgc ccccatcccg ggaggagatg accaagaacc aggtcagcct gacctgcctg     1200
gtcaaaggct tctaccccag cgacatcgcc gtggagtggg agagcaatgg gcagccggag     1260
aacaactaca agaccacacc tcccatgctg gactccgacg gctccttctt cctctacagc     1320
aagctcaccg tggacaagag caggtggcag caggggaacg tcttctcatg ctccgtgatg     1380
catgaggctc tgcacaacca ctacacgcag aagagcctct ccctgtctcc gggtaaa       1437
```

<210> SEQ ID NO 180
<211> LENGTH: 479
<212> TYPE: PRT
<213> ORGANISM: Homo sapiens

<400> SEQUENCE: 180

```
Met Asp Met Arg Val Pro Ala Gln Leu Leu Gly Leu Leu Leu Leu Trp
1               5                   10                  15

Leu Arg Gly Ala Arg Cys Glu Val Gln Leu Val Glu Ser Gly Gly Gly
                20                  25                  30

Leu Val Lys Pro Gly Gly Ser Leu Arg Leu Ser Cys Ala Ala Ser Gly
            35                  40                  45

Phe Thr Phe Ser Asn Ala Trp Met Ser Trp Val Arg Gln Ala Pro Gly
        50                  55                  60

Lys Gly Leu Glu Trp Val Gly Arg Ile Lys Ser Lys Thr Asp Gly Gly
65                  70                  75                  80

Thr Thr Asp Tyr Thr Ala Pro Val Lys Gly Arg Phe Thr Ile Ser Arg
                85                  90                  95

Asp Asp Ser Lys Asn Thr Leu Tyr Leu Gln Met Asn Ser Leu Lys Ala
            100                 105                 110

Glu Asp Thr Ala Val Tyr Tyr Cys Thr Thr Asp Arg Thr Gly Tyr Ser
        115                 120                 125

Ile Ser Trp Ser Ser Tyr Tyr Tyr Tyr Gly Met Asp Val Trp Gly
    130                 135                 140

Gln Gly Thr Thr Val Thr Val Ser Ser Ala Ser Thr Lys Gly Pro Ser
145                 150                 155                 160

Val Phe Pro Leu Ala Pro Cys Ser Arg Ser Thr Ser Glu Ser Thr Ala
                165                 170                 175

Ala Leu Gly Cys Leu Val Lys Asp Tyr Phe Pro Glu Pro Val Thr Val
            180                 185                 190

Ser Trp Asn Ser Gly Ala Leu Thr Ser Gly Val His Thr Phe Pro Ala
        195                 200                 205

Val Leu Gln Ser Ser Gly Leu Tyr Ser Leu Ser Ser Val Val Thr Val
    210                 215                 220

Pro Ser Ser Asn Phe Gly Thr Gln Thr Tyr Thr Cys Asn Val Asp His
225                 230                 235                 240

Lys Pro Ser Asn Thr Lys Val Asp Lys Thr Val Glu Arg Lys Cys Cys
                245                 250                 255

Val Glu Cys Pro Pro Cys Pro Ala Pro Pro Val Ala Gly Pro Ser Val
```

```
                260                 265                 270
Phe Leu Phe Pro Pro Lys Pro Lys Asp Thr Leu Met Ile Ser Arg Thr
            275                 280                 285

Pro Glu Val Thr Cys Val Val Val Asp Val Ser His Glu Asp Pro Glu
        290                 295                 300

Val Gln Phe Asn Trp Tyr Val Asp Gly Val Glu Val His Asn Ala Lys
305                 310                 315                 320

Thr Lys Pro Arg Glu Glu Gln Phe Asn Ser Thr Phe Arg Val Val Ser
                325                 330                 335

Val Leu Thr Val Val His Gln Asp Trp Leu Asn Gly Lys Glu Tyr Lys
            340                 345                 350

Cys Lys Val Ser Asn Lys Gly Leu Pro Ala Pro Ile Glu Lys Thr Ile
        355                 360                 365

Ser Lys Thr Lys Gly Gln Pro Arg Glu Pro Gln Val Tyr Thr Leu Pro
    370                 375                 380

Pro Ser Arg Glu Glu Met Thr Lys Asn Gln Val Ser Leu Thr Cys Leu
385                 390                 395                 400

Val Lys Gly Phe Tyr Pro Ser Asp Ile Ala Val Glu Trp Glu Ser Asn
                405                 410                 415

Gly Gln Pro Glu Asn Asn Tyr Lys Thr Thr Pro Pro Met Leu Asp Ser
            420                 425                 430

Asp Gly Ser Phe Phe Leu Tyr Ser Lys Leu Thr Val Asp Lys Ser Arg
        435                 440                 445

Trp Gln Gln Gly Asn Val Phe Ser Cys Ser Val Met His Glu Ala Leu
    450                 455                 460

His Asn His Tyr Thr Gln Lys Ser Leu Ser Leu Ser Pro Gly Lys
465                 470                 475

<210> SEQ ID NO 181
<211> LENGTH: 23
<212> TYPE: PRT
<213> ORGANISM: Homo sapiens

<400> SEQUENCE: 181

Glu Ile Val Met Thr Gln Ser Pro Ala Thr Leu Ser Val Ser Pro Gly
1               5                   10                  15

Glu Arg Ala Thr Leu Ser Cys
            20

<210> SEQ ID NO 182
<211> LENGTH: 15
<212> TYPE: PRT
<213> ORGANISM: Homo sapiens

<400> SEQUENCE: 182

Trp Tyr Arg Gln Lys Pro Gly Gln Ala Pro Arg Leu Leu Ile Tyr
1               5                   10                  15

<210> SEQ ID NO 183
<211> LENGTH: 32
<212> TYPE: PRT
<213> ORGANISM: Homo sapiens

<400> SEQUENCE: 183

Gly Ile Pro Ala Arg Phe Ser Gly Ser Gly Ser Gly Thr Glu Phe Thr
1               5                   10                  15

Leu Thr Ile Ser Ser Leu Gln Ser Glu Asp Phe Ala Val Tyr Tyr Cys
            20                  25                  30
```

<210> SEQ ID NO 184
<211> LENGTH: 10
<212> TYPE: PRT
<213> ORGANISM: Homo sapiens

<400> SEQUENCE: 184

Phe Gly Gln Gly Thr Arg Leu Glu Ile Lys
1               5                   10

<210> SEQ ID NO 185
<211> LENGTH: 23
<212> TYPE: PRT
<213> ORGANISM: Homo sapiens

<400> SEQUENCE: 185

Glu Ile Val Leu Thr Gln Ser Pro Asp Phe Gln Ser Val Thr Pro Lys
1               5                   10                  15

Glu Lys Val Thr Ile Thr Cys
            20

<210> SEQ ID NO 186
<211> LENGTH: 15
<212> TYPE: PRT
<213> ORGANISM: Homo sapiens

<400> SEQUENCE: 186

Trp Tyr Gln Gln Lys Pro Asp Gln Ser Pro Lys Leu Leu Ile Lys
1               5                   10                  15

<210> SEQ ID NO 187
<211> LENGTH: 32
<212> TYPE: PRT
<213> ORGANISM: Homo sapiens

<400> SEQUENCE: 187

Gly Val Pro Ser Arg Phe Ser Gly Ser Gly Ser Gly Thr Asp Phe Thr
1               5                   10                  15

Leu Thr Ile Asn Ser Leu Glu Ala Glu Asp Ala Ala Ala Tyr Tyr Cys
            20                  25                  30

<210> SEQ ID NO 188
<211> LENGTH: 10
<212> TYPE: PRT
<213> ORGANISM: Homo sapiens

<400> SEQUENCE: 188

Phe Gly Gly Gly Thr Lys Val Glu Ile Lys
1               5                   10

<210> SEQ ID NO 189
<211> LENGTH: 23
<212> TYPE: PRT
<213> ORGANISM: Homo sapiens

<400> SEQUENCE: 189

Asp Ile Val Met Thr Gln Thr Pro Leu Ser Ser Pro Val Thr Leu Gly
1               5                   10                  15

Gln Pro Ala Ser Ile Ser Cys
            20

<210> SEQ ID NO 190
<211> LENGTH: 15

```
<212> TYPE: PRT
<213> ORGANISM: Homo sapiens

<400> SEQUENCE: 190

Trp Leu Gln Gln Arg Pro Gly Gln Pro Pro Arg Leu Leu Ile Tyr
1               5                   10                  15

<210> SEQ ID NO 191
<211> LENGTH: 32
<212> TYPE: PRT
<213> ORGANISM: Homo sapiens

<400> SEQUENCE: 191

Gly Val Pro Asp Arg Phe Thr Gly Ser Gly Ala Gly Thr Asp Phe Thr
1               5                   10                  15

Leu Lys Ile Ser Arg Val Glu Ala Glu Asp Val Gly Val Tyr Thr Cys
            20                  25                  30

<210> SEQ ID NO 192
<211> LENGTH: 10
<212> TYPE: PRT
<213> ORGANISM: Homo sapiens

<400> SEQUENCE: 192

Phe Gly Gln Gly Thr Arg Leu Glu Ile Lys
1               5                   10

<210> SEQ ID NO 193
<211> LENGTH: 23
<212> TYPE: PRT
<213> ORGANISM: Homo sapiens

<400> SEQUENCE: 193

Glu Ile Val Leu Thr Gln Ser Pro Gly Thr Leu Ser Leu Ser Pro Gly
1               5                   10                  15

Glu Arg Ala Thr Leu Ser Cys
            20

<210> SEQ ID NO 194
<211> LENGTH: 15
<212> TYPE: PRT
<213> ORGANISM: Homo sapiens

<400> SEQUENCE: 194

Trp Tyr Gln Gln Lys Pro Gly Gln Ala Pro Arg Leu Leu Ile Tyr
1               5                   10                  15

<210> SEQ ID NO 195
<211> LENGTH: 32
<212> TYPE: PRT
<213> ORGANISM: Homo sapiens

<400> SEQUENCE: 195

Gly Ile Pro Asp Arg Phe Ser Gly Ser Gly Ser Gly Thr Asp Phe Thr
1               5                   10                  15

Leu Thr Ile Ser Arg Leu Glu Pro Glu Asp Phe Ala Val Phe Tyr Cys
            20                  25                  30

<210> SEQ ID NO 196
<211> LENGTH: 10
<212> TYPE: PRT
<213> ORGANISM: Homo sapiens

<400> SEQUENCE: 196
```

```
Phe Gly Gln Gly Thr Lys Val Glu Ile Lys
1               5                   10

<210> SEQ ID NO 197
<211> LENGTH: 23
<212> TYPE: PRT
<213> ORGANISM: Homo sapiens

<400> SEQUENCE: 197

Glu Ile Val Leu Thr Gln Ser Pro Gly Thr Leu Ser Leu Ser Pro Gly
1               5                   10                  15

Asp Arg Ala Thr Leu Ser Cys
            20

<210> SEQ ID NO 198
<211> LENGTH: 32
<212> TYPE: PRT
<213> ORGANISM: Homo sapiens

<400> SEQUENCE: 198

Gly Ile Pro Asp Arg Phe Ser Gly Ser Gly Ser Gly Thr Asp Phe Thr
1               5                   10                  15

Leu Thr Ile Ser Arg Leu Glu Pro Glu Asp Phe Ala Val Tyr Tyr Cys
            20                  25                  30

<210> SEQ ID NO 199
<211> LENGTH: 15
<212> TYPE: PRT
<213> ORGANISM: Homo sapiens

<400> SEQUENCE: 199

Trp His Gln Gln Lys Pro Gly Gln Ala Pro Arg Leu Leu Ile Tyr
1               5                   10                  15

<210> SEQ ID NO 200
<211> LENGTH: 15
<212> TYPE: PRT
<213> ORGANISM: Homo sapiens

<400> SEQUENCE: 200

Trp His Gln Gln Lys Pro Gly Gln Ala Pro Arg Leu Leu Ile Tyr
1               5                   10                  15

<210> SEQ ID NO 201
<211> LENGTH: 32
<212> TYPE: PRT
<213> ORGANISM: Homo sapiens

<400> SEQUENCE: 201

Gly Ile Pro Asp Arg Phe Ser Gly Ser Gly Ser Gly Thr Asp Phe Thr
1               5                   10                  15

Leu Thr Val Ser Arg Leu Glu Pro Glu Asp Phe Ala Val Tyr Tyr Cys
            20                  25                  30

<210> SEQ ID NO 202
<211> LENGTH: 15
<212> TYPE: PRT
<213> ORGANISM: Homo sapiens

<400> SEQUENCE: 202

Trp Phe Gln Gln Lys Pro Gly Gln Ala Pro Arg Leu Leu Ile Tyr
1               5                   10                  15
```

<210> SEQ ID NO 203
<211> LENGTH: 32
<212> TYPE: PRT
<213> ORGANISM: Homo sapiens

<400> SEQUENCE: 203

Gly Ile Pro Asp Arg Phe Ser Gly Ser Gly Ser Gly Thr Asp Phe Thr
1               5                   10                  15

Phe Thr Ile Ser Arg Leu Glu Pro Glu Asp Phe Ala Val Tyr Tyr Cys
            20                  25                  30

<210> SEQ ID NO 204
<211> LENGTH: 10
<212> TYPE: PRT
<213> ORGANISM: Homo sapiens

<400> SEQUENCE: 204

Phe Gly Gln Gly Thr Thr Val Glu Ile Lys
1               5                   10

<210> SEQ ID NO 205
<211> LENGTH: 23
<212> TYPE: PRT
<213> ORGANISM: Homo sapiens

<400> SEQUENCE: 205

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 206
<211> LENGTH: 15
<212> TYPE: PRT
<213> ORGANISM: Homo sapiens

<400> SEQUENCE: 206

Trp Tyr Gln Gln Lys Pro Gly Lys Ala Pro Lys Leu Leu Ile Tyr
1               5                   10                  15

<210> SEQ ID NO 207
<211> LENGTH: 32
<212> TYPE: PRT
<213> ORGANISM: Homo sapiens

<400> SEQUENCE: 207

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 208
<211> LENGTH: 23
<212> TYPE: PRT
<213> ORGANISM: Homo sapiens

<400> SEQUENCE: 208

Asp Ile Gln Met Thr Gln Ser Pro Ser Ser Val Ser Ala Ser Val Gly
1               5                   10                  15

Asp Arg Val Thr Ile Thr Cys
            20

-continued

```
<210> SEQ ID NO 209
<211> LENGTH: 32
<212> TYPE: PRT
<213> ORGANISM: Homo sapiens

<400> SEQUENCE: 209

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Asn Tyr Tyr Cys
            20                  25                  30

<210> SEQ ID NO 210
<211> LENGTH: 23
<212> TYPE: PRT
<213> ORGANISM: Homo sapiens

<400> SEQUENCE: 210

Asp Ile Val Met Thr Gln Ser Pro Asp Ser Leu Ala Val Ser Leu Gly
1               5                   10                  15

Glu Arg Ala Thr Ile Asn Cys
            20

<210> SEQ ID NO 211
<211> LENGTH: 15
<212> TYPE: PRT
<213> ORGANISM: Homo sapiens

<400> SEQUENCE: 211

Trp Tyr Gln Gln Lys Pro Gly Gln Pro Pro Lys Leu Leu Ile Tyr
1               5                   10                  15

<210> SEQ ID NO 212
<211> LENGTH: 32
<212> TYPE: PRT
<213> ORGANISM: Homo sapiens

<400> SEQUENCE: 212

Gly Val Pro Asp Arg Phe Ser Gly Ser Gly Ser Gly Thr Asp Phe Thr
1               5                   10                  15

Leu Thr Ile Ser Ser Leu Gln Ala Glu Asp Val Ala Val Tyr Tyr Cys
            20                  25                  30

<210> SEQ ID NO 213
<211> LENGTH: 32
<212> TYPE: PRT
<213> ORGANISM: Homo sapiens

<400> SEQUENCE: 213

Gly Val Pro Asp Arg Phe Ser Gly Ser Gly Ala Gly Thr Asp Phe Thr
1               5                   10                  15

Leu Lys Ile Ser Arg Val Glu Ala Glu Asp Val Gly Val Tyr Tyr Cys
            20                  25                  30

<210> SEQ ID NO 214
<211> LENGTH: 10
<212> TYPE: PRT
<213> ORGANISM: Homo sapiens

<400> SEQUENCE: 214

Phe Gly Pro Gly Thr Lys Val Asp Ile Lys
1               5                   10

<210> SEQ ID NO 215
```

<211> LENGTH: 23
<212> TYPE: PRT
<213> ORGANISM: Homo sapiens

<400> SEQUENCE: 215

Asp Ile Val Leu Thr Gln Ser Pro Asp Ser Leu Ala Val Ser Leu Gly
1               5                   10                  15

Glu Arg Ala Thr Ile Asn Cys
            20

<210> SEQ ID NO 216
<211> LENGTH: 32
<212> TYPE: PRT
<213> ORGANISM: Homo sapiens

<400> SEQUENCE: 216

Gly Val Pro Asp Arg Phe Ser Gly Ser Gly Ser Gly Thr Asp Phe Thr
1               5                   10                  15

Leu Thr Ile Ser Ser Leu Gln Pro Glu Asp Val Ala Val Tyr Tyr Cys
            20                  25                  30

<210> SEQ ID NO 217
<211> LENGTH: 10
<212> TYPE: PRT
<213> ORGANISM: Homo sapiens

<400> SEQUENCE: 217

Phe Gly Gln Gly Thr Arg Val Glu Ile Lys
1               5                   10

<210> SEQ ID NO 218
<211> LENGTH: 23
<212> TYPE: PRT
<213> ORGANISM: Homo sapiens

<400> SEQUENCE: 218

Asp Ile Gln Leu Thr Gln Ser Pro Ser Ser Leu Ser Ala Ser Val Gly
1               5                   10                  15

Asp Arg Val Thr Met Ser Cys
            20

<210> SEQ ID NO 219
<211> LENGTH: 32
<212> TYPE: PRT
<213> ORGANISM: Homo sapiens

<400> SEQUENCE: 219

Gly Val Pro Ser Arg Phe Ser Gly Ser Gly Ser Gly Thr Asp Phe Thr
1               5                   10                  15

Phe Thr Ile Ser Ser Leu Gln Pro Glu Asp Ile Ala Thr Tyr Tyr Cys
            20                  25                  30

<210> SEQ ID NO 220
<211> LENGTH: 10
<212> TYPE: PRT
<213> ORGANISM: Homo sapiens

<400> SEQUENCE: 220

Phe Gly Gly Gly Thr Lys Val Gln Ile Lys
1               5                   10

<210> SEQ ID NO 221
<211> LENGTH: 32

<212> TYPE: PRT
<213> ORGANISM: Homo sapiens

<400> SEQUENCE: 221

Gly Val Pro Ser Arg Phe Ser Gly Ser Gly Ser Gly Thr Asp Phe Thr
1               5                   10                  15

Phe Thr Ile Ser Ser Leu Gln Pro Glu Asp Ile Ala Thr Tyr Phe Cys
            20                  25                  30

<210> SEQ ID NO 222
<211> LENGTH: 15
<212> TYPE: PRT
<213> ORGANISM: Homo sapiens

<400> SEQUENCE: 222

Trp Tyr Gln Gln Lys Pro Gly Lys Ala Pro Lys Arg Leu Ile Tyr
1               5                   10                  15

<210> SEQ ID NO 223
<211> LENGTH: 32
<212> TYPE: PRT
<213> ORGANISM: Homo sapiens

<400> SEQUENCE: 223

Gly Val Pro Ser Arg Phe Ser Gly Ser Gly Ser Gly Thr Glu Phe Thr
1               5                   10                  15

Leu Thr Ile Ser Ser Val Gln Pro Glu Asp Phe Val Thr Tyr Tyr Cys
            20                  25                  30

<210> SEQ ID NO 224
<211> LENGTH: 23
<212> TYPE: PRT
<213> ORGANISM: Homo sapiens

<400> SEQUENCE: 224

Asp Val Val Met Thr Gln Ser Pro Leu Ser Leu Pro Val Thr Pro Gly
1               5                   10                  15

Glu Pro Ala Ser Ile Ser Cys
            20

<210> SEQ ID NO 225
<211> LENGTH: 15
<212> TYPE: PRT
<213> ORGANISM: Homo sapiens

<400> SEQUENCE: 225

Trp Tyr Leu Gln Lys Pro Gly Gln Ser Pro Gln Leu Leu Ile Tyr
1               5                   10                  15

<210> SEQ ID NO 226
<211> LENGTH: 32
<212> TYPE: PRT
<213> ORGANISM: Homo sapiens

<400> SEQUENCE: 226

Gly Val Pro Asp Arg Phe Ser Gly Ser Gly Ser Gly Thr Asp Phe Thr
1               5                   10                  15

Leu Lys Ile Ser Arg Val Glu Ala Glu Asp Val Gly Val Tyr Tyr Cys
            20                  25                  30

<210> SEQ ID NO 227
<211> LENGTH: 23
<212> TYPE: PRT

<213> ORGANISM: Homo sapiens

<400> SEQUENCE: 227

Asp Ile Val Met Thr Gln Ser Pro Leu Ser Leu Pro Val Thr Pro Gly
1               5                   10                  15

Glu Pro Ala Ser Ile Ser Cys
            20

<210> SEQ ID NO 228
<211> LENGTH: 32
<212> TYPE: PRT
<213> ORGANISM: Homo sapiens

<400> SEQUENCE: 228

Gly Val Pro Asp Arg Phe Ser Gly Ser Gly Ser Gly Thr His Leu Thr
1               5                   10                  15

Leu Lys Ile Ser Arg Val Glu Ala Glu Asp Val Gly Val Tyr Tyr Cys
            20                  25                  30

<210> SEQ ID NO 229
<211> LENGTH: 15
<212> TYPE: PRT
<213> ORGANISM: Homo sapiens

<400> SEQUENCE: 229

Trp Tyr Gln Gln Lys Pro Glu Lys Ala Pro Lys Ser Leu Ile Tyr
1               5                   10                  15

<210> SEQ ID NO 230
<211> LENGTH: 10
<212> TYPE: PRT
<213> ORGANISM: Homo sapiens

<400> SEQUENCE: 230

Phe Gly Gln Gly Thr Lys Leu Glu Ile Ser
1               5                   10

<210> SEQ ID NO 231
<211> LENGTH: 10
<212> TYPE: PRT
<213> ORGANISM: Homo sapiens

<400> SEQUENCE: 231

Phe Gly Gln Gly Thr Lys Leu Glu Ile Lys
1               5                   10

<210> SEQ ID NO 232
<211> LENGTH: 15
<212> TYPE: PRT
<213> ORGANISM: Homo sapiens

<400> SEQUENCE: 232

Trp Phe Gln Gln Lys Pro Gly Gln Ala Pro Arg Pro Leu Ile Tyr
1               5                   10                  15

<210> SEQ ID NO 233
<211> LENGTH: 32
<212> TYPE: PRT
<213> ORGANISM: Homo sapiens

<400> SEQUENCE: 233

Gly Val Pro Ala Arg Phe Ser Gly Ser Gly Ser Gly Thr Asp Phe Thr
1               5                   10                  15

Leu Thr Ile Ser Ser Leu Gln Ser Glu Asp Phe Ala Val Tyr Tyr Cys
                20                  25                  30

<210> SEQ ID NO 234
<211> LENGTH: 32
<212> TYPE: PRT
<213> ORGANISM: Homo sapiens

<400> SEQUENCE: 234

Gly Ile Pro Ala Arg Val Ser Gly Ser Gly Ser Gly Thr Glu Phe Thr
1               5                   10                  15

Leu Thr Ile Ser Ser Leu Gln Ser Glu Asp Phe Ala Val Tyr Tyr Cys
                20                  25                  30

<210> SEQ ID NO 235
<211> LENGTH: 23
<212> TYPE: PRT
<213> ORGANISM: Homo sapiens

<400> SEQUENCE: 235

Asp Val Leu Met Thr Gln Ser Pro Leu Ser Leu Pro Val Thr Leu Gly
1               5                   10                  15

Gln Pro Ala Ser Ile Ser Cys
                20

<210> SEQ ID NO 236
<211> LENGTH: 15
<212> TYPE: PRT
<213> ORGANISM: Homo sapiens

<400> SEQUENCE: 236

Trp Tyr Leu Gln Arg Pro Gly Gln Ser Pro Lys Leu Leu Ile Tyr
1               5                   10                  15

<210> SEQ ID NO 237
<211> LENGTH: 10
<212> TYPE: PRT
<213> ORGANISM: Homo sapiens

<400> SEQUENCE: 237

Phe Gly Ala Gly Thr Lys Leu Glu Ile Lys
1               5                   10

<210> SEQ ID NO 238
<211> LENGTH: 23
<212> TYPE: PRT
<213> ORGANISM: Homo sapiens

<400> SEQUENCE: 238

Glu Ile Val Leu Thr Gln Ser Pro Ala Thr Leu Ser Leu Ser Pro Gly
1               5                   10                  15

Glu Arg Ala Thr Leu Ser Cys
                20

<210> SEQ ID NO 239
<211> LENGTH: 32
<212> TYPE: PRT
<213> ORGANISM: Homo sapiens

<400> SEQUENCE: 239

Gly Ile Pro Ala Arg Phe Ser Gly Ser Gly Ser Gly Thr Asp Phe Thr
1               5                   10                  15

Leu Thr Ile Ser Ser Leu Glu Pro Glu Asp Phe Ala Val Tyr Tyr Cys

<210> SEQ ID NO 240
<211> LENGTH: 23
<212> TYPE: PRT
<213> ORGANISM: Homo sapiens

<400> SEQUENCE: 240

Asp Ile Val Met Thr Gln Thr Pro Leu Ser Leu Ser Val Thr Pro Gly
1               5                   10                  15

Gln Pro Ala Ser Ile Ser Cys
            20

<210> SEQ ID NO 241
<211> LENGTH: 15
<212> TYPE: PRT
<213> ORGANISM: Homo sapiens

<400> SEQUENCE: 241

Trp Tyr Leu Gln Lys Pro Gly Gln Pro Pro Gln Phe Leu Ile Tyr
1               5                   10                  15

<210> SEQ ID NO 242
<211> LENGTH: 32
<212> TYPE: PRT
<213> ORGANISM: Homo sapiens

<400> SEQUENCE: 242

Arg Val Pro Asp Arg Phe Ser Gly Ser Gly Ser Gly Thr Asp Phe Thr
1               5                   10                  15

Leu Arg Ile Ser Arg Val Glu Ala Glu Asp Val Gly Ile Tyr Tyr Cys
            20                  25                  30

<210> SEQ ID NO 243
<211> LENGTH: 10
<212> TYPE: PRT
<213> ORGANISM: Homo sapiens

<400> SEQUENCE: 243

Phe Gly Gln Gly Thr Gln Val Glu Ile Lys
1               5                   10

<210> SEQ ID NO 244
<211> LENGTH: 32
<212> TYPE: PRT
<213> ORGANISM: Homo sapiens

<400> SEQUENCE: 244

Gly Ile Pro Asp Arg Val Ser Gly Ser Gly Ser Gly Thr Glu Phe Thr
1               5                   10                  15

Leu Thr Ile Ser Arg Leu Glu Pro Glu Asp Phe Ala Val Tyr Tyr Cys
            20                  25                  30

<210> SEQ ID NO 245
<211> LENGTH: 15
<212> TYPE: PRT
<213> ORGANISM: Homo sapiens

<400> SEQUENCE: 245

Trp Tyr Gln Gln Lys Pro Gly Thr Ala Pro Lys Leu Leu Ile Tyr
1               5                   10                  15

<210> SEQ ID NO 246

```
<211> LENGTH: 23
<212> TYPE: PRT
<213> ORGANISM: Homo sapiens

<400> SEQUENCE: 246

Asp Ile Val Met Thr Gln Thr Pro Leu Ser Leu Pro Val Thr Pro Gly
1               5                   10                  15

Glu Pro Ala Ser Ile Ser Cys
            20

<210> SEQ ID NO 247
<211> LENGTH: 22
<212> TYPE: PRT
<213> ORGANISM: Homo sapiens

<400> SEQUENCE: 247

Glu Ser Ala Leu Thr Gln Pro Ala Ser Val Ser Gly Ser Pro Gly Gln
1               5                   10                  15

Ser Ile Thr Ile Ser Cys
            20

<210> SEQ ID NO 248
<211> LENGTH: 15
<212> TYPE: PRT
<213> ORGANISM: Homo sapiens

<400> SEQUENCE: 248

Trp Tyr Gln Gln His Pro Gly Lys Ala Pro Lys Leu Met Ile Tyr
1               5                   10                  15

<210> SEQ ID NO 249
<211> LENGTH: 32
<212> TYPE: PRT
<213> ORGANISM: Homo sapiens

<400> SEQUENCE: 249

Gly Val Ser Asn Arg Phe Ser Gly Ser Lys Ser Gly Asn Thr Ala Ser
1               5                   10                  15

Leu Thr Ile Ser Gly Leu Gln Ala Glu Asp Glu Ala Asp Tyr Tyr Cys
            20                  25                  30

<210> SEQ ID NO 250
<211> LENGTH: 10
<212> TYPE: PRT
<213> ORGANISM: Homo sapiens

<400> SEQUENCE: 250

Phe Gly Gly Gly Thr Lys Leu Thr Val Leu
1               5                   10

<210> SEQ ID NO 251
<211> LENGTH: 22
<212> TYPE: PRT
<213> ORGANISM: Homo sapiens

<400> SEQUENCE: 251

Ser Tyr Val Leu Thr Gln Pro Pro Ser Val Ser Val Ala Pro Gly Gln
1               5                   10                  15

Thr Ala Arg Ile Thr Cys
            20

<210> SEQ ID NO 252
<211> LENGTH: 15
```

```
<212> TYPE: PRT
<213> ORGANISM: Homo sapiens

<400> SEQUENCE: 252

Trp Tyr Gln Gln Lys Pro Gly Gln Ala Pro Val Leu Val Val Tyr
1               5                   10                  15

<210> SEQ ID NO 253
<211> LENGTH: 32
<212> TYPE: PRT
<213> ORGANISM: Homo sapiens

<400> SEQUENCE: 253

Trp Ile Pro Glu Arg Phe Ser Gly Ser Asn Ser Gly Asn Thr Ala Thr
1               5                   10                  15

Leu Thr Ile Ser Arg Gly Glu Ala Gly Asp Glu Ala Asp Tyr Tyr Cys
            20                  25                  30

<210> SEQ ID NO 254
<211> LENGTH: 22
<212> TYPE: PRT
<213> ORGANISM: Homo sapiens

<400> SEQUENCE: 254

Gln Ser Val Leu Thr Gln Pro Pro Ser Val Ser Ala Ala Pro Gly Gln
1               5                   10                  15

Lys Val Thr Ile Ser Cys
            20

<210> SEQ ID NO 255
<211> LENGTH: 15
<212> TYPE: PRT
<213> ORGANISM: Homo sapiens

<400> SEQUENCE: 255

Trp Tyr Gln Gln Leu Pro Gly Thr Ala Pro Lys Leu Leu Ile Tyr
1               5                   10                  15

<210> SEQ ID NO 256
<211> LENGTH: 32
<212> TYPE: PRT
<213> ORGANISM: Homo sapiens

<400> SEQUENCE: 256

Gly Ile Pro Asp Arg Phe Ser Gly Ser Lys Ser Gly Thr Ser Thr Thr
1               5                   10                  15

Leu Gly Ile Thr Gly Leu Gln Thr Gly Asp Glu Ala Asp Tyr Tyr Cys
            20                  25                  30

<210> SEQ ID NO 257
<211> LENGTH: 22
<212> TYPE: PRT
<213> ORGANISM: Homo sapiens

<400> SEQUENCE: 257

Gln Ser Val Leu Thr Gln Ser Pro Ser Ala Ser Gly Thr Pro Gly Gln
1               5                   10                  15

Arg Val Thr Ile Ser Cys
            20

<210> SEQ ID NO 258
<211> LENGTH: 15
<212> TYPE: PRT
```

<213> ORGANISM: Homo sapiens

<400> SEQUENCE: 258

Trp Tyr Gln Gln Leu Pro Gly Ala Ala Pro Lys Leu Leu Ile Leu
1               5                   10                  15

<210> SEQ ID NO 259
<211> LENGTH: 32
<212> TYPE: PRT
<213> ORGANISM: Homo sapiens

<400> SEQUENCE: 259

Gly Val Pro Asp Arg Phe Ser Gly Ser Lys Ser Gly Thr Ser Ala Ser
1               5                   10                  15

Leu Thr Ile Ser Gly Leu Arg Ser Glu Asp Glu Ala Asp Tyr Tyr Cys
            20                  25                  30

<210> SEQ ID NO 260
<211> LENGTH: 22
<212> TYPE: PRT
<213> ORGANISM: Homo sapiens

<400> SEQUENCE: 260

Ser Tyr Glu Val Thr Gln Ala Pro Ser Val Ser Val Ser Pro Gly Gln
1               5                   10                  15

Thr Ala Ser Ile Thr Cys
            20

<210> SEQ ID NO 261
<211> LENGTH: 15
<212> TYPE: PRT
<213> ORGANISM: Homo sapiens

<400> SEQUENCE: 261

Trp Tyr Gln Gln Lys Pro Gly Gln Ser Pro Val Leu Val Ile Tyr
1               5                   10                  15

<210> SEQ ID NO 262
<211> LENGTH: 32
<212> TYPE: PRT
<213> ORGANISM: Homo sapiens

<400> SEQUENCE: 262

Gly Ile Pro Glu Arg Phe Ser Gly Ser Asn Ser Gly Asn Thr Ala Thr
1               5                   10                  15

Leu Thr Ile Ser Gly Thr Gln Ala Met Asp Glu Ala Asp Tyr Tyr Cys
            20                  25                  30

<210> SEQ ID NO 263
<211> LENGTH: 22
<212> TYPE: PRT
<213> ORGANISM: Homo sapiens

<400> SEQUENCE: 263

Cys Tyr Glu Leu Thr Gln Pro Pro Ser Val Ser Val Ser Pro Gly Gln
1               5                   10                  15

Thr Ala Thr Ile Thr Cys
            20

<210> SEQ ID NO 264
<211> LENGTH: 15
<212> TYPE: PRT

<400> SEQUENCE: 264

Trp Tyr Gln Gln Arg Pro Gly Gln Ser Pro Val Leu Val Ile Tyr
1               5                   10                  15

<210> SEQ ID NO 265
<211> LENGTH: 32
<212> TYPE: PRT
<213> ORGANISM: Homo sapiens

<400> SEQUENCE: 265

Gly Ile Pro Glu Arg Phe Ser Gly Ser Asn Ser Gly Asn Thr Ala Thr
1               5                   10                  15

Leu Thr Ile Ser Gly Thr Gln Ala Met Asp Glu Ala Asp Tyr Phe Cys
            20                  25                  30

<210> SEQ ID NO 266
<211> LENGTH: 22
<212> TYPE: PRT
<213> ORGANISM: Homo sapiens

<400> SEQUENCE: 266

Ser Ser Glu Leu Thr Gln Asp Pro Thr Val Ser Val Ala Leu Gly Gln
1               5                   10                  15

Thr Val Lys Ile Thr Cys
            20

<210> SEQ ID NO 267
<211> LENGTH: 15
<212> TYPE: PRT
<213> ORGANISM: Homo sapiens

<400> SEQUENCE: 267

Trp Tyr Gln Gln Lys Pro Gly Gln Ala Pro Val Leu Val Phe Tyr
1               5                   10                  15

<210> SEQ ID NO 268
<211> LENGTH: 32
<212> TYPE: PRT
<213> ORGANISM: Homo sapiens

<400> SEQUENCE: 268

Gly Ile Pro Asp Arg Phe Ser Gly Ser Ser Ser Gly Asn Thr Ala Ser
1               5                   10                  15

Leu Thr Ile Thr Gly Ala Gln Ala Glu Asp Glu Ala Asp Tyr Tyr Cys
            20                  25                  30

<210> SEQ ID NO 269
<211> LENGTH: 10
<212> TYPE: PRT
<213> ORGANISM: Homo sapiens

<400> SEQUENCE: 269

Leu Gly Gly Gly Thr Lys Leu Thr Val Leu
1               5                   10

<210> SEQ ID NO 270
<211> LENGTH: 22
<212> TYPE: PRT
<213> ORGANISM: Homo sapiens

<400> SEQUENCE: 270

Asn Phe Met Leu Thr Gln Pro His Ser Val Ser Glu Ser Pro Gly Lys

-continued

```
                1               5                  10                 15

Thr Val Ala Ile Ser Cys
            20

<210> SEQ ID NO 271
<211> LENGTH: 15
<212> TYPE: PRT
<213> ORGANISM: Homo sapiens

<400> SEQUENCE: 271

Trp Tyr Gln Gln Arg Pro Gly Ser Ser Pro Thr Thr Val Ile Phe
1               5                  10                 15

<210> SEQ ID NO 272
<211> LENGTH: 34
<212> TYPE: PRT
<213> ORGANISM: Homo sapiens

<400> SEQUENCE: 272

Gly Val Pro Asp Arg Phe Ser Gly Ser Ile Asp Ser Ser Asn Ser
1               5                  10                 15

Ala Ser Leu Thr Ile Ser Gly Leu Lys Thr Glu Asp Glu Ala Asp Tyr
            20                  25                  30

Tyr Cys

<210> SEQ ID NO 273
<211> LENGTH: 30
<212> TYPE: PRT
<213> ORGANISM: Homo sapiens

<400> SEQUENCE: 273

Gln Val Gln Leu Gln Glu Ser Gly Pro Gly Leu Val Lys Pro Ser Glu
1               5                  10                 15

Thr Leu Ser Leu Thr Cys Thr Val Ser Gly Gly Ser Ile Ser
            20                  25                  30

<210> SEQ ID NO 274
<211> LENGTH: 14
<212> TYPE: PRT
<213> ORGANISM: Homo sapiens

<400> SEQUENCE: 274

Trp Ile Arg Gln Pro Pro Gly Lys Gly Leu Glu Trp Ile Gly
1               5                  10

<210> SEQ ID NO 275
<211> LENGTH: 32
<212> TYPE: PRT
<213> ORGANISM: Homo sapiens

<400> SEQUENCE: 275

Arg Val Thr Ile Ser Val Asp Thr Ser Lys Asn Gln Phe Ser Leu Lys
1               5                  10                 15

Leu Asn Ser Val Thr Ala Ala Asp Thr Ala Val Tyr Tyr Cys Ala Arg
            20                  25                  30

<210> SEQ ID NO 276
<211> LENGTH: 11
<212> TYPE: PRT
<213> ORGANISM: Homo sapiens

<400> SEQUENCE: 276
```

```
Trp Gly Gln Gly Thr Leu Val Thr Val Ser Ser
1               5                   10
```

<210> SEQ ID NO 277
<211> LENGTH: 30
<212> TYPE: PRT
<213> ORGANISM: Homo sapiens

<400> SEQUENCE: 277

```
Glu Val Gln Leu Met Gln Ser Gly Ala Glu Val Lys Lys Pro Gly Glu
1               5                   10                  15

Ser Leu Lys Ile Ser Cys Lys Gly Ser Gly Tyr Ser Phe Ser
            20                  25                  30
```

<210> SEQ ID NO 278
<211> LENGTH: 14
<212> TYPE: PRT
<213> ORGANISM: Homo sapiens

<400> SEQUENCE: 278

```
Trp Val Arg Gln Met Pro Gly Lys Gly Leu Glu Trp Met Gly
1               5                   10
```

<210> SEQ ID NO 279
<211> LENGTH: 32
<212> TYPE: PRT
<213> ORGANISM: Homo sapiens

<400> SEQUENCE: 279

```
Gln Val Thr Ile Ser Ala Asp Asn Ser Asn Ser Ala Thr Tyr Leu Gln
1               5                   10                  15

Trp Ser Ser Leu Lys Ala Ser Asp Thr Ala Met Tyr Phe Cys Ala Arg
            20                  25                  30
```

<210> SEQ ID NO 280
<211> LENGTH: 30
<212> TYPE: PRT
<213> ORGANISM: Homo sapiens

<400> SEQUENCE: 280

```
Gln Val Thr Leu Lys Glu Ser Gly Pro Val Leu Leu Lys Pro Thr Glu
1               5                   10                  15

Thr Leu Thr Leu Thr Cys Thr Val Ser Gly Phe Ser Leu Ser
            20                  25                  30
```

<210> SEQ ID NO 281
<211> LENGTH: 14
<212> TYPE: PRT
<213> ORGANISM: Homo sapiens

<400> SEQUENCE: 281

```
Trp Ile Arg Gln Pro Pro Gly Lys Ala Leu Glu Trp Leu Ala
1               5                   10
```

<210> SEQ ID NO 282
<211> LENGTH: 32
<212> TYPE: PRT
<213> ORGANISM: Homo sapiens

<400> SEQUENCE: 282

```
Arg Leu Thr Ile Ser Lys Asp Thr Ser Lys Ser Gln Val Val Leu Thr
1               5                   10                  15

Met Thr Asn Met Asp Pro Val Asp Thr Ala Thr Tyr Tyr Cys Ala Arg
```

20                  25                  30

<210> SEQ ID NO 283
<211> LENGTH: 11
<212> TYPE: PRT
<213> ORGANISM: Homo sapiens

<400> SEQUENCE: 283

Trp Gly Gln Gly Thr Met Val Thr Val Ser Ser
1               5                   10

<210> SEQ ID NO 284
<211> LENGTH: 30
<212> TYPE: PRT
<213> ORGANISM: Homo sapiens

<400> SEQUENCE: 284

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Leu Thr
            20                  25                  30

<210> SEQ ID NO 285
<211> LENGTH: 14
<212> TYPE: PRT
<213> ORGANISM: Homo sapiens

<400> SEQUENCE: 285

Trp Val Arg Gln Ala Pro Gly Gln Gly Leu Glu Trp Met Gly
1               5                   10

<210> SEQ ID NO 286
<211> LENGTH: 32
<212> TYPE: PRT
<213> ORGANISM: Homo sapiens

<400> SEQUENCE: 286

Arg Gly Thr Met Thr Thr Asp Pro Ser Thr Ser Thr Ala Tyr Met Glu
1               5                   10                  15

Leu Arg Ser Leu Arg Ser Asp Asp Thr Ala Val Tyr Tyr Cys Ala Arg
            20                  25                  30

<210> SEQ ID NO 287
<211> LENGTH: 11
<212> TYPE: PRT
<213> ORGANISM: Homo sapiens

<400> SEQUENCE: 287

Trp Gly Gln Gly Thr Thr Val Thr Val Ser Ser
1               5                   10

<210> SEQ ID NO 288
<211> LENGTH: 30
<212> TYPE: PRT
<213> ORGANISM: Homo sapiens

<400> SEQUENCE: 288

Gln Met Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Arg
            20                  25                  30

<210> SEQ ID NO 289

```
<211> LENGTH: 14
<212> TYPE: PRT
<213> ORGANISM: Homo sapiens

<400> SEQUENCE: 289

Trp Val Arg Gln Ala Pro Gly Lys Gly Leu Glu Trp Val Ala
1               5                   10

<210> SEQ ID NO 290
<211> LENGTH: 32
<212> TYPE: PRT
<213> ORGANISM: Homo sapiens

<400> SEQUENCE: 290

Arg Phe Thr Ile Thr Arg Asp Asn Ser Lys Asn Thr Leu Asn Leu Gln
1               5                   10                  15

Met Asn Ser Leu Arg Ala Glu Asp Thr Ala Val Tyr Tyr Cys Ala Arg
                20                  25                  30

<210> SEQ ID NO 291
<211> LENGTH: 30
<212> TYPE: PRT
<213> ORGANISM: Homo sapiens

<400> SEQUENCE: 291

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser
                20                  25                  30

<210> SEQ ID NO 292
<211> LENGTH: 14
<212> TYPE: PRT
<213> ORGANISM: Homo sapiens

<400> SEQUENCE: 292

Trp Val Arg Gln Ala Pro Gly Lys Gly Leu Glu Trp Val Ser
1               5                   10

<210> SEQ ID NO 293
<211> LENGTH: 32
<212> TYPE: PRT
<213> ORGANISM: Homo sapiens

<400> SEQUENCE: 293

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Lys
                20                  25                  30

<210> SEQ ID NO 294
<211> LENGTH: 30
<212> TYPE: PRT
<213> ORGANISM: Homo sapiens

<400> SEQUENCE: 294

Glu Val Gln Leu Val Gln Ser Gly Ala Glu Val Lys Lys Pro Gly Ser
1               5                   10                  15

Ser Val Lys Val Ser Cys Lys Ala Ser Gly Phe Thr Phe Thr
                20                  25                  30

<210> SEQ ID NO 295
<211> LENGTH: 32
```

-continued

```
<212> TYPE: PRT
<213> ORGANISM: Homo sapiens

<400> SEQUENCE: 295

Arg Val Thr Ile Thr Ala Asp Lys Ser Thr Ser Thr Ala Tyr Met Glu
1               5                   10                  15

Leu Ser Ser Leu Arg Ser Glu Asp Thr Ala Val Tyr Tyr Cys Ala Arg
                20                  25                  30

<210> SEQ ID NO 296
<211> LENGTH: 30
<212> TYPE: PRT
<213> ORGANISM: Homo sapiens

<400> SEQUENCE: 296

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Ser
                20                  25                  30

<210> SEQ ID NO 297
<211> LENGTH: 14
<212> TYPE: PRT
<213> ORGANISM: Homo sapiens

<400> SEQUENCE: 297

Trp Val Arg Gln Ala Pro Gly Lys Gly Leu Glu Trp Met Gly
1               5                   10

<210> SEQ ID NO 298
<211> LENGTH: 32
<212> TYPE: PRT
<213> ORGANISM: Homo sapiens

<400> SEQUENCE: 298

Arg Val Thr Met Thr Glu Asp Thr Ser Thr Asp Thr Ala Tyr Met Glu
1               5                   10                  15

Leu Ser Ser Leu Lys Ser Glu Asp Thr Ala Val Tyr Tyr Cys Ala Thr
                20                  25                  30

<210> SEQ ID NO 299
<211> LENGTH: 30
<212> TYPE: PRT
<213> ORGANISM: Homo sapiens

<400> SEQUENCE: 299

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr
                20                  25                  30

<210> SEQ ID NO 300
<211> LENGTH: 30
<212> TYPE: PRT
<213> ORGANISM: Homo sapiens

<400> SEQUENCE: 300

Gln Val Gln Leu Val Gln Ser Gly Ala Glu Val Lys Lys Pro Gly Ala
1               5                   10                  15

Ser Val Lys Val Ser Cys Lys Ser Ser Gly Tyr Thr Phe Thr
                20                  25                  30
```

```
<210> SEQ ID NO 301
<211> LENGTH: 32
<212> TYPE: PRT
<213> ORGANISM: Homo sapiens

<400> SEQUENCE: 301

Arg Val Thr Met Thr Arg Asp Thr Ser Ile Ser Thr Ala Tyr Met Glu
1               5                   10                  15

Leu Ser Arg Leu Arg Ser Asp Asp Thr Ala Val Tyr Tyr Cys Ala Arg
            20                  25                  30

<210> SEQ ID NO 302
<211> LENGTH: 30
<212> TYPE: PRT
<213> ORGANISM: Homo sapiens

<400> SEQUENCE: 302

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser
            20                  25                  30

<210> SEQ ID NO 303
<211> LENGTH: 33
<212> TYPE: PRT
<213> ORGANISM: Homo sapiens

<400> SEQUENCE: 303

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Arg
            20                  25                  30

Gly

<210> SEQ ID NO 304
<211> LENGTH: 30
<212> TYPE: PRT
<213> ORGANISM: Homo sapiens

<400> SEQUENCE: 304

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 305
<211> LENGTH: 32
<212> TYPE: PRT
<213> ORGANISM: Homo sapiens

<400> SEQUENCE: 305

Arg Phe Thr Ile Ser Arg Asp Asn Ala Lys Asn Ser Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 306
<211> LENGTH: 32
<212> TYPE: PRT
<213> ORGANISM: Homo sapiens

<400> SEQUENCE: 306
```

Arg Phe Thr Ile Ser Arg Asp Asn Ser Lys Asn Thr Leu Phe Leu Gln
1               5                   10                  15

Met Asn Ser Leu Arg Ala Glu Asp Thr Ala Val Tyr Tyr Cys Ala Arg
            20                  25                  30

<210> SEQ ID NO 307
<211> LENGTH: 30
<212> TYPE: PRT
<213> ORGANISM: Homo sapiens

<400> SEQUENCE: 307

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr
            20                  25                  30

<210> SEQ ID NO 308
<211> LENGTH: 14
<212> TYPE: PRT
<213> ORGANISM: Homo sapiens

<400> SEQUENCE: 308

Trp Val Arg Gln Ala Pro Gly Gln Gly Leu Glu Trp Ile Gly
1               5                   10

<210> SEQ ID NO 309
<211> LENGTH: 32
<212> TYPE: PRT
<213> ORGANISM: Homo sapiens

<400> SEQUENCE: 309

Lys Ala Thr Ile Thr Ala Asp Glu Ser Thr Asn Thr Ala Tyr Met Glu
1               5                   10                  15

Leu Ser Ser Leu Arg Ser Glu Asp Thr Ala Phe Tyr Phe Cys Ala Arg
            20                  25                  30

<210> SEQ ID NO 310
<211> LENGTH: 32
<212> TYPE: PRT
<213> ORGANISM: Homo sapiens

<400> SEQUENCE: 310

Arg Phe Thr Ile Ser Arg Asp Asn Ser Lys Asn Thr Leu Tyr Leu Gln
1               5                   10                  15

Met Asn Arg Leu Arg Ala Glu Asp Thr Ala Val Tyr Tyr Cys Ala Arg
            20                  25                  30

<210> SEQ ID NO 311
<211> LENGTH: 30
<212> TYPE: PRT
<213> ORGANISM: Homo sapiens

<400> SEQUENCE: 311

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser
            20                  25                  30

<210> SEQ ID NO 312
<211> LENGTH: 14
<212> TYPE: PRT
<213> ORGANISM: Homo sapiens

```
<400> SEQUENCE: 312

Trp Val Arg Gln Pro Pro Gly Lys Gly Leu Glu Trp Ile Gly
1               5                   10

<210> SEQ ID NO 313
<211> LENGTH: 32
<212> TYPE: PRT
<213> ORGANISM: Homo sapiens

<400> SEQUENCE: 313

Arg Val Thr Ile Ser Val Asp Lys Ser Lys Asn Gln Phe Ser Leu Lys
1               5                   10                  15

Leu Ser Ser Val Thr Ala Ala Asp Thr Ala Val Tyr Tyr Cys Ala Arg
                20                  25                  30

<210> SEQ ID NO 314
<211> LENGTH: 32
<212> TYPE: PRT
<213> ORGANISM: Homo sapiens

<400> SEQUENCE: 314

Arg Phe Ala Ile Ser Arg Asp Asn Ala Lys Asn Ser Leu Phe Leu Gln
1               5                   10                  15

Met Asn Ser Leu Arg Ala Glu Asp Thr Ala Val Tyr Tyr Cys Ala Arg
                20                  25                  30

<210> SEQ ID NO 315
<211> LENGTH: 32
<212> TYPE: PRT
<213> ORGANISM: Homo sapiens

<400> SEQUENCE: 315

Arg Phe Thr Ile Ser Arg Asp Asn Ala Arg Asn Ser Leu Tyr Leu Gln
1               5                   10                  15

Met Asn Ser Leu Arg Ala Glu Asp Thr Ala Val Tyr Tyr Cys Ala Arg
                20                  25                  30

<210> SEQ ID NO 316
<211> LENGTH: 30
<212> TYPE: PRT
<213> ORGANISM: Homo sapiens

<400> SEQUENCE: 316

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser
                20                  25                  30

<210> SEQ ID NO 317
<211> LENGTH: 14
<212> TYPE: PRT
<213> ORGANISM: Homo sapiens

<400> SEQUENCE: 317

Trp Val Arg Gln Ala Pro Gly Lys Gly Leu Glu Trp Val Gly
1               5                   10

<210> SEQ ID NO 318
<211> LENGTH: 32
<212> TYPE: PRT
<213> ORGANISM: Homo sapiens

<400> SEQUENCE: 318
```

```
Arg Phe Thr Ile Ser Arg Asp Asp Ser Lys Asn Thr Leu Tyr Leu Gln
1               5                   10                  15

Met Asn Ser Leu Lys Ala Glu Asp Thr Ala Val Tyr Tyr Cys Thr Thr
            20                  25                  30
```

<210> SEQ ID NO 319
<211> LENGTH: 30
<212> TYPE: PRT
<213> ORGANISM: Homo sapiens

<400> SEQUENCE: 319

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser
            20                  25                  30
```

<210> SEQ ID NO 320
<211> LENGTH: 14
<212> TYPE: PRT
<213> ORGANISM: Homo sapiens

<400> SEQUENCE: 320

```
Trp Ile Arg Gln Leu Pro Gly Lys Gly Leu Glu Trp Ile Gly
1               5                   10
```

<210> SEQ ID NO 321
<211> LENGTH: 32
<212> TYPE: PRT
<213> ORGANISM: Homo sapiens

<400> SEQUENCE: 321

```
Arg Val Thr Ile Ser Val Asp Thr Ser Lys Lys Gln Phe Ser Leu Arg
1               5                   10                  15

Leu Ser Ser Val Thr Ala Ala Asp Thr Ala Val Tyr Tyr Cys Ala Arg
            20                  25                  30
```

<210> SEQ ID NO 322
<211> LENGTH: 30
<212> TYPE: PRT
<213> ORGANISM: Homo sapiens

<400> SEQUENCE: 322

```
Glu Val Gln Leu Val Gln Ser Gly Ala Glu Val Lys Lys Pro Gly Glu
1               5                   10                  15

Ser Leu Lys Ile Ser Cys Lys Val Ser Gly Tyr Phe Phe Thr
            20                  25                  30
```

<210> SEQ ID NO 323
<211> LENGTH: 14
<212> TYPE: PRT
<213> ORGANISM: Homo sapiens

<400> SEQUENCE: 323

```
Trp Val Arg Gln Met Pro Gly Lys Gly Leu Glu Tyr Met Gly
1               5                   10
```

<210> SEQ ID NO 324
<211> LENGTH: 32
<212> TYPE: PRT
<213> ORGANISM: Homo sapiens

<400> SEQUENCE: 324

```
Gln Val Thr Ile Ser Ala Asp Lys Ser Ile Ser Thr Ala Tyr Leu Gln
1               5                   10                  15

Trp Ser Ser Leu Lys Ala Ser Asp Thr Ala Met Tyr Tyr Cys Ala Arg
            20                  25                  30
```

<210> SEQ ID NO 325
<211> LENGTH: 32
<212> TYPE: PRT
<213> ORGANISM: Homo sapiens

<400> SEQUENCE: 325

```
Arg Val Thr Met Thr Thr Asp Thr Ser Thr Ser Thr Ala Tyr Met Glu
1               5                   10                  15

Leu Arg Ser Leu Arg Ser Asp Asp Thr Ala Val Tyr Phe Cys Ala Arg
            20                  25                  30
```

<210> SEQ ID NO 326
<211> LENGTH: 30
<212> TYPE: PRT
<213> ORGANISM: Homo sapiens

<400> SEQUENCE: 326

```
Glu Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser
            20                  25                  30
```

<210> SEQ ID NO 327
<211> LENGTH: 30
<212> TYPE: PRT
<213> ORGANISM: Homo sapiens

<400> SEQUENCE: 327

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr
            20                  25                  30
```

<210> SEQ ID NO 328
<211> LENGTH: 32
<212> TYPE: PRT
<213> ORGANISM: Homo sapiens

<400> SEQUENCE: 328

```
Arg Val Thr Met Thr Thr Asp Thr Ser Thr Ser Thr Ala Tyr Met Glu
1               5                   10                  15

Leu Arg Ser Leu Arg Ser Asp Asp Thr Ala Val Tyr Tyr Cys Ala Arg
            20                  25                  30
```

<210> SEQ ID NO 329
<211> LENGTH: 30
<212> TYPE: PRT
<213> ORGANISM: Homo sapiens

<400> SEQUENCE: 329

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Asn Phe Thr
            20                  25                  30
```

<210> SEQ ID NO 330
<211> LENGTH: 14

-continued

<212> TYPE: PRT
<213> ORGANISM: Homo sapiens

<400> SEQUENCE: 330

Trp Val Arg Gln Met Pro Gly Lys Gly Leu Glu Leu Met Gly
1               5                   10

<210> SEQ ID NO 331
<211> LENGTH: 32
<212> TYPE: PRT
<213> ORGANISM: Homo sapiens

<400> SEQUENCE: 331

Gln Val Thr Ile Ser Ala Asp Lys Ser Ile Ser Thr Ala Tyr Leu Gln
1               5                   10                  15

Trp Ser Ser Leu Lys Ala Ser Asp Thr Ala Met Tyr Tyr Cys Gly Ser
            20                  25                  30

<210> SEQ ID NO 332
<211> LENGTH: 11
<212> TYPE: PRT
<213> ORGANISM: Homo sapiens

<400> SEQUENCE: 332

Trp Gly Arg Gly Thr Leu Val Thr Val Ser Ser
1               5                   10

<210> SEQ ID NO 333
<211> LENGTH: 30
<212> TYPE: PRT
<213> ORGANISM: Homo sapiens

<400> SEQUENCE: 333

Gln Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Arg
            20                  25                  30

<210> SEQ ID NO 334
<211> LENGTH: 32
<212> TYPE: PRT
<213> ORGANISM: Homo sapiens

<400> SEQUENCE: 334

Gln Leu Thr Ile Ser Lys Asp Thr Ser Lys Asn Gln Val Val Leu Thr
1               5                   10                  15

Met Thr Asn Met Asp Pro Val Asp Thr Ala Thr Tyr Tyr Cys Ala Arg
            20                  25                  30

<210> SEQ ID NO 335
<211> LENGTH: 30
<212> TYPE: PRT
<213> ORGANISM: Homo sapiens

<400> SEQUENCE: 335

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser
            20                  25                  30

<210> SEQ ID NO 336
<211> LENGTH: 14
<212> TYPE: PRT

<213> ORGANISM: Homo sapiens

<400> SEQUENCE: 336

Trp Ile Arg Gln Ser Pro Gly Lys Gly Leu Glu Trp Ile Gly
1               5                   10

<210> SEQ ID NO 337
<211> LENGTH: 32
<212> TYPE: PRT
<213> ORGANISM: Homo sapiens

<400> SEQUENCE: 337

Arg Leu Thr Ile Ser Ile Asp Thr Ser Lys Thr Gln Phe Ser Leu Lys
1               5                   10                  15

Leu Ser Ser Val Thr Ala Ala Asp Thr Ala Ile Tyr Tyr Cys Val Arg
                20                  25                  30

<210> SEQ ID NO 338
<211> LENGTH: 32
<212> TYPE: PRT
<213> ORGANISM: Homo sapiens

<400> SEQUENCE: 338

Arg Phe Ile Ile Ser Arg Asp Lys Ser Lys Asn Thr Leu Tyr Leu Gln
1               5                   10                  15

Met Asn Ser Leu Arg Ala Glu Asp Thr Ala Val Tyr Tyr Cys Ala Arg
                20                  25                  30

<210> SEQ ID NO 339
<211> LENGTH: 32
<212> TYPE: PRT
<213> ORGANISM: Homo sapiens

<400> SEQUENCE: 339

Arg Val Thr Met Thr Arg Asp Thr Ser Ile Ser Thr Ala Tyr Met Glu
1               5                   10                  15

Leu Ser Arg Leu Arg Ser Asp Asp Thr Ala Val Tyr Phe Cys Ala Arg
                20                  25                  30

<210> SEQ ID NO 340
<211> LENGTH: 30
<212> TYPE: PRT
<213> ORGANISM: Homo sapiens

<400> SEQUENCE: 340

Glu Val Gln Leu Val Gln Ser Gly Gly Gly Leu Val Gln Pro Gly Gly
1               5                   10                  15

Ser Leu Arg Leu Ser Cys Thr Ala Ser Gly Phe Thr Phe Ser
                20                  25                  30

<210> SEQ ID NO 341
<211> LENGTH: 32
<212> TYPE: PRT
<213> ORGANISM: Homo sapiens

<400> SEQUENCE: 341

Arg Phe Thr Ile Ser Arg Asp Asn Ala Lys Asn Thr Leu Tyr Leu Gln
1               5                   10                  15

Met Asn Ser Leu Arg Ala Glu Asp Thr Ala Val Tyr Tyr Cys Ala Arg
                20                  25                  30

<210> SEQ ID NO 342

-continued

```
<211> LENGTH: 14
<212> TYPE: PRT
<213> ORGANISM: Homo sapiens

<400> SEQUENCE: 342

Trp Val Arg Gln Ala Pro Gly Glu Gly Leu Glu Trp Val Ala
1               5                   10

<210> SEQ ID NO 343
<211> LENGTH: 30
<212> TYPE: PRT
<213> ORGANISM: Homo sapiens

<400> SEQUENCE: 343

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser
            20                  25                  30

<210> SEQ ID NO 344
<211> LENGTH: 30
<212> TYPE: PRT
<213> ORGANISM: Homo sapiens

<400> SEQUENCE: 344

Gln Val Gln Leu Val Gln Ser Gly Ala Ala Val Lys Lys Pro Gly Ala
1               5                   10                  15

Ser Val Lys Val Ser Cys Lys Ala Ser Gly Tyr Thr Phe Thr
            20                  25                  30

<210> SEQ ID NO 345
<211> LENGTH: 32
<212> TYPE: PRT
<213> ORGANISM: Homo sapiens

<400> SEQUENCE: 345

Arg Val Thr Met Thr Arg Asp Thr Ser Ile Ser Thr Ala Ser Met Glu
1               5                   10                  15

Leu Ser Arg Leu Arg Ser Asp Asp Thr Ala Val Tyr Phe Cys Ala Arg
            20                  25                  30

<210> SEQ ID NO 346
<211> LENGTH: 32
<212> TYPE: PRT
<213> ORGANISM: Homo sapiens

<400> SEQUENCE: 346

Arg Phe Thr Ile Ser Arg Asp Asn Ala Lys Asn Ser Leu Tyr Leu Gln
1               5                   10                  15

Met Asn Ser Leu Arg Ala Glu Asp Thr Ala Val Tyr Tyr Cys Thr Glu
            20                  25                  30

<210> SEQ ID NO 347
<211> LENGTH: 30
<212> TYPE: PRT
<213> ORGANISM: Homo sapiens

<400> SEQUENCE: 347

Gln Val Gln Leu Val Gln Ser Gly Thr Glu Val Lys Lys Pro Gly Ala
1               5                   10                  15

Ser Met Lys Val Ser Cys Lys Ala Ser Gly Tyr Thr Phe Thr
            20                  25                  30
```

<210> SEQ ID NO 348
<211> LENGTH: 32
<212> TYPE: PRT
<213> ORGANISM: Homo sapiens

<400> SEQUENCE: 348

Arg Val Thr Met Thr Arg Asp Thr Ser Thr Asn Thr Val Tyr Met Glu
1               5                   10                  15

Leu Ser Ser Leu Arg Ser Glu Asp Thr Ala Met Tyr Tyr Cys Ala Arg
            20                  25                  30

<210> SEQ ID NO 349
<211> LENGTH: 32
<212> TYPE: PRT
<213> ORGANISM: Homo sapiens

<400> SEQUENCE: 349

Arg Phe Thr Ile Ser Arg Asp Asn Ala Lys Asn Ser Leu Tyr Leu Gln
1               5                   10                  15

Met Asn Ser Leu Arg Asp Glu Asp Thr Ala Val Tyr Tyr Cys Ala Arg
            20                  25                  30

<210> SEQ ID NO 350
<211> LENGTH: 441
<212> TYPE: PRT
<213> ORGANISM: Homo sapiens

<400> SEQUENCE: 350

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Leu Thr Ser Tyr
            20                  25                  30

Gly Ile Ser Trp Val Arg Gln Ala Pro Gly Gln Gly Leu Glu Trp Met
        35                  40                  45

Gly Trp Val Ser Phe Tyr Asn Gly Asn Thr Asn Tyr Ala Gln Lys Leu
    50                  55                  60

Gln Gly Arg Gly Thr Met Thr Thr Asp Pro Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Tyr Gly Met Asp Val Trp Gly Gln Gly Thr Thr Val Thr
            100                 105                 110

Val Ser Ser Ala Ser Thr Lys Gly Pro Ser Val Phe Pro Leu Ala Pro
        115                 120                 125

Cys Ser Arg Ser Thr Ser Glu Ser Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Asn Phe Gly
            180                 185                 190

Thr Gln Thr Tyr Thr Cys Asn Val Asp His Lys Pro Ser Asn Thr Lys
        195                 200                 205

Val Asp Lys Thr Val Glu Arg Lys Cys Cys Val Glu Cys Pro Pro Cys
    210                 215                 220

Pro Ala Pro Pro Val Ala Gly Pro Ser Val Phe Leu Phe Pro Pro Lys

-continued

```
                225                 230                 235                 240
        Pro Lys Asp Thr Leu Met Ile Ser Arg Thr Pro Glu Val Thr Cys Val
                        245                 250                 255

Val Val Asp Val Ser His Glu Asp Pro Glu Val Gln Phe Asn Trp Tyr
                        260                 265                 270

Val Asp Gly Val Glu Val His Asn Ala Lys Thr Lys Pro Arg Glu Glu
                        275                 280                 285

Gln Phe Asn Ser Thr Phe Arg Val Val Ser Val Leu Thr Val Val His
                        290                 295                 300

Gln Asp Trp Leu Asn Gly Lys Glu Tyr Lys Cys Lys Val Ser Asn Lys
        305                 310                 315                 320

Gly Leu Pro Ala Pro Ile Glu Lys Thr Ile Ser Lys Thr Lys Gly Gln
                        325                 330                 335

Pro Arg Glu Pro Gln Val Tyr Thr Leu Pro Pro Ser Arg Glu Glu Met
                        340                 345                 350

Thr Lys Asn Gln Val Ser Leu Thr Cys Leu Val Lys Gly Phe Tyr Pro
                        355                 360                 365

Ser Asp Ile Ala Val Glu Trp Glu Ser Asn Gly Gln Pro Glu Asn Asn
                        370                 375                 380

Tyr Lys Thr Thr Pro Pro Met Leu Asp Ser Asp Gly Ser Phe Phe Leu
        385                 390                 395                 400

Tyr Ser Lys Leu Thr Val Asp Lys Ser Arg Trp Gln Gln Gly Asn Val
                        405                 410                 415

Phe Ser Cys Ser Val Met His Glu Ala Leu His Asn His Tyr Thr Gln
                        420                 425                 430

Lys Ser Leu Ser Leu Ser Pro Gly Lys
                        435                 440

<210> SEQ ID NO 351
<211> LENGTH: 215
<212> TYPE: PRT
<213> ORGANISM: Homo sapiens

<400> SEQUENCE: 351

Glu Ser Ala Leu Thr Gln Pro Ala Ser Val Ser Gly Ser Pro Gly Gln
        1               5                   10                  15

Ser Ile Thr Ile Ser Cys Thr Gly Thr Ser Ser Asp Val Gly Gly Tyr
                        20                  25                  30

Asn Ser Val Ser Trp Tyr Gln Gln His Pro Gly Lys Ala Pro Lys Leu
                        35                  40                  45

Met Ile Tyr Glu Val Ser Asn Arg Pro Ser Gly Val Ser Asn Arg Phe
        50                  55                  60

Ser Gly Ser Lys Ser Gly Asn Thr Ala Ser Leu Thr Ile Ser Gly Leu
        65                  70                  75                  80

Gln Ala Glu Asp Glu Ala Asp Tyr Tyr Cys Asn Ser Tyr Thr Ser Thr
                        85                  90                  95

Ser Met Val Phe Gly Gly Gly Thr Lys Leu Thr Val Leu Gly Gln Pro
                        100                 105                 110

Lys Ala Ala Pro Ser Val Thr Leu Phe Pro Pro Ser Ser Glu Glu Leu
                        115                 120                 125

Gln Ala Asn Lys Ala Thr Leu Val Cys Leu Ile Ser Asp Phe Tyr Pro
                        130                 135                 140

Gly Ala Val Thr Val Ala Trp Lys Ala Asp Ser Ser Pro Val Lys Ala
        145                 150                 155                 160
```

```
Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
        180                 185                 190

Ser Tyr Ser Cys Gln Val Thr His Glu Gly Ser Thr Val Glu Lys Thr
            195                 200                 205

Val Ala Pro Thr Glu Cys Ser
        210             215

<210> SEQ ID NO 352
<211> LENGTH: 441
<212> TYPE: PRT
<213> ORGANISM: Homo sapiens

<400> SEQUENCE: 352

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Leu Thr Ser Tyr
            20                  25                  30

Gly Ile Ser Trp Val Arg Gln Ala Pro Gly Gln Gly Leu Glu Trp Met
        35                  40                  45

Gly Trp Val Ser Phe Tyr Asn Gly Asn Thr Asn Tyr Ala Gln Lys Leu
    50                  55                  60

Gln Gly Arg Gly Thr Met Thr Arg Asp Pro Ser Thr Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Tyr Gly Met Asp Val Trp Gly Gln Gly Thr Thr Val Thr
            100                 105                 110

Val Ser Ser Ala Ser Thr Lys Gly Pro Ser Val Phe Pro Leu Ala Pro
        115                 120                 125

Cys Ser Arg Ser Thr Ser Glu Ser Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Asn Phe Gly
            180                 185                 190

Thr Gln Thr Tyr Thr Cys Asn Val Asp His Lys Pro Ser Asn Thr Lys
        195                 200                 205

Val Asp Lys Thr Val Glu Arg Lys Cys Cys Val Glu Cys Pro Pro Cys
    210                 215                 220

Pro Ala Pro Pro Val Ala Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser His Glu Asp Pro Glu Val Gln Phe Asn Trp Tyr
            260                 265                 270

Val Asp Gly Val Glu Val His Asn Ala Lys Thr Lys Pro Arg Glu Glu
        275                 280                 285

Gln Phe Asn Ser Thr Phe Arg Val Val Ser Val Leu Thr Val Val His
    290                 295                 300

Gln Asp Trp Leu Asn Gly Lys Glu Tyr Lys Cys Lys Val Ser Asn Lys
305                 310                 315                 320
```

```
Gly Leu Pro Ala Pro Ile Glu Lys Thr Ile Ser Lys Thr Lys Gly Gln
                325                 330                 335

Pro Arg Glu Pro Gln Val Tyr Thr Leu Pro Pro Ser Arg Glu Glu Met
            340                 345                 350

Thr Lys Asn Gln Val Ser Leu Thr Cys Leu Val Lys Gly Phe Tyr Pro
                355                 360                 365

Ser Asp Ile Ala Val Glu Trp Glu Ser Asn Gly Gln Pro Glu Asn Asn
    370                 375                 380

Tyr Lys Thr Thr Pro Pro Met Leu Asp Ser Asp Gly Ser Phe Phe Leu
385                 390                 395                 400

Tyr Ser Lys Leu Thr Val Asp Lys Ser Arg Trp Gln Gln Gly Asn Val
                405                 410                 415

Phe Ser Cys Ser Val Met His Glu Ala Leu His Asn His Tyr Thr Gln
                420                 425                 430

Lys Ser Leu Ser Leu Ser Pro Gly Lys
                435                 440

<210> SEQ ID NO 353
<211> LENGTH: 441
<212> TYPE: PRT
<213> ORGANISM: Homo sapiens

<400> SEQUENCE: 353

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Leu Thr Ser Tyr
            20                  25                  30

Gly Ile Ser Trp Val Arg Gln Ala Pro Gly Gln Gly Leu Glu Trp Met
        35                  40                  45

Gly Trp Val Ser Phe Tyr Asn Gly Asn Thr Asn Tyr Ala Gln Lys Leu
    50                  55                  60

Gln Gly Arg Gly Thr Met Thr Thr Asp Pro Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Tyr Gly Met Asp Val Trp Gly Gln Gly Thr Thr Val Thr
            100                 105                 110

Val Ser Ser Ala Ser Thr Lys Gly Pro Ser Val Phe Pro Leu Ala Pro
        115                 120                 125

Cys Ser Arg Ser Thr Ser Glu Ser Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Asn Phe Gly
            180                 185                 190

Thr Gln Thr Tyr Thr Cys Asn Val Asp His Lys Pro Ser Asn Thr Lys
        195                 200                 205

Val Asp Lys Thr Val Glu Arg Lys Cys Cys Val Glu Cys Pro Pro Cys
    210                 215                 220

Pro Ala Pro Pro Val Ala Gly Pro Ser Val Phe Leu Phe Pro Pro Lys
225                 230                 235                 240

Pro Lys Asp Thr Leu Met Ile Ser Arg Thr Pro Glu Val Thr Cys Val
```

```
                        245                 250                 255
Val Val Asp Val Ser His Glu Asp Pro Glu Val Gln Phe Asn Trp Tyr
            260                 265                 270

Val Asp Gly Val Glu Val His Asn Ala Lys Thr Lys Pro Arg Glu Glu
        275                 280                 285

Gln Phe Asn Ser Thr Phe Arg Val Val Ser Val Leu Thr Val Val His
    290                 295                 300

Gln Asp Trp Leu Asn Gly Lys Glu Tyr Lys Cys Lys Val Ser Asn Lys
305                 310                 315                 320

Gly Leu Pro Ala Pro Ile Glu Lys Thr Ile Ser Lys Thr Lys Gly Gln
                325                 330                 335

Pro Arg Glu Pro Gln Val Tyr Thr Leu Pro Pro Ser Arg Glu Glu Met
            340                 345                 350

Thr Lys Asn Gln Val Ser Leu Thr Cys Leu Val Lys Gly Phe Tyr Pro
        355                 360                 365

Ser Asp Ile Ala Val Glu Trp Glu Ser Asn Gly Gln Pro Glu Asn Asn
    370                 375                 380

Tyr Lys Thr Thr Pro Pro Met Leu Asp Ser Asp Gly Ser Phe Phe Leu
385                 390                 395                 400

Tyr Ser Lys Leu Thr Val Asp Lys Ser Arg Trp Gln Gln Gly Asn Val
                405                 410                 415

Phe Ser Cys Ser Val Met His Glu Ala Leu His Asn His Tyr Thr Gln
            420                 425                 430

Lys Lys Leu Ser Leu Ser Pro Gly Lys
        435                 440

<210> SEQ ID NO 354
<211> LENGTH: 441
<212> TYPE: PRT
<213> ORGANISM: Homo sapiens

<400> SEQUENCE: 354

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Leu Thr Ser Tyr
            20                  25                  30

Gly Ile Ser Trp Val Arg Gln Ala Pro Gly Gln Gly Leu Glu Trp Met
        35                  40                  45

Gly Trp Val Ser Phe Tyr Asn Gly Asn Thr Asn Tyr Ala Gln Lys Leu
    50                  55                  60

Gln Gly Arg Gly Thr Met Thr Arg Asp Pro Ser Thr Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Tyr Gly Met Asp Val Trp Gly Gln Gly Thr Thr Val Thr
            100                 105                 110

Val Ser Ser Ala Ser Thr Lys Gly Pro Ser Val Phe Pro Leu Ala Pro
        115                 120                 125

Cys Ser Arg Ser Thr Ser Glu Ser Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175
```

Leu Tyr Ser Leu Ser Ser Val Val Thr Val Pro Ser Ser Asn Phe Gly
            180                 185                 190

Thr Gln Thr Tyr Thr Cys Asn Val Asp His Lys Pro Ser Asn Thr Lys
        195                 200                 205

Val Asp Lys Thr Val Glu Arg Lys Cys Cys Val Glu Cys Pro Pro Cys
    210                 215                 220

Pro Ala Pro Pro Val Ala Gly Pro Ser Val Phe Leu Phe Pro Pro Lys
225                 230                 235                 240

Pro Lys Asp Thr Leu Met Ile Ser Arg Thr Pro Glu Val Thr Cys Val
            245                 250                 255

Val Val Asp Val Ser His Glu Asp Pro Glu Val Gln Phe Asn Trp Tyr
        260                 265                 270

Val Asp Gly Val Glu Val His Asn Ala Lys Thr Lys Pro Arg Glu Glu
    275                 280                 285

Gln Phe Asn Ser Thr Phe Arg Val Val Ser Val Leu Thr Val Val His
290                 295                 300

Gln Asp Trp Leu Asn Gly Lys Glu Tyr Lys Cys Lys Val Ser Asn Lys
305                 310                 315                 320

Gly Leu Pro Ala Pro Ile Glu Lys Thr Ile Ser Lys Thr Lys Gly Gln
            325                 330                 335

Pro Arg Glu Pro Gln Val Tyr Thr Leu Pro Pro Ser Arg Glu Glu Met
        340                 345                 350

Thr Lys Asn Gln Val Ser Leu Thr Cys Leu Val Lys Gly Phe Tyr Pro
    355                 360                 365

Ser Asp Ile Ala Val Glu Trp Glu Ser Asn Gly Gln Pro Glu Asn Asn
370                 375                 380

Tyr Lys Thr Thr Pro Pro Met Leu Asp Ser Asp Gly Ser Phe Phe Leu
385                 390                 395                 400

Tyr Ser Lys Leu Thr Val Asp Lys Ser Arg Trp Gln Gln Gly Asn Val
            405                 410                 415

Phe Ser Cys Ser Val Met His Glu Ala Leu His Asn His Tyr Thr Gln
        420                 425                 430

Lys Lys Leu Ser Leu Ser Pro Gly Lys
    435                 440

<210> SEQ ID NO 355
<211> LENGTH: 220
<212> TYPE: PRT
<213> ORGANISM: Homo sapiens

<400> SEQUENCE: 355

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Asp Ser
            20                  25                  30

Ser Asp Asn Lys Asn Tyr Leu Ala Trp Tyr Gln Gln Lys Pro Gly Gln
        35                  40                  45

Pro Pro Lys Leu Leu Ile Tyr Trp Ala Ser Asn Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
            85                  90                  95

Tyr Tyr Ser Asp Pro Phe Thr Phe Gly Pro Gly Thr Lys Val Asp Ile
        100                 105                 110

-continued

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
        130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 356
<211> LENGTH: 446
<212> TYPE: PRT
<213> ORGANISM: Homo sapiens

<400> SEQUENCE: 356

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Glu Ser Trp Phe Gly Glu Val Phe Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Asn Phe Gly Thr Gln Thr Tyr Thr Cys Asn Val Asp His Lys
        195                 200                 205

Pro Ser Asn Thr Lys Val Asp Lys Thr Val Glu Arg Lys Cys Cys Val
    210                 215                 220

Glu Cys Pro Pro Cys Pro Ala Pro Pro Val Ala Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val

```
                260                 265                 270
Gln Phe Asn Trp Tyr Val Asp Gly Val Glu Val His Asn Ala Lys Thr
            275                 280                 285
Lys Pro Arg Glu Glu Gln Phe Asn Ser Thr Phe Arg Val Val Ser Val
        290                 295                 300
Leu Thr Val Val His Gln Asp Trp Leu Asn Gly Lys Glu Tyr Lys Cys
305                 310                 315                 320
Lys Val Ser Asn Lys Gly Leu Pro Ala Pro Ile Glu Lys Thr Ile Ser
                325                 330                 335
Lys Thr Lys Gly Gln Pro Arg Glu Pro Gln Val Tyr Thr Leu Pro Pro
            340                 345                 350
Ser Arg Glu Glu Met Thr Lys Asn Gln Val Ser Leu Thr Cys Leu Val
        355                 360                 365
Lys Gly Phe Tyr Pro Ser Asp Ile Ala Val Glu Trp Glu Ser Asn Gly
    370                 375                 380
Gln Pro Glu Asn Asn Tyr Lys Thr Thr Pro Pro Met Leu Asp Ser Asp
385                 390                 395                 400
Gly Ser Phe Phe Leu Tyr Ser Lys Leu Thr Val Asp Lys Ser Arg Trp
                405                 410                 415
Gln Gln Gly Asn Val Phe Ser Cys Ser Val Met His Glu Ala Leu His
            420                 425                 430
Asn His Tyr Thr Gln Lys Ser Leu Ser Leu Ser Pro Gly Lys
        435                 440                 445

<210> SEQ ID NO 357
<211> LENGTH: 446
<212> TYPE: PRT
<213> ORGANISM: Homo sapiens

<400> SEQUENCE: 357

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Ser Tyr
            20                  25                  30
Gly Ile Ser Trp Val Arg Gln Ala Pro Gly Gln Gly Leu Glu Trp Met
        35                  40                  45
Gly Trp Ile Ser Ala Tyr Asn Gly Asn Thr Asn Tyr Ala Gln Lys Leu
    50                  55                  60
Gln Gly Arg Val Thr Met Thr Arg Asp Thr Ser Thr Ser Thr Ala Tyr
65                  70                  75                  80
Met Glu Leu Ser Arg Leu Arg Ser Asp Asp Thr Ala Val Tyr Tyr Cys
                85                  90                  95
Ala Arg Glu Ser Trp Phe Gly Glu Val Phe Asp Tyr Trp Gly Gln
            100                 105                 110
Gly Thr Leu Val Thr Val Ser Ser Ala Ser Thr Lys Gly Pro Ser Val
        115                 120                 125
Phe Pro Leu Ala Pro Cys Ser Arg Ser Thr Ser Glu Ser Thr Ala Ala
    130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
```

Ser Ser Asn Phe Gly Thr Gln Thr Tyr Thr Cys Asn Val Asp His Lys
            195                 200                 205

Pro Ser Asn Thr Lys Val Asp Lys Thr Val Glu Arg Lys Cys Cys Val
    210                 215                 220

Glu Cys Pro Pro Cys Pro Ala Pro Pro Val Ala Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Phe Arg Val Val Ser Val
    290                 295                 300

Leu Thr Val Val His Gln Asp Trp Leu Asn Gly Lys Glu Tyr Lys Cys
305                 310                 315                 320

Lys Val Ser Asn Lys Gly Leu Pro Ala Pro Ile Glu Lys Thr Ile Ser
                325                 330                 335

Lys Thr Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Met Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 358
<211> LENGTH: 446
<212> TYPE: PRT
<213> ORGANISM: Homo sapiens

<400> SEQUENCE: 358

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Lys Ala Tyr Asn Gly Asn Thr Asn Tyr Ala Gln Lys Leu
    50                  55                  60

Gln Gly Arg Val Thr Met Thr Arg Asp Thr Ser Thr Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Ser Trp Phe Gly Glu Val Phe Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Asn Phe Gly Thr Gln Thr Tyr Thr Cys Asn Val Asp His Lys
        195                 200                 205

Pro Ser Asn Thr Lys Val Asp Lys Thr Val Glu Arg Lys Cys Cys Val
    210                 215                 220

Glu Cys Pro Pro Cys Pro Ala Pro Pro Val Ala Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Phe Arg Val Val Ser Val
    290                 295                 300

Leu Thr Val Val His Gln Asp Trp Leu Asn Gly Lys Glu Tyr Lys Cys
305                 310                 315                 320

Lys Val Ser Asn Lys Gly Leu Pro Ala Pro Ile Glu Lys Thr Ile Ser
                325                 330                 335

Lys Thr Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Met Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 359
<211> LENGTH: 450
<212> TYPE: PRT
<213> ORGANISM: Homo sapiens

<400> SEQUENCE: 359

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Gly Met His Trp Val Arg Gln Ala Pro Gly Glu Gly Leu Glu Trp Val
        35                  40                  45

Ala Ala Ile Trp Phe Asp Ala Ser Asp Lys Tyr Tyr Ala Asp Ala Val

```
                 50                  55                  60
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Gln Ala Ile Phe Gly Val Val Pro Asp Tyr Trp Gly Gln
                100                 105                 110

Gly Thr Leu Val Thr Val Ser Ser Ala Ser Thr Lys Gly Pro Ser Val
                115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
            275                 280                 285

Asn Ala Lys Thr Lys Pro Cys Glu Glu Gln Tyr Gly Ser Thr Tyr Arg
        290                 295                 300

Cys Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
            435                 440                 445

Gly Lys
    450

<210> SEQ ID NO 360
```

<211> LENGTH: 214
<212> TYPE: PRT
<213> ORGANISM: Homo sapiens

<400> SEQUENCE: 360

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ala Thr Arg Ala Thr Gly Ile Pro Ala Arg Val Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 361
<211> LENGTH: 450
<212> TYPE: PRT
<213> ORGANISM: Homo sapiens

<400> SEQUENCE: 361

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Asn Tyr
            20                  25                  30

Gly Met His Trp Val Arg Gln Ala Pro Gly Glu Gly Leu Glu Trp Val
        35                  40                  45

Ala Ala Ile Trp Phe Asp Ala Ser Asp Lys Tyr Tyr Ala Asp Ala Val
50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gln Ala Ile Phe Gly Val Val Pro Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Cys Glu Glu Gln Tyr Gly Ser Thr Tyr Arg
290                 295                 300

Cys Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 362
<211> LENGTH: 450
<212> TYPE: PRT
<213> ORGANISM: Homo sapiens

<400> SEQUENCE: 362

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Gly Met His Trp Val Arg Gln Ala Pro Gly Glu Gly Leu Glu Trp Val

```
            35                  40                  45
Ala Ala Ile Trp Phe Asp Ala Ser Asp Lys Tyr Tyr Ala Asp Ala Val
 50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Arg Asp Gln Ala Ile Phe Gly Val Val Pro Asp Tyr Trp Gly Gln
                100                 105                 110
Gly Thr Leu Val Thr Val Ser Ser Ala Ser Thr Lys Gly Pro Ser Val
            115                 120                 125
Phe Pro Leu Ala Pro Ser Ser Lys Ser Thr Ser Gly Gly Thr Ala Ala
130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
        195                 200                 205
Pro Ser Asn Thr Lys Val Asp Lys Lys Val Glu Pro Lys Ser Cys Asp
210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
            260                 265                 270
Asp Pro Glu Val Lys Phe Asn Trp Tyr Val Asp Gly Val Glu Val His
        275                 280                 285
Asn Ala Lys Thr Lys Pro Cys Glu Glu Gln Tyr Gly Ser Thr Tyr Arg
290                 295                 300
Cys Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Glu Glu Met Thr Lys Asn Gln Val Ser Leu
        355                 360                 365
Thr Cys Leu Val Lys Gly Phe Tyr Pro Ser Asp Ile Ala Val Glu Trp
370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
        435                 440                 445
Gly Lys
450
```

<210> SEQ ID NO 363
<211> LENGTH: 214
<212> TYPE: PRT
<213> ORGANISM: Homo sapiens

<400> SEQUENCE: 363

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ala Thr Arg Ala Thr Gly Ile Pro Asp Arg Val Ser Gly
50                  55                  60

Ser Gly Ser Gly Thr Glu Phe Thr Leu Thr Ile Ser Arg Leu Glu Pro
65                  70                  75                  80

Glu Asp Phe Ala Val Tyr Tyr Cys Gln Gln Tyr Asn Asn Trp Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 364
<211> LENGTH: 450
<212> TYPE: PRT
<213> ORGANISM: Homo sapiens

<400> SEQUENCE: 364

```
Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Asn Tyr
            20                  25                  30

Gly Met His Trp Val Arg Gln Ala Pro Gly Glu Gly Leu Glu Trp Val
        35                  40                  45

Ala Ala Ile Trp Phe Asp Ala Ser Asp Lys Tyr Tyr Ala Asp Ala Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gln Ala Ile Phe Gly Val Val Pro Asp Tyr Trp Gly Gln
            100                 105                 110
```

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Cys Glu Glu Gln Tyr Gly Ser Thr Tyr Arg
    290                 295                 300

Cys Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 365
<211> LENGTH: 214
<212> TYPE: PRT
<213> ORGANISM: Homo sapiens

<400> SEQUENCE: 365

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn

```
                    20                  25                  30
Leu Ala Trp Tyr Gln Gln Lys Pro Gly Gln Ala Pro Arg Leu Leu Ile
                35                  40                  45
Tyr Gly Ala Ala Thr Arg Ala Thr Gly Ile Pro Asp Arg Val Ser Gly
            50                  55                  60
Ser Gly Ser Gly Thr Glu Phe Thr Leu Thr Ile Ser Arg Leu Glu Pro
 65                 70                  75                  80
Glu Asp Phe Ala Val Tyr Tyr Cys Gln Gln Tyr Asn Asn Trp Pro Leu
                85                  90                  95
Thr Phe Gly Gly Gly Thr Lys Val Glu Ile Lys Arg Thr Val Ala Ala
               100                 105                 110
Pro Ser Val Phe Ile Phe Pro Pro Ser Asp Glu Gln Leu Lys Ser Gly
               115                 120                 125
Thr Ala Ser Val Val Cys Leu Leu Asn Asn Phe Tyr Pro Arg Glu Ala
               130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
               165                 170                 175
Ser Thr Leu Thr Leu Ser Lys Ala Asp Tyr Glu Lys His Lys Val Tyr
               180                 185                 190
Ala Cys Glu Val Thr His Gln Gly Leu Ser Ser Pro Val Thr Lys Ser
               195                 200                 205
Phe Asn Arg Gly Glu Cys
   210

<210> SEQ ID NO 366
<211> LENGTH: 441
<212> TYPE: PRT
<213> ORGANISM: Homo sapiens

<400> SEQUENCE: 366

Glu Val Gln Leu Val Gln Ser Gly Ala Glu Val Lys Lys Pro Gly Ala
 1               5                  10                  15
Ser Val Lys Val Ser Cys Lys Ala Ser Gly Tyr Thr Leu Thr Ser Tyr
                20                  25                  30
Gly Ile Ser Trp Val Arg Gln Ala Pro Gly Gln Gly Leu Glu Trp Met
                35                  40                  45
Gly Trp Val Ser Phe Tyr Asn Gly Asn Thr Asn Tyr Ala Gln Lys Leu
            50                  55                  60
Gln Gly Arg Gly Thr Met Thr Thr Asp Pro Ser Thr Ser Thr Ala Tyr
 65                 70                  75                  80
Met Glu Leu Arg Ser Leu Arg Ser Asp Asp Thr Ala Val Tyr Tyr Cys
                85                  90                  95
Ala Arg Gly Tyr Gly Met Asp Val Trp Gly Gln Gly Thr Thr Val Thr
               100                 105                 110
Val Ser Ser Ala Ser Thr Lys Gly Pro Ser Val Phe Pro Leu Ala Pro
               115                 120                 125
Cys Ser Arg Ser Thr Ser Glu Ser Thr Ala Ala Leu Gly Cys Leu Val
               130                 135                 140
Lys Asp Tyr Phe Pro Glu Pro Val Thr Val Ser Trp Asn Ser Gly Ala
145                 150                 155                 160
Leu Thr Ser Gly Val His Thr Phe Pro Ala Val Leu Gln Ser Ser Gly
               165                 170                 175
```

Leu Tyr Ser Leu Ser Ser Val Val Thr Val Pro Ser Ser Asn Phe Gly
            180                 185                 190

Thr Gln Thr Tyr Thr Cys Asn Val Asp His Lys Pro Ser Asn Thr Lys
        195                 200                 205

Val Asp Lys Thr Val Glu Arg Lys Cys Cys Val Glu Cys Pro Pro Cys
    210                 215                 220

Pro Ala Pro Pro Val Ala Gly Pro Ser Val Phe Leu Phe Pro Pro Lys
225                 230                 235                 240

Pro Lys Asp Thr Leu Met Ile Ser Arg Thr Pro Glu Val Thr Cys Val
            245                 250                 255

Val Val Asp Val Ser His Glu Asp Pro Glu Val Gln Phe Asn Trp Tyr
        260                 265                 270

Val Asp Gly Val Glu Val His Asn Ala Lys Thr Lys Pro Arg Glu Glu
    275                 280                 285

Gln Phe Asn Ser Thr Phe Arg Val Val Ser Val Leu Thr Val Val His
290                 295                 300

Gln Asp Trp Leu Asn Gly Lys Glu Tyr Lys Cys Lys Val Ser Asn Lys
305                 310                 315                 320

Gly Leu Pro Ala Pro Ile Glu Lys Thr Ile Ser Lys Thr Lys Gly Gln
            325                 330                 335

Pro Arg Glu Pro Gln Val Tyr Thr Leu Pro Pro Ser Arg Glu Glu Met
        340                 345                 350

Thr Lys Asn Gln Val Ser Leu Thr Cys Leu Val Lys Gly Phe Tyr Pro
    355                 360                 365

Ser Asp Ile Ala Val Glu Trp Glu Ser Asn Gly Gln Pro Glu Asn Asn
370                 375                 380

Tyr Lys Thr Thr Pro Pro Met Leu Asp Ser Asp Gly Ser Phe Phe Leu
385                 390                 395                 400

Tyr Ser Lys Leu Thr Val Asp Lys Ser Arg Trp Gln Gln Gly Asn Val
            405                 410                 415

Phe Ser Cys Ser Val Met His Glu Ala Leu His Asn His Tyr Thr Gln
        420                 425                 430

Lys Lys Leu Ser Leu Ser Pro Gly Lys
    435                 440

<210> SEQ ID NO 367
<211> LENGTH: 214
<212> TYPE: PRT
<213> ORGANISM: Homo sapiens

<400> SEQUENCE: 367

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ala Thr Arg Ala Thr Gly Ile Pro Ala Arg Val Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Leu
            85                  90                  95

Thr Phe Gly Gly Gly Thr Lys Val Glu Ile Lys Arg Thr Val Ala Ala
        100                 105                 110

```
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210

<210> SEQ ID NO 368
<211> LENGTH: 450
<212> TYPE: PRT
<213> ORGANISM: Homo sapiens

<400> SEQUENCE: 368

Gln Val Gln Leu Val Glu Ser Gly Gly Gly Val Val Gln Pro Gly Arg
1               5                   10                  15
Ser Leu Arg Leu Ser Cys Ala Ala Ser Gly Phe Thr Phe Ser Asn Tyr
            20                  25                  30
Gly Met His Trp Val Arg Gln Ala Pro Gly Glu Gly Leu Glu Trp Val
        35                  40                  45
Ala Ala Ile Trp Phe Asp Ala Ser Asp Lys Tyr Tyr Ala Asp Ala Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Asp Gln Ala Ile Phe Gly Val Val Pro Asp Tyr Trp Gly Gln
            100                 105                 110
Gly Thr Leu Val Thr Val Ser Ser Ala Ser Thr Lys Gly Pro Ser Val
        115                 120                 125
Phe Pro Leu Ala Pro Ser Ser Lys Ser Thr Ser Gly Gly Thr Ala Ala
    130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
        195                 200                 205
Pro Ser Asn Thr Lys Val Asp Lys Lys Val Glu Pro Lys Ser Cys Asp
    210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
```

```
            260                 265                 270
Asp Pro Glu Val Lys Phe Asn Trp Tyr Val Asp Gly Val Glu Val His
        275                 280                 285

Asn Ala Lys Thr Lys Pro Cys Glu Glu Gln Tyr Gly Ser Thr Tyr Arg
        290                 295                 300

Cys Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Leu Ser Leu Ser Pro
        435                 440                 445

Gly Lys
    450

<210> SEQ ID NO 369
<211> LENGTH: 692
<212> TYPE: PRT
<213> ORGANISM: Homo sapiens

<400> SEQUENCE: 369

Met Gly Thr Val Ser Ser Arg Arg Ser Trp Trp Pro Leu Pro Leu Leu
1               5                   10                  15

Leu Leu Leu Leu Leu Leu Leu Gly Pro Ala Gly Ala Arg Ala Gln Glu
            20                  25                  30

Asp Glu Asp Gly Asp Tyr Glu Glu Leu Val Leu Ala Leu Arg Ser Glu
        35                  40                  45

Glu Asp Gly Leu Ala Glu Ala Pro Glu His Gly Thr Thr Ala Thr Phe
    50                  55                  60

His Arg Cys Ala Lys Asp Pro Trp Arg Leu Pro Gly Thr Tyr Val Val
65                  70                  75                  80

Val Leu Lys Glu Glu Thr His Leu Ser Gln Ser Glu Arg Thr Ala Arg
                85                  90                  95

Arg Leu Gln Ala Gln Ala Ala Arg Arg Gly Tyr Leu Thr Lys Ile Leu
            100                 105                 110

His Val Phe His Gly Leu Leu Pro Gly Phe Leu Val Lys Met Ser Gly
        115                 120                 125

Asp Leu Leu Glu Leu Ala Leu Lys Leu Pro His Val Asp Tyr Ile Glu
    130                 135                 140

Glu Asp Ser Ser Val Phe Ala Gln Ser Ile Pro Trp Asn Leu Glu Arg
145                 150                 155                 160

Ile Thr Pro Pro Arg Tyr Arg Ala Asp Glu Tyr Gln Pro Pro Asp Gly
                165                 170                 175
```

```
Gly Ser Leu Val Glu Val Tyr Leu Leu Asp Thr Ser Ile Gln Ser Asp
            180                 185                 190

His Arg Glu Ile Glu Gly Arg Val Met Val Thr Asp Phe Glu Asn Val
            195                 200                 205

Pro Glu Glu Asp Gly Thr Arg Phe His Arg Gln Ala Ser Lys Cys Asp
210                 215                 220

Ser His Gly Thr His Leu Ala Gly Val Val Ser Gly Arg Asp Ala Gly
225                 230                 235                 240

Val Ala Lys Gly Ala Ser Met Arg Ser Leu Arg Val Leu Asn Cys Gln
            245                 250                 255

Gly Lys Gly Thr Val Ser Gly Thr Leu Ile Gly Leu Glu Phe Ile Arg
            260                 265                 270

Lys Ser Gln Leu Val Gln Pro Val Gly Pro Leu Val Val Leu Leu Pro
275                 280                 285

Leu Ala Gly Gly Tyr Ser Arg Val Leu Asn Ala Ala Cys Gln Arg Leu
            290                 295                 300

Ala Arg Ala Gly Val Val Leu Val Thr Ala Ala Gly Asn Phe Arg Asp
305                 310                 315                 320

Asp Ala Cys Leu Tyr Ser Pro Ala Ser Ala Pro Glu Val Ile Thr Val
            325                 330                 335

Gly Ala Thr Asn Ala Gln Asp Gln Pro Val Thr Leu Gly Thr Leu Gly
            340                 345                 350

Thr Asn Phe Gly Arg Cys Val Asp Leu Phe Ala Pro Gly Glu Asp Ile
            355                 360                 365

Ile Gly Ala Ser Ser Asp Cys Ser Thr Cys Phe Val Ser Gln Ser Gly
            370                 375                 380

Thr Ser Gln Ala Ala Ala His Val Ala Gly Ile Ala Ala Met Met Leu
385                 390                 395                 400

Ser Ala Glu Pro Glu Leu Thr Leu Ala Glu Leu Arg Gln Arg Leu Ile
            405                 410                 415

His Phe Ser Ala Lys Asp Val Ile Asn Glu Ala Trp Phe Pro Glu Asp
            420                 425                 430

Gln Arg Val Leu Thr Pro Asn Leu Val Ala Ala Leu Pro Pro Ser Thr
            435                 440                 445

His Gly Ala Gly Trp Gln Leu Phe Cys Arg Thr Val Trp Ser Ala His
            450                 455                 460

Ser Gly Pro Thr Arg Met Ala Thr Ala Ile Ala Arg Cys Ala Pro Asp
465                 470                 475                 480

Glu Glu Leu Leu Ser Cys Ser Ser Phe Ser Arg Ser Gly Lys Arg Arg
            485                 490                 495

Gly Glu Arg Met Glu Ala Gln Gly Gly Lys Leu Val Cys Arg Ala His
            500                 505                 510

Asn Ala Phe Gly Gly Glu Gly Val Tyr Ala Ile Ala Arg Cys Cys Leu
            515                 520                 525

Leu Pro Gln Ala Asn Cys Ser Val His Thr Ala Pro Pro Ala Glu Ala
            530                 535                 540

Ser Met Gly Thr Arg Val His Cys His Gln Gln Gly His Val Leu Thr
545                 550                 555                 560

Gly Cys Ser Ser His Trp Glu Val Glu Asp Leu Gly Thr His Lys Pro
            565                 570                 575

Pro Val Leu Arg Pro Arg Gly Gln Pro Asn Gln Cys Val Gly His Arg
            580                 585                 590

Glu Ala Ser Ile His Ala Ser Cys Cys His Ala Pro Gly Leu Glu Cys
```

```
                595                 600                 605
Lys Val Lys Glu His Gly Ile Pro Ala Pro Gln Gly Gln Val Thr Val
    610                 615                 620

Ala Cys Glu Glu Gly Trp Thr Leu Thr Gly Cys Ser Ala Leu Pro Gly
625                 630                 635                 640

Thr Ser His Val Leu Gly Ala Tyr Ala Val Asp Asn Thr Cys Val Val
                645                 650                 655

Arg Ser Arg Asp Val Ser Thr Thr Gly Ser Thr Ser Glu Glu Ala Val
            660                 665                 670

Thr Ala Val Ala Ile Cys Cys Arg Ser Arg His Leu Ala Gln Ala Ser
        675                 680                 685

Gln Glu Leu Gln
    690

<210> SEQ ID NO 370
<211> LENGTH: 14
<212> TYPE: PRT
<213> ORGANISM: Homo sapiens

<400> SEQUENCE: 370

Thr Gly Thr Ser Ser Asp Val Gly Gly Tyr Asn Ser Val Ser
1               5                   10

<210> SEQ ID NO 371
<211> LENGTH: 7
<212> TYPE: PRT
<213> ORGANISM: Homo sapiens

<400> SEQUENCE: 371

Glu Val Ser Asn Arg Pro Ser
1               5

<210> SEQ ID NO 372
<211> LENGTH: 9
<212> TYPE: PRT
<213> ORGANISM: Homo sapiens

<400> SEQUENCE: 372

Asn Ser Tyr Thr Ser Thr Ser Met Val
1               5

<210> SEQ ID NO 373
<211> LENGTH: 10
<212> TYPE: PRT
<213> ORGANISM: Homo sapiens

<400> SEQUENCE: 373

Gly Tyr Thr Leu Thr Ser Tyr Gly Ile Ser
1               5                   10

<210> SEQ ID NO 374
<211> LENGTH: 16
<212> TYPE: PRT
<213> ORGANISM: Homo sapiens

<400> SEQUENCE: 374

Trp Val Ser Phe Tyr Asn Gly Asn Thr Asn Tyr Ala Gln Lys Leu Gln
1               5                   10                  15

<210> SEQ ID NO 375
<211> LENGTH: 6
<212> TYPE: PRT
```

```
<213> ORGANISM: Homo sapiens

<400> SEQUENCE: 375

Gly Tyr Gly Met Asp Val
1               5

<210> SEQ ID NO 376
<211> LENGTH: 115
<212> TYPE: PRT
<213> ORGANISM: Homo sapiens

<400> SEQUENCE: 376

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Leu Thr Ser Tyr
            20                  25                  30

Gly Ile Ser Trp Val Arg Gln Ala Pro Gly Gln Gly Leu Glu Trp Met
        35                  40                  45

Gly Trp Val Ser Phe Tyr Asn Gly Asn Thr Asn Tyr Ala Gln Lys Leu
    50                  55                  60

Gln Gly Arg Gly Thr Met Thr Thr Asp Pro Ser Thr Ser Thr Ala Tyr
65                  70                  75                  80

Met Glu Leu Arg Ser Leu Arg Ser Asp Thr Ala Val Tyr Tyr Cys
                85                  90                  95

Ala Arg Gly Tyr Gly Met Asp Val Trp Gly Gln Gly Thr Thr Val Thr
            100                 105                 110

Val Ser Ser
        115

<210> SEQ ID NO 377
<211> LENGTH: 109
<212> TYPE: PRT
<213> ORGANISM: Homo sapiens

<400> SEQUENCE: 377

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Ser Val Ser Trp Tyr Gln Gln His Pro Gly Lys Ala Pro Lys Leu
        35                  40                  45

Met Ile Tyr Glu Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Asn Ser Tyr Thr Ser Thr
                85                  90                  95

Ser Met Val Phe Gly Gly Gly Thr Lys Leu Thr Val Leu
            100                 105

<210> SEQ ID NO 378
<211> LENGTH: 115
<212> TYPE: PRT
<213> ORGANISM: Homo sapiens

<400> SEQUENCE: 378

Gln Val Gln Leu Val Gln Ser Gly Ala Glu Val Lys Lys Pro Gly Ala
1               5                   10                  15
```

```
Ser Val Lys Val Ser Cys Lys Ala Ser Gly Tyr Thr Leu Thr Ser Tyr
            20                  25                  30

Gly Ile Ser Trp Val Arg Gln Ala Pro Gly Gln Gly Leu Glu Trp Met
        35                  40                  45

Gly Trp Val Ser Phe Tyr Asn Gly Asn Thr Asn Tyr Ala Gln Lys Leu
    50                  55                  60

Gln Gly Arg Gly Thr Met Thr Thr Asp Pro Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Tyr Gly Met Asp Val Trp Gly Gln Gly Thr Thr Val Thr
                100                 105                 110

Val Ser Ser
        115

<210> SEQ ID NO 379
<211> LENGTH: 109
<212> TYPE: PRT
<213> ORGANISM: Homo sapiens

<400> SEQUENCE: 379

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Ser Val Ser Trp Tyr Gln Gln His Pro Gly Lys Ala Pro Lys Leu
        35                  40                  45

Met Ile Tyr Glu Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Asn Ser Tyr Thr Ser Thr
                85                  90                  95

Ser Met Val Phe Gly Gly Gly Thr Lys Leu Thr Val Leu
                100                 105

<210> SEQ ID NO 380
<211> LENGTH: 4
<212> TYPE: PRT
<213> ORGANISM: Homo sapiens

<400> SEQUENCE: 380

Lys Lys Lys Pro
1

<210> SEQ ID NO 381
<211> LENGTH: 4
<212> TYPE: PRT
<213> ORGANISM: Homo sapiens

<400> SEQUENCE: 381

Pro Gly Lys Pro
1

<210> SEQ ID NO 382
<211> LENGTH: 5
<212> TYPE: PRT
<213> ORGANISM: Homo sapiens

<400> SEQUENCE: 382
```

```
Pro Gly Lys Lys Pro
1               5

<210> SEQ ID NO 383
<211> LENGTH: 6
<212> TYPE: PRT
<213> ORGANISM: Homo sapiens

<400> SEQUENCE: 383

Pro Gly Lys Lys Lys Pro
1               5
```

LOW-VISCOSITY ANTIGEN BINDING PROTEINS AND METHODS OF MAKING THEM

CROSS REFERENCES TO RELATED APPLICATIONS

This application is a national stage application under 35 U.S.C. § 371 of International Application No. PCT/US17/053967, having an international filing date of Sep. 28, 2017, which claims the benefit of U.S. Provisional Application No. 62/546,469, filed on Aug. 16, 2017; U.S. Provisional Application No. 62/430,773, filed on Dec. 6, 2016; and U.S. Provisional Application No. 62/401,770, filed Sep. 29, 2016, each of which is hereby incorporated by reference in their entirety for all purposes.

FIELD OF THE INVENTION

This invention relates to biopharmaceuticals, particularly to therapeutic antigen binding proteins, methods of use thereof, pharmaceutical compositions thereof, and processes of making them. In particular, this invention relates to antigen binding proteins, particularly antibodies, mutated to reduce viscosity.

BRIEF DESCRIPTION OF THE SEQUENCE LISTING

Incorporated herein by reference in its entirety is a Sequence Listing entitled, "2063-US-PCT_ST25_SEQ_LIST_032819", comprising SEQ ID NO:1 through SEQ ID NO:383, which includes nucleic acid and/or amino acid sequences disclosed herein. The Sequence Listing has been submitted herein in ASCII text format via EFS, and thus constitutes both the paper and computer readable form thereof. The Sequence Listing was created using PatentIn on Mar. 28, 2019, and is 519 KB in size.

BACKGROUND OF THE INVENTION

Currently, monoclonal antibodies (mAbs) are the most popular modality of modern therapeutic proteins on the market and under development. The differences between antibodies are predominantly in the antigen binding domains or complementary determining regions (CDRs). These differences in the CDRs are thought to result in differences in transient protein-protein interaction propensity that manifest themselves as bulk solution viscosity. Several groups have described the presence of reversible clusters of antibodies in viscous antibody solutions (predominantly dimers). Several theoretical descriptions of polymer viscosity have been proposed to explain the interactions of these clusters as a mechanism for bulk solution viscosity behavior.

Antibodies usually work as antagonists and, therefore, large amounts, often exceeding 100 mg per dose, are required to block undesirable interactions. For patient comfort, a single subcutaneous injection of a 1 mL volume is the most preferred mode of administration. The need to administer large amounts of mAbs in a relatively small volume has required high concentration formulations at or exceeding 100 mg/ml. Antibodies are large biopolymers with molecular weights of about 150 kDa, and their high concentrations result in high sheer stress and high viscosity due to protein-protein and protein-wall interactions during filtration and passage through the injection needles and in subcutaneous space. High viscosity presents challenges in the manufacture of therapeutic antigen binding proteins as well as in their administration to patients, including prohibitively high back pressure during injections leading to malfunction of injections devices, difficulty of manual administration, decreased bio-availability and patient discomfort.

The development and use of high concentration therapeutic monoclonal antibody solutions has accelerated as the cost of biopharmaceutical production has decreased. In some cases, these antibody solutions possess viscous solution attributes that can make manufacturing and administration of the intended dose challenging. The differences in the CDRs that appear to determine if an antibody is "viscous" or "not viscous" are likely related to the propensity of the CDRs to drive protein-protein interaction.

Significant efforts are underway in the industry to understand the nature of interactions leading to high viscosity and to reduce the viscosity of high viscosity antibody formulations. The most important parameters affecting viscosity of the antibody formulations include:

intermolecular interactions defined by the pI of the protein and the pH of the solution. Cheng et al. (2013), "Linking the solution viscosity of an IgG2 monoclonal antibody to its structure as a function of pH and temperature," *J. Pharm Sci.* 102: 4291-4304.

Charge interactions. Yadav et al. (2012), "Viscosity behavior of high-concentration monoclonal antibody solutions: correlation with interaction parameter and electroviscous effects," *J. Pharm Sci.* 101: 998-1011; Yadav et al. (2012), "The influence of charge distribution on self-association and viscosity behavior of monoclonal antibody solutions." *Mol Pharm* 9(4): 791-802; Singh et al. (2014), "Dipole-Dipole Interaction in Antibody Solutions: Correlation with Viscosity Behavior at High Concentration," *Pharm Res.* 31(9): 2549-2558; Chaudhri et al. (2013), "The role of amino acid sequence in the self-association of therapeutic monoclonal antibodies: insights from coarse-grained modeling," *J. Phys. Chem. B* 117: 1269-1279.

Hydrophobic interactions. Guo et al. (2012), "Structure-activity relationship for hydrophobic salts as viscosity-lowering excipients for concentrated solutions of monoclonal antibodies," *Pharm Res* 29: 3102-3109.

The highest solution viscosity was observed under conditions with the most negative diffusion interaction parameter kD, the highest apparent radius and the lowest net charge. Neergaard et al. (2013), "Viscosity of high concentration protein formulations of monoclonal antibodies of the IgG1 and IgG4 subclass—prediction of viscosity through protein-protein interaction measurements," *Eur. J. Pharm Sci.* 49: 400-410. The diffusion interaction parameter (kD), a component of the osmotic second virial coefficient (B(2)) correlated well (R>0.9) with the viscosity of concentrated mAb solutions, while the mAb net charge correlated weakly (R<0.6), indicating that weak intermolecular interactions are important in governing the viscoelastic behavior of concentrated mAb solutions. Connolly, et al. (2012), "Weak interactions govern the viscosity of concentrated antibody solutions: high-throughput analysis using the diffusion interaction parameter," *Biophys. J.* 103: 69-78. In a study reported in this specification, primary sequences linked to 3D structure were utilized. See Honegger et al. (2001), "Yet another numbering scheme for immunoglobulin variable domains: an automatic modeling and analysis tool," *J. Mol. Biol.* 309: 657-670. Viscosity values of several mAb molecules were measured to develop a model for viscosity prediction of mAbs via machine learning algorithms. Structural position, charge and hydrophobicity were the main parameters of amino acids utilized for the model.

Viscosity of monoclonal antibodies was assessed using molecular information in the following articles: Li, L. et al. (2014), "Concentration dependent viscosity of monoclonal antibody solutions: explaining experimental behavior in terms of molecular properties," *Pharm. Res.* 31: 3161-3178; and Sharma et al. (2014), "In silico selection of therapeutic antibodies for development: viscosity, clearance, and chemical stability," *Proc. Natl. Acad. Sci. U.S.A* 111: 18601-6.

The net result of the interactions between antibodies is either an extended transient network of interactions (a percolating network) that result in a viscous solution or the formation of larger oligomers that then somehow influence the solution rheology as larger structures. In studies reported in this specification, a small number of viscous antibodies was used as the subject for biochemical and biophysical analysis in an attempt to deduce specific protein-protein interactions that might lead to a viscous antibody solution.

The Aho numbering approach was utilized in the past to improve stability and other biophysical properties. Ewert et al. (2003), "Structure-based improvement of the biophysical properties of immunoglobulin VH domains with a generalizable approach," *Biochemistry* 42: 1517-1528; Ewert et al. (2003), "Biophysical properties of human antibody variable domains," *J. Mol. Biol.* 325: 531-553; Ewert et al. (2004), "Stability improvement of antibodies for extracellular and intracellular applications: CDR grafting to stable frameworks and structure-based framework engineering," *Methods* 34: 184-199; and Rothlisberger et al. (2005), "Domain interactions in the Fab fragment: a comparative evaluation of the single-chain Fv and Fab format engineered with variable domains of different stability," *J Mol. Biol.* 347: 773-789. The Aho numbering system was also utilized in the past to reduce propensity for aggregaton. Borras et al. (2013), U.S. Pat. No. 8,545,849.

SUMMARY OF THE INVENTION

This invention relates to methods for reducing viscosity of antigen binding proteins by modifying sequences in framework regions and/or the Fc domain that are shown to be associated with high viscosity.

In the process details which follow, all variable region amino acids are identified by Aho numbering, all amino acids from conserved regions are identified by EU numbering. Aho numbering is aligned and correlated with the other main numbering schemes including EU (Edelman et al. (1969), "The covalent structure of an entire gamma immunoglobulin molecule," *Proc. Natl. Acad. Sci. U.S.A* 63: 78-85), Kabat (Kabat et al. (1991), *Sequences of proteins of immunological interest*, Fifth Edition. NIH Publication No. 91-3242), Chothia (Chothia et al., (1992), "Structural repertoire of the human VH segments," *J. Mol. Biol.* 227: 799-817); (Tomlinson et al., (1995), "The structural repertoire of the human V kappa domain," *EMBO J* 14: 4628-4638). Any of the four numbering systems can be interchangeably used to identify the preferred amino acid substitutions described in this specification.

If the antigen binding protein comprises the VH1|1-18 germline subfamily, the method comprises modifying the VH1 sequence to comprise one or more substitutions selected from $82X^1$, $94X^2$, and $95X^3$, wherein $X^1$ is a basic residues (R, K or H), $X^2$ is a polar, uncharged residue (S, T, N or Q) and $X^3$ is a basic residue (R, K, or H). All residues are identified by the Aho numbering system. Preferred mutations for the VH1|1-18 germline subfamily are 82R, 94S, and 95R. The method as applied to the VH1|1-18 germline subfamily may further comprise substitution $59X^{20}$ wherein $X^{20}$ is a basic residue (R, K or H), with the mutation 59K preferred.

If the antigen binding protein comprises the VH3|3-33 germline subfamily, the method comprises modifying the VH3 sequence to comprise one or more substitutions selected from $1X^4$, $17X^5$, and $85X^6$, wherein $X^4$ is a charged negative residue (D or E), $X^5$ is a small hydrophobic residue (G, A, V, I, L, or M), and $X^6$ is a small hydrophobic residue (G.A, V, I, L, or M). All residues are identified by the Aho numbering system. Preferred mutations for the VH3|3-33 germline subfamily are 1E, 17G, and 85A.

If the antigen binding protein comprises the VK3|L16 germline subfamily, the method comprises modifying the VK3 sequence to comprise one or more substitutions selected from $4X^{10}$, $13X^{11}$, $76X^{12}$, 78F, $95X^{13}$, $97X^{14}$, and 98P, wherein $X^{10}$ is selected from G, A, V, I, L, and M, $X^{11}$ is selected from G, A, V, I, L, and M, $X^{12}$ is selected from D and E, $X^{13}$ is selected from R, K and H, and $X^{14}$ is selected from D and E. All residues are identified by the Aho numbering system. Preferred mutations for the VK3|L16 germline subfamily are 4L, 13L, 76D, 95R, 97E, and 98P.

If the antigen binding protein comprises the VK3|L6 germline subfamily, the method comprises modifying the VK3 sequence to comprise one or more substitutions selected from $76X^{12}$ and $95X^{13}$. Preferred mutations for the VK3|L6 germline subfamily are 76D and 95R.

The methods of this invention further comprise modifying the Fc domain to comprise one or more substitutions selected from $253X^{15}$, $440X^{16}$, and $439X^{17}$, wherein $X^{15}$ is a small hydrophobic residue (G, A, V, I, L, or M), $X^{16}$ is a basic residue (R, K, or H), and $X^{17}$ is a charged negative residue (D or E), wherein the Fc domain sequence comprises only one of $440X^{16}$ and $439X^{17}$. All residues are identified by the EU numbering system. Preferred mutations of the Fc domain are 253A, 440K, and 439E.

The methods of this invention further comprise modifying the C-terminus of the Fc domain sequence to comprise $X^{18}X^{19}$ wherein $X^{18}$ is one to four amino acids selected from D and E or from H, K, and R, and $X^{19}$ is selected from P, M, G, A, V, I, L, S, T, N, Q, F, Y and W and is absent when $X^{18}$ comprises D or E, is present when $X^{18}$ comprises K or R at its C-terminal end, and is present or absent when $X^{18}$ comprises H at its C-terminal end. Preferred Fc C-terminal modifications comprise KP, KKP, KKKP (SEQ ID NO:380), E or EE at the C-terminus.

The foregoing methods are preferably applied to the high viscosity antibodies shown in FIGS. 1A and 1B hereinafter. The part of the method involving the VH1|1-18 sequence is preferably applied to antibodies AF, AK, AL, AN, and AO from FIG. 1B. The part of the method involving the VH3|3-33 sequence is preferably applied to antibodies AQ, AM, AI, and AG from FIG. 1B. The part of the method involving the VK3|L16 sequence is preferably applied to antibodies AF and AQ from FIG. 1B. The part of the method involving the VK3|L6 sequence is preferably applied to antibody AJ.

The methods of this invention further comprise a method of preparing an antigen binding protein that reaches maximum serum concentration faster than does a parental antibody when the antigen binding protein and the parental antibody are administered at the same concentration, which comprises introducing sequence modification $440X^{16}$ in the parental antibody wherein $X^{16}$ is selected from R, K, and H. In a preferred method, the sequence-modified antigen binding protein reaches maximum serum concentration after subcutaneous injection at least twice as fast as the parental antibody. Also within this invention is a method of preparing an antigen binding protein that reaches a maximum serum concentration after subcutaneous injection that is higher than that of a parental antibody when the antigen binding protein and the parental antibody are administered at the same concentration, which comprises introducing sequence modification 440X$^{16}$ in the parental antibody wherein X$^{16}$ is selected from R, K, and H. In a preferred method, the sequence-modified antigen binding protein reaches a maximum serum concentration that is at least about 25% higher than that of the parental antibody. In each of these methods, the preferred X$^{16}$ is K and the preferred parental antibody is a PCSK9 polypeptide (antibody AK most preferred).

The invention further relates to a mutant antigen binding protein, which comprises one or more sequences selected from:
 a. a VH1|1-18 germline subfamily sequence comprising one or more substitutions selected from 82X$^1$, 94X$^2$, and 95X$^3$, wherein X$^1$ is selected from R, K and H, X$^2$ is selected from S, T, N and Q and X$^3$ is selected from R, K, and H;
 b. a VH3|3-33 germline subfamily sequence comprising one or more substitutions selected from 1X$^4$, 17X$^5$, and 85X$^6$, wherein X$^4$ is selected from D and E, X$^5$ is selected from G, A, V, I, L, and M, and X$^6$ is selected from G.A, V, I, L, and M;
 c. a VK3|L16 germline subfamily, comprising one or more substitutions selected from 4X$^{10}$, 13X$^{11}$, 76X$^{12}$, 78F, 95X$^{13}$, 97X$^{14}$, and 98P, wherein X$^{10}$ is selected from G, A, V, I, L, and M, X$^{11}$ is selected from G, A, V, I, L, and M, X$^{12}$ is selected from D and E, X$^{13}$ is selected from R, K and H, and X$^{14}$ is selected from D and E, wherein the mutant antigen binding protein does not comprise only substitution 78F;
 d. a VK3|L6 germline subfamily, comprising one or more substitutions selected from 76X$^{12}$ and 95X$^{13}$;
 e. an Fc domain sequence comprising one or more substitutions selected from 253X$^{10}$ 440X$^{11}$, and 439X$^{12}$, wherein X$^{10}$ is selected from G, A, V, I, L, and M, X$^{11}$ is selected from R, K, and H, and X$^{12}$ is selected from D and E, wherein the antigen binding protein comprises at least one of 253X$^{15}$ or modifications selected from subparagraphs a, b, c, d and f when X$^{16}$ is K and X$^{17}$ is E and the antigen binding protein specifically binds CD20; and
 f. an Fc domain sequence comprising at the C-terminus X$^{18}$X$^{19}$ wherein X$^{18}$ is one to four amino acids selected from D and E or from H, K, and R, and X$^{19}$ is selected from P, M, G, A, V, I, L, S, T, N, Q, F, Y and W and is absent when X$^{18}$ comprises D or E, is present when X$^{18}$ comprises K or R at its C-terminal end, and is present or absent when X$^{18}$ comprises H at its C-terminal end, and wherein the antigen binding protein comprises at least one of 253X$^{15}$ or substitutions selected from subparagraphs a through e when PGKP (SEQ ID NO:381), PGKKP (SEQ ID NO:382), PGKKKP (SEQ ID NO:383), or PGE appears at the C-terminus and the antigen binding protein specifically binds CD20 or CD38. Preferred Fc C-terminal modifications comprise KP, KKP, KKKP (SEQ ID NO:380), E or EE at the C-terminus;

wherein the variable region amino acids are numbered according to the Aho numbering system and all amino acids from conserved regions including Fc are according to EU numbering.

Preferred antigen binding proteins in accordance with this invention are those wherein the foregoing modifications are applied to antibodies of FIGS. 1A and 1B hereinafter. Also preferred are antigen binding proteins wherein:
 the VH1|1-18 germline subfamily sequence comprises one or more substitutions selected from 82R, 94S, and 95R, with antigen binding proteins having all such substitutions most preferred;
 the VH3|3-33 germline subfamily sequence comprises one or more of substitutions 1E, 17G, and 85A, with antigen binding proteins having all such substitutions most preferred;
 the VK3|L16 germline subfamily sequence comprises one or more substitutions selected from 4L, 13L, 76D, 95R, 97E, and 98P, with antigen binding proteins having all such substitutions most preferred;
 the VK3|L6 germline subfamily sequence comprises one or more substitutions selected from 76D and 95R, with antigen binding proteins having both such substitutions most preferred;
 the Fc domain sequence comprises one or more substitutions selected from 253A, 440K, and 439E, with antigen binding proteins having all such substitutions most preferred; and
 the Fc domain C-terminus comprises a sequence selected from KP, KKP, KKKP (SEQ ID NO:380), and E.

All of the foregoing preferred amino acid substitutions in variable regions are identified by the Aho numbering system. All residues in conserved regions including Fc are identified by the EU numbering system.

Preferred antigen binding proteins in accordance with this invention include: antibodies AF, AK, AL, AN and AO from FIG. 1B having one or more, most preferably all, of the foregoing VH1|1-18 germline subfamily substitutions; antibodies AQ, AM, AI, and AG from FIG. 1B having one or more, most preferably all, of the VH3|3-33 germline subfamily substitutions; antibodies AF and AQ having one or more, most preferably all, of the VK3|L16 germline subfamily substitutions; antibody AJ from FIG. 1B having one or more, most preferably all, of the VK3|L6 germline subfamily substitutions; and antibodies BA, AH, and AN from FIG. 1B having one or more, preferably all, of the Fc substitutions noted above.

Due to the foregoing sequence modifications, the invention further relates to antigen binding proteins that specifically bind to PCSK9 comprising a heavy chain sequence selected from SEQ ID NOS: 352, 353, 354, 366, and 368, preferably also comprising a light chain sequence of SEQ ID NO: 351.

Due to the foregoing sequence modifications, the invention also relates to antigen binding proteins that specifically bind c-fms comprising a heavy chain sequence selected from SEQ ID NOS: 356, 357, and 358, preferably further comprising a light chain sequence of SEQ ID NO: 355.

Due to the foregoing sequence modifications, the invention also relates to antigen binding proteins that specifically bind GIPR comprising a heavy chain sequence selected from SEQ ID NOS: 359, 361, 362, 364, and 368, preferably further comprising a light chain sequence selected from SEQ ID NOS: 360, 363, 365, and 367.

All modified antigen binding proteins are useful for the same indications as described previously for the unmodified antibodies.

Each of the antigen binding proteins from FIGS. 1A and 1B having mutated heavy chains is preferred to further comprise a light chain sequence as noted in the unmodified parent antibody of FIGS. 1A and 1B. Each of the foregoing antigen binding proteins having a mutated light chain is preferred to further comprise a heavy chain sequence as noted above or as appearing in the unmodified parent antibody of FIGS. 1A and 1B.

The invention further comprises antigen binding proteins as described above that have improved pharmacokinetic properties. The invention comprises an antigen binding protein optionally having any of the aforementioned sequence modifications wherein:
a. the antigen binding protein comprises the sequence modification 440X$^{16}$ relative to a parental antibody lacking the 440X$^{16}$ sequence modification,
b. the antigen binding protein reaches maximum serum concentration after subcutaneous injection faster than does the parental antibody when the antigen binding protein and the parental antibody are administered at the same concentration, and
c. the antigen binding protein reaches a maximum serum concentration after subcutaneous injection that is higher than that of the parental antibody when the antigen binding protein and the parental antibody are administered at the same concentration.

The preferred parental antibody for such an antigen binding protein is a PCSK9 binding polypeptide, with antibody AK most preferred. The preferred substituent X$^{16}$ in such an antigen binding protein is K. Further within this invention is a method of treating hypercholesterolemia with such an antigen binding protein.

The invention also relates to isolated nucleic acids encoding the antigen binding proteins of the invention, as well as vectors comprising the nucleic acids, host cells comprising the vectors, and methods of making and using the antigen binding proteins.

In other embodiments, the present invention provides compositions comprising the antigen binding proteins and kits comprising the antigen binding proteins, as well as articles of manufacture comprising the antigen binding proteins.

BRIEF DESCRIPTION OF THE FIGURES

FIGS. 1A and 1B show a table of viscosity values measured for IgG1 and IgG2 monoclonal antibodies formulated at 150 mg/mL in a formulation buffer including 20 mM acetate and 9% sucrose at pH 5.2 (without polysorbate). FIGS. 1A and 1B show the targets of the antibodies studied as well as their light and heavy chain types, germline subfamilies, concentration, pI, and viscosity. Each antibody in FIGS. 1A and 1B has the amino acid sequences as noted in the figures and the Sequence Listing. The heavy and light chain amino acid sequences are encoded by nucleic acids having the SEQ ID NOS immediately preceding them in the Sequence Listing.

FIGS. 1C and 1D show the sequence identification numbers (SEQ ID NOS) for the framework regions and Fc regions of the antibodies of FIGS. 1A and 1B. FIG. 1D also shows antibody BA, which is discussed in FIG. 17.

FIG. 2 shows high viscosity and low viscosity subtype pairs identified in this specification.

FIG. 9 is a table showing global sequence parameters of mAbs high viscosity VH1|1-18 and low viscosity VH1|1-02 subtypes (germlines). The mAbs in FIG. 9 are sorted by viscosity. The table includes their mAb symbols, measured viscosity values, calculated pI values, and VL and VH germlines. For VH germlines, higher viscosity VH1|1-18 are shown in bold and underlined. Heavy chain framework 3 sequences are shown. Residues correlating with high viscosity are in bold and underlined. VBase sequences are added for VH1|1-18 and VH1|1-02 germline subfamilies for comparison to illustrate that the different residues are typical residues for the subfamilies.

FIG. 10 is a table showing produced and characterized mutants of the AK and AO antibodies.

FIG. 11 is a table showing global sequence parameters of thirteen mAbs with VH3 heavy chains. FIG. 11 includes the mAb symbols, measured viscosity values, calculated pI values, HC and LC types, and VL and VH subtypes (germlines). Higher viscosity VH3|3-33 subfamily is shown in bold and underlined. Residues correlating with high viscosity are bold and underlined. VBase sequences are added for VH3|3-33 and VH3|3-07 germline subfamilies for comparison to illustrate that the different residues are typical for those subfamilies.

FIG. 12 is a table showing global sequence parameters of fourteen mAbs with VK3 light chains. The mAbs in FIG. 12 are sorted by viscosity, including their mAb symbols, measured viscosity values, calculated pI values, HC and LC types, and VL and VH subtypes (germlines). Higher viscosity VK3|L16 and VK3|L6 subfamilies are in bold and underlined. Light chain residues that are consistently different between VK3|L16 and VK3|L6 subfamilies as compared to the VK3|A27 subfamily are shown on the right side. Residues correlating with high viscosity in the VK3|L16 and VK3|L6 subfamilies are bold and underlined. VBase sequences are added for VK3|L16 and VK3|A27 germline subfamilies for comparison to illustrate that the different residues are typical residues for the subfamilies.

FIG. 15 is a table showing the absolute and relative viscosity values of parent antibody AK and various mutants. The parent antibody AK and the mutants are used in a nonhuman primate study of the pharmacokinetics and pharmacodynamics of antibody AK and low viscosity mutants.

FIG. 17 is a table showing the viscosity of proteins selected for Fc mutations to lower viscosity variants.

FIG. 21 shows a summary of the experimental design for a single-dose subcutaneous bolus pharmacokinetic study in male cynomolgus monkeys as described in further detail in a working example hereinafter.

FIG. 22 shows mean pharmacokinetic parameter estimates of antibody AK or low viscosity mutant homologues after subcutaneous administration of 10 mg/kg to male cynomolgus monkeys (N=4 males). Introduction of a mutation in the Fc region that reduces viscosity reduces Tmax and increases Cmax.

FIG. 23 shows the percentage of LDL-C compared to pretest (Day CLAB). * Percent change is expressed as the individual animal post-dose value divided by the Day 1 pretest value. All four antibodies (parent antibody AK, AK Fc mutant, AK Fab mutant and AK double Fc/Fab mutant) all induce reductions in LDL-C.

DETAILED DESCRIPTION OF THE INVENTION

Definition of Terms

Figure 3:
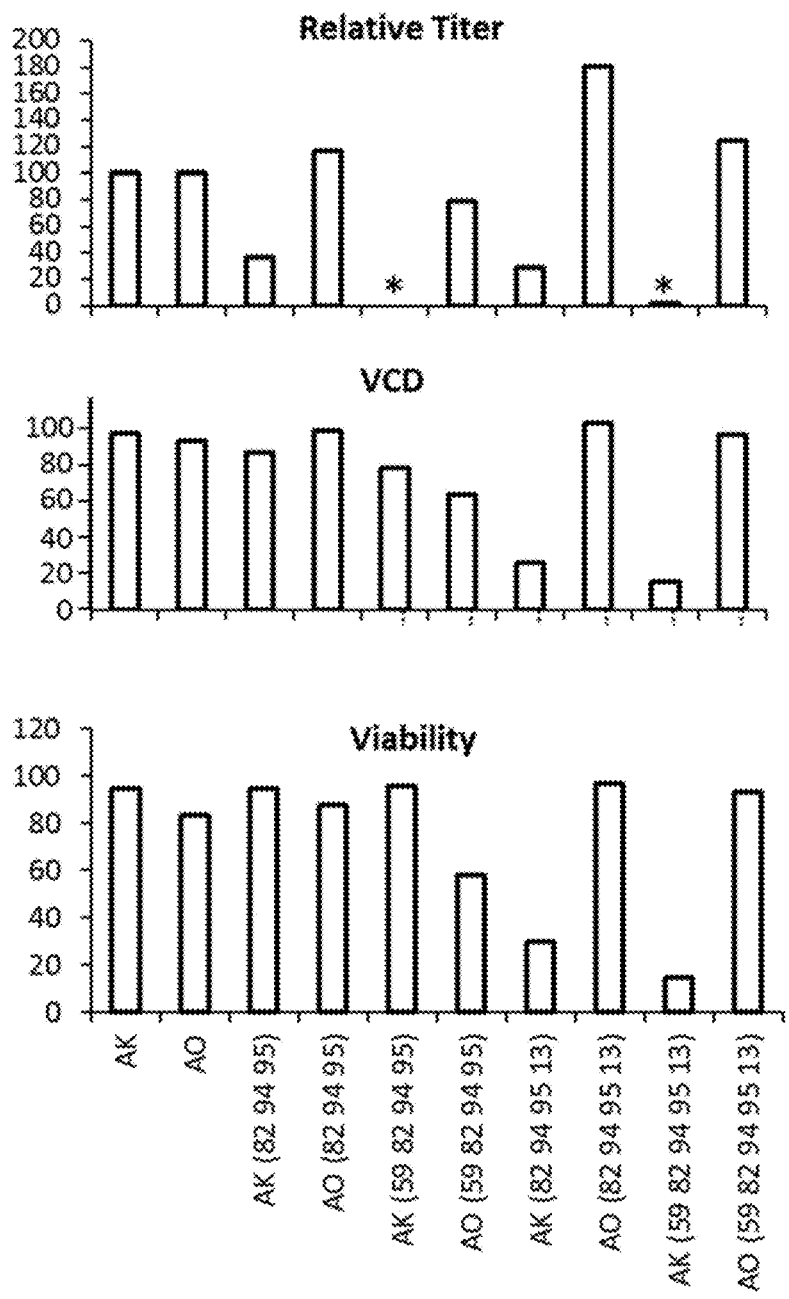
FIG. 3 shows expression results for AK and AO antibody molecules and their mutants, including relative values for titer, final viable cell density (VCD) and viability at harvest after 7 days of cell culture. AK values are at 100%.

In the description that follows, a number of terms are used extensively. The following definitions are provided to facilitate understanding of the invention.

Unless otherwise specified, "a", "an", "the", and "at least one" are used interchangeably and mean one or more than one.

"Antigen binding protein" refers to a protein or polypeptide that comprises an antigen-binding region or antigen-binding portion that has a strong affinity for another molecule to which it binds (antigen). Antigen-binding proteins encompass antibodies, peptibodies, antibody fragments (e.g., Fab, Fab', F(ab')$_2$, Fv, single domain antibody), antibody derivatives, antibody analogs, fusion proteins, and antigen receptors including chimeric antigen receptors (CARs).

"Antibodies" (Abs) and "immunoglobulins" (Igs) are glycoproteins having the same structural characteristics. While antibodies exhibit binding specificity to a specific antigen, immunoglobulins include both antibodies and other antibody-like molecules that lack antigen specificity. Polypeptides of the latter kind are, for example, produced at low levels by the lymph system and at increased levels by myelomas. Thus, as used herein, the term "antibody" or "antibody peptide(s)" refers to an intact antibody, an antibody that competes for specific binding with an antibody disclosed in this specification, or an antigen-binding fragment (e.g., Fab, Fab', F(ab')$_2$, Fv, single domain antibody) thereof that competes with the intact antibody for specific binding and includes chimeric, humanized, fully human, and bispecific antibodies. In certain embodiments, antigen-binding fragments are produced, for example, by recombinant DNA techniques. In additional embodiments, antigen-binding fragments are produced by enzymatic or chemical cleavage of intact antibodies. Antigen-binding fragments include, but are not limited to, Fab, Fab', F(ab)$^2$, F(ab')$^2$, Fv, and single-chain antibodies. Examples of antibodies suitable for use in the invention include, without limitation, the antibodies listed in FIGS. 1A and 1B as well as Abagovomab, Abciximab, Actoxumab, Adalimumab, Afelimomab, Afutuzumab, Alacizumab, Alacizumab pegol, ALD518, Alemtuzumab, Alirocumab, Alemtuzumab, Altumomab, Amatuximab, Anatumomab mafenatox, Anrukinzumab, Apolizumab, Arcitumomab, Aselizumab, Altinumab, Atlizumab, Atorolimiumab, tocilizumab, Bapineuzumab, Basiliximab, Bavituximab, Bectumomab, Belimumab, Benralizumab, Bertilimumab, Besilesomab, Bevacizumab, Bezlotoxumab, Biciromab, Bivatuzumab, Bivatuzumab mertansine, Blinatumomab, Blosozumab, Brentuximab vedotin, Briakinumab, Brodalumab, Canakinumab, Cantuzumab mertansine, Cantuzumab mertansine, Caplacizumab, Capromab pendetide, Carlumab, Catumaxomab, CC49, Cedelizumab, Certolizumab pegol, Cetuximab, Citatuzumab bogatox, Cixutumumab, Clazakizumab, Clenoliximab, Clivatuzumab tetraxetan, Conatumumab, Crenezumab, CR6261, Dacetuzumab, Daclizumab, Dalotuzumab, Daratumumab, Demcizumab, Denosumab, Detumomab, Dorlimomab aritox, Drozitumab, Duligotumab, Dupilumab, Ecromeximab, Eculizumab, Edobacomab, Edrecolomab, Efalizumab, Efungumab, Elotuzumab, Elsilimomab, Enavatuzumab, Enlimomab pegol, Enokizumab, Enokizumab, Enoticumab, Enoticumab, Ensituximab, Epitumomab cituxetan, Epratuzumab, Erenumab, Erlizumab, Ertumaxomab, Etaracizumab, Etrolizumab, Evolocumab, Exbivirumab, Exbivirumab, Fanolesomab, Faralimomab, Farletuzumab, Fasinumab, FBTAO5, Felvizumab, Fezakinumab, Ficlatuzumab, Figitumumab, Flanvotumab, Fontolizumab, Foralumab, Foravirumab, Fresolimumab, Fulranumab, Futuximab, Galiximab, Ganitumab, Gantenerumab, Gavilimomab, Gemtuzumab ozogamicin, Gevokizumab, Girentuximab, Glembatumumab vedotin, Golimumab, Gomiliximab, GS6624, Ibalizumab, Ibritumomab tiuxetan, Icrucumab, Igovomab, Imciromab, Imgatuzumab, Inclacumab, Indatuximab ravtansine, Infliximab, Intetumumab, Inolimomab, Inotuzumab ozogamicin, Ipilimumab, Iratumumab, Itolizumab, Ixekizumab, Keliximab, Labetuzumab, Lebrikizumab, Lemalesomab, Lerdelimumab, Lexatumumab, Libivirumab, Ligelizumab, Lintuzumab, Lirilumab, Lorvotuzumab mertansine, Lucatumumab, Lumiliximab, Mapatumumab, Maslimomab, Mavrilimumab, Matuzumab, Mepolizumab, Metelimumab, Milatuzumab, Minretumomab, Mitumomab, Mogamulizumab, Morolimumab, Motavizumab, Moxetumomab pasudotox, Muromonab-CD3, Nacolomab tafenatox, Namilumab, Naptumomab estafenatox, Namatumab, Natalizumab, Nebacumab, Necitumumab, Nerelimomab, Nesvacumab, Nimotuzumab, Nivolumab, Nofetumomab merpentan, Ocaratuzumab, Ocrelizumab, Odulimomab, Ofatumumab, Olaratumab, Olokizumab, Omalizumab, Onartuzumab, Oportuzumab monatox, Oregovomab, Orticumab, Otelixizumab, Oxelumab, Ozanezumab, Ozoralizumab, Pagibaximab, Palivizumab, Panitumumab, Panobacumab, Parsatuzumab, Pascolizumab, Pateclizumab, Patritumab, Pemtumomab, Perakizumab, Pertuzumab, Pexelizumab, Pidilizumab, Pintumomab, Placulumab, Ponezumab, Prezalumab, Priliximab, Pritumumab, PRO 140, Quilizumab, Racotumomab, Radretumab, Rafivirumab, Ramucirumab, Ranibizumab, Raxibacumab, Regavirumab, Reslizumab, Rilotumumab, Rituximab, Robatumumab, Roledumab, Romosozumab, Rontalizumab, Rovelizumab, Ruplizumab, Samalizumab, Sarilumab, Satumomab pendetide, Secukinumab, Sevirumab, Sibrotuzumab, Sifalimumab, Siltuximab, Simtuzumab, Siplizumab, Sirukumab, Solanezumab, Solitomab, Sonepcizumab, Sontuzumab, Stamulumab, Sulesomab, Suvizumab, Tabalumab, Tacatuzumab tetraxetan, Tadocizumab, Talizumab, Tanezumab, Taplitumomab paptox, Tefibazumab, Telimomab aritox, Tenatumomab, Tefibazumab, Telimomab aritox, Tenatumomab, Teneliximab, Teplizumab, Teprotumumab, Tezepelumab, TGN1412, Tremelimumab, Ticilimumab, Tildrakizumab, Tigatuzumab, TNX-650, Tocilizumab, Toralizumab, Tositumomab, Tralokinumab, Trastuzumab, TRBS07, Tregalizumab, Tremelimumab, Tucotuzumab celmoleukin, Tuvirumab, Ublituximab, Urelumab, Urtoxazumab, Ustekinumab, Vapaliximab, Vatelizumab, Vedolizumab, Veltuzumab, Vepalimomab, Vesencumab, Visilizumab, Volociximab, Vorsetuzumab mafodotin, Votumumab, Zalutumumab, Zanolimumab, Zatuximab, Ziralimumab and Zolimomab aritox.

The term "isolated antibody" as used herein refers to an antibody that has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The term "bind(ing)" of an antigen or other polypeptide includes, but is not limited to, the binding of a ligand polypeptide of the present invention to a receptor; the binding of a receptor polypeptide of the present invention to a ligand; the binding of an antibody of the present invention to an antigen or epitope; the binding of an antigen or epitope of the present invention to an antibody; the binding of an antibody of the present invention to an anti-idiotypic antibody; the binding of an anti-idiotypic antibody of the present invention to a ligand; the binding of an anti-idiotypic antibody of the present invention to a receptor; the binding of an anti-anti-idiotypic antibody of the present invention to a ligand, receptor or antibody, etc.

The term "immunoglobulin" refers to a protein consisting of one or more polypeptides substantially encoded by immunoglobulin genes. One form of immunoglobulin constitutes the basic structural unit of an antibody. This form is a tetramer and consists of two identical pairs of immunoglobulin chains, each pair having one light and one heavy chain. In each pair, the light and heavy chain variable regions are together responsible for binding to an antigen, and the constant regions are responsible for the antibody effector functions.

Full-length immunoglobulin "light chains" (about 25 Kd or about 214 amino acids) are encoded by a variable region gene at the NH2-terminus (about 110 amino acids) and a kappa or lambda constant region gene at the COOH-terminus. Full-length immunoglobulin "heavy chains" (about 50 Kd or about 446 amino acids), are similarly encoded by a variable region gene (about 116 amino acids) and one of the other aforementioned constant region genes (about 330 amino acids). Heavy chains are classified as gamma, mu, alpha, delta, or epsilon, and define the antibody's isotype as IgG (such as IgG1, IgG2, IgG3 and IgG4), IgM, IgA, IgD and IgE, respectively. Within light and heavy chains, the variable and constant regions are joined by a "J" region of about 12 or more amino acids, with the heavy chain also including a "D" region of about 10 more amino acids. (See generally, *Fundamental Immunology* (Paul, W., ed., 2nd Edition, Raven Press, NY (1989)), Chapter 7 (incorporated by reference in its entirety for all purposes).

An immunoglobulin light or heavy chain variable domain or region comprises "framework regions" (FRs) interrupted by "complementarity determining regions" (CDRs). Kabat et al. (1991), *Sequences of Proteins of Immunological Interest*, 5th Edition, Public Health Service, National Institutes of Health, Bethesda, Md. (1991); Chothia et al. (1987), *J. Mol. Biol.* 196: 901-917 (both of which are incorporated herein by reference). FR residues are those variable domain residues other than CDR region residues as herein defined. The sequences of the framework regions of different light or heavy chains are relatively conserved within a species. Thus, a "human framework region" is a framework region that is substantially identical (about 85% or more, usually 90-95% or more) to the framework region of a naturally occurring human immunoglobulin. The framework region of an antibody, that is the combined framework regions of the constituent light and heavy chains, serves to position and align the CDR's. The CDR's are primarily responsible for binding to an epitope of an antigen. Accordingly, the term "humanized" immunoglobulin refers to an immunoglobulin comprising a human framework region and one or more CDR's from a non-human (usually a mouse or rat) immunoglobulin. The non-human immunoglobulin providing the CDR's is called the "donor" and the human immunoglobulin providing the framework is called the "acceptor". Constant regions need not be present, but if they are, they must be substantially identical to human immunoglobulin constant regions—i.e., at least about 85-90%, preferably about 95% or more identical. Hence, all parts of a humanized immunoglobulin, except possibly the CDR's, are substantially identical to corresponding parts of natural human immunoglobulin sequences. Further, one or more residues in the human framework region may be back mutated to the parental sequence to retain optimal antigen-binding affinity and specificity. In this way, certain framework residues from the non-human parent antibody are retained in the humanized antibody in order to retain the binding properties of the parent antibody while minimizing its immunogenicity. The term "human framework region" as used herein includes regions with such back mutations. A "humanized antibody" is an antibody comprising a humanized light chain and a humanized heavy chain immunoglobulin. For example, a humanized antibody would not encompass a typical chimeric antibody as defined below, e.g., because the entire variable region of a chimeric antibody is non-human.

The monoclonal antibodies and antibody constructs of the present invention specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is/are identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al. (1984), Proc. Natl. Acad. Sci. USA, 81: 6851-6855). Chimeric antibodies of interest herein include "primitized" antibodies comprising variable domain antigen-binding sequences derived from a non-human primate (e.g., Old World Monkey, Ape, etc.) and human constant region sequences. A variety of approaches for making chimeric antibodies have been described. See e, Morrison et al. (1985), Proc. Natl. Acad. Sci. U.S.A. 81:6851; Takeda et al. (1985), Nature 314:452, Cabilly et al., U.S. Pat. No. 4,816,567; Boss et al., U.S. Pat. No. 4,816,397; Tanaguchi et al., EP 0171496; EP 0173494; and GB 2177096.

The terms "human antibody" and "fully human antibody" each refer to an antibody that has an amino acid sequence of a human immunoglobulin, including antibodies isolated from human immunoglobulin libraries or from animals transgenic for one or more human immunoglobulins and that do not express endogenous immunoglobulins; for example, Xenomouse® antibodies and antibodies as described by Kucherlapati et al. in U.S. Pat. No. 5,939,598.

The term "genetically altered antibodies" means antibodies wherein the amino acid sequence has been varied from that of a native antibody. Because of the relevance of recombinant DNA techniques in the generation of antibodies, one need not be confined to the sequences of amino acids found in natural antibodies; antibodies can be redesigned to obtain desired characteristics. The possible variations are many and range from changes to just one or a few amino acids to complete redesign of, for example, the variable and/or constant region. Changes in the constant region will, in general, be made in order to improve or alter characteristics, such as complement fixation, interaction with membranes and other effector functions, as well as manufacturability and viscosity. Changes in the variable region will be made in order to improve the antigen binding characteristics.

A "Fab fragment" is comprised of one light chain and the $C_{H1}$ and variable regions of one heavy chain. The heavy chain of a Fab molecule cannot form a disulfide bond with another heavy chain molecule.

A "Fab' fragment" contains one light chain and one heavy chain that contains more of the constant region, between the $C_{H1}$ and $C_{H2}$ domains, such that an interchain disulfide bond can be formed between two heavy chains to form a $F(ab')_2$ molecule.

A "$F(ab')_2$ fragment" contains two light chains and two heavy chains containing a portion of the constant region between the $C_{H1}$ and $C_{H2}$ domains, such that an interchain disulfide bond is formed between two heavy chains.

The terms "Fv fragment" and "single chain antibody" refer to polypeptides containing antibody variable regions from both heavy and light chains but lacking constant regions. Like a whole antibody, it is able to bind selectively to a specific antigen. With a molecular weight of only about 25 kDa, Fv fragments are much smaller than common antibodies (150-160 kD) which are composed of two heavy protein chains and two light chains, and even smaller than Fab fragments (about 50 kDa, one light chain and half a heavy chain).

A "single domain antibody" is an antibody fragment consisting of a single domain Fv unit, e.g., $V_H$ or $V_L$. Like a whole antibody, it is able to bind selectively to a specific antigen. With a molecular weight of only 12-15 kDa, single-domain antibodies are much smaller than common antibodies (150-160 kDa) which are composed of two heavy protein chains and two light chains, and even smaller than Fab fragments (.about.50 kDa, one light chain and half a heavy chain) and single-chain variable fragments (.about.25 kDa, two variable domains, one from a light and one from a heavy chain). The first single-domain antibodies were engineered from heavy-chain antibodies found in camelids. Although most research into single-domain antibodies is currently based on heavy chain variable domains, light chain variable domains and nanobodies derived from light chains have also been shown to bind specifically to target epitopes.

The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

In some embodiments, an antigen binding protein of the present invention selectively inhibits the human antigen of the antibody from which it is derived. For example, the antigen binding protein having the sequence of antibody AF as substituted as described herein will selectively inhibit the antigen in FIG. 1B of antibody AF. An antibody or functional fragment thereof "selectively inhibits" a specific receptor or ligand relative to other receptors or ligands when the IC50 of the antibody in an inhibition assay of the specific receptor is at least 50-fold lower than the IC50 in an inhibition assay of another "reference" ligand or receptor. An "IC50" is the dose/concentration required to achieve 50% inhibition of a biological or biochemical function. With radioactive ligands, IC50 is the concentration of a competing ligand that displaces 50% of the specific binding of the radioactive ligand. The IC50 of any particular substance or antagonist can be determined by constructing a dose-response curve and examining the effect of different concentrations of the drug or antagonist on reversing agonist activity in a particular functional assay. IC50 values can be calculated for a given antagonist or drug by determining the concentration needed to inhibit half of the maximum biological response of the agonist. Thus, the IC50 value for any anti-PCSK9 antibody or functional fragment thereof, for example, can be calculated by determining the concentration of the antibody or fragment needed to inhibit half of the maximum biological response of PCSK9 in activating the human PCSK9 receptor in any functional assay. An antibody or functional fragment thereof that selectively inhibits a specific ligand or receptor is understood to be a neutralizing antibody or neutralizing fragment with respect to that ligand or receptor. Thus, in some embodiments, the anti-PCSK9 antibody or functional fragment is a neutralizing antibody or fragment of human PCSK9.

The substituted antigen binding proteins of the present invention can cross-block the unsubstituted antibodies from which they are derived. The terms "cross-block," "cross-blocked," and "cross-blocking" are used interchangeably herein to mean the ability of an antigen binding protein to interfere with the binding of other antigen binding proteins (e.g., antibodies or binding fragments) to a target (e.g., human PCSK9). The extent to which an antibody or binding fragment is able to interfere with the binding of another to a target and therefore whether it can be said to cross-block, can be determined using competition binding assays. In some embodiments, a cross-blocking antigen binding protein of this invention reduces binding of a reference antibody to the target antigen between about 40% and 100%, such as about 60% and about 100%, specifically preferably between about 70% and 100%, and more specifically preferably between about 80% and 100%. A particularly suitable quantitative assay for detecting cross-blocking uses a Biacore machine which measures the extent of interactions using surface plasmon resonance technology. Another suitable quantitative cross-blocking assay uses a FACS-based approach to measure competition between antibodies in terms of their binding to the target antigen.

The term "nucleic acid" or "nucleic acid molecule" refers to polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Nucleic acid molecules can be composed of monomers that are naturally-occurring nucleotides (such as DNA and RNA), or analogs of naturally-occurring nucleotides (e.g., .alpha.-enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. The term "nucleic acid molecule" also includes so-called "peptide nucleic acids", which comprise naturally-occurring or modified nucleic acid bases attached to a polyamide backbone. Nucleic acids can be either single stranded or double stranded.

The term "complement of a nucleic acid molecule" refers to a nucleic acid molecule having a complementary nucleotide sequence and reverse orientation as compared to a reference nucleotide sequence.

The term "degenerate nucleotide sequence" denotes a sequence of nucleotides that includes one or more degenerate codons as compared to a reference nucleic acid molecule that encodes a polypeptide. Degenerate codons contain different triplets of nucleotides, but encode the same amino acid residue (i.e., GAU and GAC triplets each encode Asp).

An "isolated nucleic acid molecule" is a nucleic acid molecule that is not integrated in the genomic DNA of an organism. For example, a DNA molecule that encodes a heavy chain of an antibody that has been separated from the genomic DNA of a cell is an isolated DNA molecule. Another example of an isolated nucleic acid molecule is a chemically-synthesized nucleic acid molecule that is not integrated in the genome of an organism. A nucleic acid molecule that has been isolated from a particular species is smaller than the complete DNA molecule of a chromosome from that species.

A "nucleic acid molecule construct" is a nucleic acid molecule, either single- or double-stranded, that has been modified through human intervention to contain segments of nucleic acid combined and juxtaposed in an arrangement not existing in nature.

"Complementary DNA (cDNA)" is a single-stranded DNA molecule that is formed from an mRNA template by the enzyme reverse transcriptase. Typically, a primer complementary to portions of mRNA is employed for the initiation of reverse transcription. Those skilled in the art also use the term "cDNA" to refer to a double-stranded DNA molecule consisting of such a single-stranded DNA molecule and its complementary DNA strand. The term "cDNA" also refers to a clone of a cDNA molecule synthesized from an RNA template.

A "promoter" is a nucleotide sequence that directs the transcription of a structural gene. Typically, a promoter is located in the 5' non-coding region of a gene, proximal to the transcriptional start site of a structural gene. Sequence elements within promoters that function in the initiation of transcription are often characterized by consensus nucleotide sequences. These promoter elements include RNA polymerase binding sites, TATA sequences, CAAT sequences, differentiation-specific elements (DSEs; McGehee et al. (1993), *Mol. Endocrinol.*, 7:551), cyclic AMP response elements (CREs), serum response elements (SREs; Treisman (1990), *Seminars in Cancer Biol.*, 1:47), glucocorticoid response elements (GREs), and binding sites for other transcription factors, such as CRE/ATF (O'Reilly et al. (1992), *J. Biol. Chem.*, 267:19938), AP2 (Ye et al. (1994), *J. Biol. Chem.*, 269:25728), SP1, cAMP response element binding protein (CREB; Loeken (1993), *Gene Expr.*, 3:253) and octamer factors (see, in general, Watson et al. (1987), eds., Molecular Biology of the Gene, 4th Edition, The Benjamin/Cummings Publishing Company, Inc., and Lemaigre et al. (1994), *Biochem. J.*, 303:1). If a promoter is an inducible promoter, then the rate of transcription increases in response to an inducing agent. In contrast, the rate of transcription is not regulated by an inducing agent if the promoter is a constitutive promoter. Repressible promoters are also known.

A "regulatory element" is a nucleotide sequence that modulates the activity of a core promoter. For example, a regulatory element may contain a nucleotide sequence that binds with cellular factors enabling transcription exclusively or preferentially in particular cells, tissues, or organelles. These types of regulatory elements are normally associated with genes that are expressed in a "cell-specific", "tissue-specific", or "organelle-specific" manner.

An "enhancer" is a type of regulatory element that can increase the efficiency of transcription, regardless of the distance or orientation of the enhancer relative to the start site of transcription.

"Heterologous DNA" refers to a DNA molecule, or a population of DNA molecules, that does not exist naturally within a given host cell. DNA molecules heterologous to a particular host cell may contain DNA derived from the host cell species (i.e., endogenous DNA) so long as that host DNA is combined with non-host DNA (i.e., exogenous DNA). For example, a DNA molecule containing a non-host DNA segment encoding a polypeptide operably linked to a host DNA segment comprising a transcription promoter is considered to be a heterologous DNA molecule. Conversely, a heterologous DNA molecule can comprise an endogenous gene operably linked with an exogenous promoter. As another illustration, a DNA molecule comprising a gene derived from a wild-type cell is considered to be heterologous DNA if that DNA molecule is introduced into a mutant cell that lacks the wild-type gene.

An "expression vector" is a nucleic acid molecule encoding a gene that is expressed in a host cell. Typically, an expression vector comprises a transcription promoter, a gene, and a transcription terminator. Gene expression is usually placed under the control of a promoter, and such a gene is said to be "operably linked to" the promoter. Similarly, a regulatory element and a core promoter are operably linked if the regulatory element modulates the activity of the core promoter.

A "recombinant host" is a cell that contains a heterologous nucleic acid molecule, such as a cloning vector or expression vector. In the present context, an example of a recombinant host is a cell that produces an antagonist of the present invention from an expression vector. In contrast, such an antagonist can be produced by a cell that is a "natural source" of said antagonist, and that lacks an expression vector.

The terms "amino-terminal" and "carboxyl-terminal" are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide.

A "fusion protein" is a hybrid protein expressed by a nucleic acid molecule comprising nucleotide sequences of at least two genes. For example, a fusion protein can comprise at least part of an antibody heavy chain fused with a polypeptide that binds an affinity matrix or another target of interest.

The term "receptor" denotes a cell-associated protein that binds to a bioactive molecule termed a "ligand." This interaction mediates the effect of the ligand on the cell. Receptors can be membrane-bound, cytosolic or nuclear; monomeric (e.g., thyroid stimulating hormone receptor, beta-adrenergic receptor) or multimeric (e.g., PDGF receptor, growth hormone receptor, IL-3 receptor, GM-CSF receptor, G-CSF receptor, erythropoietin receptor and IL-6 receptor). Membrane-bound receptors are characterized by a multi-domain structure comprising an extracellular ligand-binding domain and an intracellular effector domain that is typically involved in signal transduction. In certain membrane-bound receptors, the extracellular ligand-binding domain and the intracellular effector domain are located in separate polypeptides that comprise the complete functional receptor. In general, the binding of ligand to receptor results in a conformational change in the receptor that causes an interaction between the effector domain and other molecule(s) in the cell, which in turn leads to an alteration in the metabolism of the cell. Metabolic events that are often linked to receptor-ligand interactions include gene transcription, phosphorylation, dephosphorylation, increased cyclic AMP production, mobilization of cellular calcium, mobilization of membrane lipids, cell adhesion, hydrolysis of inositol lipids and hydrolysis of phospholipids.

The term "expression" refers to the biosynthesis of a gene product. For example, in the case of a structural gene, expression involves transcription of the structural gene into mRNA and the translation of mRNA into one or more polypeptides.

The term "complement/anti-complement pair" denotes non-identical moieties that form a non-covalently associated, stable pair under appropriate conditions. For instance, biotin and avidin (or streptavidin) are prototypical members of a complement/anti-complement pair. Other exemplary complement/anti-complement pairs include receptor/ligand pairs, antibody/antigen (or hapten or epitope) pairs, sense/antisense polynucleotide pairs, and the like. Where subsequent dissociation of the complement/anti-complement pair is desirable, the complement/anti-complement pair preferably has a binding affinity of less than $10^9$ $M^{-1}$.

A "detectable label" is a molecule or atom which can be conjugated to an antibody moiety to produce a molecule useful for diagnosis. Examples of detectable labels include chelators, photoactive agents, radioisotopes, fluorescent agents, paramagnetic ions, or other marker moieties.

The term "affinity tag" is used herein to denote a polypeptide segment that can be attached to a second polypeptide to provide for purification or detection of the second polypeptide or provide sites for attachment of the second polypeptide to a substrate. In principal, any peptide or protein for which an antibody or other specific binding agent is available can be used as an affinity tag. Affinity tags include a polyhistidine tract, protein A (Nilsson et al. (1985), *EMBO J.* 4:1075; Nilsson et al. (1991), *Methods Enzymol.*, 198:3), glutathione S transferase (Smith et al. (1988), *Gene,* 67:31), Glu-Glu affinity tag (Grussenmeyer et al (1985)., *Proc. Natl. Acad. Sci. USA* 82:7952), substance P, FLAG® peptide (Hopp et al. (1988), *Biotechnology* 6:1204), streptavidin binding peptide, or other antigenic epitope or binding domain. See, in general, Ford et al. (1991), *Protein Expression and Purification,* 2:95. DNA molecules encoding affinity tags are available from commercial suppliers (e.g., Pharmacia Biotech, Piscataway, N.J.).

The terms "acidic residue" and "charged negative residue" refer to amino acid residues having sidechains comprising acidic groups. Exemplary acidic or charged negative residues include D and E.

The term "amide residue" refers to amino acids having sidechains comprising amide derivatives of acidic groups. Exemplary amide residues include N and Q.

The term "aromatic residue" refers to amino acid residues having sidechains comprising aromatic groups. Exemplary aromatic residues include F, Y, and W.

The terms "basic residue" and "charged positive residue" refer to amino acid residues having sidechains comprising basic groups. Exemplary basic or charged positive residues include H, K, and R.

The terms "hydrophilic residue" and "polar uncharged residue" refer to amino acid residues having sidechains comprising polar groups. Exemplary hydrophilic or polar uncharged residues include C, S, T, N, and Q.

The terms "non-functional residue" and "small hydrophobic residue" refer to amino acid residues having sidechains that lack acidic, basic, or aromatic groups. Exemplary non-functional, small hydrophobic residues include M, G, A, V, I, L and norleucine (Nle).

One aspect of this invention concerns PCSK9 binding polypeptides. "PCSK9-binding polypeptide" means a polypeptide that binds proprotein convertase subtilisin/kexin type 9 (PCSK9) protein. In some cases, the PCSK9-binding polypeptide blocks binding of PCSK9 to low-density lipid receptors (LDLRs). Such blocking PCSK9-binding polypeptides can be monoclonal antibodies (mAbs) and can be one of the following:

a. a mAb comprising a heavy chain polypeptide having an amino acid sequence of SEQ ID NO: 136 and a light chain polypeptide having an amino acid sequence of SEQ ID NO: 134 (antibody AK, evolocumab), or an antigen-binding fragment thereof;

b. a mAb that competes with evolocumab for binding to PCSK9;

c. a mAb comprising:
  i. a heavy chain polypeptide comprising the following complementarity determining regions (CDRs): a heavy chain CDR1 that is a CDR1 in SEQ ID NOs: 376 or 378; a heavy chain CDR2 that is a CDR2 in SEQ ID Nos: 376 or 378; a heavy chain CDR3 that is a CDR3 in SEQ ID NOs: 376 or 378, and
  ii. a light chain polypeptide comprising the following CDRs: a light chain CDR1 that is a CDR1 in SEQ ID NOs: 377 or 379; a light chain CDR2 that a CDR2 in SEQ ID NOs: 377 or 379; and a light chain CDR3 that is a CDR3 in SEQ ID NOs: 377 or 379;

d. a mAb that binds to at least one of the following residues of PCSK9, the PCSK9 comprising an amino acid sequence of SEQ ID NO: 369: S153, D188, I189, Q190, S191, D192, R194, E197, G198, R199, V200, D224, R237, and D238, K243, S373, D374, S376, T377, F379, I154, T1897, H193, E195, I196, M201, V202, C223, T228, S235, G236, A239, G244, M247, I369, S372, C375, C378, R237, and D238;

e. a mAb that binds to PCSK9 at an epitope on PCSK9 that overlaps with an epitope that is bound by an antibody that comprises:
  i. a heavy chain variable region of the amino acid sequence in SEQ ID NO: 136; and
  ii. a light chain variable region of the amino acid sequence in SEQ ID NO: 134, and
  iii. wherein the epitope of the mAb further overlaps with a site to which binds an epidermal growth factor-like repeat A (EGF-A) domain of the low density lipoprotein receptor (LDLR) protein (Horton, Cohen, & Hobbs (2007), *Trends Biochem Sci*, 32(2), 71-77. doi: 10.1016/j.tibs.2006.12.008; Seidah & Prat (2007), *J Mol Med (Berl)*, 85(7), 685-696;

f. a mAb that comprises a heavy chain polypeptide comprising the following complementarity determining regions (CDRs):
  i. heavy chain CDR1, CDR2, and CDR3 having an amino acid sequence of SEQ ID NOs: 373, 374, and 375, respectively; and
  ii. light chain CDR1, CDR2, and CDR3 having an amino acid sequence of SEQ ID NOs: 369, 370, and 371, respectively; or g. a mAb that comprises the heavy chain variant region sequence of SEQ ID NO: 378 and the light chain variant region sequence of SEQ ID NO: 379.

PREFERRED EMBODIMENTS

Correlation of Global Sequence Features to Viscosity

The main goal of the study reported in Example 1 of this specification was to identify a link between viscosity and amino acid sequence, or global sequence features of IgG monoclonal antibodies with the purpose of reducing viscosity of high-concentration monoclonal antibody formulations. For that, viscosity values of 43 different monoclonal antibodies were measured at 150 mg/ml to provide a wide range of values from 5 to 33 cP (FIGS. 1A and 1B). Main global sequence features of the monoclonal antibodies, such as light and heavy chain types, their subtypes (germlines), and pI were calculated and correlated to viscosity, but did not immediately reveal significant correlations (FIGS. 1A and 1B). Polymorphisms (known as allotypes) within the IgG isotypes were described using serological reagents derived from humans (Ropartz, C., Schanfield, M. S., and Steinberg, A. G. (1976), "Review of the notation for the allotypic and related markers of human immunoglobulins," WHO meeting on human immunoglobulin allotypic markers, held 16-19 Jul. 1974, Rouen, France; report amended June 1976, *J Immunogenet*. 3, 357-362) and correlated to certain amino acid residues in several specific positions in conserved regions of heavy and light chains (Jefferis and Lefranc (2009) Human immunoglobulin allotypes: possible implications for immunogenicity, mAbs 1, 332-338.) (Vidarsson, G., Dekkers, G., and Rispens, T. (2014) IgG subclasses and allotypes: from structure to effector functions, *Front Immunol*. 5, 1-17). The allotypes introduce a few different residues (described below) in otherwise conserved regions of light and heavy chains. All kappa light chains used in this study were the same (3) allotype (featuring residues A153, V191 in EU numbering). All IgG2 heavy light chains were the same (n-) allotype (featuring P189). Four IgG1 heavy chain allotypes were described (including the following related residues in EU numbering): f(R214); z (K214); a (D356, L358) and x (G431) (Jefferis & Lefranc, 2009) (Vidarsson et al., 2014). IgG1 heavy chains with alternative residues in the positions E356, M358 and A431 do not constitute allotypes because these amino acid residues are present in other IgG subclasses. IgG1 allotype (x) was not present in the study; all IgG1 heavy chains had A431. IgG1 heavy chain allotypes (f), (z), (a) and related residues are shown in FIGS. 1A and 1B.

The antibodies in FIGS. 1A and 1B are sorted by viscosity. The table in FIGS. 1A and 1B includes the monoclonal antibody name, measured concentrations, measured viscosity values and global sequence parameters including type, subtype and calculated pI. IgG1 type, lambda light chains and VH1 heavy chain subtype are in boldface type.

IgG1 and IgG2 heavy chains and kappa and lambda light chains were rather evenly distributed across the viscosity range. A sequence assessment of subtypes revealed several high viscosity and low viscosity subtype pairs: VH1|1-18 and VH1|1-02; VH3|3-33 and VH3|3-07; VK3|L16 and VK3|A27 with the probability of random correlation at 0.0002; 0.076 and 0.031, respectively, correlating to viscosity residues (FIG. 2). The study looked for viscosity correlations to D and J region sequences but found no significant correlation.

FIG. 2 shows p-values, which indicate probability of random correlation to viscosity. FIG. 2 also shows residues in high viscosity subtype, positions in Aho numbering, and residues in low viscosity subtypes.

Among the fourteen IgG molecules of VH1 subtype, high viscosity was strongly associated with VH1|1-18 subtype and low viscosity with VH1|1-01 subtype with the very low probability of this being a random coincidence (FIG. 9).

In order to assess the correlation between the two subtypes and viscosity, probability of the same population mean by Student's t-test was calculated for VH1|1-02 versus VH1|1-18, VH3|3-33 versus VH3|3-07 and VK3|L16 versus VK3|A27 using t-test two-sample equal variants with a two-tailed distribution.

An association (t-test, p=0.031) of light chain VK3|L16 with high viscosity and VK3|A27 with low viscosity was detected (FIG. 2, FIG. 12, left side). VK3|L16 versus VK3|A27 and VH3|3-33 versus VH3|3-07 are discussed further in this specification. Due to the strong correlation to viscosity, VH1|1-18 and VH1|1-02 were further evaluated as follows. As the next step, 43 antibody chain sequences were aligned and assessed as follows.

Sequence Alignment and Numbering System

Several IgG numbering systems exist, including:

EU—Edelman et al. (1969), "The covalent structure of an entire gamma immunoglobulin molecule," *Proc. Natl. Acad. Sci. U.S.A* 63, 78-85;

Kabat—Kabat et al. (1991), *Sequences of proteins of immunological interest*, Fifth Edition. NIH Publication No. 91-3242;

Chothia—Chothia et al. (1992), "*Structural repertoire of the human VH segments,*" *J. Mol. Biol.* 227: 799-817; Tomlinson et al., (1995), "The structural repertoire of the human V kappa domain. *EMBO J.* 14: 4628-4638;

Aho—Hoenegger et al. (2001), "Yet another numbering scheme for immunoglobulin variable domains: an automatic modeling and analysis tool," *J. Mol. Biol.* 309, 657-670;

and others. All four numbering systems mentioned above are illustrated in FIG. 9, right side for frame region 3 of the heavy chain of VH1 subtype. The Aho scheme was built by utilizing spatial positions of amino acid residues derived from more than 400 crystal structures of variable domains of different antibodies. The Aho numbering system defined by A. Honegger (citation above) was used in this work because it is a 3D structure-based numbering system. This creates an advantage specifically for residues in CDRs: Residues with the same numbers are located in similar spatial areas and are comparable across different IgG sequences. Since residue positions in the Aho numbering scheme are related to tertiary structure, they should be more associated with biophysical and biochemical properties and, possibly, viscosity. Aho numbering is aligned and correlated with the other main numbering schemes as it is shown in several tables of this specification. Any of the four numbering systems can be interchangeably used to identify the preferred amino acid substitutions. The heavy chain variable region ends at the following residues for different numbering systems: 149 Aho, 117 EU, 113 Kabat, 113 Chothia. The light chain variable region ends at 149 Aho, 107 EU, 107 Kabat, 107 Chothia. Aho numbering allocates more numbers for CDR regions instead of using letters for CDR residues as in Kabat and Chothia (for example 82b for Kabat and Chothia). As a result, Aho numbers for the same residues are often larger. Each variable region includes three complementarity determining regions (CDRs) and four framework regions (FRs) in the following sequence: FR1-CDR1-FR2-CDR2-FR3-CDR3-FR4. While CDRs provide great sequence diversity with the purpose of binding to antigens (CDR3 regions bind most often), FR sequences are more conserved and contain only a few differences, some of which are subtype specific.

Correlation of Sequences to Viscosity

In addition to assessing the global sequence features, the variable regions' sequences were aligned to identify the residues responsible for the viscosity differences. In addition to visual observations, a software machine learning algorithm was developed and applied to identify the residues impacting viscosity the most and to predict antibodies' viscosity values from their sequences. The predictive model was constructed using charge and hydrophobicity of residues in Aho-aligned positions.

Heavy chain VH1 sequence alignment and assessment of the five sequences of high-viscosity VH1|1-18 subtype and five sequences of low-viscosity VH1|1-02 subtype molecules revealed that only 4 residues were different between the two subtypes in frames, all four located in framework 3 (FIG. 9, right side). A larger number of sequence differences were observed in CDRs, but they were left beyond the scope of the study, since CDRs are often involved in binding to the antigens, and engineering (mutating residues in) CDRs with a goal of reducing viscosity would carry a significant risk of losing potency. The subtype-related differences in viscosity and residues in FR3 indicated that the following amino acid substitutions could potentially reduce viscosity in Aho numbering: T82R, T86I, R94S and S95R. The software algorithm supported the four substitutions and also suggested that the following two substitutions correlated with reduction of viscosity: light chain G13V/L in FR1 and heavy chain S59R/K from the edge of CDR2, the latter correlation observed in VH3 subtype (FIG. 9, right side).

In Silico Assessment of Suggested Amino Acid Substitutions

VH T82R.

R82 occurs with high frequency in VH1-02. IgG structure modeling indicated that heavy chain Aho position 82 is a part of the upper core of the globulin fold and does not typically contact the antigen, but it can directly contact CDR backbones according to Ewert et al. (2003), "Biophysical properties of human antibody variable domains," *J. Mol. Biol.* 325: 531-553. HC82 has very conserved main chain—side chain H-bond interactions with CDR 1 and CDR2 backbone amides (Honegger et al., supra). R82 may also coordinate the backbone oxygen atoms of the CDR2 loop.

VH R94S and S95R.

S94 and R95 occur with high frequency in VH1-02. These positions are located on the surface, away from the antigen binding domain and are considered a part of the lower core.

T86I.

I86 occurs with high frequency in VH1-02. The data suggest substituting a hydrophobic residue (I) for hydrophilic one (T) on the surface, which can potentially lead to aggregation.

VH S59R/K—

Within VH1 and VH3, a hydrophilic position 59 associates with lower viscosity. VH S59R/K position has high structural and sequence variability, is fairly solvent exposed, and is directly in between residues 58 and 60, which are part of the upper core and may affect binding. The structure will likely depend directly on the differences in residues 58 and 60 (especially 58 if it is buried). R/K59 has low frequency of occurrence (below 2%), and was not observed in VH1 according to the amino acid residue frequency analysis. All R/K59s are accommodated within the VH3 dataset except one (VH4).

VL G13V/L—

This position is structurally buried and is a part of the lower core of the variable domain according to Ewert et al., supra. From this point of view, a G13V mutation to a more hydrophobic residue should make the core stronger.

To summarize, in silico sequence analysis indicated that the proposed mutations do not introduce any additional glycosylation sites or sites susceptible to rapid degradation under physiological or mildly acidic formulation conditions (NG, NS, NT, DG, DH). VH T82R, T86I, R94S and S95R mutations would provide a switch from subtype VH1-18 to VH1-02 in frame region 3, so they should not introduce any unusual or rare motifs. The addition of VH S59R and VL G13V mutations was suggested by the software from the VH3 subtype, outside of VH1. None of the mutation sites is positioned close to the binding regions, except for S59R, which is at the edge of HC CDR2 and, therefore, represents a mild risk of interfering with potency/binding. Arginine is a very low frequency residue in position 59 (R59), so prediction of its impact is difficult. T86I was identified as a high risk for aggregation and removed from the list of mutations.

Produced Mutants and their Expression, Potency, Chemical Modifications, Glycosylation and Viscosity.

Taking into account the above considerations, several mutants were produced for two IgG2 antibodies AK and AO of the high-viscosity VH1-18 subtype with the goal of reducing viscosity while maintaining potency (FIG. 9B). FIG. 9B includes monoclonal antibody mutant symbols and related mutations on the heavy and light chain.

A very low expression level was observed for both AK mutants containing the S59R substitution (marked with * on FIG. 3). Viability and viable cell density was also low for one of them, AK (59 82 94 95 13). On the other hand, antibody AO mutants containing the S59R substitution produced a titer comparable to that of the AO parent molecule. Although the statistics were not sufficient to make a general conclusion about heavy chain position 59, the case suggested that a single amino acid substitution may dramatically alter expression. Chemical modifications, including oxidation, deamidation, isomerization and the glycosylation pattern, were similar among the two parents and their mutants as measured by peptide mapping LC-MS analysis.

Figure 4:
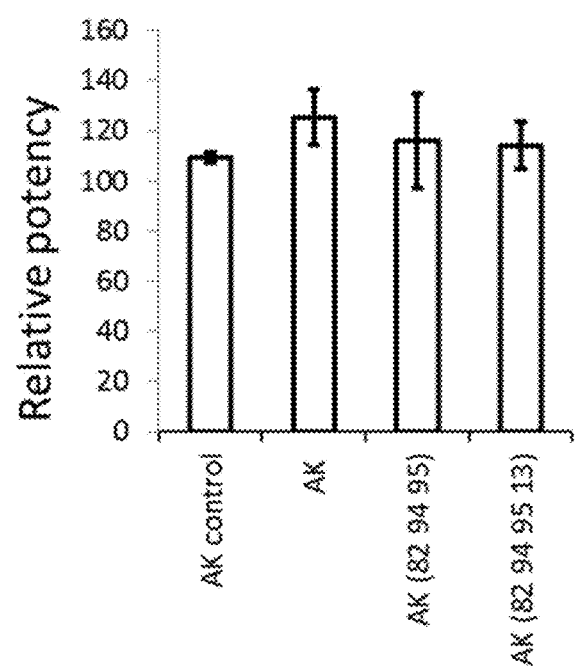
FIG. 4 shows potency of AK parent antibodies (AK control, AK) and their mutants.
Figure 5:
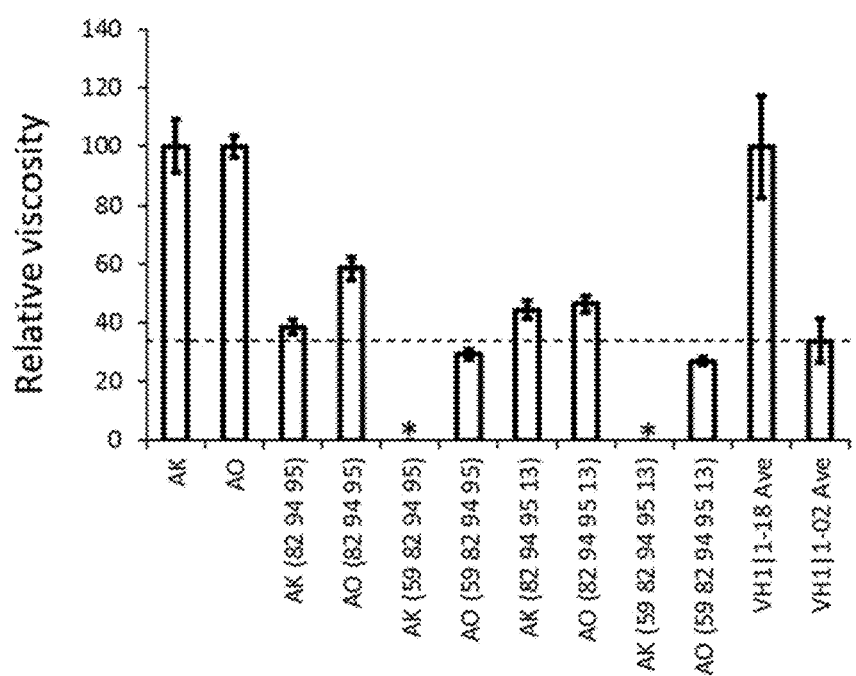
FIG. 5 shows viscosity of mutants relative to the parent AK and AO antibodies. Average viscosity values of high viscosity VH1|1-18 and low viscosity VH1|1-02 from the set of 43 antibodies are also shown for comparison.

Potency values of the parent AK antibody and the two well-expressed mutants, measured through binding to PCSK9, were similar (FIG. 4). Finally, measured viscosity values of the AK and AO mutants were significantly lower than the parents, as predicted (FIG. 5). For example, the AK (82 94 95) mutant was at only 39% of the parent's viscosity. Viscosity of both AO mutants containing the S59R substitution was even lower, at approximately 28% of the parent's viscosity (FIG. 5). The S59R mutants did not express well for the AK antibody and the viscosity could not be measured. Average viscosity values for VH1|1-18 and VH1|1-02 germline subfamilies were added for comparison. A total of 12 consistent sequence differences were identified between VH1|1-18 and VH1|1-02 subfamilies, including 8 in CDRs and 4 in frame regions (FIG. 9). Three sites, all in frame region 3, were selected for amino acid substitutions from high viscosity VH1|1-18 to low viscosity VH1|1-02. The three point mutations in frames were introduced in two mAbs of VH1|1-18 subfamily (AK and AO) to convert only these residues to the residues present in VH1|1-02. Although chances to achieve the possible 2-fold decrease in viscosity were theoretically low (3/12), these substitutions rather unexpectedly produced desirable outcome: with only three substitutions the viscosity decreased approximately two-fold in both antibody molecules.

Viscosity Versus pI

Figure 6:
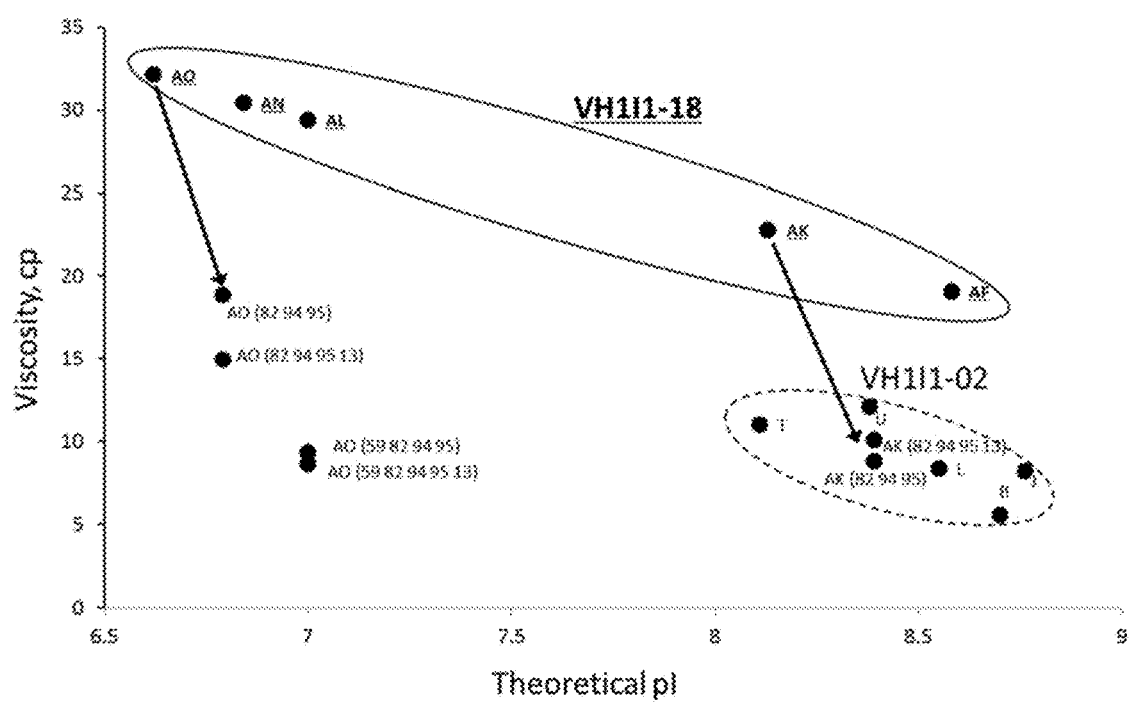
FIG. 6 shows measured viscosity values of mAbs of the high viscosity VH1|1-18 and the low viscosity VH1|1-02 subtypes versus calculated whole molecule pI values. The low-viscosity mutants of AK and AO antibodies are also shown.

Although the dependence of viscosity from pI was not clear from the whole set of the 43 mAbs, the VH1 subset clearly showed that viscosity steadily increased when pI values of the mAbs decrease from pI 8.5 to pI 6.5 in the pH 5.2 formulation (FIG. 6). The shift between the high-viscosity VH1|1-18 mAbs and low-viscosity VH1|1-02 mAbs can be also seen. As predicted, T82R, R94S and S95R mutants of AK and AO antibodies moved approximately two fold down along the viscosity scale from the VH1|1-18 to the VH1|1-02 area on the plot (FIG. 6). Mutants AO (59 82 94 95) and AO (59 82 94 95 13) moved to even lower viscosity and to slightly higher pI, indicating that the S59R substitution, adopted from outside of the VH1 group, was effective in further reducing viscosity. Unfortunately, AK mutants containing R59 were not expressed well, suggesting that appearance of the low-frequency arginine residue in position 59 may affect expression.

An increase in pI for antibodies in formulations with pH<pI (for example, the mildly acidic formulation used in this study) typically leads to a decrease in viscosity. This result can be explained by the columbic repulsion of the positively charged antibody molecules. It is known that proteins, including antibodies, show poor solubility and high precipitation, which affect viscosity, at high concentrations. It is interesting that the VH1|1-18 to VH1|1-02 substitutions in frame region 3 resulted in a two-fold decrease in viscosity and only a minor increase in antibody pI values, suggesting that not the charge increase, but rather some structural changes may be responsible for the dramatic decrease in viscosity.

After superimposing crystallography structures of hundreds of Fab domains, hydrogen bond interactions for every VH and VL position were identified (Honegger et al. (2001), "Yet another numbering scheme for immunoglobulin variable domains: an automatic modeling and analysis tool," *J. Mol. Biol.* 309: 657-670). The data indicate that the identified positions may be bound to other residues through main-chain and side-chain hydrogen bond interactions (for Type III AK and AO antibody molecules). For example, 94 was bound to 77 in some VH Type III immunoglobulin structures; 95 to 18; 59 to 67, 66, 65, 61, 60 and VL13 to 146, 148. Hence, residue substitutions at these positions may change the interactions and the immunoglobulin fold. The crystal structure of AK antibody (Jackson et al., 2007), "The Crystal Structure of PCSK9: a Regulator of Plasma LDL-Cholesterol," *Structure* 15: 545-52) suggests that all three positions 82, 94 and 95 are on the very periphery of the Fab regions and exposed to solvent and other antibody molecules. Changes in FR3 positions in VH3 (FIG. 11) and VK3 (FIG. 12) also correlate to viscosity. One explanation of their role in viscosity is that these positions in FR3 are on the periphery of the molecule and are actively engaged in the intermolecular interactions during shear stress associated with motion through the injection needles and viscosity measurements.

Figure 8:
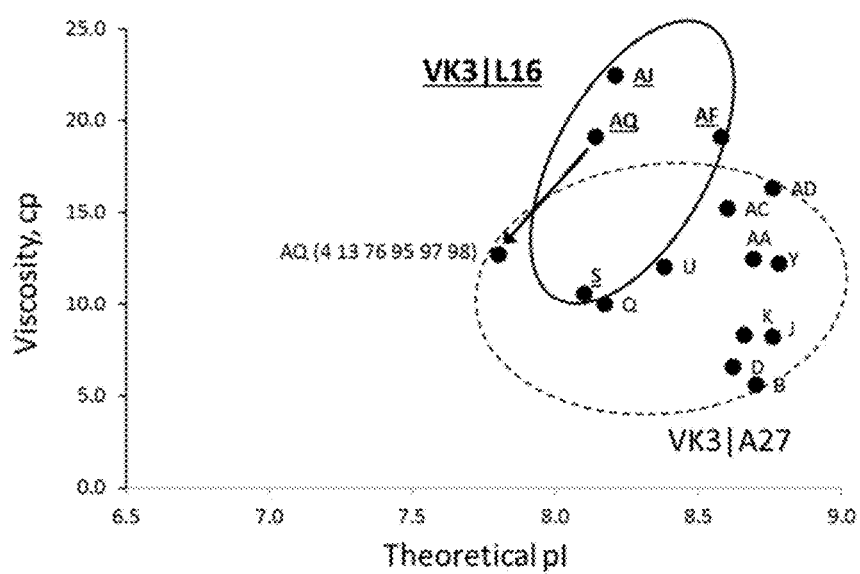
FIG. 8 shows measured viscosity values of mAbs with high viscosity VK3|L16 and VK3|L6 subfamilies and the low viscosity VK3|A27 subfamily versus calculated whole molecule pI values. The low-viscosity mutant AQ (4 13 76 95 97 98) is also shown.

Lower viscosity VK3|A27 and higher viscosity VK3|L16 antibodies showed inverse correlation between viscosity and pI (FIG. 8, FIG. 12).

Figure 7:
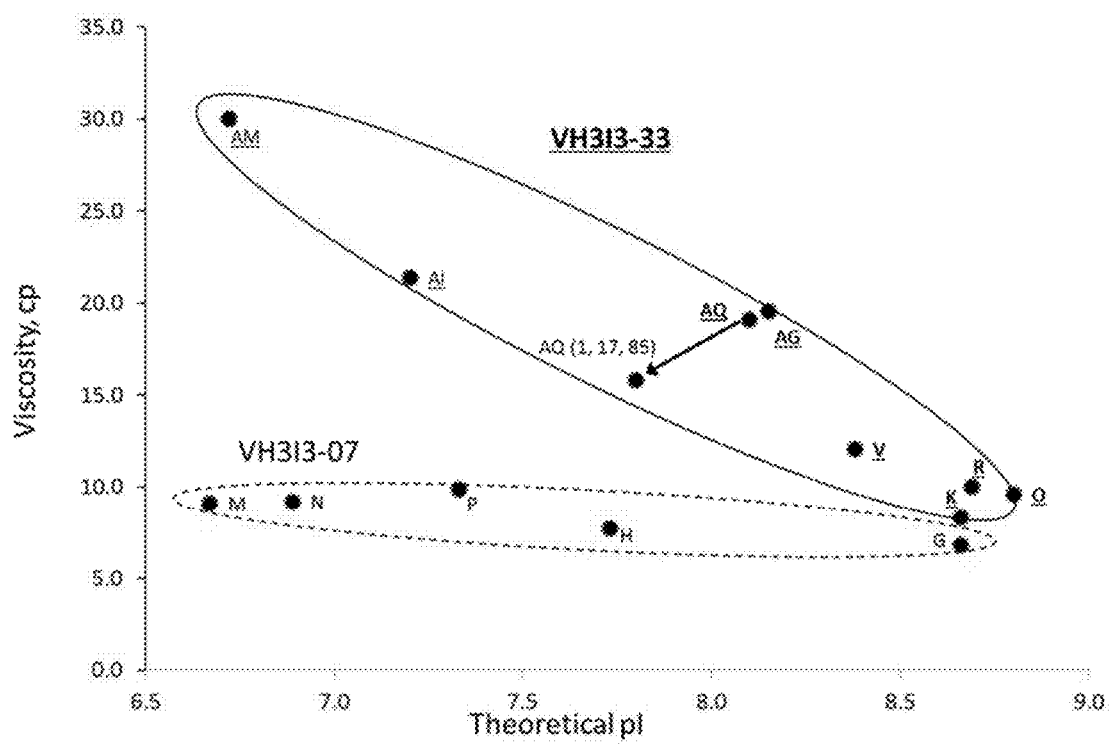
FIG. 7 shows measured viscosity values of mAbs of the high viscosity VH3|3-33 and the low viscosity VH3|3-07 subtypes versus calculated whole molecule pI. The low-viscosity mutant AQ (1, 17, 85) is also shown.

It needs to be mentioned that pI was a not very strong but in some cases useful predictor of viscosity. In general, viscosity decreased with increasing pI, and pI should be taken into account. For example, viscosity values of VH3|3-33 become lower and similar to VH3|3-07 for higher pI antibody molecules (FIG. 7). Hence, pI should be taken into account when predicting viscosity of VH3|3-33.

Proposed Viscosity Reduction for VH3 and VK3 Germline Families

High-viscosity VH3|3-33 and low-viscosity VH3|3-07 antibodies on average have a large difference in viscosity, while occupying a similar pI range (FIG. 7). Unexpectedly, on average, VH3|3-07 had lower viscosity and also lower pI, which contradicts typical behavior reported in the literature. Viscosity values of the following VH3|3-33 molecules can be reduced by the mutations: AQ, AM, AI, AG.

Monoclonal antibodies with high-viscosity VK3|L16 and low-viscosity VK3|A27 light chains also showed a large viscosity difference while showing relatively small difference in pI values, again suggesting a structural difference between subfamilies (FIG. 8). Viscosity values of the following VK3|L16 molecule can be reduced by the mutations described in FIG. 11: antibodies AQ and AF.

Figure 13:
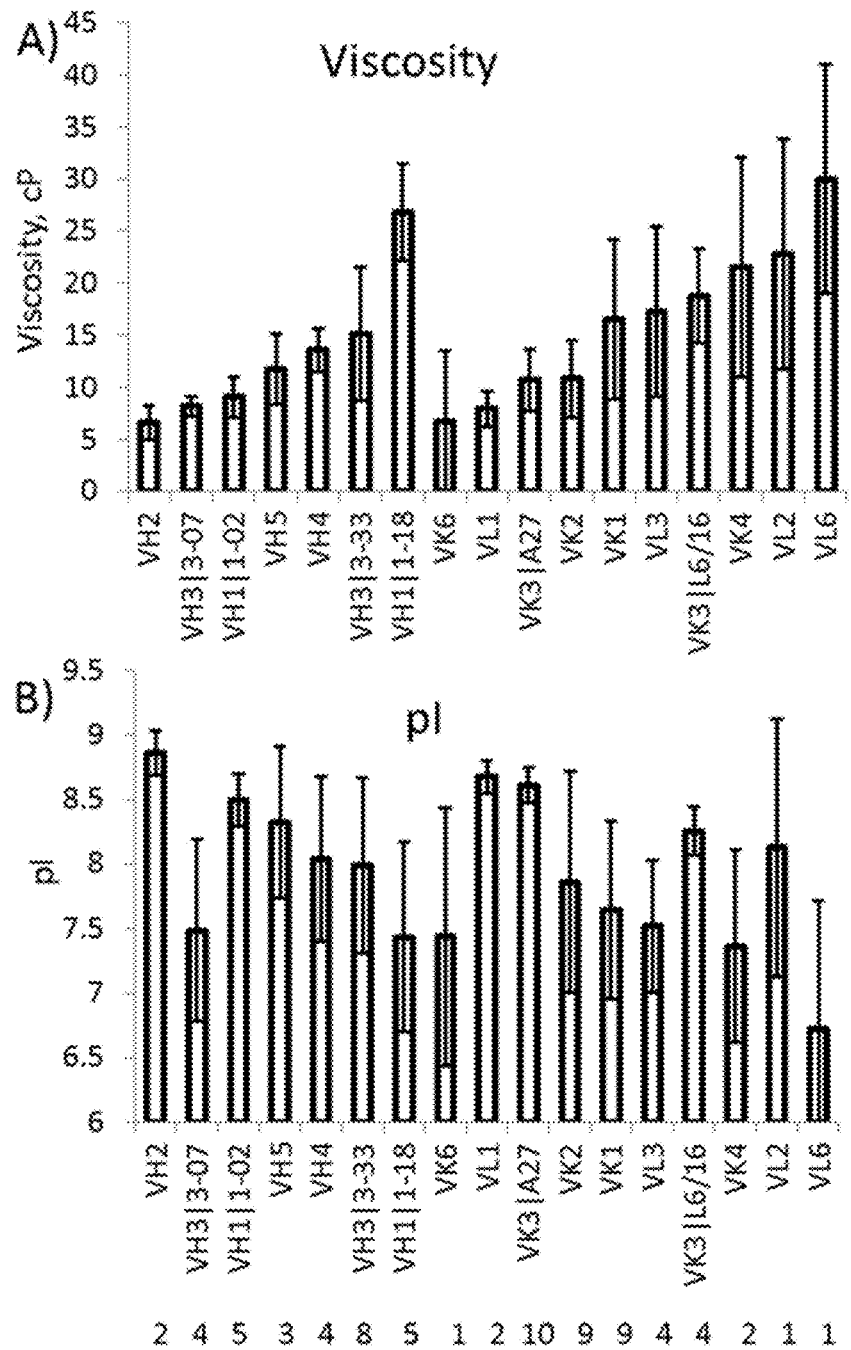
FIGS. 13A and 13B show average values for measured viscosity and calculated pI values for intact antibody molecules containing the specified heavy chain and light chain germline families and germline subfamilies of VH1, VH3 and VK3. The X-axis contains families and the number of members in each family and subfamily.
Figure 14A:
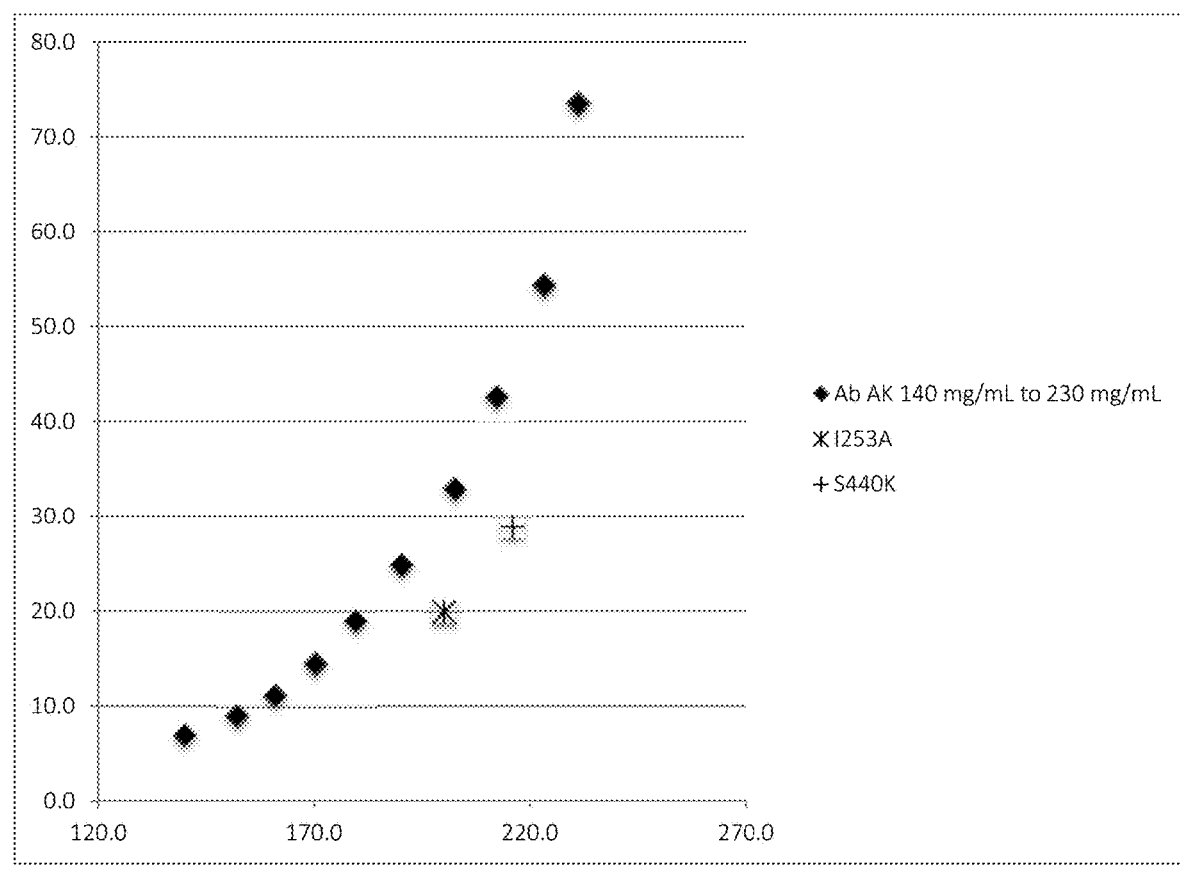
FIG. 14A shows that mutations in the Fc-Fc interaction surface can decrease solution viscosity. The viscosity of concentrations of antibody AK and antibody AK mutants I253A and S440K are shown.
Figure 14B:
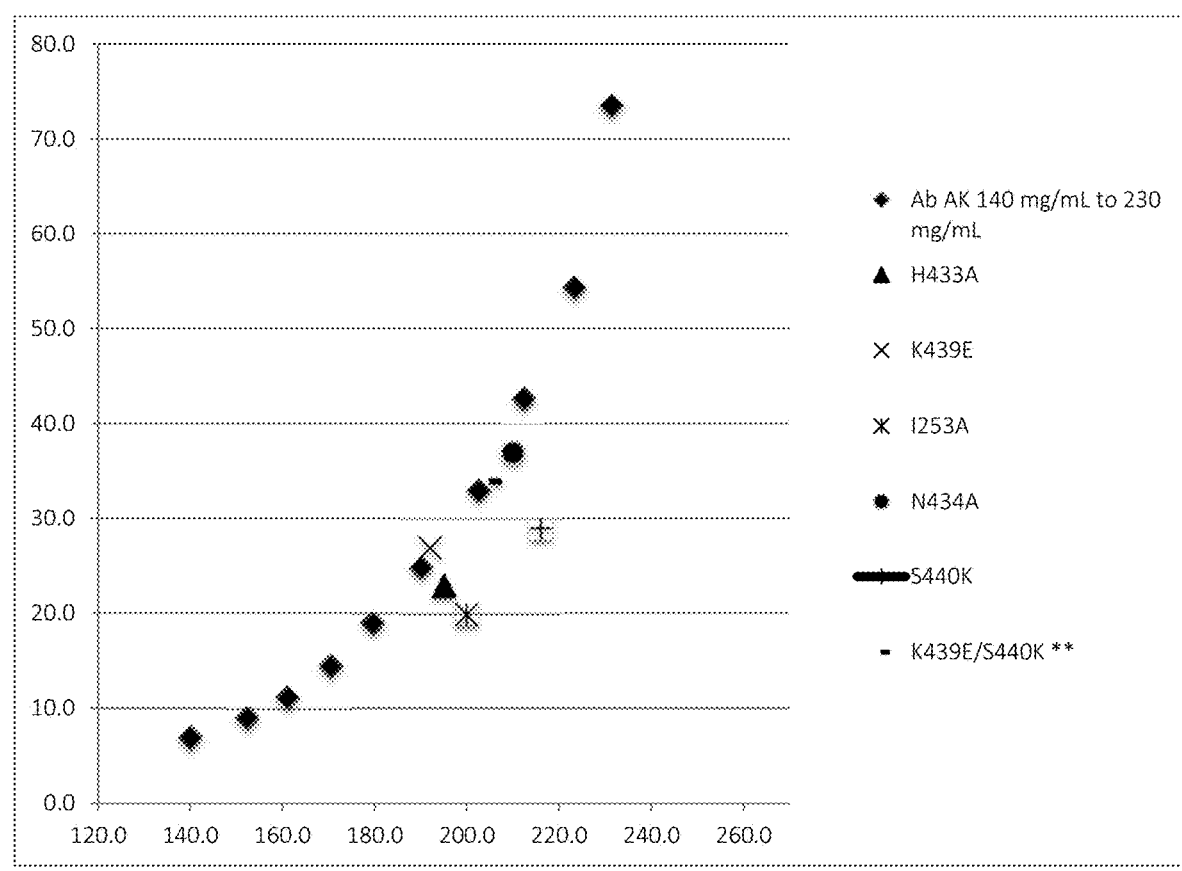
FIG. 14B shows that a double mutant that restores wild type complement activity also restores wild type viscosity. The figure shows the viscosity of concentrations of antibody AK, antibody AK mutant I253A, antibody AK mutant S440K, and antibody AK double mutant K439E/S440K. The figure also shows the viscosity of antibody AK mutant K439E, antibody AK mutant H433A, and antibody AK mutant N434A which do not decrease viscosity relative to the antibody AK parent.

The analysis of global sequence features revealed the following high/low viscosity pairs: VH1|1-18/VH1|1-02; VK3|L16/VK3|A27; and VH3|3-33/VH3|3-07 with p-values of the correlation at 0.0002, 0.031 and 0.076, respectively (FIG. 2). Sequence positions and residues correlating to the viscosity differences were identified, and can be considered as candidates for viscosity lowering point mutations (FIG. 2). The performed above correlation of VH and VL families to viscosity indicates that theoretically antibodies with the following VH and VL combinations should have the lowest viscosity (FIGS. 13A and B): VH2, VH3|3-07, VH1|1-02 for VH and VK3, VL1, VK3|A27 for VL. Three antibodies of VH1|1-02 and VK3|A27 configuration practically occurred in our set and they indeed exhibited low viscosity values: B (5.6 cP), J (8.2 cP), Y (12.1 cP).

Chemical Cross-Linking Studies

A broad survey of the potential protein-protein interactions in viscous antibody solutions was attempted using chemical cross-linking at high protein concentrations. Chemical cross-linking is a classic biochemical technique used to demonstrate that specific portions of proteins interact with each other. In this paper we describe the use of a zero length chemical cross-linking reagent to identify potential protein-protein interactions in high concentration viscous antibody solutions. The chemical cross-linking results of viscous and non-viscous antibodies are used to construct a model of potential protein-protein interactions in solution.

Chemical cross-linking with EDC reveals the presence of a common chemically cross-linkable oligomeric distribution. The chemical cross-link that results in the oligomeric pattern is surprisingly not inter-molecular but rather an intra-molecular cross-link. The intra-molecular cross-link between the top of the Fc and the bottom of a Fab results in an antibody conformation that may favor the formation of Fc-Fc mediated antibody oligomers. The 1HZH antibody crystal structure contains an antibody hexamer in the asymmetric unit that has one Fab arm pinned against the Fc domain to facilitate the Fc-Fc interaction critical to form the IgG1 hexamer. The appearance of this conformation may or may not be critical to the formation of the hexamer in the protein crystal. The increased propensity to form the hexamer in solution when the Fab-Fc intra-molecular chemical cross-link is present suggests that the Fab arm pinned to the Fc may have increased propensity to form Fc-Fc based antibody oligomers.

Decreasing Fc-Fc Interactions can Decrease Solution Viscosity

The scientific literature includes research on hexamer formation of antibodies related to interaction with C1q1 and CDC activity. Diebolder et al. found that anti-CD20 antibodies with certain Fc point mutations, including K439E and S440K, abrogated CDC activity but that the associated K439E/S440K double mutant restored CDC activity. Also I253A mutation decreased CDC activity. Diebolder et al. (2014), "Complement is Activated by IgG Hexamers Assembled at the Cell Surface," Science 343: 1260-3. Diebolder et al. did not associate the mutants they disclose with an effect on antibody viscosity. Similarly, van den Bremer et al (2015) found that charged residues at the C-terminus of an antibody could decrease C1q1 interaction due to a decreased ability to form IgG hexamer structures. The authors did not associate the presence of charged residues at the C-terminus of IgGs to an effect on antibody solution viscosity.

The observation of a hexamer of antibodies in viscous antibody solutions suggested that the Fc-Fc interactions that are present in the antibody hexamer crystal structure as well as the structure thought to form prior to the recruitment of C1q1 (complement) are likely present in viscous antibody solutions in the absence of the chemical cross-linker EDC. In order to test whether the Fc-Fc interaction might contribute to solution viscosity, Fc mutants based on the work done by Diebolder et al. were generated at Amgen. The materials were then evaluated in anti-PCSK9 formulation buffer by cone and plate rheology. The comparison of parent anti-PCSK9 antibody AK and Fc mutant anti-PCSK9 antibodies demonstrated that decreasing the affinity of Fc for Fc does decrease the solution viscosity of the antibody. The point mutants retained FcRn binding capacity and there were no changes to bioactivity. The ability of a double mutant which restored wild-type complement activity to return to wild type viscosity demonstrates that the decrease in viscosity can be reversed if the ability of Fc-Fc interactions is restored to wild-type levels. Taken together with the observation of Fc-Fc mediated oligomeric species increasing solution viscosity, there is a common Fc-mediated protein-protein interaction that contributes to antibody solution viscosity. It needs to be noted that out of five mutations, S440K, I253A, K439E, H433A, N434A identified by Diebolder et al. as reducing CDC activity and tested for viscosity in this work, only the first two showed reduced viscosity in high concentration anti-PCSK9 formulation, while K439E, H433A and N343A did not reduce viscosity in high concentration anti-PCSK9 formulation, indicating that direct correlation does not exist and that people skilled in the art could not correctly anticipate lower viscosity from the information provided by Diebolder et al. The K439E mutant was also evaluated in a high protein concentration sucrose formulation and found to be less viscous than the parent anti-PCSK9 mutant at the same concentration. The presence of Arginine in the anti-PCSK9 formulation may have contributed to charge screening that may have decreased the effectiveness of the negative charge introduced in the K439E mutant to decrease Fc-Fc interactions. The H433A and the N434A mutants have no obvious charge screening sensitivity like the K439E mutant.

The Fc-Fc interaction may influence solution viscosity by increasing the number of potential interactions possible in two potential ways. It could increase the number of interactions per antibody from two CDR mediated interactions to two CDR mediated interactions plus 2 Fc mediated interactions per antibody or it could change the number of free CDR ends available in oligomers present in solution. Given the fact that the Fc domain of IgG1, IgG2, IgG3 and IgG4 antibodies are highly similar, it is likely that the Fc-Fc mediated interactions are present in all antibodies. The analysis of non-viscous antibodies shows that the intramolecular cross-link which indicates the presence of an Fc-Fc interaction is absent in contrast to a viscous antibody at the same concentration. This suggests that the Fc-Fc interaction, although theoretically possible, is absent in non-viscous antibodies. The CDR next nearest neighbor interaction may influence the relative distance between Fc's as well as the relative orientation to enhance Fc-Fc interaction. This may explain why viscous antibodies have an Fc-Fc interaction while non-viscous antibodies do not at room temperature.

The presence of an Fc-Fc interaction also increases the likelihood that an oligomer of antibodies (dimer, trimer, tetramer, etc.) contains the maximum number of free CDR ends. The larger number of free CDR ends increases the number of CDR next nearest neighbor interactions. This in turn may increase network formation propensity and increase solution viscosity as a result of more efficient "percolation."

C-Terminal Modifications to Reduce Viscosity

Certain modifications at the antibody C-terminus interfere with C1q binding and complement-dependent cytotoxicity (CDC). Van den Bremer et al. (2015), "Human IgG is produced in a pro-form that requires clipping of C-terminal lysines for maximal complement activation," *mAbs* 7(4): 672-80. The authors found that C-terminal lysine and C-terminal glutamic acid likely decreases the propensity of the Fc-Fc interactions that lead to a hexamer of antibodies that can most efficiently interact with C1q1. The authors constructed mutants of a CD20 antibody and a CD38 antibody having PGKP (SEQ ID NO:381), PGKKP(SEQ ID NO:382), PGKKKP (SEQ ID NO:383), and PGE at the C-terminus. They found that these mutants showed significantly reduced or completely lost CDC activity. Thus, one may conclude that the mutations blocked the hexamerization previously correlated by the authors with CDC activity. Given the present correlation of hexamerization with viscosity, such mutations should also reduce viscosity of antigen binding proteins. It is thus reasonable to conclude that placement of positively charged or negatively charged amino acids at the C-terminus, whether placed there by addition or substitution of existing C-terminal amino acids, will reduce the viscosity of an antigen binding protein.

Sequence Modification to Improve Pharmacokinetic Parameters

This invention also includes the discovery of improved pharmacokinetic properties in antigen binding proteins having mutations that may also reduce viscosity. In particular, S440K mutations have been found to improve both Tmax (the time after dosing at which the maximum concentration was observed) and Cmax (the maximum observed concentration measured after dosing). Mutants of antibody AK having S440K, optionally with other mutations, have been found to have Tmax reduced by more than half that of the parental antibody AK after subcutaneous injection of the mutants and the parental antibody at the same concentration. Such mutants have also been found to have Cmax that is 28% or 42% higher after subcutaneous injection of the mutants and the parental antibody. See FIG. 22.

Nucleic Acids, Vectors, Host Cells

The invention also includes isolated nucleic acids encoding the bispecific antibodies of the invention, which includes, for instance, the light chain, light chain variable region, light chain constant region, heavy chain, heavy chain variable region, heavy chain constant region, linkers, and any and all components and combinations thereof of the bispecific antibodies disclosed herein. Nucleic acids of the invention include nucleic acids having at least 80%, more preferably at least about 90%, more preferably at least about 95%, and most preferably at least about 98% homology to nucleic acids of the invention. The terms "percent similarity", "percent identity" and "percent homology" when referring to a particular sequence are used as set forth in the University of Wisconsin GCG® software program. Nucleic acids of the invention also include complementary nucleic acids. In some instances, the sequences will be fully complementary (no mismatches) when aligned. In other instances, there may be up to about a 20% mismatch in the sequences. In some embodiments of the invention are provided nucleic acids encoding both a heavy chain and a light chain of an antibody of the invention.

Nucleic acids of the invention can be cloned into a vector, such as a plasmid, cosmid, bacmid, phage, artificial chromosome (BAC, YAC) or virus, into which another genetic sequence or element (either DNA or RNA) may be inserted so as to bring about the replication of the attached sequence or element. In some embodiments, the expression vector contains a constitutively active promoter segment (such as but not limited to CMV, SV40, Elongation Factor or LTR sequences) or an inducible promoter sequence such as the steroid inducible pIND vector (Invitrogen), where the expression of the nucleic acid can be regulated. Expression vectors of the invention may further comprise regulatory sequences, for example, an internal ribosomal entry site. The expression vector can be introduced into a cell by transfection, for example.

In another embodiment, the present invention provides an expression vector comprising the following operably linked elements; a transcription promoter; a first nucleic acid molecule encoding the heavy chain of a bispecific antigen binding protein, antibody or antigen-binding fragment of the invention; a second nucleic acid molecule encoding the light chain of a bispecific antigen binding protein, antibody or antigen-binding fragment of the invention; and a transcription terminator. In another embodiment, the present invention provides an expression vector comprising the following operably linked elements; a first transcription promoter; a first nucleic acid molecule encoding the heavy chain of a bispecific antigen binding protein, antibody or antigen-binding fragment of the invention; a first transcription terminator; a second transcription promoter a second nucleic acid molecule encoding the light chain of a bispecific antigen binding protein, antibody or antigen-binding fragment of the invention; and a second transcription terminator.

A secretory signal peptide sequence can also, optionally, be encoded by the expression vector, operably linked to the coding sequence of interest, so that the expressed polypeptide can be secreted by the recombinant host cell, for more facile isolation of the polypeptide of interest from the cell, if desired.

Recombinant host cells comprising such vectors and expressing the heavy and light chains are also provided.

Purification

Methods of antibody purification are known in the art and can be employed with production of the antibodies and bispecific antibodies of the present invention. In some embodiments of the invention, methods for antibody purification include filtration, affinity column chromatography, cation exchange chromatography, anion exchange chromatography, and concentration. The filtration step preferably comprises ultrafiltration, and more preferably ultrafiltration and diafiltration. Filtration is preferably performed at least about 5-50 times, more preferably 10 to 30 times, and most preferably 14 to 27 times. Affinity column chromatography, may be performed using, for example, PROSEP® Affinity Chromatography (Millipore, Billerica, Mass.). In a preferred embodiment, the affinity chromatography step comprises PROSEP®-vA column chromatography. Eluate may be washed in a solvent detergent. Cation exchange chromatography may include, for example, SP-Sepharose Cation Exchange Chromatography. Anion exchange chromatography may include, for example but not limited to, Q-Sepharose Fast Flow Anion Exchange. The anion exchange step is preferably non-binding, thereby allowing removal of contaminants including DNA and BSA. The antibody product is preferably nanofiltered, for example, using a Pall DV 20 Nanofilter. The antibody product may be concentrated, for example, using ultrafiltration and diafiltration. The method may further comprise a step of size exclusion chromatography to remove aggregates. Further parameters of purification appear in the working examples hereinafter.

The bispecific antibodies, antibodies or antigen-binding fragments may also be produced by other methods known in the art, for example by chemical coupling of antibodies and antibody fragments.

Each manuscript, research paper, review article, abstract, patent application, patent or other publication cited in this specification is hereby incorporated by reference in its entirety.

WORKING EXAMPLES

The invention is further illuminated by the following working examples, which exemplify but do not limit the scope of the invention

Example 1

Fab Mutations

Materials

A set of 43 human and humanized recombinant monoclonal antibody molecules with different targets and different sequences were produced and purified according to a standard procedure (FIGS. 1A and 1B). The set with equivalent purity of >98% by size exclusion chromatography (SEC) was collected. Samples were concentrated in a 3 mL maximum volume using Amicon Ultrafiltration Stirred Cell Model 8003 (Millipore, Billerica, Mass.) at 2-8° C. at a maximum pressure of 30±10 psi. They were concentrated up to 150 mg/mL according to approximate volume depletion in a formulation buffer containing 20 mM acetate, 9% sucrose at pH 5.2 (without polysorbate), and final concentrations were determined (+10%) using the protein's absorbance at 280 nm (after dilution to end up within 0.1-1 absorbance units (AU)) and a protein-specific extinction coefficient.

Several low viscosity mutants of two mAbs were produced, purified and formulated according to a similar standard procedure. They included an antibody against proprotein convertase subtilisin/kexin type 9 (PCSK9, antibody AK) and against macrophage colony-stimulating factor (M-CSF, AO).

Viscosity Measurements

Viscosity analysis was performed on a Brookfield LV-DVIII cone and plate instrument (Brookfield Engineering, Middleboro, Mass., USA) using a CP-40 spindle and sample cup. All measurements were performed at 25° C., controlled by a water bath attached to the sample cup. Multiple viscosity measurements were collected, manually within a defined torque range (10-90%) by increasing the RPM of the spindle. Measurements were averaged in order to report one viscosity value per sample to simplify the resulting comparison chart Sequence Alignment A structure-based sequence alignment was performed by an Ab Initio software tool developed using Excel Macros downloaded from the Department of Biochemistry of Zürich University.

Example 2

Fc Mutations

Figure 16:
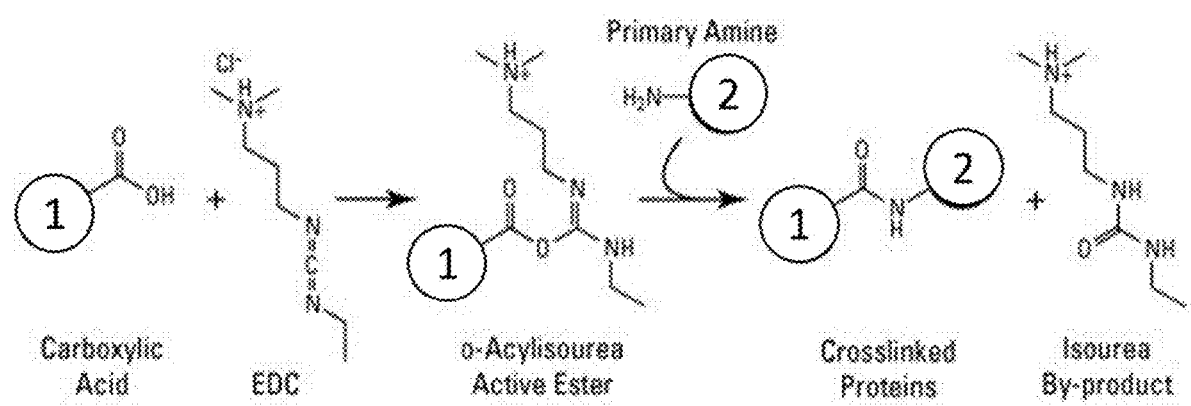
FIG. 16 is a schematic of EDC chemical cross-linking (see Example 2).
Figure 18:
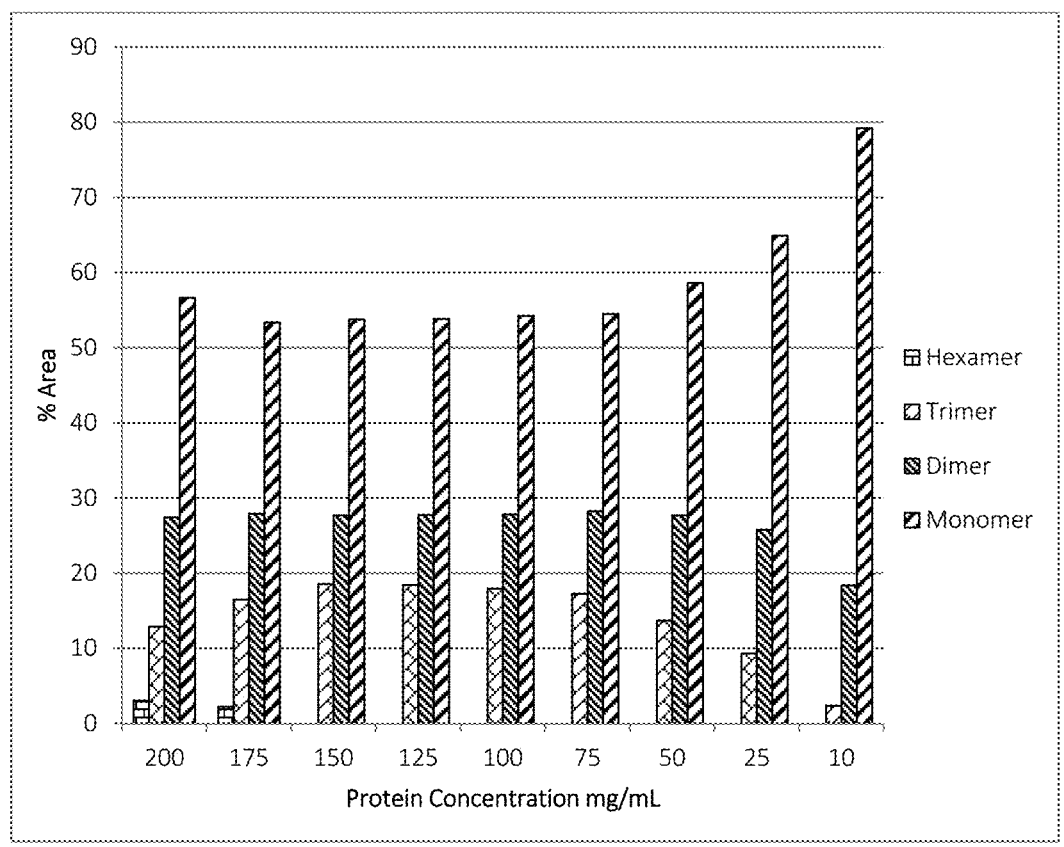
FIG. 18 shows concentration-dependent formation of antibody system oligomers by EDC chemical cross-linking of antibody AH.
Figure 19A:
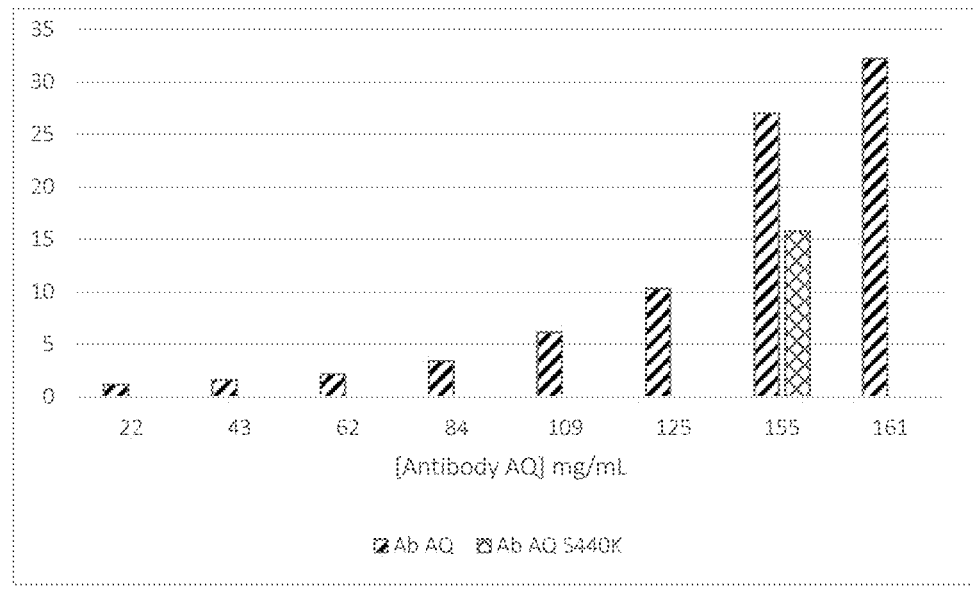
FIG. 19A shows that a S440K mutation in the Fc region reduces viscosity in antibody AQ. (Note that the concentration of the mutant is actually 150 mg/mL.)
Figure 19B:
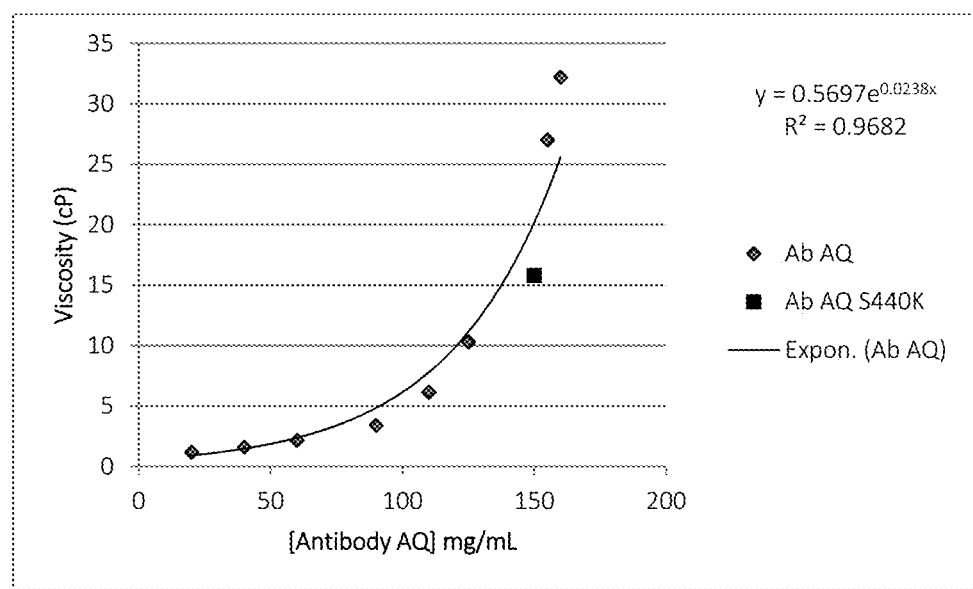
FIG. 19B is a scatter plot of the same data with an exponential fit. The diamonds in FIG. 19B denote the unmodified antibody AQ at the concentrations shown and the square shows the S440K mutant at 150 mg/mL.

Expression and Purification of Mutants
Materials and Methods
 Anti-C-kit antibody (antibody BA, SEQ ID NOS: 174 and 176, encoded by nucleic acids of SEQ ID NOS: 173 and 175, respectively), anti-sclerostin antibody AH, and anti-PCSK9 antibody AK
 Anti-streptavidin IgG1 and IgG2.
 1-ethyl-3-[3-dimethylaminopropyl] carbodiimide hydrochloride (EDC)
 Solubilization with n-methyl-2-pyrrolidone
 Size Exclusion High Performance Liquid Chromatography (SE-HPLC) with Light Scattering (LS)
 Reduced and alkylated reversed phase High Performance Liquid Chromatography (RA RP-HPLC)
 Trypsin peptide map with electro spray ionization mass spectrometry (ESI-MS)
 Cone and plate viscometer
Results
SE-HPLC of EDC Cross-Linking of High Concentration Monoclonal Antibody Solutions Reveals Propensity to Form Oligomers The compound 1-ethyl-3-[3-dimethylaminopropyl] carbodiimide hydrochloride (EDC) was used to chemically cross-link acidic residues in the antibody to primary amines in the antibody (N-terminus and/or Lys residues) and has been used in other studies to determine the regions of protein-protein interaction. The proximity of the carboxyl group to the primary amine is critical as an amide bond is formed between the two groups (FIG. 16). The cross-links that form are likely salt bridges that are present in solution. Carraway and Koshland, Jr. (1972). "Carbodiimide modification of proteins." *Methods Enzymol* 25: 616-623. A panel of antibodies was chemically cross-linked with EDC under identical solution conditions. Previous rheological studies had determined that some of the antibodies in the panel were viscous and some were not (FIG. 17). The non-viscous antibodies had small increases in dimer content but did not contain large amounts of higher order. In contrast, the viscous antibodies contained large amounts of dimer as well as higher order oligomers. A summary is provided in FIG. 17. All of the antibodies that were identified as viscous contained EDC cross-linked species that appeared to be larger than dimer. The appearance of the larger oligomeric species is concentration dependent (antibody AH is shown in FIG. 18 as an example). In order to facilitate further analysis, chemical cross-linking conditions were changed to drive the cross-linking reaction to completion. The solutions became solids after chemical cross-linking at 200 mg/mL. The solids were re-solubilized with buffer or a buffered 3% NMP solution. SE-HPLC analysis of both samples showed that the samples were similar. The buffered 3% NMP solution solubilized the protein significantly faster with more of the material going into solution. Antibody AH was re-solubilized and analyzed further as an example.

Size Analysis by SE-HPLC with Online LS

The cross-linked antibody solutions were analyzed by SE-HPLC with online light scattering to determine the size of the eluting species. SE-HPLC was conducted with online light scattering analysis of antibody AH after EDC chemical cross-linking and resolublization with 3% NMP. SE-HPLC revealed three peaks present in the UV and RI. The first peak was identified as a species with a mass of 840.5 kD. This is close to the expected mass for a hexamer of antibody AH of 873.2 kD. Another species had a mass of 494.6 kD, which is close to the predicted mass of 436.6 kD for a trimer of antibody AH. The third species showed a mass of 139.9 kD, which is close to the predicted mass of 145.5 kD for a monomer of antibody AH.

Reduced and Alkylated Reversed Phase HPLC of EDC Cross-Linked Antibody AH

The cross-linked antibody solutions were analyzed by reduced and alkylated reversed phase high performance liquid chromatography. The recovery of the majority of both light chain (LC) and heavy chain (HC) was unexpected as it was presumed that either the HC or the LC would be cross-linked to one another to form non-native LC-HC peptides or non-native LC-LC or HC-HC peptides reflecting the cross-linked oligomers observed by SEC analysis. In the case of antibody AH, the LC eluted in the same place with the exact same mass as non-cross-linked antibody AH LC. There were changes in the HC in antibody AH that are concentration dependent. There is a small amount of HC-HC cross-linked material (eluting at about 33 minutes, FIG. 21) that had an identified mass of 100 kD. At 150 mg/mL and 200 mg/mL, the distribution of HC species is similar. At lower protein concentrations, the distribution includes more of a species that elutes at about 28.5 min. The distribution of HC species correlates with the amount of oligomer present in each sample as analyzed by SEC with the 200 mg/mL sample containing the largest amount of hexamers and the 10 mg/mL sample containing very little oligomer. The pattern was observed in other viscous antibody solutions.

Example 3

Nonhuman Primate Study of Pharmacokinetics and Pharmacodynamics (PKPD) of the Anti-PCSK9 Parent Antibody AK and Low Viscosity Mutants Materials: antibody AK and its mutants. All mutations in heavy chain.

Fab Mutant: T82(72)R, R94(84)S, S95(85)R; Aho numbering (actual numbering)

Fc Mutant S(434)K (S440K in EU numbering):

Double Mutant: T82(72)R, R94(84)S, S95(85)R; S(434)K:

Four groups of 4 male cynomolgus monkeys were used in this study. Each group received 1 subcutaneous (SC) dose of 10 mg/kg as follows. Group 1 received parent antibody AK (140 mg/ml); Group 2 received Fab mutant (210 mg/ml); Group 3 received Fc mutant (210 mg/ml); Group 4: Fab/Fc mutant (210 mg/ml). Groups 1 and 2 also had diluent control SC dose. Fab mutant included the following substitutions in positions T82(72)R, R94(84)S, S95(85)R. Fc mutant included substitution in position S(434)K.

To measure viscosity at 210 mg/ml, the parent and all mutants were formulated at 210 mg/mL in 10 mM Acetate, 155 mM N-acetyl arginine (NAR), 70 mM ArgHCl, pH 5.4, 0.01% Polysorbate 80. Viscosity was measured using ARG2 cone/plate at 1000 sec−1 and 25 C. See FIG. 15.

Study Design Outline:
4 groups of 4 male cynomolgus monkeys
  Each group received 1 SC dose (10 mg/kg) of:
Group 1: parent antibody AK (140 mg/ml)
Group 2: Fab mutant (210 mg/ml)
Group 3: Fc mutant (210 mg/ml)
Group 4: Fab/Fc mutant (210 mg/ml)
  Groups 1 and 2 also had diluent control subcutaneous dose
  Skin biopsies taken at injection site 3 days after dosing
  Histopath analysis performed
  Plasma LDL, HDL, total cholesterol and PK followed for 6 weeks post-dose
Study Conclusions
All 4 homologues produced marked LDL lowering
  Maximal reduction 2 weeks after dosing: 1 week later than previously observed for parent
  The nadir of the effect was not quite as profound for the Fab/Fc mutant (~78% vs ~90%)
  Return to baseline appears slightly more accelerated for the Fc mutant
  PK: Mean exposures were similar (based on Cmax and AUClast) between all treatment groups (within 1.4-fold)
  Fab and/or Fc mutations in anti-PCSK9 antibody AK had no significant effect on injection site reactions (ISR) or Pharmacokinetics and Pharmacodynamics (PKPD) profile in nonhuman primates (NHPs) (cynomolgus monkeys).

Fab Mutant: T82(72)R, R94(84)S, S95(85)R; Aho numbering (actual numbering).

Fc Mutant: S(434)K (S440K in EU numbering).

Example 4

Production and Characterization of Low-Viscosity Mutants of GIPR (2G10.006) Antibody AO Cloning. Expression, Purification and High Concentration Formulation of Low Viscosity Mutants of Antibody AQ GIPR (2G10.006) AQ parent is described in U.S. Provisional Application 62/387,486 as 2G10_LC1.006 (SEQ ID NO: 74 of the cited patent application). The aforementioned US Patent Application is hereby incorporated by reference. Heavy chain mutant AQ (HC 1, 17, 85) with mutation sites Q1(1)E, R17(16)G, S85(75)A and light chain mutant AQ (LC 4 13 76 95 97 98) with mutation sites M4(4)L, V13(13)L, A76(60)D, S95(77)R, Q97(79)E, S98(80)P were produced as follows. Synthetic genes for GIPR (2G10.006) (antibody AQ) low viscosity mutants were produced, digested and ligated into plasmid expression vectors. Constructs were verified by DNA sequencing. Stable cell pools were created by electroporation of a clonal CHO host cell line. The pools were cultured under selection until viability reached greater than 85%. Pools were seeding into a fed-batch production culture for 10 days and centrifuged media was harvested.

Figures 20A, 20B:
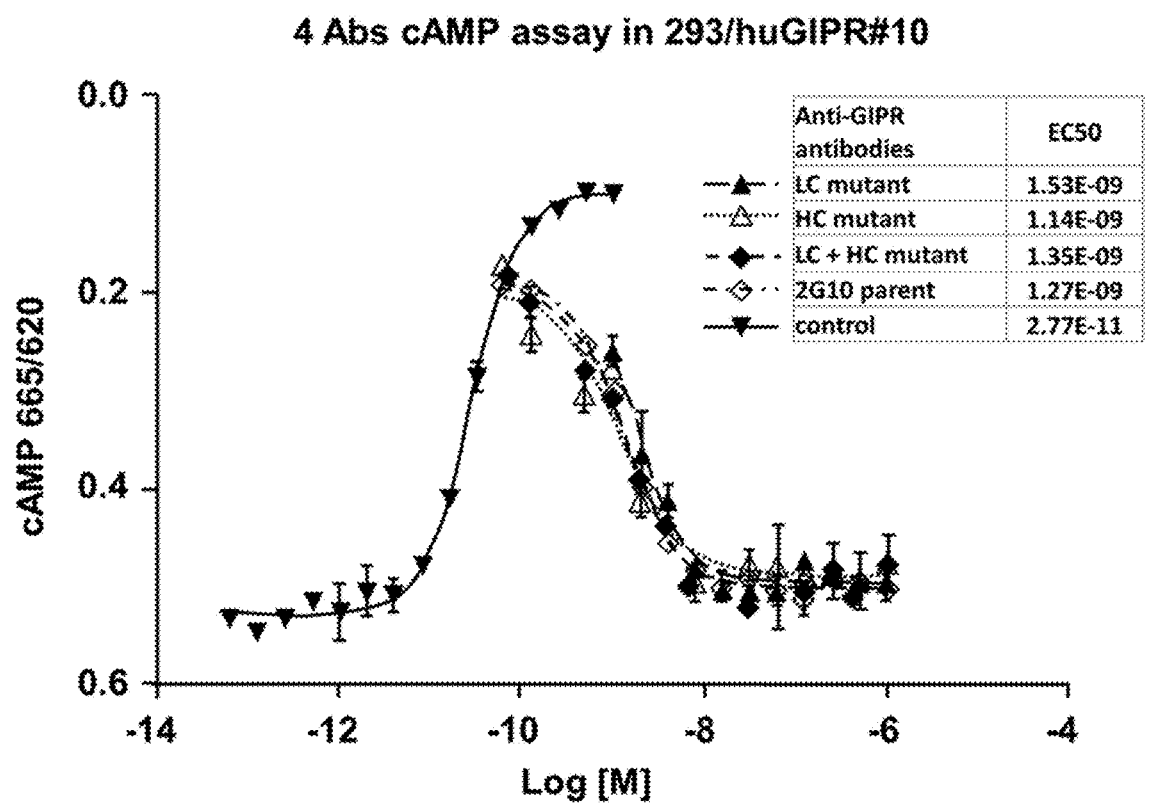
FIG. 20A is a table showing produced and characterized mutants of antibody AQ, including measured concentration and viscosity.
FIG. 20B shows cAMP response of 293/huGIPR cells expressing human GIP receptors activated by GIP and blocked by the anti-GIPR antibodies. The in vitro cAMP activity was equally unaffected by viscosity mutations. The potency remained the same within the error margin of the assay.

Harvested supematants were sterile filtered and purified through a three column chromatography process consisting of Protein A, cation exchange, and anion exchange, similar to the process described earlier (Shukla et al. (2007), "Downstream processing of monoclonal antibodies—Application of platform approaches," *J. Chrom. B* 848: 28-39). The resulting purified pools were dialyzed into formulation buffer containing 20 mM acetate and 9% sucrose at pH 5.2 (without polysorbate), achieving a final pH of ~5.2 and concentrated to approximately 150 mg/mL above 30 kDa cutoff filter via centrifugal ultrafiltration (FIG. 20A).

Potency Measurements

Potency was measured by an assay utilizing mammalian cells 293/huGIPR expressing glucose-dependent insulinotropic polypeptide receptor (GIPR). The increasing concentrations of anti-GIPR parent AQ and the low-viscosity mutants were blocking the interaction of GIP with GIPR which induced cAMP changes monitored during the assay. An application of the assay was earlier described in Tseng C. C. et al. (1996), "Postprandial stimulation of insulin release by glucose-dependent insulinotropic polypeptide (GIP). Effect of a specific glucose-dependent insulinotropic polypeptide receptor antagonist in the rat," *J. Clin. Invest.* 98: 2440-2445.

Viscosity Measurements

Viscosity analysis of AQ and two low viscosity mutants was performed on an Anton Paar Rheometer using a CP25-1/TG spindle. All measurements were performed at 25° C., controlled by a water bath attached to the sample cup. Viscosity measurements were collected manually with increasing shear rate from 0-2000 rpm. 10 viscosity measurement results at shear rate 1000 l/s and 10 viscosity measurement results at shear rate 2000 l/s were collected for each sample and averaged to report one viscosity value per sample.

It needs to be noted that precision of viscosity measurements is much better that accuracy, because the viscosity measurements are sensitive to even minor changes in some parameters, such as the state of the viscometer, temperature in the room and some other minor parameters at the time of the measurements. Therefore, it is important to measure all samples of interest in one setting or, if samples of interest are measured in two settings, have the same reference standard in both settings.

Results

Anti-GIPR (2G10.006) antibody AQ belongs to high-viscosity germline subfamilies of heavy chain VH3|3-33 and light chain VK3|L16. Several mutations derived from FIGS. 11 and 12 were made in frames in the effort to reduce viscosity of AQ. The viscosity of the parent AQ and the two mutants measured in one viscometer setting revealed the following values: AQ—19.1 cP, AQ (HC 1, 17, 85)—15.8 cP, AQ (LC 4 13 76 95 97 98)—12.7 cP (FIG. 20). The heavy chain mutant AQ (HC 1, 17, 85) mutant was at 83% and the light chain mutant AQ (LC 4 13 76 95 97 98) was at 67% relative to the parent AQ. FIGS. 7 and 8 illustrate positions of the mutants on the viscosity versus pI plots for VH3 and VK3 family members. The in vitro cAMP activity was equally unaffected by viscosity mutations. The potency remained the same within the error margin of the in vitro cell-based assay (See FIG. 20B). To summarize, introduced mutations reduced viscosity without loss of the potency.

Example 5

GIPR Low Viscosity Mutant Light Chain V78F (LC V78F in Aho Numbering and LC V62F in Linear Numbering)

GIPR (2G10.006) antibody AQ showed a high viscosity of 23 cP at 150 mg/mL in A52Su formulation. This antibody featured a low-frequency residue V78 in Aho numbering (V62 in linear numbering) in the kappa light chain (LC V78 Aho). The frequency of occurrence of V78 is <1%, while F78 is >98% in light chain sequences related to the kappa germline. The residue LC V78 attracted attention, because it was a covariance violator. Covariance analysis allows establishing pair-wise conserved-residue positions based on the physiochemical properties of the residues in variable regions of antibodies, identifying incorrectly positioned residues (which are often non-germline residues). Covariance analysis further may suggest replacing the amino acids at the deviating positions with more common germline sequences that lead to a large conformational change uncovered by molecular-dynamics simulations (Kannan G., "Method of correlated mutational analysis to improve therapeutic antibodies," U.S. Ser. No. 61/451,929, PCT/US 2012/028596, WO 2012/125495). In an effort to eliminate the covariance violation and increase the percentage of human sequences, the LC V78F mutation was introduced in the GIPR (2G10.006) antibody AQ.

Unexpectedly, viscosity of the mutant decreased by 25%, while maintaining similar potency for human GIPR as measured in cAMP (cell-based) assays. Both sequences, the GIPR (2G10.006) AQ parent and its LC V78F mutant are described in U.S. Provisional Application 62/387,486 as 2G10_LC1.006 (SEQ ID NO: 74 of the cited application) and 2G10_LC1.003 (SEQ ID NO: 71 of the cited application), respectively. The US Patent Application is hereby incorporated by reference. Newly discovered in the present invention is that such substitution resulted in about 25% reduction of viscosity by LC V78F mutation. Viscosity analysis of the GIPR_2G10.006 AQ and its V78F mutant was performed at 150 mg/ml in formulation containing 20 mM acetate, 9% sucrose at pH 5.2, 0.01% polysorbate 80, 1000 shear rate and 25 C using AR-G2 Magnetic Bearing Cone and Plate Rheometer from TA Instruments—Waters LLC. Cone plate size was 20 mm in diameter, 1.988° cone angle, equipped with Steel-990918 Peltier plate and operated using the Flow Sweep procedure. The measured viscosity values were 21 cP for GIPR_2G10.006 and 15.3 cP for GIPR (2G10.003) LC V78F mutant, which is 25% decrease in viscosity.

As noted in the previous example, precision of viscosity measurements is much better that accuracy. Viscosity at 150 mg/mL with 0.01% polysorbate is typically 10% lower than without polysorbate, which was observed in case of GIPR (2G10.006). Its viscosity was 23 cP without polysorbate (as for all 43 antibodies) and 21 cP with polysorbate.

Example 6

Cynomolgus Monkey Study

The antibodies designated as AK (control, also known as AMG 145 and evolocumab) and the Fab mutant, Fc mutant, and double mutant shown in Example 3 were generated using the methodology disclosed in Examples 1 and 2. The pharmacokinetic properties of these antibodies were tested in vivo by single subcutaneous bolus injection into male cynomolgus monkeys.

Study Design

The study was conducted in male cynomolgus monkeys. The animals were 2.7 to 3.8 years old and weighted between 2.9 to 3.8 kg. The animals were acclimated to laboratory housing for 7 days before the initiation of dosing. Criteria for selection included acceptable results from the pretreatment cholesterol levels (including LDL and HDL) levels.

Before the initiation of dosing, all animals were randomized and assigned to groups using a computer-based randomization procedure.

The test and control articles were administered subcutaneously into the mid-dorsal areas to the appropriate animals once on Day 1. The injection site(s) were shaved prior to administration and marked with indelible ink. The animals were temporarily restrained for dose administration and were not sedated. The dose volume for each animal was based on the most recent body weight measurement. For Groups 1 and 2, dose solutions were administered via 2 subcutaneous injections on the back of each animal (1 with test material, 1 with diluent). Injection sites were at least 5-6 cm apart. The test material was administered on the right of the spinal column for each animal. The diluent was delivered on the left of the spinal column for each animal. For Groups 3 and 4, dose solutions were administered via a single subcutaneous injection on the back of each animal. Dose levels and volumes for each group are summarized in FIG. 21.

Blood samples were collected by venipuncture into tubes containing Potassium (K2) EDTA at various time points over the duration of the in-life portion of this study (43 days). Animals were not fasted prior to serum chemistry blood collections.

Samples were chilled following blood collections, and split for preparation of either serum or plasma. Samples were mixed gently and centrifuged. Blood samples were maintained on wet ice immediately after collection until centrifuged (1500-2000×g for approximately 10 minutes) at approximately 4° C. The resultant plasma or serum was separated and divided into 2 aliquots (primary and backup), transferred to appropriately labeled polypropylene tubes, and stored in a freezer set to maintain at −80° C. until analysis. Plasma samples were used to determine test article concentration for pharmacokinetic evaluation, serum samples were analyzed for cholesterol, HDL, and LDL.

Pharmacokinetic Evaluation

Plasma samples were analyzed for concentration of each test antibody (antibody AK, AK Fab mutant, AK S440K Fc mutant, and AK Fab/S440K double mutant) using an enzyme-linked immunosorbent assay (ELISA). The assay uses recombinant human PCSK9 as the capture reagent and a horseradish peroxidase labeled antibody to human IgG1 as the detection reagent. Standards and quality control samples (QCs) are prepared by spiking antibody AK or low viscosity homologs into 100% cynomolgus monkey K2-EDTA pool. Costar 96-well microplate wells (Corning Incorporated) are coated with recombinant human PCSK9. After a blocking step, the standards, matrix blank (NSB), QCs (QCs) and test samples are loaded into the microplate wells after pretreating with a dilution factor of 100 in Blocker™ BLOTTO in TBS (Thermo Scientific). The antibody AK in the samples is captured by the immobilized recombinant human PCSK9 coated on the microplate. Unbound material is removed by washing the microplate wells. Following washing, mouse anti-human IgG, Ab35, HRP conjugated detection antibody is added to the microplate wells to bind the captured antibody AK. Unbound detection antibody is removed by washing the microplate wells. A one component TMB solution is added to the microplate wells for the detection of bound mouse anti-human IgG Ab35 HRP conjugate. The TMB substrate solution reacts with peroxide and, in the presence of HRP, creates a colorimetric signal that is proportional to the amount of antibody AK, or low viscosity mutant homolog, bound by the capture reagent. The color development is stopped using 2N sulfuric acid and the intensity of the color (optical density or OD) is measured at 450 nm minus 650 nm. Data are reduced using Watson version 7.4 SP3 (or later) data reduction package using a 4 parameter (Marquardt) regression model with a weighting factor of 1.

Pharmacokinetic parameters were estimated using WinNonlin pharmacokinetic software. A non-compartmental approach consistent with the subcutaneous route of administration was used for parameter estimation. All parameters were generated from individual concentrations in plasma from Day 1. The following parameters were determined Tmax (the time after dosing at which the maximum observed concentration was observed), Cmax (the maximum observed concentration measured after dosing), AUC (0-t) (the area under the concentration versus time curve from the start of dose administration to the time after dosing at which the last observed quantifiable concentration using the linear or linear/log trapezoidal method), AUC (0-t)/D (the AUC(0-t) divided by the dose administered), and RAUC (the area under the curve from T1 and T2 at steady state divided by the area under the curve from T1 to T2 during the initial dosing interval).

Results and Discussion

Figure 24A:
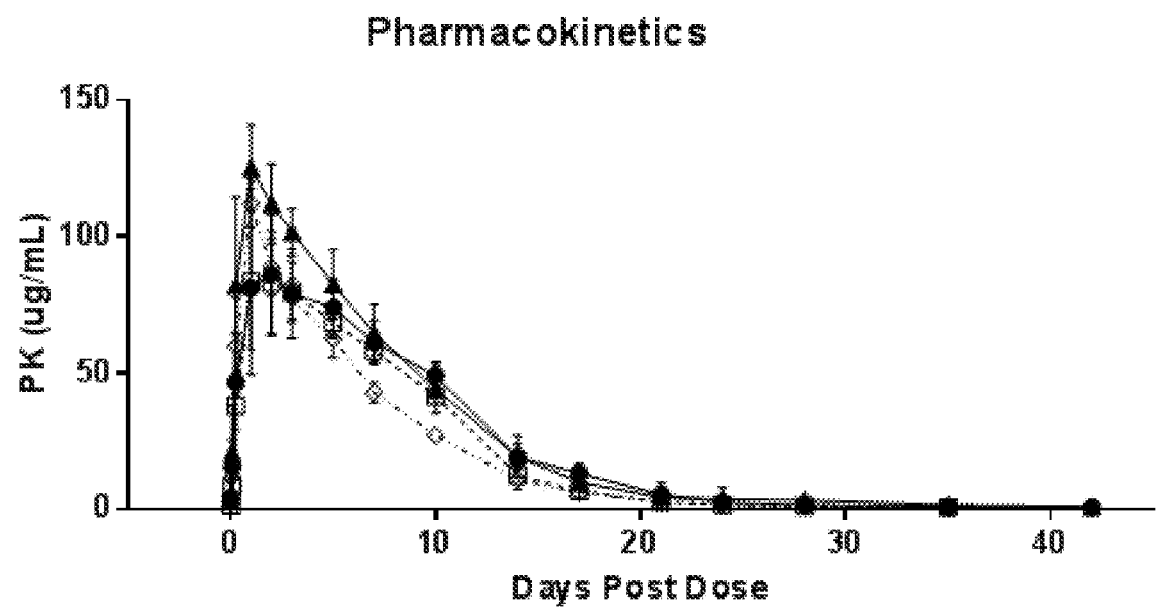
FIGS. 24A and 24B show a pharmacokinetic profile (µg/mL) with corresponding low density lipoprotein (LDL) concentration (mg/dL) profile in plasma. LDL concentrations and test article serum concentrations are presented as mean values from four animals. Solid circles with a solid line indicate the serum concentrations of the parent antibody AK. Open squares with a dashed line indicate the serum concentrations of the antibody bearing the Fab mutation. Solid triangles with a solid line indicate the serum concentrations of the antibody bearing the Fc mutation. Open diamonds with a dashed line indicate the serum concentrations of the antibody bearing both the Fab and Fc mutations. These data indicate that presence of a mutation in the Fc region that reduces viscosity of the antibody formulation results in a reduced time to Tmax and a higher Cmax. All the mutant forms of the parent antibody retain the ability to lower serum LDL-C(lower panel).
Figure 24B:
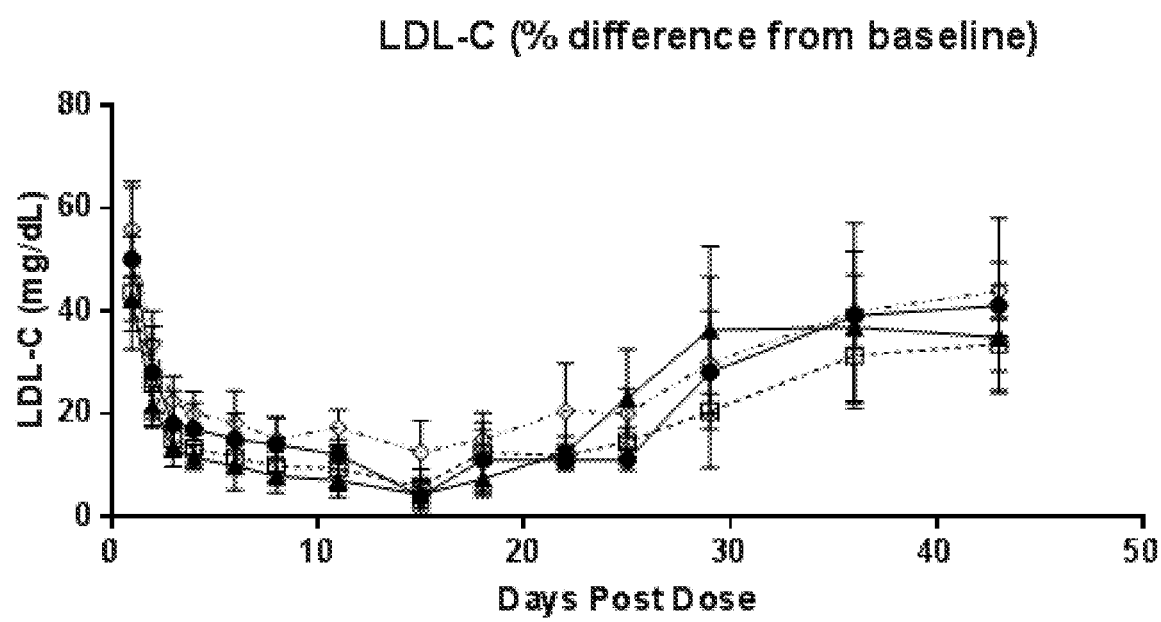

Test article concentrations plotted versus time are shown in FIGS. 24A and 24B (mean concentrations for each test article, n=4 at each time point). Pharmacokinetic parameters for the four test articles are summarized in FIG. 22. Antibodies containing the Fc mutation S440K (both antibody AK (Fc mutant) and antibody AK (Fc and Fab double mutant)) show a reduced Tmax (0.81 and 1 days respectively versus 2.5 days) and increased Cmax (125 and 112 µg/mL respectively versus 87.8 µg/mL) relative to antibody AK (control) and antibody AK (Fab mutant) indicating antibodies containing an Fc mutation that reduces viscosity are distributing more rapidly to the circulation following subcutaneous injection.

Administration of all low viscosity homologues of antibody AK resulted in expected pharmacologic mild to moderate decreases in low density lipoprotein (LDL) associated with decreased total cholesterol concentration compared to baseline (Day −6). The magnitude of decrease for total and low density lipoprotein cholesterol following administration of AK Fab mutant and AK S440K Fc mutant was generally similar to control animals with a trend toward recovery to baseline of AK S440K Fc mutant on Day 25 and AK (control) and AK Fab mutant on Day 29. The magnitude of decrease in total and low density lipoprotein cholesterol for AK Fab/S440K double mutant was generally less pronounced compared to control (antibody AK at 10 mg/kg). There were no changes in high density lipoprotein in any AK low viscosity homologue. Percentage changes in LDL-C relative to baseline are tabulated in FIG. 23 and are plotted versus time in FIGS. 24A and 24B.

Abbreviations

Abbreviated terms used throughout this specification are defined as follows.
AEI allelic expression imbalance
ANOVA analysis of variance
AUC area under the curve
BSA bovine serum albumin
DMEM Dulbecco's Modified Eagle Medium DMSO dimethyl sulfoxide
EDC  1-ethyl-3-[3-dimethylaminopropyl] carbodiimide hydrochloride
EDTA ethylenediaminetetraacetic acid
ELISA enzyme-linked immunosorbent assay
eQTL expression quantitative trait loci
ESI-TOF electrospray ionization time of flight
FACS fluorescence-activated cell sorting
FBS fetal bovine serum
FPLC fast protein liquid chromatography
FVB a strain of mice inbred for the Friend leukemia virus 1b (Fvlb) allele
H&E Hematoxylin and eosin
HA hypoxanthine
HIC hydrophobic interaction chromatography
HPLC high performance liquid chromatography
HRP horseradish peroxidase
HUVEC human umbilical vein epithelial cell
IBD inflammatory bowel disease
IDMEM DMEM without glutamine
IFN interferon
IL interleukin
MCP monocyte chenmotactic protein
MSD macromolecular structure database
PBMC peripheral blood mononuclear cell
PBS phosphate-buffered saline
PCR polymerase chain reaction
PEG polyethylene glycol
PEI polyethylenimine
QTL quantitative trait loci
RPMI media developed at Roswell Park Memorial Institute
SNP single nucleotide polymorphism
TFA trifluoroacetic acid
TMB 3,3',5,5'-Tetramethylbenzidine

What is claimed is:

1. An antigen binding protein that specifically binds to GIPR, wherein the antigen binding protein comprises sequences of SEQ ID NOS: 158 and 160, wherein the antigen binding protein further comprises one or more sequence modifications selected from:
   a. a VH1|1-18 germline subfamily sequence comprising one or more substitutions selected from $82X^1$, $94X^2$, and $95X^3$, wherein $X^1$ is selected from R, K and H, $X^2$ is selected from S, T, N and Q and $X^3$ is selected from R, K, and H;
   b. a VH3|3-33 germline subfamily sequence comprising one or more substitutions selected from $1X^4$, $17X^5$, and $85X^6$, wherein $X^4$ is selected from D and E, $X^5$ is selected from G, A, V, I, L, and M, and $X^6$ is selected from GA, V, I, L, and M;
   c. a VK3 L 16 germline subfamily sequence comprising one or more substitutions selected from $4X^{10}$, $13X^{11}$, $76X^{12}$, $95X^{13}$, $97X^{14}$, and 98P, wherein $X^{10}$ is selected from G, A, V, I, L, and M, $X^{11}$ is selected from G, A, V, I, L, and M, $X^{12}$ is selected from D and E, $X^{13}$ is selected from R, K and H, and $X^{14}$ is selected from D and E, wherein the antigen binding protein does not comprise only substitution 78F;
   d. a VK3jL6 germline subfamily sequence comprising one or more substitutions selected from $76X^{12}$ and $95X^{13}$;
   e. an Fe domain sequence comprising one or more substitutions selected from $253X^{15}$, $440X^{16}$, and $439X^{17}$, wherein $X^{15}$ is selected from G, A, V, I, L, and M, $X^{16}$ is selected from R, K, and H, and) $X^{17}$ is selected from D and E, wherein the Fc domain sequence comprises only one of $440X^{16}$ and $439X^{17}$ and wherein the antigen binding protein comprises at least one of $253X^{15}$ or modifications selected from subparagraphs a, b, c, d and f when $X^{16}$ is K or $X^{17}$ is E and the antigen binding protein specifically binds CD20; and
   f. an Fc domain sequence comprising $X^{18}X^{19}$ at its C-terminus wherein $X^{18}$ is one to four amino acids selected from D and E or from H, K, and R, and $X^{19}$ is selected from P, M, G, A, V, I, L, S, T, N, Q F, Y and W and is absent when $X^{18}$ comprises D or E, is present when $X^{18}$ comprises K or R at its C-terminal end, and is present or absent when $X^{18}$ comprises H at its C-terminal end, and wherein the antigen binding protein comprises at least one of $253X^{15}$ or substitutions selected from subparagraphs a through e when PGKP (SEQ ID NO:381), PGKKP (SEQ ID NO:382), PGKKKP (SEQ ID NO:383), or PGE appears at the C-terminus of the Fc domain and the antigen binding protein specifically binds CD20 or CD38;

wherein the amino acids in subparagraphs a, b, c, and d are numbered according to the Aho numbering system and the amino acids in subparagraph e are numbered according to the EU numbering system.

2. The antigen binding protein of claim 1, wherein the VH1|1-18 germline subfamily sequence comprises one or more substitutions selected from 82R, 94S, and 95R.

3. The antigen binding protein of claim 1, wherein the VH1|1-18 germline subfamily sequence comprises substitution $59X^{20}$ wherein $X^{20}$ is selected from R, K and H.

4. The antigen binding protein of claim 1, wherein the VH3|3-33 germline subfamily sequence comprises one or more substitutions selected from 1E, 17G, and 85A.

5. The antigen binding protein of claim 1, wherein the VH3|3-33 germline subfamily sequence comprises substitutions 1E, 17G, and 85A.

6. The antigen binding protein of claim 1, wherein the VK3|L16 sequence comprises one or more substitutions selected from 4L, 13L, 76D, 78F, 95R, 97E, and 98P.

7. The antigen binding protein of claim 1, wherein the antigen binding protein comprises, prior to substitution:
   a. a heavy chain framework 1 sequence of SEQ ID NO: 302;
   b. a heavy chain framework 2 sequence of SEQ ID NO.: 342;
   c. a heavy chain framework 3 sequence of SEQ ID NO.: 303;
   d. a heavy chain framework 4 sequence of SEQ ID NO.: 276;
   e. a light chain framework 1 sequence of SEQ ID NO.: 181;
   f. a light chain framework 2 sequence of SEQ ID NO.: 194;
   g. a light chain framework 3 sequence of SEQ ID NO.: 234; and
   h. a light chain framework 4 sequence of SEQ ID NO.: 188.

8. The antigen binding protein of claim 1 comprising an amino acid sequence selected from SEQ ID NOS: 359, 361, 362, 364, and 368.

9. The antigen binding protein of claim 8 further comprising an amino acid sequence selected from SEQ ID NOS: 360, 363, 365, and 367.

* * * * *